US011141483B2

(12) United States Patent
Makings et al.

(10) Patent No.: US 11,141,483 B2
(45) Date of Patent: Oct. 12, 2021

(54) METHODS FOR MANUFACTURING PHTHALOCYANINE DYE CONJUGATES AND STABLE CONJUGATES

(71) Applicant: Rakuten Medical, Inc., San Mateo, CA (US)

(72) Inventors: Lewis R. Makings, Encinitas, CA (US); Roger Heim, Del Mar, CA (US); Miguel Garcia-Guzman, San Diego, CA (US)

(73) Assignee: Rakuten Medical, Inc., San Mateo, CA (US)

( * ) Notice: Subject to any disclaimer, the term of this patent is extended or adjusted under 35 U.S.C. 154(b) by 355 days.

(21) Appl. No.: 15/753,151

(22) PCT Filed: Aug. 18, 2016

(86) PCT No.: PCT/US2016/047636
§ 371 (c)(1),
(2) Date: Feb. 15, 2018

(87) PCT Pub. No.: WO2017/031363
PCT Pub. Date: Feb. 23, 2017

(65) Prior Publication Data
US 2019/0015510 A1    Jan. 17, 2019

Related U.S. Application Data

(60) Provisional application No. 62/206,774, filed on Aug. 18, 2015.

(51) Int. Cl.
*A61K 41/00* (2020.01)
*A61K 47/68* (2017.01)
(Continued)

(52) U.S. Cl.
CPC ...... *A61K 41/0076* (2013.01); *A61K 47/6835* (2017.08); *A61K 47/6839* (2017.08);
(Continued)

(58) Field of Classification Search
None
See application file for complete search history.

(56) References Cited

U.S. PATENT DOCUMENTS 2,915,392 A   12/1959  Pedersen
5,196,005 A    3/1993  Doiron
(Continued)

FOREIGN PATENT DOCUMENTS

CN    101023084        8/2007
CN    102585003 A      7/2012
(Continued)

OTHER PUBLICATIONS

Maawy et al., PLOS ONE, vol. 10, No. 3, Mar. 23, 2015 (Mar. 23, 2015) (Year: 2015).*
(Continued)

*Primary Examiner* — Karl J Puttlitz
(74) *Attorney, Agent, or Firm* — Morrison & Foerster LLP

(57) ABSTRACT

Provided are methods for manufacturing a conjugate containing a phthalocyanine dye, including methods that include one or more steps of preparing or producing the conjugate, formulating the conjugate and packaging the conjugate. In some aspects, the manufacturing methods result in the generation of a stable conjugate. Also provided are stable phthalocyanine dye conjugates, compositions and articles of manufacture containing the stable conjugates, and methods for their administration to subjects for photoimmunotherapy. In some embodiments, the phthalocyanine dye conjugates are conjugated to a targeting molecule, such as an
(Continued)

antibody, that targets the conjugate to a cell or pathogen, such as by binding to a cell surface protein.

17 Claims, 19 Drawing Sheets

Specification includes a Sequence Listing.

(51) Int. Cl.
*A61P 35/00* (2006.01)
*A61K 45/06* (2006.01)

(52) U.S. Cl.
CPC ...... *A61K 47/6843* (2017.08); *A61K 47/6851* (2017.08); *A61P 35/00* (2018.01); *A61K 45/06* (2013.01); *A61K 2300/00* (2013.01)

(56) References Cited

U.S. PATENT DOCUMENTS

| | | | |
|---|---|---|---|
| 5,494,793 | A | 2/1996 | Schindele |
| 5,585,089 | A | 12/1996 | Queen et al. |
| 6,344,050 | B1 | 2/2002 | Chen |
| 6,534,041 | B1 | 3/2003 | Licha |
| 7,005,518 | B2 | 2/2006 | Peng et al. |
| 7,498,029 | B2 | 3/2009 | Hasan |
| 8,524,239 | B2 | 9/2013 | Kobayashi |
| 8,623,354 | B2 | 1/2014 | Brown |
| 9,358,306 | B2 | 6/2016 | Kobayashi |
| 10,064,943 | B2 | 9/2018 | Dilley et al. |
| 10,295,719 | B2 | 5/2019 | Rose et al. |
| 10,416,366 | B2 | 9/2019 | Rose et al. |
| 10,527,771 | B2 | 1/2020 | Rose et al. |
| 10,537,641 | B2 | 1/2020 | Kobayashi |
| 10,538,590 | B2 | 1/2020 | Kobayashi |
| 10,588,972 | B2 | 3/2020 | Kovar |
| 2001/0044124 | A1 | 11/2001 | Bacus |
| 2003/0092667 | A1 | 5/2003 | Tachibana et al. |
| 2004/0120949 | A1 | 6/2004 | Adolf |
| 2004/0171827 | A1 | 9/2004 | Peng et al. |
| 2005/0157292 | A1 | 7/2005 | Saitoh |
| 2006/0231107 | A1 | 10/2006 | Glickman |
| 2007/0020272 | A1 | 1/2007 | Hasan |
| 2007/0133086 | A1 | 6/2007 | Wilhelm |
| 2008/0073566 | A1 | 3/2008 | Frangioni |
| 2008/0095699 | A1 | 4/2008 | Zheng et al. |
| 2008/0095950 | A1 | 4/2008 | Hall-Goulle et al. |
| 2008/0253960 | A1 | 10/2008 | Zheng |
| 2010/0215575 | A1 | 8/2010 | O'Neill et al. |
| 2010/0255057 | A1 | 10/2010 | Hyde et al. |
| 2011/0082412 | A1 | 4/2011 | Hyde et al. |
| 2012/0010558 | A1* | 1/2012 | Kobayashi ............ C07K 16/32 604/20 |
| 2012/0070377 | A1 | 3/2012 | Yahioglu et al. |
| 2012/0070853 | A1 | 3/2012 | Johansen et al. |
| 2012/0171290 | A1 | 7/2012 | Pierre |
| 2012/0263651 | A1 | 10/2012 | Widen et al. |
| 2013/0287688 | A1 | 10/2013 | Jain |
| 2013/0336995 | A1 | 12/2013 | Kobayashi |
| 2014/0050662 | A1 | 2/2014 | Ho |
| 2014/0120119 | A1 | 5/2014 | Kobayashi |
| 2014/0309578 | A1 | 10/2014 | Anvari |
| 2014/0314778 | A1* | 10/2014 | Alavattam ............ C12Q 1/28 424/141.1 |
| 2015/0343060 | A1 | 12/2015 | Kovar |
| 2015/0343084 | A1 | 12/2015 | Dilley |
| 2015/0343484 | A1 | 12/2015 | Kukas |
| 2015/0374819 | A1 | 12/2015 | Kovar |
| 2016/0256564 | A2 | 9/2016 | Kobayashi |
| 2016/0345834 | A1 | 12/2016 | Hasan et al. |
| 2017/0122853 | A1 | 5/2017 | Kobayashi |
| 2018/0113246 | A1 | 4/2018 | Rose |
| 2018/0113247 | A1 | 4/2018 | Rose |
| 2018/0236076 | A1 | 8/2018 | Kobayashi |
| 2018/0239074 | A1 | 8/2018 | Rose |
| 2018/0250405 | A1 | 9/2018 | Biel |
| 2018/0339048 | A1 | 11/2018 | Dilley et al. |
| 2019/0070296 | A1 | 3/2019 | Wang et al. |
| 2019/0282696 | A1 | 9/2019 | Biel |
| 2019/0365897 | A1 | 12/2019 | Garcia-Guzman et al. |
| 2020/0085950 | A1 | 3/2020 | Kobayashi et al. |
| 2020/0095331 | A1 | 3/2020 | Kobayashi et al. |
| 2020/0166690 | A1 | 5/2020 | Rose et al. |
| 2020/0179514 | A1 | 6/2020 | Kovar |

FOREIGN PATENT DOCUMENTS

| | | |
|---|---|---|
| CN | 103781495 | 5/2014 |
| CN | 104203286 | 12/2014 |
| DE | 19717904 A1 | 10/1998 |
| EP | 1512963 A1 | 3/2005 |
| JP | 2003284757 A | 10/2003 |
| JP | 2003344284 A | 12/2003 |
| JP | 2006515892 A | 6/2006 |
| JP | 2006517230 A | 7/2006 |
| JP | 2007155722 A | 6/2007 |
| JP | 2014523907 A5 | 6/2015 |
| JP | 2017524002 A5 | 8/2018 |
| WO | WO 2001057495 | 8/2001 |
| WO | WO03011106 A2 | 2/2003 |
| WO | WO03083811 A1 | 10/2003 |
| WO | WO 2004038378 | 5/2004 |
| WO | WO2004067038 A1 | 8/2004 |
| WO | WO2004071571 A1 | 8/2004 |
| WO | WO 2005099689 | 10/2005 |
| WO | WO2006092598 A2 | 9/2006 |
| WO | WO2008120134 A1 | 10/2008 |
| WO | WO 2008152424 | 12/2008 |
| WO | WO 2009038776 | 3/2009 |
| WO | WO 2009092062 | 7/2009 |
| WO | WO2010047611 A1 | 4/2010 |
| WO | WO2010085651 A1 | 7/2010 |
| WO | WO 2010121163 | 10/2010 |
| WO | WO 2011025950 | 3/2011 |
| WO | WO 2011038006 | 3/2011 |
| WO | WO 2011123742 | 10/2011 |
| WO | WO 2012076631 | 6/2012 |
| WO | WO 2012082118 | 6/2012 |
| WO | WO 2013009475 | 1/2013 |
| WO | WO 2013044156 | 3/2013 |
| WO | WO 2013080187 | 6/2013 |
| WO | WO 2013139391 | 9/2013 |
| WO | WO 2014084394 | 6/2014 |
| WO | WO 2014089247 | 6/2014 |
| WO | WO 2014120974 | 8/2014 |
| WO | WO 2014127365 | 8/2014 |
| WO | 2014160497 A1 | 10/2014 |
| WO | WO 2014168950 | 10/2014 |
| WO | WO 2014176284 | 10/2014 |
| WO | WO 2015042325 | 3/2015 |
| WO | WO 2015057692 | 4/2015 |
| WO | WO 2015061247 | 4/2015 |
| WO | WO 2015120198 | 8/2015 |
| WO | WO2015175750 A1 | 11/2015 |
| WO | WO 2015187651 | 12/2015 |
| WO | WO 2015187677 | 12/2015 |
| WO | WO 2016022896 | 2/2016 |
| WO | WO2017027247 A1 | 2/2017 |
| WO | WO 2017031367 | 2/2017 |
| WO | WO 2018080952 | 5/2018 |
| WO | WO 2018156815 | 8/2018 |
| WO | WO2019009941 A1 | 1/2019 |
| WO | WO 2019036249 | 2/2019 |
| WO | WO2019232478 A1 | 12/2019 |
| WO | WO 2020205623 | 10/2020 |
| WO | WO 2021021882 | 2/2021 |
| WO | WO 2021026393 | 2/2021 |
| WO | WO 2021046100 | 3/2021 |

OTHER PUBLICATIONS

Rosas Arellano et al., Histochem Cell Biol (2016) 146:421-430 (Year: 2016).*

(56) References Cited

OTHER PUBLICATIONS

Anonymous, "Near Infrared Light for the Treatment of Painful Peripheral Neuropathy," U.S. National Institutes of Health, Aug. 2, 2012, XP002686617, retrieved from the internet: URL:http://clinicaltrials.gov/ct2/show/NCT00125268, retrieved on Nov. 7, 2011.
Ballou et al., "Tumor labeling in vivo using cyanine-conjugated monoclonal antibodies." Cancer Immunol Immunother. Oct. 1995;41(4):257-263.
Carcenac et al., "Internalisation enhances photo-induced cytotoxicity of monoclonal antibody-phthalocyanine conjugates." British Journal of Cancer, (2001) 85(11); 1787-1793.
Carter et al., "Identification and Validation of Cell Surface Antigens for Antibody Targeting in Oncology," Endocr Relat Cancer (2004) 11:659-687.
Chen et al., "Tumor vascular permeabilization by vascular-targeting photosensitization: effects, mechanism, and therapeutic implications," Clin Cancer Res. (2006) 12: 917-923.
Clinical Trial Identifier NCT02422979, first posted on Apr. 22, 2015. Last updated on Sep. 20, 2019.
Del Governatore et al., "Experimental Photoimmunotherapy of Hepatic Metastases of Colorectal Cancer with a 17.1A Chlorine6 Immunoconjugate," Cancer Res. (2000) 60:4200-4205.
Dixit et al., "Transferrin Receptor-Targeted Theranostic Gold Nanoparticles for Photosensitizer Delivery in Brain Tumors," Nanoscale, (2015) 7(5):1782-1790.
Duska et al., "Combination Photoimmunotherapy and Cisplatin: Effects on Human Ovarian Cancer Ex Vivo," J Nat Cancer Inst. (1999) 91:1557-1563.
Gajewski et al., Current Protocols in Immunology (2001) 20.4.1-20.4.18 by John Wiley & Sons, Inc., 2001.
Greish, K., "Enhanced permeability and retention of macromolecular drugs in solid tumors: a royal gate for targeted anticancer nanomedicines," J Drug Target. (2007) 15: 457-464.
Kines et al., "HPV Based Photodynamic Therapy: A New Approach for Anti-Cancer Therapy," J. Immunol. (2014) 192 (1): Supplement 206.8.
Kirveliene et al., "Schedule-Dependent Interaction Between Doxorubicin and mTHPC-Mediated Photodynamic Therapy in Murine Hepatoma In Vitro and In Vivo," Cancer Chemother. Pharmacol. (2005) 57:65-72.
Kobayashi "Activatable Fluorescent Imaging Probes for Cancer Detection and Diagnosis," Abstract presented at the American Chemical Society meeting in San Francisco, 2014.
Kobayashi, "Near infrared photoimmunotherapy: A new cancer therapy kills cancer cells with exposure of harmless near infrared light," Poster Presentation, at NEST Conference, Tokyo, Japan, Apr. 2018.
Kovar et al., "A Systematic Approach to the Development of Fluorescent Contrast Agents for Optical Imagining of Mouse Cancer Models," Anal. Biochem. (2007) 367: 1-12.
Maya et al., "Synthesis, Aggregation Behavior and Nonlinear Absorption Properties of Lead Phthalocyanines Substituted with Siloxane Chains," J Materials Chem. (2003) 13: 1603-1613.
Mchugh et al., "The role of suppressor T cells in regulation of immune responses." J Allergy Clin Immunol. (2002) 110(5): 693-702.
Mitchell et al., "Comparison of Two Infrared Devices in Their Effectiveness in Reducing Symptoms Associated with RLS," Physiother. Theory Pract. (2011) 27:352-359.
Mitsunaga et al., "Abstract 3618: Target-Specific Photo-Activatable Immunotherapy (PIT) for Cancer Based on a Monoclonal Antibody-Photosensitizer Conjugate," in Proceedings of the 102nd Annual Meeting of the American Association for Cancer Research; Apr. 2-6, 2011; Orlando, FL. Philadelphia (PA): AACR; Cancer Res. 71:3618, 2011.
Mitsunaga et al., "Cancer Cell-Selective in Vivo Near Infrared Photomimmunotherapy Targeting Specific Membrane Molecules," Nat. Med. 17:1685-1691, 2011. Supplementary materials.
Nagaya et al., "Host Immunity Following Near-Infrared Photoimmunotherapy Is Enhanced with PD-1 Checkpoint Blockade to Eradicate Established Antigenic Tumors," Cancer Immunol Res. (2019) 7:401-413.
Nagaya et al., "Near infrared photoimmunotherapy targeting bladder cancer with a canine anti-epidermal growth factor receptor (EGFR) antibody," Oncotarget (2018) 9:19026-19038.
Nagaya et al., "Near infrared photoimmunotherapy with avelumab, an antiprogrammed death-ligand 1 (PD-L1) antibody," Oncotarget (2017) 8: 8807-8817.
Nagaya et al., "Syngeneic Mouse Models of Oral Cancer Are Effectively Targeted by Anti-CD44-Based NIR-PIT," Mol Cancer Res. (2017) 15: 1667-1677.
Nowis et al., "The influence of photodynamic therapy on the immune response," Photodiagnosis Photodyn Ther. (2005) 2(4): 283-98.
Rosenthal et al., "In Vivo Detection of Head and Neck Cancer Orthotopic Xenografts by Immunofluorescence," Laryngoscope (2006) 116: 1636-1641.
Sanchez-Barcelo et al., "Recent Patents on Light Based Therapies: Photodynamic Therapy, Photothermal Therapy and Photoimmunotherapy," Recent Patents on Endocrine, Metabolic & Immune Drug Discovery (2014) 8: 1-8.
Sato et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy," ACS Cent Sci. (2018) 4: 1559-1569.
Sato et al., "Spatially selective depletion of tumor-associated regulatory T cells with near-infrared photoimmunotherapy." Sci Transl Med. (2016) 8(352): 352ra110.
Savellano et al., "Multiepitope HER2 Targeting Enhances Photoimmunotherapy of HER2-Overexpressing Cancer Cells with Pyropheophorbide-a Immunoconjugates," Cancer Res. (2005) 65:6371-6379.
Scully et al., "Application of Fluorescence Lifetime Imaging Microscopy to the Investigation of Intracellular PDT Mechanisms," Bio imaging (1997) 5 :9-18.
Serebrovskaia et al., "Genetically Encoded Photoimmunosensitizer," abstract (in English); Bioorg. Khim. 2011 37 (1):137-44.
Serebrovskaya et al., "Targeting Cancer Cells by Using an Antireceptor Antibody-Photo sensitizer Fusion Protein," Proc Nat A cad Sci. (2009) 106: 9221-9225.
Snyder et al., "Photodynamic therapy: a means to enhanced drug delivery to tumors," (2003) Cancer Res. 63:8126-8131.
Soukos et al., "Epidermal Growth Factor Receptor-Targeted Immunophotodiagnosis and Photoimmunotherapy of Oral Precancer in Vivo," Cancer Res. (2001) 61: 4490-4496.
Steele et al., "Suppressor deletion therapy: selective elimination of T suppressor cells in vivo using a hematoporphyrin conjugated monoclonal antibody permits animals to reject syngeneic tumor cells." Cancer Immunol Immunother. (1988) 26(2): 125-131.
Sugiyama et al., "Anti-CCR4 mAb selectively depletes effector-type FoxP3+CD4+ regulatory T cells, evoking antitumor immune responses in humans." Proc Natl Acad Sci U S A. (2013) 110(44): 17945-17950.
Supplementary materials from Sugiyama et al., "Anti-CCR4 mAb selectively depletes effector-type FoxP3+CD4+ regulatory T cells, evoking antitumor immune responses in humans." Proc Natl Acad Sci U S A. Oct. 29, 2013;110 (44):17945-50.
Supplementary materials from Zhang et al., "Target-selective phototherapy using a ligand-based photosensitizer for type 2 cannabinoid receptor," Chem Biol. (2014) 21(3): 338-44.
Supplementary materials from Zhang et al., "Tumor mitochondria-targeted photodynamic therapy with a translocator protein (TSPO)-specific photosensitizer," Acta Biomater. Dec. 2015;28:160-70.
Van Dongen et al., "Photosensitizer-Antibody Conjugates for Detection and Therapy of Cancer," Adv Drug Deliv Rev. (2004) 56: 31-52.
Vrouenraets et al., "Targeting of aluminum (III) phthalocyanine tetrasulfonate by use of internalizing monoclonal antibodies: improved efficacy in photodynamic therapy." Cancer Research (2001) (61)5; 1970-1975.

(56) References Cited

OTHER PUBLICATIONS

Waite et al., "Nanoscale drug delivery systems for enhanced drug penetration into solid tumors: current progress and opportunities," (2012) Crit Rev Biomed Eng. 40: 21-41.
Wessels et al., "Advances in cellular, subcellular, and nanoscale imaging in vitro and in vivo," Cytometry (2010) A:77: 667-676.
Xu et al., "Antibody Conjugated Magnetic Iron Oxide Nanoparticles for Cancer Cell Separation in Fresh Whole Blood," Biomaterials (2011) 32: 9758-9765.
Yoon et al., "Advance in Photosensitizers and Light Delivery for Photodynamic Therapy," Clin Endosc. (2013) 46(1): 7-23.
Zhu et al., "Visualization of P53264-2n/HLA-A *0201 Complexes Naturally Presented on Tumor Cell Surface by a Multimeric Soluble Single-Chain T Cell Receptor," J Immunol. (2006) 176: 3223-3232.
Zinn et al., "IND-Directed Safety and Biodistribution Study of Intravenously Injected Cetuximab-IRDye800 in Cynomolgus Macaques." Molecular Imaging Biology, (2015) 17(1); 49-57.
Zuluaga et al., "Combination of Photodynamic Therapy With Anti-Cancer Agents," Curr Med Chem. (2008) 15:1655-1673.
Ali et al., "Dynamic fluorescent imaging with indocyanine green for monitoring the therapeutic effects of photoimmunotherapy," Contrast Media Mol Imaging. Jul.-Aug. 2014;9(4):276-82.
Amoury et al., "Photoimmunotheranostic agents for triple-negative breast cancer diagnosis and therapy that can be activated on demand," Oncotarget. (2016) 7(34):54925-54936.
Barrett et al., "In vivo diagnosis of epidermal growth factor receptor expression using molecular imaging with a cocktail of optically labeled monoclonal antibodies," Clin Cancer Res. Nov. 15, 2007;13(22 Pt 1):6639-48.
Chopra, "IRDye 700DX-Labeled annexin V," Molecular Imaging and Contrast Agent Database (MICAD) [Internet]. Bethesda (MD): National Center for Biotechnology Information (US); 2004-2013. Oct. 27, 2009 [updated Dec. 17, 2009].
De Boer et al., "A standardized light-emitting diode device for photoimmunotherapy," J Nucl Med. Nov. 2014;55(11):1893-8.
De Boer et al., "Biodistribution Study of Intravenously Injected Cetuximab-IRDye700DX in Cynomolgus Macaques," Mol Imaging Biol (2016) 18(2):232-42.
Denis et al., "Synthesis, bioanalysis and biodistribution of photosensitizer conjugates for photodynamic therapy," Bioanalysis (2013) 5:1099-1114.
Elliott et al., "Direct characterization of arterial input functions by fluorescence imaging of exposed carotid artery to facilitate kinetic analysis," Mol Imaging Biol. Aug. 2014;16(4):488-94.
Gao et al., "In vivo cancer targeting and imaging with semiconductor quantum dots," Nat Biotechnol. Aug. 2004;22(8):969-76.
Gleysteen et al., "Update on Aspyrian Trial: Study of RM-1929 and Photoimmunotherapy in Patients with Recurrent Head and Neck Cancer," Abstract, submitted for 2017 Combined Otolaryngology Spring Meetings, American Head and Neck Cancer Society, Apr. 26, 2017, San Diego, CA, available online at: https://www.researchposters.com/display_posters.aspx?page=eposter&code=COSM2017.
Gleysteen et al., "Update on Aspyrian Trial: Study of RM-1929 and Photoimmunotherapy in Patients with Recurrent Head and Neck Cancer," Poster, Presented at 2017 Combined Otolaryngology Spring Meetings, American Head and Neck Cancer Society, Apr. 26, 2017, San Diego, CA, available online at https://www.researchposters.com/Posters/COSM/COSM2017/B043.pdf.
Glysteen et al., "Fluorescently Labeled Cetuximab to Evaluate Head and Neck Cancer Response to Treatment," Cancer Biology & Therapy. 2007 6(8):e1-e5.
Hanaoka et al., "Glypican-3 targeted human heavy chain antibody as a drug carrier for hepatocellular carcinoma therapy," Mol Pharm. Jun. 1, 2015;12(6):2151-7.
Hanaoka et al., "Photoimmunotherapy of hepatocellular carcinoma-targeting Glypican-3 combined with nanosized albumin-bound paclitaxel," Nanomedicine (Lond). (2015);10(7):1139-47.
Heukers et al., "Nanobody-photosensitizer conjugates for targeted photodynamic therapy," Nanomedicine (2014) 10:14441-51.
Hiroshima et al., "Photoimmunotherapy Inhibits Tumor Recurrence After Surgical Resection on a Pancreatic Cancer Patient-Derived Orthotopic Xenograft (PDOX) Nude Mouse Model," Ann Surg Oncol. Dec. 2015;22 Suppl 3:S1469-74.
Ishida et al., "Trastuzumab-Based Photoimmunotherapy Integrated with Viral HER2 Transduction Inhibits Peritoneally Disseminated HER2-Negative Cancer," Mol Cancer Ther. Mar. 2016;15(3):402-11.
Ito et al., "Combination photoimmunotherapy with monoclonal antibodies recognizing different epitopes of human epidermal growth factor receptor 2: an assessment of phototherapeutic effect based on fluorescence molecular imaging," Oncotarget. Mar. 22, 2016;7(12):14143-52.
Ito et al., "Molecular targeted photoimmunotherapy for HER2-positive human gastric cancer in combination with chemotherapy results in improved treatment outcomes through different cytotoxic mechanisms," BMC Cancer. Jan. 25, 2016;16:37.
Jia et al., "Cannabinoid CB2 receptor as a new phototherapy target for the inhibition of tumor growth," Mol Pharm. Jun. 2, 2014;11(6):1919-29.
Jing et al., "Imaging and Selective Elimination of Glioblastoma Stem Cells with Theranostic Near-Infrared-Labeled CD133-Specific Antibodies," Theranostics. Apr. 12, 2016;6(6):862-74.
Kijanka et al., "Optical imaging of pre-invasive breast cancer with a combination of VHHs targeting CAIX and HER2 increases contrast and facilitates tumour characterization," EJNMMI Res. (2016) 6(1):14.
Kishimoto et al., "Evaluation of oxygen dependence on in vitro and in vivo cytotoxicity of photoimmunotherapy using IR-700-antibody conjugates," Free Radic Biol Med. Aug. 2015;85:24-32.
Kochuparambil et al., "A Phase 1, Multicenter, Open-label, Dose-escalation, Combination Study of RM-1929 and Photoimmunotherapy in Patients with Recurrent Head and Neck Cancer," Abstract, Annals of Oncology, vol. 28, Issue suppl_5, Sep. 1, 2017, mdx374.008, Published: Sep. 18, 2017, available online at: https://doi.org/10.1093/annonc/mdx374.008.
Kochuparambil et al., "A Phase 1, Multicenter, Open-label, Dose-escalation, Combination Study of RM-1929 and Photoimmunotherapy in Patients with Recurrent Head and Neck Cancer," Poster, Presented at 2017 European Society for Medical Oncology, Sep. 8-12, 2017, Madrid, Spain.
Licor, "High Photostability of IRDye® 700DX," Retrieved on Aug. 23, 2018. Retrieve on https://www.licor.com/bio/products/reagents/irdye/700dx/photostability.html.
Lin et al., "Comparison of Cherenkov excited fluorescence and phosphorescence molecular sensing from tissue with external beam irradiation," Phys Med Biol. May 21, 2016;61(10):3955-68.
Maawy et al., "Near infra-red photoimmunotherapy with anti-CEA-IR700 results in extensive tumor lysis and a significant decrease in tumor burden in orthotopic mouse models of pancreatic cancer," PLoS One. Mar. 23, 2015;10(3):e0121989.
Maawy et al., "Photoimmunotherapy lowers recurrence after pancreatic cancer surgery in orthotopic nude mouse models," J Surg Res. Jul. 2015;197(1):5-11.
Master et al. "A Cell-targeted Photodynamic Nanomedicine Strategy for Head & Neck Cancers," Mol. Pharm., (2013) 6:1988-1997.
Mitsunaga et al., "Cancer cell-selective in vivo near infrared photoimmunotherapy targeting specific membrane molecules," Nat Med. Nov. 6, 2011;17(12):1685-91.
Mitsunaga et al., "Immediate in vivo target-specific cancer cell death after near infrared photoimmunotherapy," BMC Cancer. Aug. 8, 2012;12:345.
Mitsunaga et al., "Near-infrared theranostic photoimmunotherapy (PIT): repeated exposure of light enhances the effect of immunoconjugate," Bioconjug Chem. Mar. 21, 2012;23(3):604-9.
Moore et al., "Photoimmunotherapy of residual disease after incomplete surgical resection in head and neck cancer models," Cancer Med. Jul. 2016;5(7):1526-34.
Nagaya et al., "Improved micro-distribution of antibody-photon absorber conjugates after initial near infrared photoimmunotherapy (NIR-PIT)," J Control Release. (2016) 232:1-8.
Nagaya et al., "Near infrared photoimmunotherapy of B-cell lymphoma," Mol Oncol. (2016) 10(9):1404-1414.

(56) References Cited

OTHER PUBLICATIONS

Nagaya et al., "Near Infrared Photoimmunotherapy Targeting EGFR Positive Triple Negative Breast Cancer: Optimizing the Conjugate-Light Regimen," PLoS One. Aug. 27, 2015;10(8):e0136829.
Nagaya et al., "Near infrared photoimmunotherapy with an anti-mesothelin antibody," Oncotarget. Apr. 26, 2016;7(17):23361-9.
Nakajima et al., "Improving the efficacy of Photoimmunotherapy (PIT) using a cocktail of antibody conjugates in a multiple antigen tumor model," Theranostics. Apr. 23, 2013;3(6):357-65.
Nakajima et al., "Real-time monitoring of in vivo acute necrotic cancer cell death induced by near infrared photoimmunotherapy using fluorescence lifetime imaging," Cancer Res. Sep. 15, 2012;72(18):4622-8.
Nakajima et al., "The effects of conjugate and light dose on photo-immunotherapy induced cytotoxicity," BMC Cancer. May 30, 2014;14:389.
Nakamura et al., "MR imaging biomarkers for evaluating therapeutic effects shortly after near infrared photoimmunotherapy," Oncotarget. Mar. 29, 2016;7(13):17254-64.
Ogawa et al., "In vivo molecular imaging of cancer with a quenching near-infrared fluorescent probe using conjugates of monoclonal antibodies and indocyanine green," Cancer Res. Feb. 15, 2009;69(4):1268-72.
Olejko et al., "An ion-controlled four-color fluorescent telomeric switch on DNA origami structures," Nanoscale. May 21, 2016;8(19):10339-47.
Peng et al., "A nonfluorescent, broad-range quencher dye for Förster resonance energy transfer assays," Anal Biochem. May 15, 2009;388(2):220-8.
Peng et al., "Phthalocyanine dye as an extremely photostable and highly fluorescent near-infrared labeling reagen," Proc SPIE Int Soc Opt Eng. vol. 6097, 60970E (2006).
Samkoe et al., "High vascular delivery of EGF, but low receptor binding rate is observed in AsPC-1 tumors as compared to normal pancreas," Mol Imaging Biol. Aug. 2012;14(4):472-9.
Sano et al., "Acute cytotoxic effects of photoimmunotherapy assessed by 18F-FDG PET," J Nucl Med. May 2013;54(5):770-5.
Sano et al., "The effect of photoimmunotherapy followed by liposomal daunorubicin in a mixed tumor model: a demonstration of the super-enhanced permeability and retention effect after photoimmunotherapy," Mol Cancer Ther. Feb. 2014;13(2):426-32.
Sano et al., "Markedly Enhanced Permeability and Retention Effects Induced by Photo-Immunotherapy of Tumors," ACS Nano. Jan. 22, 2013; 7:717-724.
Sato et al., "Comparative effectiveness of light emitting diodes (LEDs) and Lasers in near infrared photoimmunotherapy," Oncotarget. Mar. 22, 2016;7(12):14324-35.
Sato et al., "Near infrared photoimmunotherapy for lung metastases," Cancer Lett. Aug. 28, 2015;365(1):112-21.
Sato et al., "Near infrared photoimmunotherapy in the treatment of disseminated peritoneal ovarian cancer," Mol Cancer Ther. Jan. 2015;14(1):141-50.
Sato et al., "Near infrared photoimmunotherapy in the treatment of pleural disseminated NSCLC: preclinical experience," Theranostics. Mar. 19, 2015;5(7):698-709.
Sato et al., "Photoimmunotherapy of gastric cancer peritoneal carcinomatosis in a mouse model," PLoS One. Nov. 17, 2014;9(11):e113276.
Sato et al., "Photoimmunotherapy: comparative effectiveness of two monoclonal antibodies targeting the epidermal growth factor receptor," Mol Oncol. May 2014;8(3):620-32.
Sato et al., "Selective cell elimination in vitro and in vivo from tissues and tumors using antibodies conjugated with a near infrared phthalocyanine," RSC Adv. Mar. 3, 2015;5(32):25105-25114.
Shimoyama et al., "Viral transduction of the HER2-extracellular domain expands trastuzumab-based photoimmunotherapy for HER2-negative breast cancer cells," Breast Cancer Res Treat. Feb. 2015;149(3):597-605.
Shirasu et al., "Potent and specific antitumor effect of CEA-targeted photoimmunotherapy," Int J Cancer. Dec. 1, 2014;135(11):2697-710.
Specenier et al., "Cetuximab: its unique place in head and neck cancer treatment," Biologics (2013) 7:77-90.
Steiner et al., "Efficient Selection of DARPins with Sub-nanomolar Affinities using SRP Phage Display," J Mol Biol (2008) 382(5):1211-1227.
Tamaskovic et al., "Designed ankyrin repeat proteins (DARPins) from research to therapy," Methods Enzymol (2012) 503:101-134.
Therasse et al., "New guidelines to evaluate the response to treatment in solid tumors. European Organization for Research and Treatment of Cancer, National Cancer Institute of the United States, National Cancer Institute of Canada," J Natl Cancer Inst (2000)92(3):205-216.
Topalian et al., "Safety, Activity, and Immune Correlates of Anti-PD-1 Antibody in Cancer," N Engl J Med (2012) 366:2443-2454.
Tynan et al., "Multicolour single molecule imaging in cells with near infra-red dyes," PLoS One. (2012);7(4):e36265.
Van Driel et al., "EGFR targeted nanobody-photosensitizer conjugates for photodynamic therapy in a pre-clinical model of head and neck cancer," J Control Release. May 10, 2016;229:93-105.
Von Felbert et al., "A specific photoimmunotheranostics agent to detect and eliminate skin cancer cells expressing EGFR," J Cancer Res Clin Oncol. May 2016;142(5):1003-11.
Wang et al., "Theranostic Agents for Photodynamic Therapy of Prostate Cancer by Targeting Prostate-Specific Membrane Antigen," Mol Cancer Ther. Aug. 2016;15(8):1834-44.
Watanabe et al., "Photoimmunotherapy targeting prostate-specific membrane antigen: are antibody fragments as effective as antibodies?," J Nucl Med. Jan. 2015;56(1):140-4.
Whiteside, "The tumor microenvironment and its role in promoting tumor growth," Oncogene (2008) 27(45):5904-5912.
Zhang et al., "Target-selective phototherapy using a ligand-based photosensitizer for type 2 cannabinoid receptor," Chem Biol. Mar. 20, 2014;21(3):338-44.
Zhang et al., "Tumor mitochondria-targeted photodynamic therapy with a translocator protein (TSPO)-specific photosensitizer," Acta Biomater. Dec. 2015;28:160-70.
Chiarello, K., "In between the light and the dark: developments in Photosensitive Pharmaceuticals," Dec. 2005 48-54.
Iqbal et al., "Phthalocyanine-Biomolecule Conjugated Photosensitizers for Targeted Photodynamic Therapy and Imaging," Current Drug Metabolism (2015) 16(9):816-832.
Porter, W., "Shining Some Light on Photostability Testing | IVT," Dec. 16, 2014, available online at: http://www.ivtnetwork.com/article/shiningsomelightphotostabilitytesting.
Templeton et al., "Implications of Photostability on the Manufacturing, Packaging, Storage, and Testing of Formulated Pharmaceutical Products," Pharmaceutical Technology Mar. 2005 68-86.
New Pharmacology (New Yakurigaku), Nankodo Co., Ltd., 2012, the third impression of the revised sixth edition, p. 558-559.
Butcher et al., "Visible Light," Tour of the Electromagnetic Spectrum, National Aeronautics and Space Administration, 2016, available at https://smd-prod.s3.amazonaws.com/science-pink/s3fs-public/atoms/files/Tour-of-the-EMS-TAGGED-v7_0.pdf.
Jeong et al., "Indium gallium nitride-based ultraviolet, blue, and green lightemitting diodes functionalized with shallow periodic hole patterns," (2017) Scientific Reports 7:45726.
U.S. Appl. No. 17/057,589, filed Nov. 20, 2020, by Manibusan et al.
Agostinis et al., "Photodynamic Therapy of Cancer: An Update," CA Cancer J Clin. (2011) 61(4): 250-281.
Busch et al., "Increasing Damage to Tumor Blood Vessels during Motexafin Lutetium-PDT through Use of Low Fluence Rate," Radiat Res.(2010) 174(3): 331-340.
Chauhan et al., "Angiotensin inhibition enhances drug delivery and potentiates chemotherapy by decompressing tumour blood vessels," Nat Commun. (2013) 4: 2516.
Chothia et al., "Canonical Structures for the Hypervariable Regions of Immunoglobulins," J Mol Biol. Aug. 20, 1987;196(4):901-17.
Cozaar (losartan potassium) FDA datasheet. Revised Mar. 2013.

(56) References Cited

OTHER PUBLICATIONS

Diop-Frimpong et al., "Losartan inhibits collagen I synthesis and improves the distribution and efficacy of nanotherapeutics in tumors," Proc Natl Acad Sci U S A.(2011) 108(7): 2909-2914.

Dolmans et al., "Targeting Tumor Vasculature and Cancer Cells in Orthotopic Breast Tumor by Fractionated Photosensitizer Dosing Photodynamic Therapy," (2002) Cancer Res. 62(15):4289-94.

Han, Weiwei, Radio Exploration of the Four Colors, Jilin Fine Arts Publishing House, Jan. 2014, p. 139. (Including English summary).

Houston et al., "Quality analysis of in vivo near-infrared fluorescence and conventional gamma images acquired using a dual-labeled tumor-targeting probe," J. Biomed. Optics 2005, 10, 054010-1 to 054010-11.

Kovar et al., "Abstract C4: Specific targeting of spontaneous medulloblastoma tumors in mice by IRDye 800CW chlorotoxin.", AACR-NCI-EORTC International Conference: Molecular Targets and Cancer Therapeutics, vol. 10, Issue 11, Nov. 12-16, 2011; San Francisco, CA.

Lee et al., "Peptides and Peptide Hormones for Molecular Imaging and Disease Diagnosis," Chem Rev. May 12, 2010; 110(5): 3087-3111.

Li et al., "Structural basis for inhibition of the epidermal growth factor receptor by cetuximab," Cancer Cell Apr. 2005;7(4):301-11.

Li-Cor, "IRDye® Infrared Dyes: Advancing Discovery with Infrared Imaging," 2010.

National Optical Astronomy Observatory, "Recommended Light Levels," retrieved from https://www.noao.edu/education/QLTkit/ACTIVITY_Documents/Safety/LightLevels_outdoor+indoor.pdf.

North et al., "A new clustering of antibody CDR loop conformations," J Mol Biol. Feb. 18, 2011; 406(2): 228-256.

Supplementary materials from Gao et al., "In vivo cancer targeting and imaging with semiconductor quantum dots," Nat Biotechnol. Aug. 2004;22(8):969-76.

Turner et al., Administration of substances to laboratory animals: routes of administration and factors to consider. J Am Assoc Lab Anim Sci. 2011;50(5):600-613.

U.S. Department of Veterans Affairs, "Lighting Design Manual," Dec. 2015, retrieved from https://www.cfm.va.gov/til/dManual/dmLighting.pdf.

U.S. Environmental Protection Agency, "Laboratories for the 21st Century: Best Practice Guide," Aug. 2006, U.S. Environmental Protection Agency, retrieved from http://labs21.lbl.gov/docs/Lighting_reduced_R11.pdf.

Van Cutsem et al., "Intrapatient cetuximab dose escalation in metastatic colorectal cancer according to the grade of early skin reactions: the randomized EVEREST study," J Clin Oncol. Aug. 10, 2012;30(23):2861-8.

Wang, Changhui et al., New Progress in the Diagnosis and Treatment of Respiratory Interventional Therapy, Shanghai Science and Technology Press, Jun. 2015, p. 152. (Including English summary).

Xu, Deyu et al., Tumor Photodynamic Therapy Principles, Drugs, and Clinical Introduction, China Medical Science and Technology Press, May 1996, pp. 172-174. (Including English summary).

Zhang et al., "Inhibition of tumor growth and metastasis by photoimmunotherapy targeting tumor-associated macrophage in a sorafenib-resistant tumor model," Biomaterials Jan. 2016; vol. 84:1-12.

Zhen et al. Tumor vasculature targeted photodynamic therapy for enhanced delivery of nanoparticles. (2014) ACS Nano. 8(6):6004-6013.

Algeria-Schaffer, "General Protein-Protein Cross-Linking," Methods Enzymol (2014) 539:81-87.

Bartl et al., "Emissivity of aluminium and its importance for radiometric measurement," Measurement of Physical Quantities (2004) 31-36.

Cheng et al., "Near infrared light-triggered drug generation and release from gold nanoparticle carriers for photodynamic therapy," Small (2014) 10(9):1799-1804.

Li et al., "A Novel Tumor Targeting Drug Carrier for Optical Imaging and Therapy," Theranostics (2014) 4(6):642-659.

Sekkat et al., "Like a bolt from the Blue: Phthalocyanines in Biomedical Optics," Molecules (2012) 17:98-144.

Wagner-Rousset et al., "Antibody-drug conjugate model fast characterization by LC-MS following IdeS proteolytic digestion," mAbs (2014) 6(1):173-184.

\* cited by examiner

METHODS FOR MANUFACTURING PHTHALOCYANINE DYE CONJUGATES AND STABLE CONJUGATES

CROSS REFERENCE TO RELATED APPLICATIONS

This application is a U.S. National Phase Application of International Application No. PCT/US2016/047636, filed Aug. 18, 2016, which claims priority from U.S. provisional application No. 62/206,774, filed Aug. 18, 2015, entitled "Methods for Manufacturing Phthalocyanine Dye-Macromolecule Conjugates and Stable Conjugates" the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 751702000100SeqList.txt, created Feb. 15, 2018, which is 9,917 bytes in size. The information in the electronic format of the Sequence Listing is incorporated by reference in its entirety.

FIELD

The present disclosure relates in some aspects to methods for manufacturing a conjugate containing a phthalocyanine dye, including methods that include one or more steps of preparing or producing the conjugate, formulating the conjugate and packaging the conjugate for storage. In some aspects, the manufacturing methods result in the generation of a stable conjugate. In some aspects, the disclosure further relates to stable phthalocyanine dye conjugates, compositions and articles of manufacture containing the stable conjugates, and methods for their administration to subjects for photoimmunotherapy. In some embodiments, the phthalocyanine dye conjugates are conjugated to a targeting molecule, such as an antibody, that targets the conjugate to a cell or pathogen, such as by binding to a cell surface protein.

BACKGROUND

Various therapies are available for treating disease, such as cancer. For example, photoimmunotherapy (PIT) is a method that uses a photosensitizer conjugated to an antibody or other targeting molecule to target to a cell surface target molecule, e.g., a cell surface receptor, in order to permit the targeted killing of specific cells. In some cases, PIT can selectively target disease cells, such as tumor cells, and thereby selectively kill such cells without damaging healthy cells. Improved strategies are needed to improve phthalocyanine dye conjugates for use in such methods, for example, strategies that minimize or avoid photodegradation and improve the activity of the conjugate when used for PIT. Provided are methods and conjugates that meet such needs.

SUMMARY

Provided in some embodiments is a method of manufacturing a phthalocyanine dye-conjugate. In some embodiments, the method includes contacting a targeting molecule, such as a macromolecule, with a phthalocyanine dye, which in some cases contains a reactive chemical group, under conditions to produce a conjugate containing the phthalocyanine dye linked to, such as covalently bound to, the targeting molecule. In some embodiments, the method includes formulating the conjugate in a pharmaceutically acceptable buffer. In some embodiments, before, during, and/or after preparation of the conjugate, the only light to which the dye and conjugate are exposed has a wavelength within a range from about 400 nm to about 650 nm. In some embodiments, before, during, and/or after preparation of the conjugate, such as during the contacting and/or formulating steps, the only light to which the dye and conjugate are exposed has an intensity of less than 500 lux.

In some embodiments, the method includes contacting a targeting molecule with a phthalocyanine dye at a molar ratio of dye to targeting molecule of from or from about 1:1 to 1000:1. In some embodiments, the dye includes a reactive chemical group, under conditions to produce a conjugate containing the phthalocyanine dye covalently linked to an attachment group of the targeting molecule. In some embodiments, the method includes formulating the conjugate in a pharmaceutically acceptable buffer to a concentration from or from about 0.01 mg/mL to 1000.0 mg/mL. In some embodiments, before, during, and/or after preparation of the conjugate, such as during the contacting and/or formulating steps, the only light to which the dye and conjugate are exposed has an intensity of less than 500 lux.

In some embodiments, the conjugate is formulated to a concentration from or from about 0.01 mg/mL to about 200.0 mg/mL or from about 0.5 mg/mL to about 10.0 mg/mL. In some embodiments, the conjugate is formulated to a concentration from or from about 0.5 mg/mL to about 5.0 mg/mL.

In some embodiments, prior to the contacting step, the phthalocyanine dye is dissolved in a solvent under conditions in which the only light to which the dye is exposed has a wavelength within a range from about 400 nm to about 650 nm. In some embodiments, the only light to which the dye is exposed during or after being dissolved in solvent has an intensity of less than 500 lux. In some embodiments, the dye is dissolved in the solvent to a concentration in a range from or from about 0.1 mg/mL to about 100 mg/mL. In some embodiments, the dye is dissolved in the solvent to a concentration from or from about 1 mg/mL to about 50 mg/mL. In some embodiments, the concentration of the phthalocyanine dye in the solvent is about 10 mg/mL. In some embodiments, the solvent is dimethylsulfoxide (DMSO) or DMF and water-based solvents.

In some embodiments, the formulating step includes concentrating the conjugate.

In some embodiments, the contacting step is carried out for at least 5 minutes, at least 15 minutes, at least 30 minutes, at least 60 minutes, at least 90 minutes, at least 120 minutes, at least 240 minutes, at least 360 minutes, at least 24 hours, at least 72 hours, or at least 120 hours. In some embodiments, the contacting step is carried out for 5 minutes to 150 hours, 5 minutes to 100 hours, 5 minutes to 48 hours, 5 minutes to 24 hours, 5 minutes to 6 hours, 5 minutes to 2 hours, 5 minutes to 90 minutes, 5 minutes to 60 minutes, 5 minutes to 30 minutes, 30 minutes to 150 hours, 30 minutes to 100 hours, 30 minutes to 48 hours, 30 minutes to 24 hours, 30 minutes to 6 hours, 30 minutes to 2 hours, 30 minutes to 90 minutes, 30 minutes to 60 minutes, 60 minutes to 150 hours, 60 minutes to 100 hours, 60 minutes to 48 hours, 60 minutes to 24 hours, 60 minutes to 6 hours, 60 minutes to 2 hours, 60 minutes to 90 minutes, 90 minutes to 150 hours, 90 minutes to 100 hours, 90 minutes to 48 hours, 90 minutes to 24 hours, 90 minutes to 6 hours, 90 minutes to 2 hours, 2 hours to 150 hours, 2 hours to 100 hours, 2 hours to 48 hours, 2 hours to 24 hours, 2 hours to 6 hours, 6 hours to 150 hours, 6 hours to 100 hours, 6 hours to 48 hours, 6 hours to 24 hours, 24 hours to 150 hours, 24 hours to 100 hours, 24 hours to 48 hours, 48 hours to 150 hours, 48 hours to 100 hours or 100 hours to 150 hours. In some embodiments, the contacting step is carried out at a temperature between or between about 4° C. and about 37° C. In some embodiments, the contacting step is carried out at a temperature of about 25° C.±2.0° C., 25° C.±1.0° C. or 25° C.±0.3° C.

In some embodiments, the phthalocyanine dye is covalently or non-covalently linked to the targeting molecule. In some embodiments, the phthalocyanine dye contains a reactive chemical group and contacting the phthalocyanine dye and targeting molecule produces a conjugate comprising the phthalocyanine dye covalently bound to an attachment group of the targeting molecule.

In some embodiments, the method further includes quenching the conjugate, such as to remove unconjugated dye. In some embodiments, the only light to which the conjugate is exposed during the quenching step has a wavelength within a range from about 400 nm to about 650 nm. In some embodiments, the only light to which the conjugate is exposed during the quenching step has an intensity of less than 500 lux.

In some embodiments, the formulating step includes ultrafiltration, diafiltration or dialysis. In some embodiments, the method further includes sterile filtration of the conjugate.

In some embodiments, the method includes packaging the conjugate, such as in one or more light-protected container. In some embodiments, during the packaging step the only light to which the conjugate is exposed has a wavelength within a range from about 400 nm to about 650 nm. In some embodiments, during the packaging step, the only light to which the dye and conjugate are exposed has an intensity of less than 500 lux.

In some embodiments, the methods include dissolving a phthalocyanine dye, which, in some cases contains a reactive chemical group, in a solvent to a concentration of about 0.1-100 mg/mL. In some embodiments, the method further includes contacting a targeting molecule with the phthalocyanine dye at a molar ratio of dye to targeting molecule from 1:1 to 1000:1, under conditions to produce a conjugate containing the phthalocyanine dye linked to, e.g., covalently bound to, the targeting molecule. In some embodiments, the method further includes formulating the conjugate in a pharmaceutically acceptable buffer to a concentration from or from about 0.01 to 1000.0 mg/mL. In some embodiments, the method further includes packaging the conjugate in one or more light-protected container. In some embodiments, before, during and/or after the steps of the method, such as the dissolving, contacting, formulating, and packaging steps, the only light to which the dye and conjugate are exposed has a wavelength within a range from about 400 nm to about 650 nm, or the only light to which the dye and conjugate are exposed has an intensity of less than 500 lux.

Provided in some embodiments is a method of manufacturing a phthalocyanine dye-targeting molecule conjugate, comprising: a) dissolving a phthalocyanine dye in a solvent to a concentration of about 0.1-100 mg/mL; b) contacting a targeting molecule with the phthalocyanine dye at a molar ratio of dye to targeting molecule from 1:1 to 1000:1 under conditions to produce a conjugate comprising the phthalocyanine dye linked to the targeting molecule; c) formulating the conjugate in a pharmaceutically acceptable buffer to a concentration from or from about 0.01 to about 200.0 mg/mL; and d) packaging the conjugate in one or more light-protected container, wherein in each of steps a)-d): the only light to which the dye and conjugate are exposed has a wavelength within a range from about 400 nm to about 650 nm, or the only light to which the dye and conjugate are exposed has an intensity of less than 500 lux.

In some of any such embodiments, the phthalocyanine dye is covalently or non-covalently linked to the targeting molecule. In some of any such embodiments, the phthalocyanine dye includes a reactive chemical group and contacting the phthalocyanine dye and targeting molecule produces a conjugate comprising the phthalocyanine dye covalently bound to an attachment group of the targeting molecule.

In some embodiments, during the steps of the provided methods, the total exposure of the dye and conjugate to any light is for no more than 5000 lux hours, no more than 2500 lux hours, no more than 1000 lux hours, no more than 500 lux hours, no more than 250 lux hours, no more than 100 lux hours or no more than 80 lux hours. In some embodiments, during the packaging step of the provided method, the total exposure of the conjugate to any light is for no more than 5000 lux hours, no more than 2500 lux hours, no more than 1000 lux hours, no more than 500 lux hours, no more than 250 lux hours, no more than 100 lux hours or no more than 80 lux hours.

In some embodiments, the dye has a maximum absorption wavelength from or from about 600 nm to about 850 nm. In some embodiments, the dye has a maximum absorption wavelength from or from about 650 nm to about 850 nm. In some embodiments, the dye has a maximum absorption wavelength from or from about 680 nm to about 850 nm.

In some embodiments, the phthalocyanine dye contains the formula:

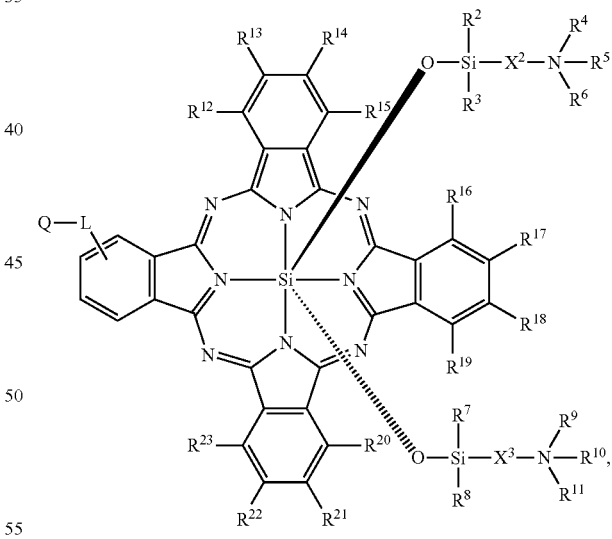

wherein:

L is a linker;

Q is a reactive group for attachment of the dye to the targeting molecule;

$R^2$, $R^3$, $R^7$, and $R^8$ are each independently selected from among optionally substituted alkyl and optionally substituted aryl;

$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from among hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

In some embodiments, the phthalocyanine dye includes the formula:

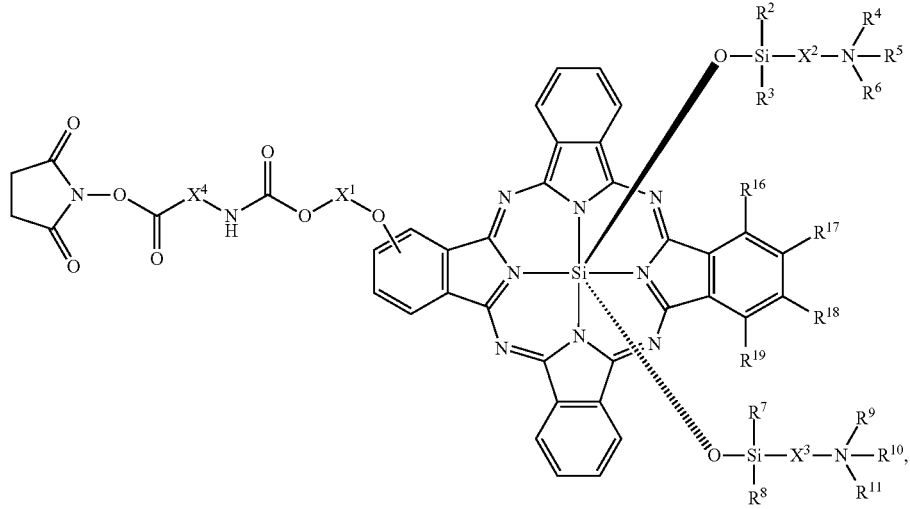

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from among hydrogen, halogen, optionally substituted alkylthio, optionally substituted alkylamino and optionally substituted alkoxy.

In some embodiments, the reactive group is selected from among an amine-reactive chemical group, a sulfhydryl-reactive chemical group, an activated ester, an acyl halide, an alkyl halide, an anhydride, a carboxylic acid, a carbodiimide, a carbonate, a carbamate, a haloacetamide, an isocyanate, an isothiocyanate, a maleimide, an NHS ester, a phosphoramidite, a platinum complex, a sulfonate ester and a thiocyanate. In some embodiments, the reactive chemical group is a sulfhydryl-reactive chemical group selected from among maleimides, haloacetyls and pyridyl disulfides. In some embodiments, the phthalocyanine dye is covalently bound to a lysine residue of the targeting molecule. In some embodiments, the reactive group is an amine-reactive chemical group. In some embodiments, the reactive chemical group is an amine-reactive chemical group that is an N-hydroxysuccinimide (NHS) ester.

In some embodiments, the phthalocyanine dye is IRDye 700DX-NHS (IR700-NHS).

In some embodiments, the targeting molecule binds to an antigen or protein directly or indirectly. For example, in some embodiments, the targeting molecule is a second binding molecule that binds to a first binding molecule, said first binding molecule being capable of binding to the antigen or protein. In some embodiments, the targeting molecule is a secondary antibody.

In some embodiments, the targeting molecule binds a cell surface target molecule on a surface of a cell or pathogen, such as a stem cell, a proliferating cell, a cancer cell, a cell in a hyperplasia, a tumor cell, an inflammatory cell, a neuron, a pathogen, or a pathogen infected cell. In some embodiments, the pathogen is selected from among viruses, bacteria, fungi, biofilms, and other prokaryote cell systems. In some embodiments, the cell is a cancer cell, a tumor cell, an inflammatory cell or, a neuron. In some embodiments, the cell is present in the microenvironment of a lesion associated with a disease or condition. In some embodiments, the lesion is a tumor and the cell is a cancer cell or a tumor cell. In some embodiments, the cell is a cancer stem cell or a circulating tumor cell.

In some such embodiments, the inflammatory cell is a leukocyte such as a neutrophil, an eosinophil, a basophil, a lymphocyte, or a monocyte. In some embodiments, the targeting molecule is a neuron, such as a peripheral nervous system neuron or a central nervous system neuron. In some embodiments, the neuron is a nociceptor such as a nociceptor, mechanical nociceptor, chemical nociceptor or polymodal nociceptor. In some embodiments, the targeting molecule binds to a pathogen, such as a virus, bacterium, fungus, biofilm, or other prokaryote cell system. In some embodiments, the pathogen is a gram-negative or gram-positive bacterium.

In some embodiments, the cell surface target molecule includes an antigen, a polypeptide, a lipid, or a carbohydrate, or a combination thereof.

In some embodiments, the cell surface target molecule is selected from among cell membrane phospholipids, prokaryotic peptidoglycans, bacterial cell envelop proteins, viral capsid proteins, ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, an interleukin receptor (e.g. IL-2R, IL11-R, IL-13R) ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g. P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g. TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4 and Y5.

In some embodiments, the cell surface target molecule is selected from among HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-lantigen, Bcr-abl, RET, MET, TRKB, TIE2, ALK, ROS, EML4-ALK, ROS1, BRAFV600E, SRC, c-KIT, PDGFR, mTOR, TSC1, TSC2, BTK, KIT, BRCA, CDK 4/6, JAK1, JAK2, BRAF, FLT-3, MEK1, MEK2, and SMO. In some embodiments, the cell surface target molecule is HER1/EGFR, HER2, PD-L1, CD25, EpCAM, EphA2, CD206, CD20, CD44, CD133, Mesothelin, Glypican-3, or carcinoembryonic antigen (CEA).

In some embodiments, at least part of the targeting molecule is or is a combination of a protein, a glycoprotein, an antibody, an antibody fragment, an antigen, an antigen binding fragment, a peptide, a polypeptide, a tissue homing peptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, an aptamer, nucleotide triphosphates, acyclo terminator triphosphates, or PNA.

In some embodiments, the targeting molecule is a tissue-specific homing peptide. In some embodiments, the homing peptide has the sequence of amino acids as set forth in any of SEQ ID NOS: 1-52.

In some embodiments, the targeting molecule is an RGD polypeptide, an iRGD polypeptide, a Lyp-1 polypeptide, a cripto-1 binding polypeptide, a somatostatin receptor binding polypeptide, a prohibitin binding polypeptide, a NGR polypeptide, an iNGR polypeptide, or an activatable cell penetrating peptide (ACPP) comprised of a polycationic cell penetrating peptide (CPP) connected via a cleavable linker to a neutralizing polyanion.

In some embodiments, the ACPP comprises the structure: A-X1-B—, wherein B is a peptide portion of about 5 to about 20 basic amino acid residues, which is suitable for cellular uptake; A is a peptide portion of about 2 to about 20 acidic amino acid residues, which when linked with portion B is effective to inhibit or prevent cellular uptake of portion B; X1 is a cleavable linker of about 2 to about 100 atoms; and one or more of L-Y is linked to the C-terminus of peptide portion B.

In some embodiments, the targeting molecule is selected from among adrenocorticotropic hormone (ACTH), angiotensin II, atrial natriuretic factor (ANF), bombesin, bradykinin, brain derived neurotropihic factor (BDNF), bone morphogenetic protein 2 (BMP-2), bone morphogenetic protein 6 (BMP-6), bone morphogenetic protein 7 (BMP-7), calcitonin, cardiotrophin 1 (BMP-2), CD22, CD40, cholecystokinin (CCK), ciliary neurotrophic factor (CNTF), CCL1-CCL28, CXCL1-CXCL17, XCL1, XCL2, CX3CL1, cripto 1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-a), interferon beta (IFN-b), interferon gamma (IFNg), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 3G (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMA5A), semaphorin 5B (SEMA5B), semaphorin 6A (SEMA6A), semaphorin 6B (SEMA6B), semaphorin 6D (SEMA6D), semaphorin 7A (SEMA7A), SLIT1, SLIT2, SLITS, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-α), transforming growth factor beta (TGF-b), tumor necrosis factor alpha (TNF-α), thrombin, vasoactive intestinal peptide (VIP), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

In some embodiments, the targeting molecule is an antibody or an antibody fragment.

In some embodiments, the antibody is cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A, Pidilizumab (CT-011), AMP-224, MSB001078C, or MEDI4736, or is an antigen-binding fragment thereof. In some embodiments, the antibody binds to a cell surface target molecule, such as HER1/EGFR, HER2, PD-L1, CD25, EpCAM, EphA2, CD206, CD20, CD44, CD133, Mesothelin, Glypican-3, or carcinoembryonic antigen (CEA). In some embodiments, the antibody is cetuximab, Panitumumab, Trastuzumab, BMS-935559, MEDI4736, MPDL3280A or MSB0010718C or is an antigen-binding fragment thereof.

In some embodiments, the dye-targeting molecule conjugate is cetuximab-IR700, Panitumumab-IR700, Trastuzumab-IR700, BMS-935559-IR700, MEDI4736-IR700, MPDL3280A-IR700 or MSB0010718C-IR700.

In some embodiments, the targeting molecule is contacted with the phthalocyanine dye at a molar ratio of dye to targeting molecule from 1:1 to 100:1 or 1:1 to 10:1. In some embodiments, the molar ratio of dye to targeting molecule is at least or at least about 4:1 or is at least or at least about 10:1. In some embodiments, the conjugate includes from or from about 1 to about 1000 phthalocyanine dye molecules per targeting molecule, from or from about 1 to about 10 phthalocyanine dye molecules per targeting molecule or from or from about 2 to about 5 phthalocyanine dye molecules per targeting molecule.

In some embodiments, the conjugate is formulated to a concentration that is from or from about 1.0 to about 5.0 mg/mL, such as in a pharmaceutically acceptable buffer. In some embodiments, the pharmaceutically acceptable buffer is phosphate buffered saline. In some embodiments, the pharmacologically acceptable buffer has a pH from or from about pH 6.0 to about pH 8.0. In some embodiments, the conjugate is stable for greater than 3 months with greater than 90% of the conjugate present as a main monomer component. In some embodiments, the conjugate is stable if it retains greater than or greater than about 30%, 40%, 50%, 60%, 70%, 80%, 90% or more of its potency, activity or purity for greater than 3 months compared to the conjugate prior to the storage for the time. In some embodiments, the conjugate is stable if greater than 90% of the conjugate is present as a main monomer component. In some embodiments, the pharmacologically acceptable buffer has a pH from or from about pH 6.8 to about pH 7.4.

In some embodiments, the only light to which the dye and conjugate are exposed has a wavelength within a range from about 425 nm to about 575 nm. In some embodiments, the only light to which the dye and conjugate are exposed has an intensity of less than 200 lux.

In some embodiments, the container comprising the conjugate protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, container protects from transmission of light such that the percentage of light transmission by the container is less than 50%, less than 40%, less than 30%, less than 20%, less than 10% or less than 5%. In some embodiments, the container is green, blue, amber, translucent, opaque, or is wrapped in an opaque foil. In some embodiments, the container is green, blue, amber, translucent, opaque, or is covered by material with light transmission of less than 50%, less than 40%, less than 30%, less than 20%, less than 10% or less than 5%. In some embodiments of the methods provided herein, the container is selected from among a vial, a tube, a syringe, a bag, a pouch, and a box.

In some embodiments, the light-protected container is a first light-protected container and the method further includes packing the first light-protected container into a second light-protected container. In some embodiments, the second container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the second container protects from transmission of light such that the percentage of light transmission is less than 50%, less than 40%, less than 30%, less than 20%, less than 10% or less than 5%. In some embodiments, the second container is green, blue, amber, translucent, opaque, or is covered by a material with light transmission of less than 50%, less than 40%, less than 30%, less than 20%, less than 10% or less than 5%. In some embodiments, the second container is selected from among a vial, a tube, a syringe, a bag, a pouch, and a box.

In some embodiments, the method provided herein further includes packaging the second container into a third light-protected container. In some embodiments, the third container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the third container protects from transmission of light such that the percentage of light transmission is less than 50%, less than 40%, less than 30%, less than 20%, less than 10% or less than 5%. In some embodiments, the third container is green, blue, amber, translucent, opaque, or is covered by a material with light transmission of less than 50%, less than 40%, less than 30%, less than 20%, less than 10% or less than 5%. In some embodiments, the third container is selected from among a vial, a tube, a syringe, a bag, a pouch, and a box.

In some embodiments, the amount of the conjugate produced by the method is greater than or greater than about 1 gram, greater than or greater than about 2 grams, greater than or greater than about 3 grams, greater than or greater than about 4 grams, greater than or greater than about 5 grams or greater than or greater than about 10 grams. In some embodiments, the conjugate is produced using good manufacturing practice (GMP).

Provided in some embodiments is a conjugate produced, formulated or packaged by the method described herein. In some embodiments, the conjugate is stable for greater than three months, such as with greater than 90% of the conjugate present as a main monomer component.

Provided in some embodiments is a stable conjugate containing a phthalocyanine dye linked to a targeting molecule. In some embodiments, the stable conjugate is stable for greater than three months, such as with greater than 90% of the conjugate present as a main monomer component.

In some embodiments, the conjugate is stable if it retains greater than or greater than about 30%, 40%, 50%, 60%, 70%, 80%, 90% or more of its potency, activity or purity for greater than 3 months compared to the conjugate prior to the storage for the time. In some embodiments, the conjugate is stable if greater than 90% of the conjugate or stable conjugate is present as a main monomer component. In some embodiments, the conjugate is stable if greater than 95% of the conjugate or stable conjugate is present as a main monomer component. In some embodiments, the conjugate or stable conjugate is stable for greater than 6 months or greater than 12 months. In some embodiments, the conjugate or stable conjugate is stable at a temperature of less than 30° C.

In some embodiments, the phthalocyanine dye contained in the stable conjugate includes the formula:

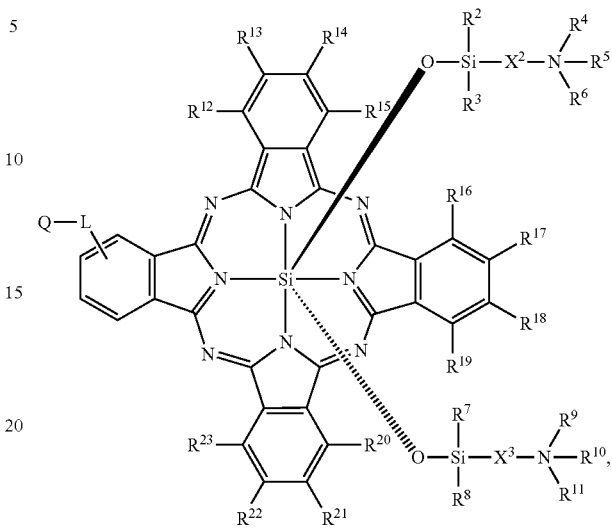

wherein:

L is a linker;

Q is a reactive group for attachment of the dye to the targeting molecule;

$R^2$, $R^3$, $R^7$, and $R^8$ are each independently selected from among optionally substituted alkyl and optionally substituted aryl;

$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from among hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

In some embodiments, the stable conjugate containing the phthalocyanine dye includes the formula:

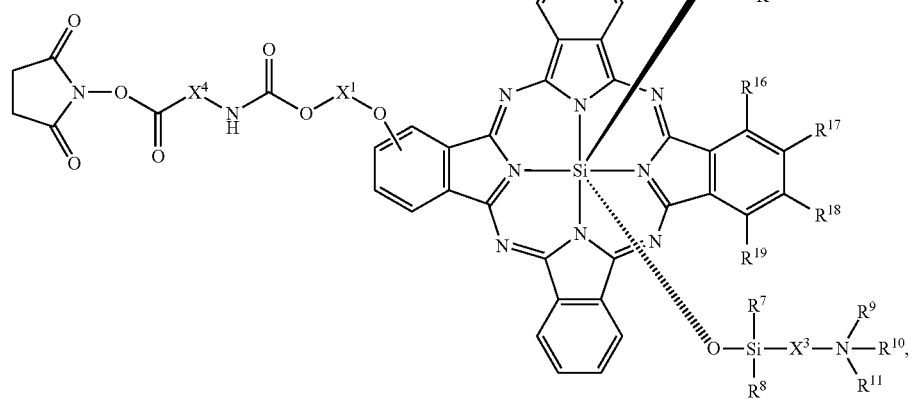

wherein:

X¹ and X⁴ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from among hydrogen, halogen, optionally substituted alkylthio, optionally substituted alkylamino and optionally substituted alkoxy In some embodiments, the dye contained in the stable conjugate has a maximum absorption wavelength from or from about 600 nm to about 850 nm, from or from about 650 nm to about 850 nm, or from or from about 680 nm to about 850 nm.

In some embodiments, the dye contained in the stable conjugate is IRDye 700DX (IR700).

In some embodiments, the targeting molecule contained in the stable conjugate binds to a cell surface target molecule on a surface of a cell or pathogen, such as a proliferating cell, a cancer cell, a cell in hyperplasia, a tumor cell, an inflammatory cell, a neuron, or a pathogen. In some embodiments, the cell is a stem cell, a proliferating cell, a cell in a hyperplasia, or a pathogen infected cell. In some embodiments, the pathogen is selected from among viruses, bacteria, fungi, biofilms, and other prokaryote cell systems. In some embodiments, the inflammatory cell is a leukocyte, such as a neutrophil, an eosinophil, a basophil, a lymphocyte, or a monocyte. In some embodiments, the targeting molecule is a neuron, such as a peripheral nervous system neuron or a central nervous system neuron. In some embodiments, the neuron is a nociceptor such as a nociceptor, mechanical nociceptor, chemical nociceptor or polymodal nociceptor. In some embodiments, the targeting molecule binds to a pathogen, such as a virus, bacterium, fungus, biofilm, or other prokaryote cell system. In some embodiments, the pathogen is a gram-negative or gram-positive bacterium.

In some embodiments, the cell surface target molecule bound by the targeting molecule contained in the stable conjugate includes an antigen, a polypeptide, a lipid, or a carbohydrate, or a combination thereof.

In some embodiments, the cell surface target molecule is selected from among cell membrane phospholipids, prokaryotic peptidoglycans, bacterial cell envelop proteins, viral capsid proteins, ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, an interleukin receptor (e.g. IL-2R, IL11-R, IL-13R), ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g. P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g. TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

In some embodiments, the cell surface target molecule is selected from among HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-1antigen, Bcr-abl, RET, MET, TRKB, TIE2, ALK, ROS, EML4-ALK, ROS1, BRAFV600E, SRC, c-KIT, PDGFR, mTOR, TSC1, TSC2, BTK, KIT, BRCA, CDK 4/6, JAK1, JAK2, BRAF, FLT-3, MEK1, MEK2, and SMO. In some embodiments, the cell surface target molecule is HER1/EGFR, HER2, PD-L1, CD25, EpCAM, EphA2, CD206, CD20, CD44, CD133, Mesothelin, Glypican-3, or carcinoembryonic antigen (CEA).

In some embodiments, at least part of the targeting molecule is or is a combination of a protein, a glycoprotein, an antibody, an antibody fragment, an antigen, an antigen binding fragment, a peptide, a polypeptide, a tissue homing peptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, an aptamer, nucleotide triphosphates, acyclo terminator triphosphates, or PNA.

In some embodiments, the targeting molecule is a tissue-specific homing peptide. In some embodiments, the homing peptide has the sequence of amino acids as set forth in any of SEQ ID NOS: 1-52.

In some embodiments, the targeting molecule is an RGD polypeptide, an iRGD polypeptide, a Lyp-1 polypeptide, a cripto-1 binding polypeptide, a somatostatin receptor binding polypeptide, a prohibitin binding polypeptide, a NGR polypeptide, an iNGR polypeptide, or an activatable cell penetrating peptide (ACPP) comprised of a polycationic cell penetrating peptide (CPP) connected via a cleavable linker to a neutralizing polyanion.

In some embodiments, the ACPP comprises the structure: A-X1-B—, wherein B is a peptide portion of about 5 to about 20 basic amino acid residues, which is suitable for cellular uptake; A is a peptide portion of about 2 to about 20 acidic amino acid residues, which when linked with portion B is effective to inhibit or prevent cellular uptake of portion B; X1 is a cleavable linker of about 2 to about 100 atoms; and one or more of L-Y is linked to the C-terminus of peptide portion B.

In some embodiments, the targeting molecule is selected from among adrenocorticotropic hormone (ACTH), angiotensin II, atrial natriuretic factor (ANF), bombesin, bradykinin, brain derived neurotropihic factor (BDNF), bone morphogenetic protein 2 (BMP-2), bone morphogenetic protein 6 (BMP-6), bone morphogenetic protein 7 (BMP-7), calcitonin, cardiotrophin 1 (BMP-2), CD22, CD40, cholecystokinin (CCK), ciliary neurotrophic factor (CNTF), CCL1-CCL28, CXCL1-CXCL17, XCL1, XCL2, CX3CL1, cripto 1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-a), interferon beta (IFN-b), interferon gamma (IFNg), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 36 (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMA5A), semaphorin 5B (SEMA5B), semaphorin 6A (SEMA6A), semaphorin 6B (SEMA6B), semaphorin 6D (SEMA6D), semaphorin 7A (SEMA7A), SLIT1, SLIT2, SLITS, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-α), transforming growth factor beta (TGF-b), tumor necrosis factor alpha (TNF-α), thrombin, vasoactive intestinal peptide (VIP), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

In some embodiments, the targeting molecule is an antibody or an antibody fragment.

In some embodiments, the antibody is cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, lambrolizumab, MPDL3280A, Pidilizumab (CT-011), MSB001078C, BMS-935559 or MEDI4736, AMP-224, or is an antigen-binding fragment thereof. In some embodiments, the antibody binds to a cell surface target molecule, such as HER1/EGFR, HER2, PD-L1, CD25, EpCAM, EphA2, CD206, CD20, CD44, CD133, Mesothelin, Glypican-3, or carcinoembryonic antigen (CEA). In some embodiments, the antibody is cetuximab, Panitumumab, Trastuzumab, BMS-935559, MEDI4736, MPDL3280A or MSB0010718C or is an antigen-binding fragment thereof.

In some embodiments, the stable dye-targeting molecule conjugate is cetuximab-IR700, Panitumumab-IR700, Trastuzumab-IR700, BMS-935559-IR700, MEDI4736-IR700, MPDL3280A-IR700 or MSB0010718C-IR700.

In some embodiments, the stable conjugate includes from or from about 1 to about 1000 phthalocyanine dye molecules per targeting molecule, from or from about 1 to about 10 or from or from about 2 to about 5 phthalocyanine dye molecules per targeting molecule.

Provided in some embodiments is a composition containing the conjugate or stable conjugate.

Provided in some embodiments is a pharmaceutical composition containing the conjugate or stable conjugate and a pharmaceutically acceptable excipient.

In some embodiments, the composition is formulated in phosphate buffered saline. In some embodiments, composition has a pH of greater than 6.0.

Provided in some embodiments is a pharmaceutical composition containing a phthalocyanine dye linked to a targeting molecule and a pharmaceutically acceptable excipient. In some such embodiments, the composition has a pH of greater than 6.0 and the conjugate in the composition is stable for greater than three months, such as with greater than 90% of the conjugate present as a main monomer component. In some such embodiments, the conjugate in the composition is stable if it retains greater than or greater than about 30%, 40%, 50%, 60%, 70%, 80%, 90% or more of its potency, activity or purity for greater than 3 months compared to the conjugate prior to the storage for the time. In some such embodiments, the conjugate in the composition is stable if greater than 90% of the conjugate is present as a main monomer component. In some embodiments, the pH of the composition is greater than 6.0 or is from or from about pH 6.0 to about 8.0, inclusive.

In some embodiments, the concentration of the conjugate in the composition is from or from about 0.01 mg/mL to about 200 mg/mL. In some embodiments, the concentration of the conjugate in the composition is from or from about 0.5 mg/mL to about 10 mg/mL. In some embodiments, the concentration of the conjugate in the composition is from or from about 1.0 to about 5.0 mg/mL. In some embodiments, the concentration of the conjugate in the composition is from or from about 1.8 to about 2.1 mg/mL.

In some embodiments, the volume of the composition is from or from about 0.5 mL to about 100 mL, from or from about 1 mL to about 50 mL or from or from about 1 mL to about 10 mL.

Provided in some embodiments is a container comprising the conjugate or stable conjugate. In some embodiments, the container protects from transmission of light having a wavelength from or from about 500 nm to 725 nm or 650 nm to 725 nm. In some embodiments, the container protects from transmission of light such that the percentage of light transmission by the container is less than 50%, less than 40%, less than 30%, less than 20%, less than 10% or less than 5%. In some embodiments, the container is green, blue, amber, translucent, opaque, or is covered by a material with light transmission of less than 50%, less than 40%, less than 30%, less than 20%, less than 10% or less than 5%. In some embodiments, the container is wrapped in an opaque foil.

Provided in some embodiments is a packaging system for protecting a phthalocyanine dye-targeting molecule conjugate from light. In some embodiments, the packaging system includes an internal packaging material comprising the container described herein. In some embodiments, the internal packaging material has a light transmittance of no more than 5%. In some embodiments, an external packaging material contains the internal packaging material. In some embodiments, the external packaging material has a light transmittance of no more than 5%. In some embodiments, the internal packaging material includes an opaque foil.

Provided in some embodiments is a packaging system for protecting a phthalocyanine dye-targeting molecule conjugate from light that includes a first container, such as any container provided herein, and a second container comprising the first container, wherein the second container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the second container protects from transmission of light such that the percentage of light transmission is less than 50%, less than 40%, less than 30%, less than 20%, less than 10% or less than 5%. In some embodiments, the second container is green, blue, amber, translucent, opaque, or is covered by a material with light transmission of less than 50%, less than 40%, less than 30%, less than 20%, less than 10% or less than 5%. In some embodiments, the first and second container are independently selected from among a vial, a tube, a syringe, a bag, a pouch, and a box.

In some embodiments, any of the provided packaging system further includes a third container comprising the second container, wherein the third container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the third container protects from transmission of light such that the percentage of light transmission is less than 50%, less than 40%, less than 30%, less than 20%, less than 10% or less than 5%. In some embodiments, the third container is green, blue, amber, translucent, opaque, or is covered by a material with light transmission of less than 50%, less than 40%, less than 30%, less than 20%, less than 10% or less than 5%. In some embodiments, the third container is selected from among a vial, a tube, a syringe, a bag, a pouch, and a box.

Provided in some embodiments is a kit that includes any of the containers described herein or any of the packaging systems described herein; a light-protected cover capable of covering a device capable of administering a composition comprising a phthalocyanine dye-targeting molecule conjugate; and optionally instructions for use. In some embodiments, the administration device is an intravenous infusion bag. In some embodiments, the light-protected cover protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the light-protected cover protects from transmission of light such that the percentage of light transmission is less than 50%, less than 40%, less than 30%, less than 20%, less than 10% or less than 5%. In some embodiments, the light-protected cover is green, blue, amber, translucent, opaque, or is covered by a material with light transmission of less than 50%, less than 40%, less than 30%, less than 20%, less than 10% or less than 5%.

Provided in some embodiments is a method of preparing a composition comprising a phthalocyanine-dye conjugate for administration that includes: unpacking one or more of any of the containers described herein or one or more of any of the packaging system described herein that includes any of the containers described herein; and transferring the composition present in the one or more containers into a device capable of administering the composition to a subject, wherein the only light to which the composition is exposed has a wavelength within a range from about 400 nm to about 650 nm, or the only light to which the composition is exposed has an intensity of less than 500 lux. In some embodiments, the only light in which the composition is exposed has an intensity of less than 200 lux or less than 100 lux. In some embodiments, the method provided is performed in a biosafety cabinet, biosafety hood or a sterile environment. In some embodiments, the one or more containers together comprise a therapeutically effective dose of the phthalocyanine-dye conjugate. In some embodiments, the one or more containers include at least or about at least or 2, 4, 6, 8, 10, 12, 18 or 24 containers. In some embodiments, the provided method is carried out for no more than 1 hour, no more than 30 minutes or no more than 15 minutes; or the total exposure of the composition to any light during the method is no more than 500 lux hours, no more than 250 lux hours, no more than 100 lux hours, no more than 50 lux hours or no more than 25 lux hours.

In some embodiments, the administration device is an intravenous infusion bag. In some embodiments, the administration device comprises a light-protected cover capable of covering the device. In some embodiments, the light-protected cover protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

In some embodiments, the light-protected cover protects from transmission of light such that the percentage of light transmission is less than 50%, less than 40%, less than 30%, less than 20%, less than 10% or less than 5%. In some embodiments, the light-protected cover is green, blue, amber, translucent, opaque, or is covered by a material with light transmission of less than 50%, less than 40%, less than 30%, less than 20%, less than 10% or less than 5%.

Provided in some embodiments is a light-protected device that includes the composition prepared using the methods provided herein.

Provided in some embodiments is a method of removing unwanted cells or pathogens in a subject, that includes: (a) administering a composition comprising a phthalocyanine-dye conjugate from any of the light-protected device provided herein to a subject, wherein prior to and during the administration step the composition is not exposed to an intensity of environmental light greater than 500 lux; and (b) irradiating the unwanted cells or pathogens at a wavelength of 660 to 740 nm at a dose of at least 1 J cm$^{-2}$ or 1 J/cm of fiber length thereby removing the unwanted cell in the subject.

Provided in some embodiments is a method of removing unwanted cells or pathogens in a subject that includes: a) administering to a subject a therapeutically effective amount of any of the conjugates or compositions described herein, wherein prior to and during the administration step the conjugate is not exposed to an intensity of environmental light greater than 500 lux; and b) irradiating the unwanted cells or pathogens at a wavelength of 660 to 740 nm at a dose of at least 1 J cm$^{-2}$ or 1 J/cm of fiber length thereby removing the unwanted cell in the subject.

Provided in some embodiments is a method of removing unwanted cells or pathogens in a subject that includes: a) administering to a subject a therapeutically effective amount of a conjugate comprising IRDye 700DX (IR700) linked to a targeting molecule capable of binding an unwanted cell or pathogen, wherein prior to and during the administration step the conjugate is not exposed to an intensity of environmental light greater than 500 lux; and b) irradiating the unwanted cells or pathogens at a wavelength of 600 to 800 nm at a dose of at least 1 J cm$^{-2}$ or 1 J/cm of fiber length thereby removing the unwanted cells or pathogens in the subject.

Provided in some embodiments is a method of removing unwanted cells or pathogens in a subject that includes: a) administering to a subject a therapeutically effective amount of a first binding molecule capable of binding an unwanted cell or pathogen; b) administering to the subject a conjugate molecule comprising IRDye 700DX (IR700) linked to a targeting molecule, wherein the targeting molecule is a second binding molecule that is capable of binding to the first binding molecule; and c) irradiating the unwanted cells or pathogens at a wavelength of 600 to 800 nm at a dose of at least 1 J cm$^{-2}$ or 1 J/cm of fiber length thereby removing the unwanted cells or pathogens in the subject.

Provided in some embodiments is a method of removing unwanted cells or pathogens in a sample, that includes: (a) administering a composition comprising a phthalocyanine-dye conjugate from any of the light-protected device provided herein to a sample, wherein prior to and during the administration step the composition is not exposed to an intensity of environmental light greater than 500 lux; and (b) irradiating the unwanted cells or pathogens at a wavelength of 660 to 740 nm at a dose of at least 1 J cm$^{-2}$ or 1 J/cm of fiber length thereby removing the unwanted cell in the sample.

Provided in some embodiments is a method of removing unwanted cells or pathogens in a sample that includes: a) administering to a sample a therapeutically effective amount of any of the conjugates or compositions described herein, wherein prior to and during the administration step the conjugate is not exposed to an intensity of environmental light greater than 500 lux; and b) irradiating the unwanted cells or pathogens at a wavelength of 660 to 740 nm at a dose of at least 1 J cm$^{-2}$ or 1 J/cm of fiber length thereby removing the unwanted cell in the sample.

Provided in some embodiments is a method of removing unwanted cells or pathogens in a sample that includes: a) administering to a sample a therapeutically effective amount of a conjugate comprising IRDye 700DX (IR700) linked to a targeting molecule capable of binding an unwanted cell or pathogen, wherein prior to and during the administration step the conjugate is not exposed to an intensity of environmental light greater than 500 lux; and b) irradiating the unwanted cells or pathogens at a wavelength of 600 to 800 nm at a dose of at least 1 J cm$^{-2}$ or 1 J/cm of fiber length thereby removing the unwanted cells or pathogens in the sample.

Provided in some embodiments is a method of removing unwanted cells or pathogens in a sample that includes: a) administering to a sample a therapeutically effective amount of a first binding molecule capable of binding an unwanted cell or pathogen; b) administering to the sample a conjugate molecule comprising IRDye 700DX (IR700) linked to a targeting molecule, wherein the targeting molecule is a second binding molecule that is capable of binding to the first binding molecule; and c) irradiating the unwanted cells or pathogens at a wavelength of 600 to 800 nm at a dose of at least 1 J cm$^{-2}$ or 1 J/cm of fiber length thereby removing the unwanted cells or pathogens in the sample.

In some embodiments, the method is performed in vitro or ex vivo. In some embodiments, the method is performed using an extracorporeal device.

In some embodiments of the methods provided herein, the first binding molecule is administered to the subject prior to the conjugate or the first binding molecule and conjugate are administered simultaneously to the subject. In some embodiments, the targeting molecule is a secondary antibody. In some embodiments, prior to and during the administration of the conjugate, the conjugate is not exposed to an intensity of environmental light greater than 500 lux.

In some embodiments, the cell is a stem cell, a proliferating cell, a cell in a hyperplasia, an inflammatory cell, a negative regulatory immune cell, which optionally is a T cell, a pathogen infected cell, a neuron, a fat cell or adipocyte. In some embodiments, the cell is a cancer cell or a tumor cell. In some embodiments, the cell is associated with, causes or contributes to the etiology of a disease or condition. In some embodiments, the disease of condition is a tumor or cancer, an infection, an inflammatory disease or condition, or a neuronal disease or condition. In some embodiments, the cell is a neuron and the disease or condition is a neurological disorder, which optionally is pain; the cell is a fat cell or adipocyte and the disease or condition involves excess fat; the cell is a pathogen infected cell and the disease or condition is an infection; the cell is a pathogen and the disease or condition is an infection; the cell is an inflammatory cell and the disease or condition is an inflammatory disease; the cell is a an immune cell, which optionally is a regulatory T cell, and the disease or condition is a tumor or cancer; or the cell is a tumor or cancer cell and the disease or condition is a tumor or a cancer.

In some embodiments, the cell is present in the microenvironment of a lesion associated with a disease or condition or is in a hyperplasia. In some embodiments, the lesion is a tumor and the disease or condition is a tumor or cancer. In some embodiments, the method treats the disease or condition.

Provided in some embodiments is a method of removing a pathogen infected cell in a subject that includes: a) administering to a subject a therapeutically effective amount of a conjugate molecule comprising IRDye 700DX (IR700) linked to a targeting molecule, wherein the targeting molecule is capable of binding to the pathogen infected cell directly or indirectly; and b) irradiating the pathogen infected cell at a wavelength of 600 to 800 nm at a dose of at least 1 J $cm^{-2}$ or 1 J/cm of fiber length thereby removing the pathogen infected cell in the subject. In some embodiments, the pathogen is a virus, bacterium, fungus, biofilm, or other prokaryote cell system. In some embodiments, prior to and during the administration of the conjugate, the conjugate is not exposed to an intensity of environmental light greater than 500 lux.

Provided in some embodiments is a method of removing a pathogen infected cell in a sample that includes: a) administering to a sample a therapeutically effective amount of a conjugate molecule comprising IRDye 700DX (IR700) linked to a targeting molecule, wherein the targeting molecule is capable of binding to the pathogen infected cell directly or indirectly; and b) irradiating the pathogen infected cell at a wavelength of 600 to 800 nm at a dose of at least 1 J $cm^{-2}$ or 1 J/cm of fiber length thereby removing the pathogen infected cell in the sample. In some embodiments, the pathogen is a virus, bacterium, fungus, biofilm, or other prokaryote cell system. In some embodiments, prior to and during the administration of the conjugate, the conjugate is not exposed to an intensity of environmental light greater than 500 lux.

In some embodiments, the method is performed in vitro or ex vivo. In some embodiments, the ex vivo irradiation is method is performed using an extracorporeal device. Provided in some embodiments is a method of treating hyperplasia or a tumor in a subject. In some embodiments, the method includes administering to the subject a therapeutically effective amount of the conjugate or stable conjugate or composition, where prior to and during the administration step the conjugate is not exposed to an intensity of environmental light greater than 500 lux. In some embodiments, the method further includes irradiating the hyperplasia or the tumor at a wavelength of 660 to 740 nm at a dose of at least 1 J $cm^{-2}$ or 1 J/cm of fiber length, thereby treating the tumor in the subject.

Provided in some embodiments is a method of treating hyperplasia or a tumor in a subject. In some such embodiments, the method includes administering to the subject a therapeutically effective amount of a conjugate containing IRDye 700DX (IR700) linked to a targeting molecule. In some embodiments, the conjugate is targeted to the hyperplasia or the tumor and prior to and during the administration step the conjugate is not exposed to an intensity of environmental light greater than 500 lux. In some embodiments, the method further includes irradiating the tumor at a wavelength of 600 to 800 nm at a dose of at least 1 J $cm^{-2}$ or 1 J/cm of fiber length thereby treating the tumor in the subject.

Provided in some embodiments is a method of treating hyperplasia or a tumor in a sample. In some embodiments, the method includes administering to the sample a therapeutically effective amount of the conjugate or stable conjugate or composition, where prior to and during the administration step the conjugate is not exposed to an intensity of environmental light greater than 500 lux. In some embodiments, the method further includes irradiating the hyperplasia or the tumor at a wavelength of 660 to 740 nm at a dose of at least 1 J $cm^{-2}$ or 1 J/cm of fiber length, thereby treating the tumor in the sample.

Provided in some embodiments is a method of treating hyperplasia or a tumor in a sample. In some such embodiments, the method includes administering to the sample a therapeutically effective amount of a conjugate containing IRDye 700DX (IR700) linked to a targeting molecule. In some embodiments, the conjugate is targeted to the hyperplasia or the tumor and prior to and during the administration step the conjugate is not exposed to an intensity of environmental light greater than 500 lux. In some embodiments, the method further includes irradiating the tumor at a wavelength of 600 to 800 nm at a dose of at least 1 J $cm^{-2}$ or 1 J/cm of fiber length thereby treating the tumor in the sample.

In some embodiments, the method is for treating a tumor, wherein the targeting molecule of the conjugate targets the conjugate to the tumor or a microenvironment of the tumor. In some embodiments, irradiating the tumor is at a wavelength of 600 to 800 nm and at a dose of at least 1 J $cm^{-2}$ or 1 J/cm of fiber length, thereby treating the tumor, e.g., the tumor in the subject or in the sample.

In some embodiments, the targeting molecule is an antibody, an antigen binding fragment, a protein, a glycoprotein, a peptide, a polypeptide, a virus, a viral capsid, or a viral particle. In some embodiments, the targeting molecule is an antibody or an antibody fragment.

In some embodiments, administration is performed under fluorescent lighting or LED lighting and in the absence of direct or indirect sunlight.

In some embodiments, any exposure of the conjugate to light less than 500 lux is for less than 20 minutes, less than 15 minutes, less than 10 minutes or less than 5 minutes. In some embodiments, the exposure of the conjugate to any light is light with an intensity that is not greater than 50 lux.

In some embodiments, the tumor is a cancer. In some embodiments, the cancer is a cancer located at the head and neck, breast, liver, colon, ovary, prostate, pancreas, brain, cervix, bone, skin, eye, bladder, stomach, esophagus, peritoneum, or lung. In some embodiments, the cancer is a cancer of the blood.

In some embodiments, the conjugate is targeted to a protein expressed in the tumor. In some embodiments, the conjugate is targeted to a protein expressed on the surface of a cell present in the tumor microenvironment. In some embodiments, the cell is a tumor cell, an immune cell or a cancer stem cell.

In some embodiments, the protein expressed in the tumor is ACTHR, endothelial cell Anxa-1, aminopetidase N, anti- IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g. P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g. TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, or Y5.

In some embodiments, the protein expressed in the tumor is HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-1 antigen, Bcr-abl, RET, MET, TRKB, TIE2, ALK, ROS, EML4-ALK, ROS1, BRAFV600E, SRC, c-KIT, PDGFR, mTOR, TSC1, TSC2, BTK, KIT, BRCA, CDK 4/6, JAK1, JAK2, BRAF, FLT-3, MEK1, MEK2, or SMO.

In some embodiments, the conjugate is targeted to a protein expressed in the tumor. In some embodiments, the cell, hyperplasia or tumor is irradiated at a wavelength from or from about 600 nm to about 850 nm. In some embodiments, the tumor is irradiated at a wavelength of 690±50 nm or 690±20 nm.

In some embodiments, the cell, hyperplasia or tumor is irradiated at a dose of from or from about 2 J cm$^{-2}$ to about 400 J cm$^{-2}$ or from or from about 2 J/cm fiber length to about 500 J/cm fiber length. In some embodiments, the cells, hyperplasia or tumor are irradiated at a dose of at least or at least about 2 J cm$^{-2}$, 5 J cm$^{-2}$, 10 J cm$^{-2}$, 25 J cm$^{-2}$, 50 J cm$^{-2}$, 75 J cm$^{-2}$, 100 J cm$^{-2}$, 150 J cm$^{-2}$, 200 J cm$^{-2}$, 300 J cm$^{-2}$, 400 J cm$^{-2}$, or 500 J cm$^{-2}$; or the cells, tumor or hyperplasia are irradiated at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.

In some embodiments, the disease or condition is a tumor and the tumor is a superficial tumor. In some embodiments, the tumor is irradiated at a dose of at least or about at least or about 10 J/cm$^2$, 25 J/cm$^2$, 50 J/cm$^2$, 150 J/cm$^2$, or 250 J/cm$^2$.

In some embodiments, the disease or condition is a tumor and the tumor is an interstitial tumor. In some embodiments, the tumor is irradiated at a dose of at least or about at least or about 50 J/cm fiber length, 100 J/cm fiber length, 200 J/cm fiber length, or 300 J/cm fiber length.

In some embodiments, the cells, hyperplasia or tumor is irradiated within or within about or about 12 hours, 24 hours, 36 hours, 72 hours or 96 hours after administering the conjugate. In some embodiments, the targeting molecule is administered up to 96 hours prior to administration of the conjugate. In some embodiments, the conjugate is administered in an amount that is from or from about 0.5 mg/kg to about 100 mg/kg or 20 mg/m$^2$ to about 4000 mg/m$^2$.

In some embodiments, the conjugate is administered in an amount that is at least or about at least or is or is about 0.5 mg/kg, 2.0 mg/kg, 4.0 mg/kg, 8.0 mg/kg, 16.0 mg/kg, 32.0 mg/kg or 64 mg/kg; or the conjugate is administered in an amount that is at least or about at least or is or is about 20 mg/m$^2$, 40 mg/m$^2$, 160 mg/m$^2$, 320 mg/m$^2$, 640 mg/m$^2$, 1280 mg/m$^2$ or 2560 mg/m$^2$.

In some embodiments of the methods provided herein, prior to administration of the conjugate the targeting molecule is administered, e.g., administered to the subject or the sample. In some embodiments, the targeting molecule is administered at a dose within a range from or from about 10 mg/m$^2$ to about 500 mg/m$^2$.

In some embodiments, the targeting molecule is an antibody or antigen binding fragment. In some embodiments, the antibody is cetuximab.

Provided in some embodiments is a conjugate containing a phthalocyanine dye and a targeting molecule. In some such embodiments, the targeting molecule is a tissue-specific homing peptide, an RGD polypeptide, an iRGD polypeptide, a Lyp-1 polypeptide, a cripto-1 binding polypeptide, a somatostatin receptor binding polypeptide, a prohibitin binding polypeptide, a NGR polypeptide, an iNGR polypeptide, an activatable cell penetrating peptide (ACPP) comprised of a polycationic cell penetrating peptide (CPP) connected via a cleavable linker to a neutralizing polyanion, or an antibody, such as Ado-trastuzumab emtansine, Afatinib, Axitinib, Bosutinib, Cabozantinib, Ceritinib, Crizotinib, Dabrafenib, Dasatinib, Everolimus, Ibrutinib, Imatinib, Lenvatinib, Nilotinib, Olaparib, Palbociclib, Pazopanib, Ramucirumab, Regorafenib, Ruxolitinib, Sorafenib, Sunitinib, Temsirolimus, Trametinib, Vandetanib, Vemurafenib, Vismodegib, Ipilimumab, Nivolumab, pembrolizumab, MPDL3280A, Pidilizumab (CT-011), AMP-224, MSB001078C, or MEDI4736, or an antigen-binding fragment thereof.

In some embodiments, the ACPP comprises the structure: A-X1-B—, wherein B is a peptide portion of about 5 to about 20 basic amino acid residues, which is suitable for cellular uptake; A is a peptide portion of about 2 to about 20 acidic amino acid residues, which when linked with portion B is effective to inhibit or prevent cellular uptake of portion B; X1 is a cleavable linker of about 2 to about 100 atoms; and one or more of L-Y is linked to the C-terminus of peptide portion B.

In some embodiments, the homing peptide has a sequence as set forth in any of SEQ ID NOs: 1-52. In some embodiments, the dye is IR700.

DETAILED DESCRIPTION

Figure 1A:
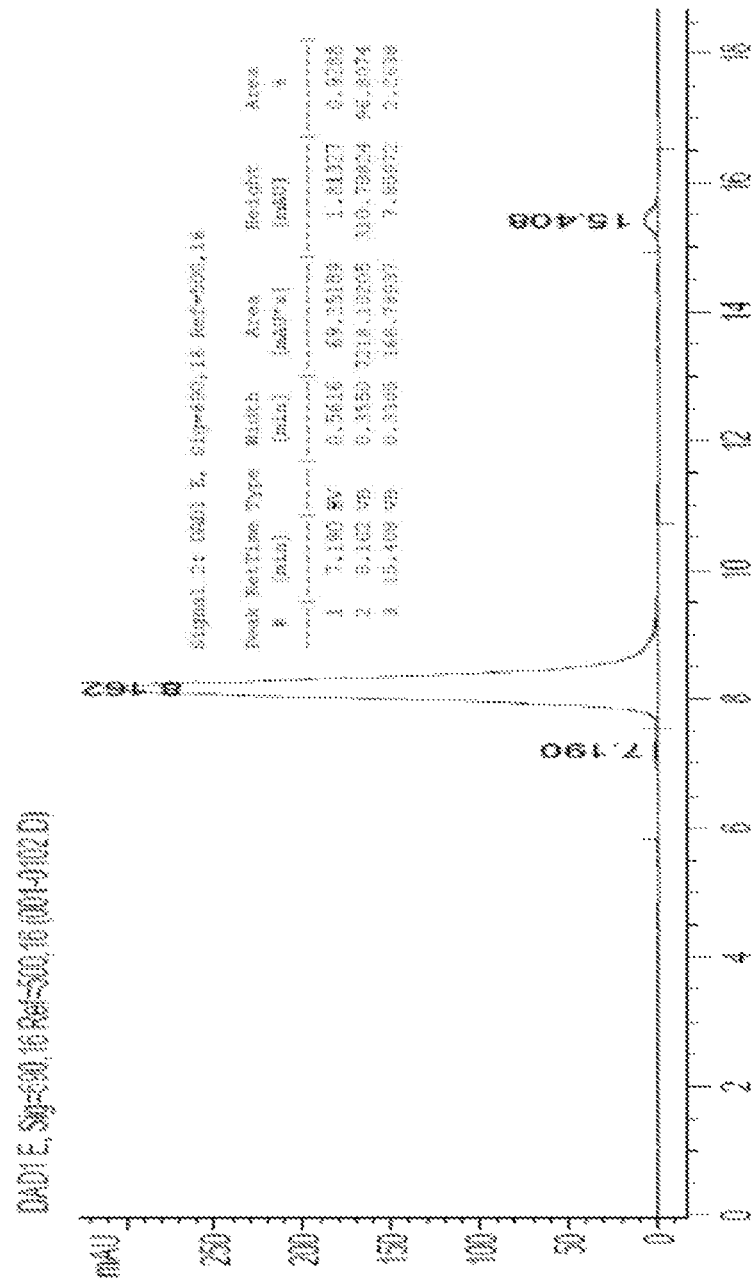
FIG. 1A displays the relative amounts of high molecular weight species (aggregates) and monomer form of the Cetuximab-IRDye 700DX as assessed by High Pressure Liquid Chromatography using a Size Exclusion column (HPLC-SEC) of a sample in a clear vial before 24 hours of light exposure.

I. Methods for Manufacturing Phthalocyanine Dye-Targeting Molecule Conjugates In some embodiments, provided are methods for preparing or manufacturing phthalocyanine dye-targeting molecule conjugates, such as an IRDye 700DX (IR700)-targeting molecule (e.g. antibody) conjugate, including producing, formulating and/or packaging the conjugates. In some embodiments, the methods are performed under conditions to reduce or prevent aggregation or degradation of the dye, such as by protecting the conjugate from light that may photoactivate the dye of the conjugate during manufacturing processes. In some embodiments, the provided methods also include protecting the conjugate from exposure to an acidic pH, such as an acidic pH less than 6.0. The provided methods produce a dye-conjugate that is stable for greater than 3 months, and generally greater than 6 months or greater than 12 months, including a dye-conjugate that is stable under conditions of storage.

In some embodiments, the methods are performed to produce a phthalocyanine dye-targeting molecule conjugate for use in photoimmunotherapy methods. Photoimmunotherapy is a molecular targeted therapy that utilizes a target-specific photosensitizer based on phthalocyanine dye, such as a near infrared (NIR) phthalocyanine dye (e.g., IR700), conjugated to a targeting molecule, e.g., targeting to a cell surface protein on tumor cells. For example, in some cases a phthalocyanine dye-conjugate used in photoimmunotherapy can include conjugation to a monoclonal antibody (mAb) targeting tumor-specific cell surface proteins, e.g., a tumor-specific cell surface receptor. In some embodiments, activation of the dye-conjugate by irradiation with absorbing light, such as NIR light, excites the photosensitizer and results in cell killing. In some cases, the use of light in the NIR range leads to deeper tissue penetration resulting in successful eradication of tumors after only a single dose of external NIR light irradiation.

Typically, PIT results in cell death primarily of those cells to which the phthalocyanine-dye conjugate, such as IR700-antibody conjugate, binds after the cells are irradiated with NIR, while cells that do not express the cell surface protein recognized the targeting molecule (e.g., antibody) are not killed in significant numbers. Thus, because the therapy is targeted specifically to disease cells, such as tumor cells, its effects are highly selective to disease tissue compared to healthy tissue or cells. For example, although a targeted photosensitizer can distribute throughout the body, it is only active where intense light is applied, reducing the likelihood of off-target effects.

Generally, targeted phototoxicity appears to be primarily dependent on binding of the dye-conjugate to the cell membrane via the specific targeting molecule (e.g., a macromolecule, such as an antibody). For example, studies using an exemplary antibody-IR700 molecule indicate that the conjugate must be bound to the cellular membrane to be active, and that cell killing does not require intracellular localization to be effective (see. e.g., U.S. Pat. No. 8,524,239 and U.S. published application No. US20140120119). Photo-activation of the conjugate-bound cells results in rapid cell death and necrosis.

Generally, phthalocyanine dyes, and in particular IRDye 700DX (IR700), are extremely photostable dyes. For example, IR700 is reported to be 45 to 128 times more photostable than other near-infrared dyes and is free of aggregation (Peng et al. (2006) Proc. SPIE 6097, 60970E; see also www.licor.com/bio/products/reagents/irdye/700dx/photostability.html). IR700 dye also is reported not to exhibit the same aggregation problems as other dyes when formulated at acidic pH. Likewise, Peng et al. reports that when IR700 is conjugated to an antibody, it exhibits virtually the same fluorescence excitation and absorption spectra as the non-conjugated dye, thereby indicating the conjugate retains its fluorescent properties. In some aspects, the photostability of IR700 can permit its use in applications in which the dye is exposed to continuous excitation with light for extended time periods and without the need to be protected from light. This is in contrast to other fluorophore dyes that are not photostable and cannot remain fluorescent when exposed to light for an extended period.

It is found herein, however, that conjugating the dye to a targeting molecule, which is necessary for PIT activity, reduces the stability of the dye, such that the conjugate is more prone to aggregation and has a decreased activity (e.g. PIT activity). This effect occurs even though the dye in the monomer retains its photostability and fluorescent properties. In some cases, particularly for therapeutic applications, this can reduce the activity and thereby limit the efficacy of the conjugate as a PIT agent. This result is not shown for other dye conjugates (e.g. IRDye 680 conjugates) where such dyes exhibit less photostability but are not prone to aggregate when conjugated to another molecule. Thus, it is found therein that conjugates of phthalocyanine dyes, such as IR700, used for PIT are particular sensitive to soluble aggregate formation when exposed to light compared to conjugates of other dyes, including other 700 nm dyes. In some aspects, this is a problem because the fraction of monomer purity and pharmacological activity (e.g. PIT activity) are necessary for therapeutic use of the phthalocyanine dye conjugate (e.g. IR700 conjugate), since changes in purity or activity can lead to a significant impact on the light-activated killing activity.

These observations are based, in part, on HPLC-SEC analysis of dye conjugates prepared or exposed to different conditions. For example, the Examples provided herein demonstrate that aggregation of the bound dye portion of an antibody-dye conjugate can occur when the conjugate is exposed to light for increasing amounts of time as evidenced by an increase in a high molecular weight species that is greater in size than the main monomer peak (compare FIGS. 1A and 1B). The results also show that substantial aggregation of an IR700 conjugate occurs in the presence of white light, which is not observed for IRDye 680 conjugates when conjugated to the same molecule (see e.g. FIG. 15A). In some cases, the reduced stability of the dye can mean that the dye conjugate is more susceptible to light-induced aggregation that can minimize the use of the dye conjugate after it has been exposed to light for an extended time. It also is found that the general instability of the dye conjugate also is evident when the conjugate is formulated at acidic pH. For example, as shown in the Examples, the dye conjugate exhibits increased aggregation at pH less than 6.0.

The provided observations establish that, in some cases, light protection of phthalocyanine dye conjugates is necessary to minimize aggregation and retain activity, particularly to ensure consistency in product manufacturing, such as used in accord with good manufacturing production (GMP) methods. Thus, provided herein are methods to improve the stability, e.g. integrity, purity, activity, or potency, of the dye conjugate. In some embodiments, the methods include protecting the dye or dye conjugate from excitation light during one or more of the steps of handling or preparing the dye, performing the conjugation of the dye with a targeting molecule (e.g. antibody), formulating the dye and/or packaging the dye. In some embodiments, where light is necessary, for example, to visualize the processes of making or producing the conjugate, the light protection includes performing one or more of, and in some cases all of, the above steps only in the presence of green light, such as at a wavelength that is not absorbed by the dye, for example a wavelength from or from about 400 nm to about 650 nm. In some embodiments, any light that is present during one or more of the above steps is at an intensity that is less than 500 lux, such as less than 200 lux. In some embodiments, the total light exposure to any light of the dye and the conjugate during the process of making, manufacturing or producing the conjugate is no more than 5000 lux hours, such as no more than 80 lux hours. In some embodiments, the total light exposure to any light of the dye and the conjugate during the process of packaging the conjugate is no more than 5000 lux hours, such as no more than 80 lux hours.

In some embodiments, the methods include formulating the dye in a pharmaceutically acceptable buffer at a pH greater than 6.0, such as generally from or from about pH 6.0 to about 8.0.

In some embodiments, methods also are provided that include protecting the dye conjugate from excitation light by packaging the drug product in a container(s) or other article of manufacture(s) that protects from transmission of light such that the container(s) or other article of manufacture(s) exhibits no more than 40% transmission of light having a wavelength of from or from about 250 nm to about 800 nm, from about 250 nm to about 450 nm, from about 400 nm to about 800 nm, from about 450 nm to about 650 nm, or from about 600 nm to about 720 nm. In some embodiments, the container or other article of manufacture is one in which the transmittance of any light is less than 5% or no more than 5%. In some embodiments, such a container or article of manufacture containing the dye conjugate product is an internal packaging material and one or more other external containers or articles of manufacture are provided that enclose or encase the internal packaging material, such as to provide further light protection.

In some embodiments, provided is a dye conjugate that is stable. In some embodiments, by practice of the provided methods, the purity, impurities, integrity, composition and potency of the conjugate are not changed greater than acceptable specifications for manufacturing purposes to support clinical or commercial uses. In embodiments, the conjugate is stable and exhibits minimal aggregation and retains potency and activity, such as after processing, manufacture or storage of the dye. In some embodiments, the dye conjugate is stable for greater than three months, four months, five months, such as generally for greater than 6 months, greater than 7 months, 8 months, 9 months, 10 months, 11 months, 12 months or more. In some embodiments, such stability is present when stored for the time at a temperature that is less than 30° C., such as generally at a temperature that is at 2-8° C.

With reference to the dye conjugate, the term "stable" refers to a conjugate in which, after storage for greater than a requisite time, such as greater than three months, for example greater than or greater than about 6 months, 12 months or 24 months, greater than or greater than about 90% of the conjugate is present as a main monomer component as a percentage of the total molecular weight of the conjugate present in the sample, no more than 10.0% of the conjugate exists as a high molecular weight component as a percentage of the total molecular weight of the conjugate present in the sample or the conjugate retains at least 20% and up to 100% of its integrity, such as its physical and functional qualities, including one or more of its purity (e.g. percent monomer content vs. aggregates, such as content of higher molecular weight components), identity (e.g. chemical composition, such as structural characteristics), potency (e.g. concentration or amount required to produce a pharmacologic response) or activity (e.g. PIT killing) compared to the conjugate prior to the storage for the requisite time (e.g. t=0).

In some embodiments, a conjugate is stable if, after storage for greater than a requisite time, such as greater than three months, such as greater than 6 months, 12 months or 24 months, greater than 90% of the conjugate exists as a main monomer component as a percentage of the total molecular weight of the conjugate present in the sample, such as greater than 91%, greater than 92%, greater than 93%, greater than 94%, greater than 95%, greater than 96%, greater than 97%, greater than 98% or more exists as a main monomer component as a percentage of the total molecular weight of the conjugate present in the sample. In some embodiments, the dye conjugate is stable if, after storage for greater than three months, such as greater than 6 months, 12 months or 24 months, no more than 10.0% of the conjugate exists as a high molecular weight component as a percentage of the total molecular weight of the conjugate present in the sample, and generally no more than 9.0%, no more than 8.0%, no more than 7.0%, no more than 6.0%, no more than 5.0%, no more than 4.0% or no more than 3.0% exists as a high molecular weight component as a percentage of the total molecular weight of the conjugate present in the sample. In some embodiments, the presence of a high molecular weight component or a main monomer component can be identified using any method that can separate molecules based on size, such as by performing HPLC-SEC.

In some embodiments, a conjugate is stable if, after greater than three months, such as greater than or greater than about 6 months, 12 months or 24 months, its integrity, purity, identity, potency or activity is retained to at least or about at least 30%, 40%, 50%, 60%, 70%, 80%, 90% or 95% of the integrity, purity, identity, potency or activity, respectively, of the conjugate prior to the storage for the time (e.g. conjugate at t=0). In some embodiments, the potency of the conjugate can relate to the affinity of the conjugate for binding to its target molecule. In some embodiments, the potency can be assessed by its $ED_{50}$, i.e. the measure of the dose or amount of the conjugate that is pharmacologically effective or that exhibits a desired effect in 50% of the subjects exposed to the conjugate. In some embodiments, the activity relates to the biological activity, including the therapeutic effect and pharmacologic activity, of the conjugate that result upon in vivo administration, such as the activity of the conjugate to induce PIT killing. In some embodiments, biological activity can be observed in in vitro systems designed to test such activities. In some embodiments, the purity of the conjugate is related to the presence of monomers of the conjugate as compared to aggregates (e.g. high molecular weight components). In some embodiments, the purity can be assessed based on the percentages of monomers (e.g. main monomer peak) versus aggregates (e.g. high molecular weight components) in the composition. In some embodiments, the presence of a high molecular weight component or a main monomer component can be identified using any method that can separate molecules based on size, such as by performing HPLC-SEC.

In some embodiments, the main monomer component of a dye conjugate generally refers to a molecular weight species of the dye conjugate that represents the combined molecular weight of the dye and targeting molecule present in the conjugate. Generally, the main monomer component is the species present in the greatest amount in a sample of a dye conjugate. For example, by HPLC-SEC methods, the main monomer component is generally the species of dye conjugate present as the largest peak in a preparation of a dye conjugate. Its exact molecular weight range in a dye-conjugate sample depends upon the particular sample (e.g. the particular dye and targeting molecule) and the methods of preparation (e.g. the ratio of dye to targeting molecule). The skilled artisan will recognize such a species. For example, for a conjugate containing an IR700 dye (having a molecular weight of about 1954.22 Da) and an antibody (having an average molecular weight of about 150,000 Da for a full-length antibody), the molecular weight range of the main monomer component typically is about 151,000 Da to 165,000 Da, such as 154,000 Da to 158,000 Da. In the exemplary experiment depicted in FIGS. 1A and 1B, the main monomer component of an exemplary antibody-dye conjugate include those that elute by HPLC-SEC between 8 and 9 minutes.

In some embodiments, the high molecular weight component of a dye conjugate generally refers to the molecular weight species of the dye conjugate that exhibit a molecular weight that is greater than the molecular weight of the main monomer component. In some embodiments, the increased or greater molecular weight can be due to aggregation of the dye. In some embodiments, the aggregation can be due to the formation of dimers, trimers or higher ordered oligomers. The exact molecular weight range of a high molecular weight component in a dye-conjugate sample will depend upon the particular sample (e.g. the particular dye and targeting molecule), the methods of preparation (e.g. the ratio of dye to targeting molecule) and, in some cases, the degree or extent of aggregation. The skilled artisan will recognize such a species. In some embodiments, for a dye conjugate of a full-length antibody and dye, such as IR700 dye, the high molecular weight component can be due to the presence of a dimer, trimer or higher ordered oligomer any that has a molecular weight generally greater than 200,000 Da, such as greater than 300,000 Da, 350,000 Da, 400,000 Da, 450,000 Da, 500,000 Da or greater. In the exemplary experiment depicted in FIGS. 1A and 1B, the high molecular components of an exemplary antibody-dye conjugate include those that elute by HPLC-SEC before 8 minutes, such as between 6 minutes and 8 minutes.

A. Conjugates Containing a Phthalocyanine Dye and Targeting Molecule

The methods provided herein include manufacturing a conjugate containing a photosensitizer, such as a phthalocyanine dye, for example IR700, and a targeting molecule (e.g. antibody), such as an antibody that binds to a cell surface protein. In some embodiments, the targeting molecule that is conjugated to the photosensitizer, such as a phthalocyanine dye (e.g., IR700), permits the targeting of the conjugate to a cell surface molecule, e.g., a cell surface receptor, of cells involved in a disease or condition, such as a tumor or cancer, infection, inflammatory disease or condition, neuronal disease or condition or other disease or condition. In some embodiments, cell targeting increases the efficacy of PIT induced upon local irradiation of the subject, such as irradiation of a tumor in the subject, at a wavelength that is absorbed by the phthalocyanine dye, such as at a near-infrared (NIR) wavelength.

The phthalocyanine dye conjugates for use in the combination therapy provided herein include a dye molecule conjugated to a targeting molecule via a linker group. In one aspect, the conjugate is of Formula I:

$$A\text{-}[(L)_n\text{-}D]_p \qquad (I)$$

wherein:
A is a targeting molecule that can bind to cells or tissues;
L is an independently selected linker for each p;
n is 1 or 2;
D is an independently selected hydrophilic phthalocyanine dye for each p; and
p is independently 1, 2, 3, 4, 5 or greater than 5, such as up to 1000. For example, p can be 1 to 1000, such as generally 1 to 10 or 2 to 5.

Phthalocyanines are a group of photosensitizer compounds having the phthalocyanine ring system. Phthalocyanines are azaporphyrins that contain four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy are described in International Publication WO 2005/099689 and U.S. Pat. No. 7,005,518.

In some embodiments, phthalocyanines strongly absorb red or near IR radiation with absorption peaks falling between about 600 and 810 nm, which, in some cases, allow deep penetration of tissue by the light. Phthalocyanines are generally photostable. This photo stability is typically advantageous in pigments and dyes and in many of the other applications of phthalocyanines.

In some embodiments, the phthalocyanine dye is water soluble and contains a luminescent fluorophore moiety having at least one aqueous-solubilizing moiety. In some embodiments, the aqueous solubilizing moiety contains silicon. In some embodiments, the phthalocyanine dye has a core atom such as Si, Ge, Sn, or Al. In some embodiments, the phthalocyanine dye exists as a single core isomer, essentially free of other isomers. In some embodiments, the phthalocyanine dye contains a linker that has a reactive or activatable group, which is able to form a bond between the linker and targeting molecule. In some embodiments, the phthalocyanine dye can be tailored to fluoresce at a particular wavelength.

In some embodiments, the phthalocyanine dye contains a linker, i.e., is a linker-phthalocyanine dye moiety (L-D). In some embodiments, the linker contains a reactive group. In some embodiments, the phthalocyanine dye is of Formula II:

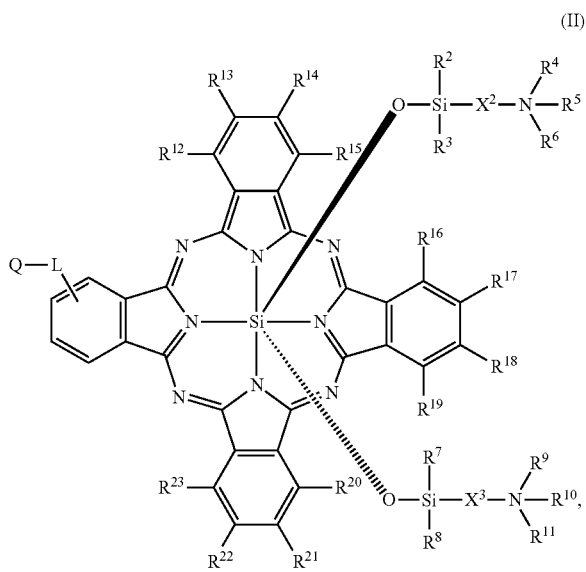

wherein
L is selected from a direct link, or a covalent linkage;
Q is a reactive group or an activatable group that can be part of the linker L, and is any group that can react to form a bond between L and the targeting molecule A;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$, if present, are each independently selected from hydrogen, optionally substituted alkyl, optionally substituted alkanoyl, optionally substituted alkoxycarbonyl, optionally substituted alkylcarbamoyl, or a chelating ligand, wherein at least one of $R^4$, $R^5$, $R^6$, $R^9$, $R^{10}$, and $R^{11}$ comprises a water soluble group;
$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each functional groups that can be independently selected from hydrogen, halogen, optionally substituted alkylthio, optionally substituted alkylamino or optionally substituted alkoxy;
or in an alternative embodiment, at least one of i) $R^{13}$ and $R^{14}$, and the carbons to which they are attached, or ii) $R^{17}$ and $R^{18}$, and the carbons to which they are attached, or iii) $R^{21}$ and $R^{22}$, and the carbons to which they are attached, join to form a fused ring; and $X^2$ and $X^3$ are each independently $C_1$-$C_{10}$ alkylene, optionally interrupted by a hetero atom.

In some embodiments, L is a covalent linkage. In some embodiments, the covalent linkage is linear or branched, cyclic or heterocyclic, saturated or unsaturated, having 1-60 atoms, such as 1-45 atoms or 1-25 atoms. In some cases, such atoms can be selected from C, N, P, O, and S. In some embodiments, L can have additional hydrogen atoms to fill valences (in addition to the 1-60 atoms). Generally, the linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds.

In some embodiments, L is of the formula —$R^1$—Y—$X^1$—$Y^1$—, wherein $R^1$ is a bivalent radical or direct link; Y and $Y^1$ are each independently selected from t a direct link, oxygen, an optionally substituted nitrogen, or sulfur; and $X^1$ is selected from t a direct link and $C_1$-$C_{10}$ alkylene optionally interrupted by an atom. Bivalent radicals include, but are not limited to, optionally substituted alkylene, optionally substituted alkyleneoxycarbonyl, optionally substituted alkylenecarbamoyl, optionally substituted alkylenesulfonyl, and optionally substituted arylene.

Exemplary $R^1$ substituents include, but are not limited to, optionally substituted alkylene, optionally substituted alkyleneoxycarbonyl, optionally substituted alkylenecarbamoyl, optionally substituted alkylenesulfonyl, optionally substituted alkylenesulfonylcarbamoyl, optionally substituted arylene, optionally substituted arylenesulfonyl, optionally substituted aryleneoxycarbonyl, optionally substituted arylenecarbamoyl, optionally substituted arylenesulfonylcarbamoyl, optionally substituted carboxyalkyl, optionally substituted carbamoyl, optionally substituted carbonyl, optionally substituted heteroarylene, optionally substituted heteroaryleneoxycarbonyl, optionally substituted heteroarylenecarbamoyl, optionally substituted heteroarylenesulfonylcarbamoyl, optionally substituted sulfonylcarbamoyl, optionally substituted thiocarbonyl, a optionally substituted sulfonyl, and optionally substituted sulfinyl.

In some embodiments, Q contains a reactive group for optional attachment to a material, such as a targeting molecule. As used herein, the term "reactive group" or ""reactive chemical group" means a moiety on the compound that is capable of chemically reacting with the functional group on a different material (e.g., targeting molecule) to form a linkage, such as a covalent linkage. Typically, the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the targeting molecule to be conjugated results in one or more atoms of the reactive group Q incorporated into a new linkage attaching the dye to the conjugated targeting molecule.

In some embodiments, Q contains a reactive group that is reactive with a carboxyl group, an amine, or a thiol group on the targeting molecule. Suitable reactive groups include, but are not limited to, an amine-reactive chemical group, a sulfhydryl-reactive chemical group, an activated ester, an acyl halide, an alkyl halide, an anhydride, a carboxylic acid, a carbodiimide, a carbonate, a carbamate, a haloacetamide (e.g., iodoacetamide), an isocyanate, an isothiocyanate, a maleimide, an NHS ester, a phosphoramidite, a platinum complex, a sulfonate ester and a thiocyanate for optional attachment to the targeting molecule. In some embodiments, the reactive groups are reactive with a carboxyl group, an amine, or a thiol group on a targeting molecule. In some embodiments, the reactive group is a sulfhydryl-reactive chemical group such as maleimide, haloacetyl, and pyridyl disulfide. In some embodiments, the reactive group is amine-reactive. In some embodiments, the reactive group is an NHS ester.

In some embodiments, $R^2$, $R^3$, $R^7$, and $R^8$ are each optionally substituted alkyl such as optionally substituted methyl, ethyl, or isopropyl groups.

In some embodiments, at least one of $R^4$, $R^5$, $R^6$, $R^9$, $R^{10}$, and $R^{11}$ contains a water soluble group. For example, the alkyl portion of $R^4$, $R^5$, $R^6$, $R^9$, $R^{10}$, and $R^{11}$ is substituted with a water soluble substituent. As used herein, "water soluble group" refers to a group comprising one or more polar and/or ionic substituents that improves the solubility of the overall molecule in aqueous media. In some cases, at least two of $R^4$, $R^5$, $R^6$, $R^9$, $R^{10}$, and $R^{11}$ comprise water soluble groups. In other embodiments, three or more comprise water soluble groups. Water soluble groups include, but are not limited to, a carboxylate (—$CO_2^-$) group, a sulfonate (—$SO_3^-$) group, a sulfonyl (—$SO_2^-$) group, a sulfate (—$SO_4^{-2}$) group, a hydroxyl (—OH) group, a phosphate (—$OPO_3^{-2}$) group, a phosphonate (—$PO_3^{-2}$) group, an amine (—$NH_2$) group and an optionally substituted quaternized nitrogen with each having an optional counter ion.

Suitable counter ions include, but are not limited to, sodium, potassium, calcium, ammonium, organic amino salt, or magnesium salt, or a similar salt. Preferably, the counter ion is a biologically acceptable counter ion.

In some embodiments, the nitrogen atom(s) to which $R^4$, $R^5$, $R^6$, $R^9$, $R^{10}$, and $R^{11}$ are attached can be trivalent or tetravalent.

In some embodiments $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each hydrogen.

In some embodiments, $X^2$ and $X^3$ are each independently selected from $C_1$-$C_{10}$ alkylene optionally interrupted by an atom. In some embodiments, the nitrogens appended to $X^2$ and/or $X^3$ can be optionally quaternized.

In some embodiments, the phthalocyanine dye is of Formula III:

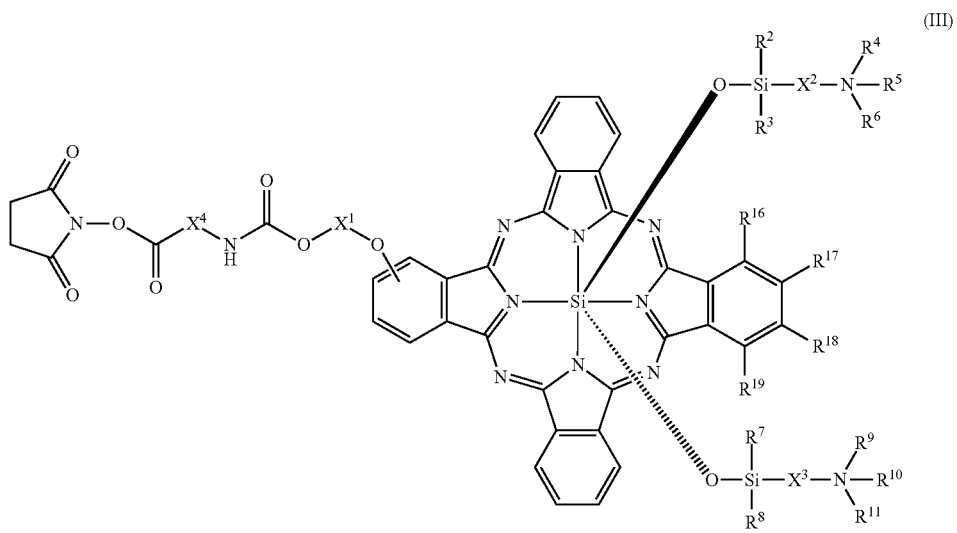

(III)

wherein $X^1$ and $X^4$ are each independently a $C_1$-$C_{10}$ alkylene optionally interrupted by a heteroatom; and $R^2$, $R^3$, $R^4$, $R^5$, $R^6$, $R^7$, $R^8$, $R^9$, $R^{10}$, $R^{11}$, $R^{16}$, $R^{17}$, $R^{18}$, $R^{19}$, $X^2$, and $X^3$ are as defined herein.

In some embodiments, the reactive group is an NHS ester. In some embodiments, the reactivity of the NHS ester can be adjusted by varying the length of the alkylene group of $X^4$, between the NHS ester and carbamate functionality. In some embodiments, the length of the alkylene group of $X^4$ between the NHS ester and the carbamate functionality is inversely proportional to the NHS ester reactivity. In some embodiments, $X^4$ is $C_5$-alkylene. In other embodiments, $X^4$ is $C_3$-alkylene. In some embodiments, $X^1$ is $C_6$-alkylene. In other embodiments, $X^1$ is $C_3$-alkylene.

In some embodiments, the phthalocyanine dye has an overall electronic charge of zero. This charge neutrality can in certain instances by obtained with one or more optional counterions, or quaternized nitrogens.

In some embodiments, the phthalocyanine dye has sufficient solubility in aqueous solutions that once it is attached to a soluble targeting molecule, the targeting molecule retains its solubility. In some embodiments, the dye also is soluble in organic media (e.g., DMSO or DMF).

In some embodiments, the phthalocyanine dye has a maximum light absorption in the near infrared (NIR range). In some embodiments, the phthalocyanine dye has a maximum light absorption wavelength between 600 nm and 850 nm, such as between 680 nm and 850 nm, for example at approximately 690 nm±50 nm or 690±20 nm. In some embodiments, the phthalocyanine dye can be excited efficiently by commercially available laser diodes that emit light at these wavelengths.

In some embodiments, the phthalocyanine dye containing the reactive group is IR700 NHS ester, such as IRDye 700DX NHS ester (LiCor 929-70010, 929-70011). Thus, in some embodiments, the dye is a compound having the following formula:

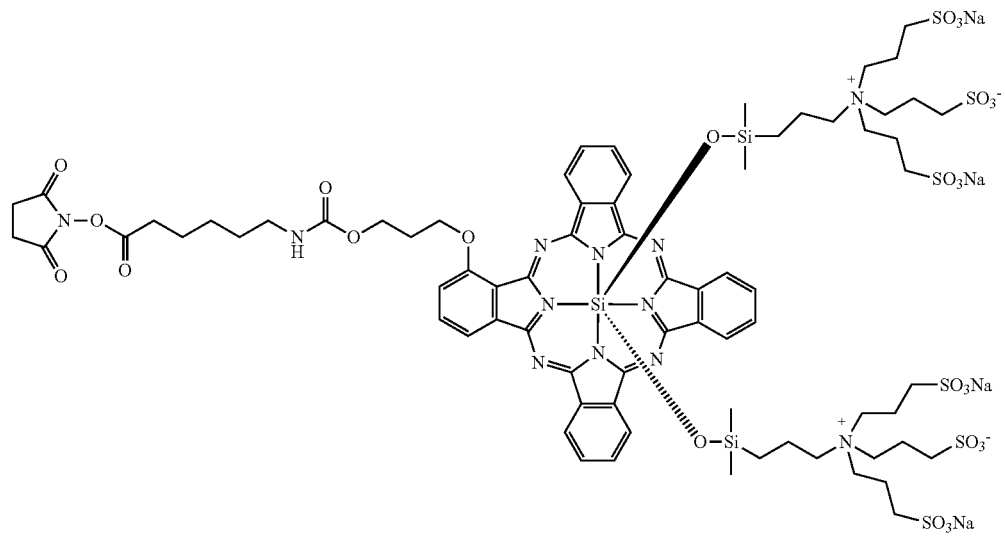

Chemical Formula: $C_{74}H_{96}N_{12}Na_4O_{27}S_6Si_3$
Exact Mass: 1952.37
Molecular Weight: 1954.22
IRDye 700DX NHS Ester For purposes herein, the term "IR700," "IRDye 700DX," or variations thereof refer to the above formula when the dye is conjugated to a targeting molecule, e.g. via a reactive group. Generally, IR700 has several favorable chemical properties. Amino-reactive IR700 is a relatively hydrophilic dye and can be covalently conjugated with an antibody using the NHS ester of IR700. Typically, IR700 also has more than 5-fold higher extinction coefficient ($2.1 \times 10^5$ $M^{-1}cm^{-1}$ at the absorption maximum of 689 nm), than conventional photosensitizers such as the hematoporphyrin derivative Photofrin® ($1.2 \times 10^3$ $M^{-1}cm^{-1}$ at 630 nm), meta-tetrahydroxyphenylchlorin; Foscan® ($2.2 \times 10^4$ $M^{-1}cm^{-1}$ at 652 nm), and mono-L-aspartylchlorin e6; NPe6/Laserphyrin® ($4.0 \times 10^4$ $M^{-1}cm^{-1}$ at 654 nm).

The phthalocyanine dyes described herein can be made with commercially available starting material. The core structure is synthesized by condensation of two or more different diiminoisoindolines. Synthetic strategies using different dinitriles or diiminoisoindolines can lead to various degrees of substitution of the phthalocyanine and/or distribution of regioisomers. Exemplary synthetic schemes for generating the dyes are described in U.S. Pat. No. 7,005,518.

In some embodiments, the phthalocyanine dye is conjugated to a targeting molecule via a reactive group of the dye molecule. In some embodiments, the targeting molecule is one that is able to target the conjugate to a cell or pathogen, for example, by binding to a cell surface molecule (e.g. cell surface receptor) on the cell or pathogen. In some embodiments, the targeting molecule, e.g., a macromolecule, can selectively bind to a desired cell type, cells with a particular phenotype, or cells displaying one or more cell surface markers or antigens. In some cases, the targeting molecule binds to a cell that is a cancer cell, a tumor cell, an inflammatory cell, an immune cell, a neuron, a stem cell, a proliferating cell, or a cell in a hyperplasia. In some cases, the targeting molecule binds to a pathogen or a pathogen infected cell. In some embodiments, the cell is an inflammatory cell, such a leukocyte, for example, a neutrophil, an eosinophil, a basophil, a lymphocyte, or a monocyte. In some embodiments, the cell is an immune cell, such as a T cell, a B cell, a Natural Killer (NK) cell, a dendritic cell, a macrophage or a neutrophil. In some embodiments, the cell is a neuron that is a peripheral nervous system neuron or a central nervous system neuron, such as a nociceptor, for example, thermal nociceptors, mechanical nociceptors, chemical nociceptors or polymodal nociceptors. In some cases, the targeting molecule binds to a pathogen or a pathogenic cell, such as a virus, bacterium, fungus, biofilm or other prokaryotic cell system. In some embodiments, the targeting molecule hinds to a pathogen that is a gram-negative or gram-positive bacterium.

In some embodiments, the targeting molecule (e.g., antibody) of the phthalocyanine dye conjugate bind to a protein on the surface of a cell or cells present in a microenvironment of a lesion that is associated with or present as a result of a disease or condition. For example, in some embodiments, the conjugate binds to a protein on the surface of a cell or cells present in a tumor microenvironment associated with or present in a tumor. In some embodiments, the conjugate binds to a protein present in the extracellular matrix in the microenvironment of the tumor.

As used herein, a "cell present in the microenvironment of a lesion" refers to any cell present in the cellular environment associated with a lesion, a disease or a disorder, such as any cell present in or immediately adjacent to a tumor, such as cells present in a tumor microenvironment, or the extracellular matrix in the tumor microenvironment.

As used herein, a "cell present in a tumor microenvironment" refers to any cell present in the cellular environment in which the tumor exists, such as any cell present in or immediately adjacent to the tumor, including the proliferating tumor cells (e.g., cancer cells), the tumor stroma, blood vessels, infiltrating inflammatory cells (e.g., immune cells) and a variety of associated tissue cells (e.g., fibroblasts). Thus, it is understood that reference to the tumor refers not only to the tumor cells, which can include malignant or cancer cells, but also to other cells present in the tumor microenvironment that regulate the growth of the tumor, including immune cells. In some cases, immune cells present in a tumor microenvironment can include T lymphocytes, including regulatory T lymphocytes (Treg), dendritic cells, natural killer (NK) cells, B cells, macrophages and other immune cells (Whiteside (2008) Oncogene, 27:5904-5912). It is recognized that, in some aspects, many non-cancerous cells present in and around the tumor can regulate the proliferation, angiogenesis, invasion and/or metastasis of tumor cells, thereby promoting the growth of the tumor. Thus, in some cases, targeting such non-cancerous cells, such as immune cells (e.g., T cells, such as regulatory T cells), present in a tumor can be an effective therapy for killing a tumor by PIT.

Generally, cancerous cells contain tumor-specific antigens that should be recognized by the immune system. Typically, in an active immune system, immune cells, such as cytotoxic T cells, attack and eradicate these cancerous cells. Under normal physiological conditions, the T cell-mediated immune response is initiated by antigen recognition by the T cell receptor (TCR) and is regulated by a balance of co-stimulatory and inhibitory signals (e.g., immune checkpoint proteins). In particular, CD4+ and CD8+ T cells expressing a TCR can become activated upon recognition of antigenic peptides presented on antigen-presenting cells on major histocompatibility complex (MHC) class I or class II molecules, respectively. In some aspects, activated CD8+ cells, or cytotoxic T cells, can kill tumor cells expressing the antigen, which can be helped by the presence of CD4+ T cells.

In the case of tumors, however, the tumor microenvironment has mechanisms to suppress the immune system, thereby evading immune recognition and preventing or reducing killing of tumor cells. For example, in some cases, immune checkpoint proteins can be dysregulated in tumors, thereby resulting in a suppression of the immune response in the tumor microenvironment as a mechanism of evading the immune system. In some cases, tumor-infiltrating lymphocytes can include Tregs (e.g., CD4+CD25+ T cells), which are cells that are capable of suppressing proliferation of other T cells in the microenvironment (Whiteside, T L (2008) Oncogene, 27:5904-5912). In some cases, other mechanisms can act to inhibit access of immune cells to tumor antigens, thereby also contributing to the tumors ability to evade the immune system.

In some embodiments, the targeting molecule is a molecule that binds to a cell surface protein on a tumor or cancer cell. In some embodiments, the targeting molecule binds to a cell surface protein on the surface of a T lymphocyte, such as a Treg, a dendritic cell, a natural killer (NK) cell, a B cell, a macrophage or other immune cell that is present in a tumor microenvironment. For example, the tumor or cancer cell can be one associated with a cancer located at the head and neck, breast, liver, colon, ovary, prostate, pancreas, brain, cervix, bone, skin, eye, bladder, stomach, esophagus, peritoneum, or lung. In some embodiments, the targeting molecule binds a cell is a cancer stem cell or a circulating tumor cell.

Exemplary of targeting molecules, such as macromolecules, including those that target a tumor or cancer, include, but are not limited to, any as described in published international PCT appl. Nos. WO2014120974, WO2014176284, WO2015042325, U.S. Pat. No. 8,524,239 or U.S. patent publication No. US20140120119.

Exemplary targeting molecules include, but are not limited to, a protein, a glycoprotein, an antibody, an antibody fragment, an antigen, an antigen binding fragment, a peptide, a polypeptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, or PNA.

In some embodiments, the targeting molecule is an amino acid, peptide, protein, tyramine, polysaccharide, ion-complexing moiety, nucleoside, nucleotide, oligonucleotide, psoralen, drug, hormone, lipid, lipid assembly, polymer, polymeric microparticle, a biological cell, or virus. In some embodiments, the targeting molecule is an antigen, steroid, vitamin, drug, metabolite, toxin, environmental pollutant, nucleic acid polymer, carbohydrate, lipid, or glass, plastic or other non-biological polymer. In some embodiments, the targeting molecules is a cell, cellular system, cellular fragment, or subcellular particle, e.g. a virus particle, bacterial particle, virus component, biological cell (such as animal cell, plant cell, bacterium, yeast, or protist), or cellular component. In some embodiments, reactive dyes may label functional groups at the cell surface, in cell membranes, organelles, or cytoplasm.

In some embodiments, the targeting molecule can selectively bind to a desired cell type, cells with a particular phenotype, or cells displaying one or more cell surface markers or antigens. In some embodiments, the targeting molecule is a tumor targeting molecule. In some embodiments, the targeting molecule can bind to tumor or cancer cells. In some embodiments, the targeting molecule targets or binds to a marker or antigen on a cell surface, for example, a cell surface of a tumor cell.

In some embodiments, the targeting molecule targets or binds to an antigen, such as any structural substance that serves as a target capable of being bound by the molecule. In some embodiments, the antigen is or is comprised as part of a cell surface molecule, such as a protein, e.g., a receptor, that is expressed on a cell surface. In some embodiments, for example, the antigen is or is comprised as part of a molecule expressed on the surface of a cell present in a tumor, including any cell present in the tumor microenvironment. Examples of cell surface molecules to which a targeting molecule can bind, include, but are not limited to, an antigen, peptides, lipids, polysaccharides, carbohydrate, or nucleic acids containing antigenic determinants, such as those recognized by an immune cell. In some examples, an antigen includes a tumor-specific peptide (such as one found on the surface of a cancer cell) or immunogenic fragment thereof.

In some embodiments, the targeting molecule is a binding partner, such as a ligand, capable of binding to a cell surface molecule, such as a cell surface protein, e.g., a cell surface receptor. In some embodiments, the targeting molecule is selected from adrenocorticotropic hormone (ACTH), angiotensin II, atrial natriuretic factor (ANF), bombesin, bradykinin, brain derived neurotropihic factor (BDNF), bone morphogenetic protein 2 (BMP-2), bone morphogenetic protein 6 (BMP-6), bone morphogenetic protein 7 (BMP-7), calcitonin, cardiotrophin 1 (BMP-2), CD22, CD40, cholecystokinin (CCK), ciliary neurotrophic factor (CNTF), CCL1-CCL28, CXCL1-CXCL17, XCL1, XCL2, CX3CL1, cripto 1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-a), interferon beta (IFN-b), interferon gamma (IFNg), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 3G (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMA5A), semaphorin 5B (SEMA5B), semaphorin 6A (SEMA6A), semaphorin 6B (SEMA6B), semaphorin 6D (SEMA6D), semaphorin 7A (SEMA7A), SLIT1, SLIT2, SLIT3, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-α), transforming growth factor beta (TGF-b), tumor necrosis factor alpha (TNF-α), thrombin, vasoactive intestinal peptide (VIP), Wnt1, Wnt2, Wnt2b/13, Wnt3, Wnt3a, Wnt4, Wnt5a, Wnt5b, Wnt6, Wnt7a, Wnt7b, Wnt7e, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog, or is a binding fragment thereof that is capable of binding to its cognate cell surface molecule, such as a cell surface protein, e.g., cell surface receptor.

In some embodiments, the targeting molecule can be an immune modulating agent, which can bind to a cell surface molecule or protein on an immune cell to either suppress or activate the body's immune response. In some embodiments, binding of the immune modulating agent to the cell surface molecule or protein can stimulate an immune response to a tumor and/or a pathogen, such as by inhibiting immune suppression or by enhancing immunostimulation. In some embodiments, the cell surface molecule or protein can be CD25, PD-1 (CD279), PD-L1 (CD274, B7-H1), PD-L2 (CD273, B7-DC), CTLA-4, LAGS (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GALS, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR or VEGF.

In some embodiments, the cell surface molecule can be a cell membrane phospholipid, a prokaryotic peptidoglycan, a bacterial cell envelop protein, a viral capsid protein, ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, an interleukin receptor (e.g. IL-2R, IL11-R, IL-13R), ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/ HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g. P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g. TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, or Y5.

In some embodiments, the cell surface molecule can be HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, or SK-lantigen.

In some embodiments, the targeting molecule is an antibody or antibody fragment that specifically binds to an antigen, such as a cell surface molecule on a tumor cell. Included among such antibodies are antibodies or antigen-binding antibody fragments capable of binding to a cell surface molecule, such as a cell surface protein, e.g., cell surface receptor, described herein. In some cases, the antibody can bind to an antigen of a protein expressed on a cell in a tumor, including a tumor-specific protein.

In some embodiments, the targeting molecule binds to an antigen or protein directly or indirectly. For example, in some embodiments, the targeting molecule is a second binding molecule that binds to a first binding molecule which is capable of binding to the antigen or protein. For example, the targeting molecule is a secondary antibody, which binds to a first binding molecule, e.g., a primary antibody, capable of binding the protein or antigen, e.g., a cell surface protein or a cell surface receptor. Thus, in some embodiments, the dye is conjugated to a secondary antibody.

An "antibody" is a polypeptide ligand comprising at least a light chain or heavy chain immunoglobulin variable region that specifically recognizes and binds an epitope of an antigen, such as a tumor-specific protein. Generally, antibodies are composed of a heavy and a light chain, each of which has a variable region, termed the variable heavy ($V_H$) region and the variable light ($V_L$) region. Together, the $V_H$ region and the $V_L$ region are responsible for binding antigen recognized by the antibody.

Antibodies include intact immunoglobulins and fragments of antibodies that exhibit antigen-binding, such as Fab fragments, Fab' fragments, F(ab)'$_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies, for example, humanized murine antibodies, and heteroconjugate antibodies, such as bispecific antibodies. See also, *Pierce Catalog and Handbook*, 1994-1995 (Pierce Chemical Co., Rockford, Ill.); Kuby, J. *Immunology*, 3$^{rd}$ Ed., W.H. Freeman & Co., New York, 1997

Typically, a naturally occurring immunoglobulin has heavy (H) chains and light (L) chains interconnected by disulfide bonds. There are two types of light chain, lambda (λ) and kappa (k). There are five main heavy chain classes, or isotypes, which determine the functional activity of an antibody molecule: IgM, IgD, IgG, IgA and IgE.

Each heavy and light chain contains a constant region and a variable region, also known as "domains." In combination, the heavy and the light chain variable regions generally specifically bind the antigen. Light and heavy chain variable regions may contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are typically responsible for binding to an epitope of an antigen. The CDRs of each chain are typically referred to as CDR1, CDR2, and CDR3, numbered sequentially starting from the N-terminus, and are also generally identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities, such as different combining sites for different antigens, have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "$V_L$" refer to the variable region of an immunoglobulin light chain, including that of an Fv, scFv, dsFv or Fab.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. Other antibody fragments or multispecific antibodies formed from antibody fragments include a multivalent scFv, a bispecific scFv or an scFv-CH3 dimer. Antibody fragments can be made by various techniques, including but not limited to proteolytic digestion of an intact antibody as well as production by recombinant host cells.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs, which generally confer antigen binding, from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In some embodiments, the CDRs are from the donor immunoglobulin in a humanized immunoglobulin. Constant regions need not be present, but if they are, they may be substantially identical to human immunoglobulin constant regions, such as at least about 85-90%, such as about 95% or more identical. Hence, parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and CDRs from a human immunoglobulin. In some embodiments, the framework and the CDRs are from the same originating human heavy and/or light chain amino acid sequence. However, frameworks from one human antibody can be engineered to include CDRs from a different human antibody. Parts of a human immunoglobulin may be substantially identical to corresponding parts of natural human immunoglobulin sequences.

"Specifically binds" refers to the ability of a molecule, such as an antibody or antigen-binding fragment, to specifically bind an antigen, such as a tumor-specific antigen, relative to binding to unrelated proteins, such as non-tumor proteins, for example β-actin. In some embodiments, a molecule, such as an antibody or fragment, including a molecule, such as an antibody or fragment, attached to a phthalocyanine dye molecule, specifically binds to a target, such as a cell surface protein, with a binding constant that is at least $10^3$ M$^{-1}$ greater, $10^4$ M$^{-1}$ greater or $10^5$ M$^{-1}$ greater than a binding constant for other molecules in a sample or subject. In some embodiments, a molecule, such as an antibody or fragments thereof, has an equilibrium association constant ($K_A$) of greater than or equal to about $10^6$ M$^{-1}$, greater than or equal to about $10^7$ M, greater than or equal to about $10^8$ M$^{-1}$, or greater than or equal to about $10^9$ M$^{-1}$, $10^{10}$ M$^{-1}$, $10^{11}$ M$^{-1}$ or $10^{12}$ M$^{-1}$. Antibodies also can be characterized by an equilibrium dissociation constant ($K_D$) of $10^{-6}$ M, $10^{-7}$ M, $10^{-8}$ M, $10^{-10}$ M, $10^{-11}$ M or $10^{-12}$ M or lower. In some embodiments, an equilibrium dissociation constant ($K_D$) can be 1 nM or less. Affinity constants, such as $K_D$ or $K_A$, can be estimated empirically or affinities can be determined comparatively, e.g. by comparing the affinity of one antibody and another antibody for a particular antigen. For example, such affinities can be readily determined using techniques known in the art, such as, for example, by competitive ELISA (enzyme-linked immunosorbent assay) or using a surface-plasmon resonance device, such as the Biacore T100 (available from Biacore, Inc., Piscataway, N.J), a radioimmunoassay using radiolabeled target antigen, or by another method known to the skilled artisan.

In some embodiments, the phthalocyanine dye (e.g., IR700) is conjugated to an antibody or an antigen-binding antibody fragment. For example, in some aspects, the phthalocyanine dye-targeting molecule conjugate is an IR700-antibody conjugate. Exemplary antibodies to which the phthalocyanine dye (e.g., IR700) can be conjugated to include, but are not limited to, cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A, Pidilizumab (CT-011), MK-3475, BMS-936559, MPDL3280A, tremelimumab, IMP321, BMS-986016, LAG525, urelumab, PF-05082566, TRX518, MK-4166, dacetuzumab, lucatumumab, SEQ-CD40, CP-870, CP-893, MEDI6469, MEDI6383, MOXR0916, AMP-224, MSB0010718C, MEDI4736, PDR001, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or an antibody-binding fragment thereof.

In some embodiments, the targeting molecule is a tissue-specific homing peptide. For example, in some embodiments, the homing polypeptide can contain the sequence of amino acids set forth in any of SEQ ID NOS: 1-52. In some embodiments, the targeting molecule is an RGD polypeptide, such as an iRGD polypeptide, a Lyp-1 polypeptide, a cripto-1 binding polypeptide, a somatostatin receptor binding polypeptide, or a prohibitin binding polypeptide, a NGR polypeptide, or an iNGR polypeptide.

In some embodiments, the targeting molecule is an activatable cell penetrating peptide (ACPP) comprised of a polycationic cell penetrating peptide (CPP) connected via a cleavable linker to a neutralizing polyanion. For example, in some embodiments, the ACPP comprises the structure: A-X1-B—, wherein B is a peptide portion of about 5 to about 20 basic amino acid residues, which is suitable for cellular uptake; A is a peptide portion of about 2 to about 20 acidic amino acid residues, which when linked with portion B is effective to inhibit or prevent cellular uptake of portion B; X1 is a cleavable linker of about 2 to about 100 atoms; and one or more of L-Y is linked to the C-terminus of peptide portion B.

In some embodiments, the targeting molecule is a viral particle, such as a virus-like particle, a viral-like nanoparticle, or a viral capsid. In some embodiments, the targeting molecule is a viral-like nanoparticle. In some embodiments, the viral-like nanoparticle is assembled from L1 capsid proteins. In some embodiments, the viral-like nanoparticle is assembled from a combination of L1 and L2 capsid proteins. In some embodiments, the targeting molecule and bind to and infect cells. In some embodiments, the targeting molecule is one described in WO2015042325.

In some embodiments, a virus-like particle (VLP) refers to an organized capsid-like structure, such as roughly spherical or cylindrical in shape, that comprises self-assembling ordered arrays of L1 or L1 and L2 capsomers and does not include a viral genome. In some embodiments, virus-like particles are morphologically and antigenically similar to authentic virions, but they lack viral genetic material, such as viral nucleic acid, rendering the particles noninfectious. A VLP may be used to deliver to a recipient cell an agent, such as prophylactic agent, therapeutic agent or diagnostic agent, or an enclosed circular or linear DNA or RNA molecule.

In some embodiments, VLPs may have modified immunogenicity and/or antigenicity with respect to the wild type VLPs. The VLPs may, for example, be assembled from capsomers having a variant capsid protein with modified immunogenicity and/or antigenicity. In some embodiments, a variant capsid protein with modified immunogenicity and/or antigenicity is one that is modified naturally or synthetically, such as mutated, substituted, deleted, pegylated or inserted, at an amino acid to reduce or prevent recognition of the capsid protein by pre-existing, such as endogenous, viral serotype-specific antibodies. A variant capsid protein may be a human papillomavirus (HPV) L1 variant, a non-human papillomavirus L1 variant, or a papillomavirus L1 variant based on a combination of amino acids from different HPV serotypes.

In some embodiments, a VLP is a papilloma virus VLP. The VLP may be a human papilloma virus VLP, such as derived from a virus that can infect human, while in other embodiments, the VLP may be a non-human papilloma virus VLP. Examples of non-human VLPs include those derived from, without limitation, bovine papilloma viruses, murine papilloma viruses, cotton-rabbit papilloma viruses and macaque or rhesus papilloma virus particles. In some embodiments, the VLPs are bovine papilloma virus viral-like nanoparticles, such as type 1 viral-like nanoparticles, such as assembled from BPV L1 capsid proteins or a combination of BPV L1 and BPV L2 capsid proteins.

In some embodiments, a capsid protein refers to a protein monomer, several of which form a capsomer oligomer. In some embodiments, a capsomer refers to the basic oligomeric structural unit of a viral capsid, which is an outer covering of protein that protects the genetic material of a virus. Capsid proteins may include in some embodiments, papillomavirus L1 major capsid proteins and papillomavirus L2 minor capsid proteins. In some embodiments, the VLPs contain only L1 capsid proteins, while in other embodiments, the VLPs contain a mixture, or combination, of L1 and L2 capsid proteins.

In some embodiments, the percentage of L1 capsid proteins in a virus-like particle is greater than the percentage of L2 capsid proteins in the virus-like particle. For example, in some embodiments, the percentage of L1 capsid proteins in a virus-like particle is 80% to 100% of the total number of capsid proteins in the virus-like particle. In some embodiments, the percentage of L1 capsid proteins in a virus-like particle is at least or is about 80%, 85%, 90%, 91%, 92%, 93%, 94%, 95%, 96%, 97%, 98%, 99% or 100%. In some embodiments, the percentage of L2 capsid proteins in a virus-like particle is 1% to 25% of the total number of capsid proteins in the virus-like particle. For example, in some embodiments, the percentage of L2 capsid proteins in a virus-like particle is at least or about 1%, 2%, 3%, 4%, 5%, 6%, 7%, 8%, 9%, 10%, 11%, 12%, 13%, 14%, 15%, 16%, 17%, 18%, 19% or 20%.

In some embodiments, a virus-like particle contains 12 to 72 L2 proteins. In some embodiments, a virus-like particle contains 360 L1 proteins and 12 to 72 L2 proteins. In some embodiments, capsid proteins assemble into viral-like nanoparticles having a diameter of 20 to 60 nm. For example, capsid proteins may assemble into viral-like nanoparticles having a diameter of at least or about 20, 25, 30, 35, 40, 45, 50, 55 or 60 nm.

In some embodiments, the targeting molecule is a DARPin (designed ankyrin repeat protein). Typically, DARPins are derived from natural ankyrin repeat proteins and bind to proteins including e.g., human receptors, cytokines, kinases, human proteases, viruses and membrane proteins (Molecular Partners AG Zurich Switzerland; see Chapter 5. "Designed Ankyrin Repeat Proteins (DARPins): From Research to Therapy", Methods in Enzymology, vol 503: 101˜134 (2012); and "Efficient Selection of DARPins with Sub-nanomolar Affinities using SRP Phage Display", J. Mol. Biol. (2008) 382, 1211-1227, the entire disclosures of which are hereby incorporated by reference. In some embodiments, the DARPin is an antibody mimetic protein having high specificity and high binding affinity to a target protein, which is prepared via genetic engineering. In some embodiments, DARPins have a structure comprising at least 2 ankyrin repeat motifs, for example, comprising at least 3, 4 or 5 ankyrin repeat motifs. The DARPins can have any suitable molecular weight depending on the number of repeat motifs. For example, the DARPins including 3, 4 or 5 ankyrin repeat motifs may have a molecular weight of about 10 kDa, about 14 kDa, or about 18 kDa, respectively.

In some embodiments, the DARPin includes a core part that provides structure and a target binding portion that resides outside of the core and binds to a target. In some embodiments, the structural core includes a conserved amino acid sequence and the target binding portion includes an amino acid sequence that differs depending on the target.

In some embodiments, the conjugate contains a number of dye residues per targeting molecule that is from or from about 1 to about 1000, such as from or from about 1 to about 100, from or from about 1 to about 50, from or from about 1 to about 25, from or from about 1 to about 10, from or from about 1 to about 5. In some embodiments, the ratio of dye molecules to targeting molecule is or is about 2:1, 3:1, 4:1, 5:1, 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1 or 1000:1, or is between or between about any two of such values. In some embodiments, the targeting molecule may contain up to 2, 3, 4, 5, 6, 7, 8, 9, 10, 15, 20, 50, 75, 100, 150, 200, 250, 300, 350, 400, 450, 500, 550, 600, 650, 700, 750, 800, 850, 900, 950 or 1000 dye molecules. In some embodiments, the targeting molecule may contain more than 1000 dye molecules or less than 10 dye molecules.

In some embodiments, such as when the targeting molecule is a polypeptide, such as an antibody or antigen-binding fragment, the number of dye molecule per targeting molecule can be from or from about 2 to 5, such as from or from about 2 to 4, for example about 3 or 3. In some embodiments, for example where the targeting molecule is a nanoparticle, such as a virus-like particle (VLP), the number of dye molecules to targeting molecule can be from or from about 10 to 1000, 10 to 500, 50 to 500, or 50 to 1000. Thus, in some embodiments, the targeting molecule may contain about 10 to about 1000 dye molecules.

In some embodiments, such as where the targeting molecule is a VLP, more than one dye molecule may be conjugated to a single capsid protein. For example, a single capsid protein, such as L1 or L2 capsid protein, may be conjugated to 1 to 5, such as 1, 2, 3, 4 or 5, dye molecules. Thus, more than one amino acid of a capsid protein may be conjugated to a dye molecule. In some embodiments, a single capsid protein may be conjugated to 1 to 2, 1 to 3, or 2 to 3 dye molecules. Thus, a dye molecule may be conjugated to 1, 2, 3, 4 or 5 different amino acids, such as lysine, arginine and/or histidine, or other amino acid, of a single capsid protein.

B. Light-Protected Preparation of Dye-Targeting Molecule Conjugate

In some embodiments, provided is a method or process for preparing a phthalocyanine dye-targeting molecule conjugate, such as an IR700-targeting molecule (e.g. IR700-antibody) conjugate, under light-protected conditions. In some embodiments, the method includes 1) preparing or providing a phthalocyanine dye and a targeting molecule; 2) contacting the targeting molecule and phthalocyanine dye under conditions to produce or generate the conjugate with minimal exposure of the dye; and 3) formulating, purifying and/or isolating the conjugate to produce a composition containing the drug substance, where one or more of the steps, such as in some cases all of the steps, are performed with minimal exposure of the dye or the conjugate containing the dye to environmental light.

In some embodiments, prior to, during, and following the preparation of the dye and/or conjugate are not exposed to any environmental light or are not exposed to light with an intensity greater than 700 lux, greater than 600 lux, greater than 500 lux, greater than 400 lux, greater than 300 lux, greater than 200 lux, or greater than 100 lux. In some embodiments, the dye and/or conjugate is not exposed to light with an intensity of greater than 700 lux for more than 20 minutes, for more than 10 minutes, or for more than 5 minutes. In some embodiments, the dye and/or conjugate is not exposed to light with an intensity of greater than 200 lux for more than 20 minutes, for more than 10 minutes, or for more than 5 minutes.

In some embodiments, prior to, during, or following one or more steps of the method or all steps of the method, the dye and/or conjugate are protected from environmental light, such as light in the near infrared (IR) range. In some embodiments, the only light to which the dye and conjugate are exposed prior to, during, and following the preparation of the conjugate has a wavelength that is not absorbed by the dye or is not substantially absorbed by the dye. In some embodiments, the only light to which the dye and conjugate are exposed prior to, during, and following the preparation of the drug substance is green light. In some embodiments, the only light to which the dye and conjugate are exposed prior to, during, and following the preparation of the drug substance has a wavelength in a range from or from about 400 nm to 650 nm, such as 400 nm to 600 nm, 425 nm to 575 nm or 450 nm to 550 nm.

In some embodiments, the only light to which the dye and/or conjugate are exposed during one or more or all of the steps of the method has a wavelength that is not absorbed by the dye or is not substantially absorbed by the dye and an intensity of less than 700 lux, less than 600 lux, less than 500 lux, less than 400 lux, less than 300 lux, less than 200 lux, or less than 100 lux. In some embodiments, the only light to which the dye and/or conjugate are exposed during one or more or all of the steps of the method is green light that has an intensity of less than 700 lux, less than 600 lux, less than 500 lux, less than 400 lux, less than 300 lux, less than 200 lux, or less than 100 lux. In some embodiments, the only light to which the dye and conjugate are exposed during one or more or all of the steps of the method has a wavelength in a range from or from about 400 nm to 650 nm, such as 400 nm to 600 nm, 425 nm to 575 nm or 450 nm to 550 nm and has an intensity of less than 700 lux, less than 600 lux, less than 500 lux, less than 400 lux, less than 300 lux, less than 200 lux, or less than 100 lux.

In some embodiments, prior to, during, and following the preparation, production, formulation and/or packaging of the dye and/or conjugate are not exposed to any environmental light or have total light exposure of no more than 5000 lux hours, no more than 2500 lux hours, no more than 1000 lux hours, no more than 500 lux hours, no more than 250 lux hours, no more than 100 lux hours or no more than 80 lux hours. In some embodiments, in the methods provided herein, the dye and/or conjugate are not exposed to any environmental light or have total light exposure of no more than 5000 lux hours, no more than 2500 lux hours, no more than 1000 lux hours, no more than 500 lux hours, no more than 250 lux hours, no more than 100 lux hours or no more than 80 lux hours, during performance of the entire method. For example, the total light exposure of the dye and/or conjugate during the entire method or prior to, during, and following the preparation, production, formulation and/or packaging of the dye and/or conjugate is no more than 500 lux hours, no more than 250 lux hours, no more than 100 lux hours, no more than 50 lux hours or no more than 25 lux hours. Total light exposure is determined by multiplying intensity of illumination (lux) by time of exposure (hours).

In some embodiments, during one or more or all of the steps of the methods provided herein, the total exposure of the dye and/or conjugate to any light is for no more than 5000 lux hours, no more than 2500 lux hours, no more than 1000 lux hours, no more than 500 lux hours, no more than 250 lux hours, no more than 100 lux hours or no more than 80 lux hours. For example, the total light exposure of the dye and/or conjugate during the packaging step is no more than 500 lux hours, no more than 250 lux hours, no more than 100 lux hours, no more than 50 lux hours or no more than 25 lux hours.

In some embodiments, the dye and/or conjugate are protected from light during one or more or all of the steps of the method by performing procedures of the method using one or more containers that protect contents from light, or certain wavelengths or intensities of light. For example, in some embodiments, one, two or three or more light-protected container are used in the methods. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 250 nm and 800 nm, such as between or between about 250 nm and 450 nm, 400 nm and 800 nm, 450 nm and 650 nm, 500 nm and 725 nm, 600 nm and 720 nm or 650 nm and 725 nm, or does not transmit an intensity of light greater than 700 lux, 600 lux, 500 lux, 400 lux, 300 lux, 200 lux, or 100 lux. In some embodiments, the dye and/or conjugate is prepared in a translucent or opaque container. In some embodiments, the container is green, blue or amber. In some embodiments, the container is covered with an opaque substance, such as a foil, such as aluminum foil. In some embodiments, the container is covered with material with light transmission of less than 50%, less than 40%, less than 30%, less than 20%, less than 10% or less than 5%. In some embodiments, the container is a vial, a tube, a syringe, a bag, a pouch, and/or a box.

In some embodiments, the methods of manufacturing a conjugate include a step of preparing or producing the conjugate. In some embodiments, such methods include providing a phthalocyanine dye. In some embodiments, the phthalocyanine dye is provided in an aqueous form, such as an aqueous solution. In some embodiments, the dye is provided in a lyophilized form, such as a lyophilized powder, and is reconstituted or dissolved into a solvent to form an aqueous solution. For example, in some embodiments, the phthalocyanine dye containing the reactive group, e.g., IR 700 NHS ester, is dissolved in a solvent. In some embodiments, the methods include a step of dissolving the phthalocyanine dye in a solvent, such as prior to conjugation of the dye to a targeting molecule. In some embodiments, the solvent is an organic solvent, such as dimethyl sulfoxide (DMSO) or DMF. In some examples, the solvent is a water-based solvent. In some embodiments, the dye is dissolved in solvent to a concentration in a range from or from about 0.1 mg/mL to 100 mg/ml, 1 mg/mL to 50 mg/mL, 1 mg/mL to 15 mg/mL, or is dissolved in solvent to a concentration of or of about 10 mg/mL.

In some embodiments, during the steps of preparing the dye for use in the method, the phthalocyanine dye, such as IR700 NHS ester, is protected from exposure to environmental light. In some embodiments, prior to, during, and following preparation of the phthalocyanine dye, the dye is not exposed to light, such as environmental light, or is only exposed to light with a wavelength in a range from or from about 400 nm to 650 nm, such as from or from about 425 nm to 475 nm. In some embodiments, the phthalocyanine dye is not exposed to light with an intensity of greater than 700 lux, or is not exposed to light with an intensity of greater than 700 lux for more than 10 minutes, or for more than 5 minutes. In some embodiments, the phthalocyanine dye is not exposed to light with an intensity of greater than 200 lux, or is not exposed to light with an intensity of greater than 200 lux for more than 10 minutes, or for more than 5 minutes.

In some embodiments, the steps of preparing or producing a conjugate include providing a targeting molecule (e.g. antibody) for conjugation with the phthalocyanine dye, such as IR700. In some embodiments, the targeting molecule is prepared prior to conjugation with the phthalocyanine dye. In some embodiments, preparing the targeting molecule includes concentrating or diluting the targeting molecule to a particular amount or concentration prior to the conjugation reaction. In some embodiments, preparing the targeting molecule includes exchanging the targeting molecule into a buffer, such as a buffer that is compatible or suitable for the conjugation reaction. In some embodiments, preparing the targeting molecules includes adjusting the pH to a pH suitable for use in the conjugation reaction. For example, the targeting molecule, such as antibody, is prepared at a pH that is between or between about 6 and 10, such as between or between about 8 and 9, such as about 8.5, such as 8.46.

In some embodiments, the targeting molecule, such as antibody, is buffer exchanged into a buffer, such as using ultrafiltration/diafiltration such as using tangential flow filtration (TFF). In some embodiments, the TFF comprises a regenerated membrane, such as a regenerated cellulose membrane. In some embodiments, the buffer into which the targeting molecule is exchanged is a sodium phosphate buffer, such as 100 mM sodium phosphate, such as with a pH of 8.5 or pH 8.65. In some embodiments, tangential flow filtration is performed until a desired pH of the filtrate is reached. In some embodiments, the desired pH is between or between about 6 and 10, such as between or between about 8 and 9, such as about 8.5, such as 8.46.

In some embodiments, the targeting molecule is provided in an amount that is between or between about 0.01 g and 100 g, between or between about 1 g and 50 g, between or between about 1 g and 25 g, between or between about 5 g and 15 g, or is or is about 12 g. In some embodiments, the volume of targeting molecule preparation is between or between about 0.01 L and 100 L, between or between about 1 L and 50 L, between about 1 L and 15 L, or is or is about 6 L. In some embodiments, the concentration of the targeting molecule, such as antibody, is less than 0.01 mg/mL, or is between or between about 0.1 mg/mL and 100.0 mg/mL, between or between about 0.1 mg/mL and 50 mg/mL, between or between about 0.1 mg/mL and 10 mg/mL, or between or between about 1 mg/mL and 5 mg/mL, or is or is about 5 mg/mL or 4.5 mg/mL, or is or is about 2 mg/mL. In some embodiments, the targeting molecule, such as antibody, is diluted, such as to a concentration between or between about 0.1 mg/mL and 100.0 mg/mL, between or between about 0.1 mg/mL and 50 mg/mL, between or between about 0.1 mg/mL and 10 mg/mL, between or between about 1 mg/mL and 5 mg/mL, or between or between about 1.8 mg/mL and 2.4 mg/mL, or is diluted to a concentration of or of about 2 mg/mL.

In some embodiments, the targeting molecule, e.g., antibody, is filtered through a sterile filter, such as a 0.2 μm filter or 0.22 μm filter. In some embodiments, the prepared targeting molecule is stored, such as at a temperature below 30° C., such as generally below 26° C., 20° C., 15° C., 10° C., such as generally between or between about 2 and 8° C. In some embodiments, the weight of the targeting molecule is determined.

In some embodiments, the methods of manufacturing a conjugate include a step of contacting a targeting molecule, such as any described above (e.g. an antibody), with a phthalocyanine dye (e.g. IR700). In some embodiments, the phthalocyanine dye and targeting molecule are mixed together in a container, such as a reaction vessel. In some embodiments, the contacting step is carried out in a container or vessel, such as a reaction vessel. In some embodiments, the vessel is a tube a bottle, or a carboy. In some embodiments, the vessel has a maximum volume of about or at least 1 L, 2 L, 5 L, 10 L, 15 L, 20 L, 30 L, 40 L, 50 L or 100 L. In some embodiments, the vessel is a 40 L carboy. In some embodiments, the vessel has a maximum volume of about or at least 100 μL, 500 μL, 1 mL, 1.5 mL, 5 mL, 15 mL, 50 mL, 250 mL, or 500 mL. In some embodiments, the container or vessel is translucent or opaque, is green or amber, and/or is covered, such as wrapped, in an opaque, such as aluminum, foil.

In some embodiments, the amount of dye used for contacting the targeting molecule is calculated based on the weight of the targeting molecule present in the container or vessel. For example, in some embodiments, an amount of dye is added such that the final molar ratio of dye to targeting molecule is from or from about 1:1 to 1000:1, from or from about 1:1 to 100:1, from or from about 1:1 to 10:1, from or from about 1:1 to 4:1, or about 4:1 or 4:1.

In some embodiments, for example where the targeting molecule is a virus-like particle (VLP), the ratio of dye molecules to targeting molecule is between or between about 10:1 and 1000:1, 10:1 and 500:1, 50:1 and 500:1, or 50:1 and 1000:1. Thus, in some embodiments, the targeting molecule may comprise about 10 to about 1000 dye molecules. In some embodiments, the ratio of dye molecules to targeting molecule is or is about or 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1 or 1000:1, or is between or between about any two of such values. In some embodiments, the targeting molecule may comprise up to 10, 15, 20, 50, 75, 100, 150, 200, 250, 300, 350, 400, 450, 500, 550, 600, 650, 700, 750, 800, 850, 900, 950 or 1000 dye molecules. In some embodiments, the targeting molecule may comprise more than 1000 dye molecules or less than 10 dye molecules.

In some embodiments, the ratio of dye to targeting molecule is chosen such that a desired number of dye residues are incorporated per targeting molecule. In some embodiments, the desired number of dye residues per targeting molecule is from or from about 1 to 50, from or from about 1 to 25, from or from about 1 to 10, from or from about 1 to 5, from or from about 2-5, from or from about 2-3, or is about 3 or 3.

In some embodiments, such as where the targeting molecule is a VLP, more than one dye molecule may be conjugated to a single capsid protein. For example, a single capsid protein, such as L1 or L2 capsid protein, may be conjugated to 1 to 5, such as 1, 2, 3, 4 or 5, dye molecules. Thus, more than one amino acid of a capsid protein may be conjugated to a dye molecule. In some embodiments, a single capsid protein may be conjugated to 1 to 2, 1 to 3, or 2 to 3 dye molecules. Thus, a dye molecule may be conjugated to 1, 2, 3, 4 or 5 different amino acids, such as lysine, arginine and/or histidine, or other amino acid, of a single capsid protein.

In some embodiments, the contacting step is performed under conditions in which the dye and the targeting molecule are made to become covalently or non-covalently associated, such as are reacted or otherwise associated or linked together.

In some embodiments, the phthalocyanine dye comprises a reactive chemical group and contacting the phthalocyanine dye and targeting molecule produces a conjugate comprising the phthalocyanine dye covalently bound to an attachment group of the targeting molecule.

In some embodiments, the dye and the targeting molecule are contacted at a controlled temperature, or are contacted in a unit with a controlled temperature, such as an incubator or refrigerator. In some embodiments, the method involves contacting the phthalocyanine dye (e.g. IR700) and the targeting molecule (e.g. antibody) at a temperature in a range from or from about 4° C. to 37° C., such as from or from about 10° C. to 30° C., from or from about 20° C. to 30° C., or from or from about 23° C. to 27° C., or that is about 25° C.±2.0° C., 25° C.±1.0° C. or 25° C.±0.3° C., such as that is or is about 25° C. In some embodiments, the contacting step is carried out at room temperature, such as between 21° C. and 25° C., such as about 23° C.

In some embodiments, the contacting step includes incubating, such as reacting, the dye and targeting molecule. In some embodiments, the contacting can be carried out in a reaction vessel. In some embodiments, the contacting includes mixing, for example by stirring, the combined dye and targeting molecule compositions for at least a portion of the contacting. In some embodiments, the contents are stirred, such as on a stir plate. In some embodiments, the contents are stirred for about or at least 5 to 30 minutes, such as about 5 to 20 minutes, such as about 10 to 15 minutes.

In some embodiments, the contacting step is carried out for at least 5 minutes, at least 15 minutes, at least 30 minutes, at least 60 minutes, at least 90 minutes, at least 120 minutes, at least 240 minutes, at least 360 minutes, at least 24 hours, at least 72 hours, or at least 120 hours. In some embodiments, the contacting step is carried out for 5 minutes to 150 hours, 5 minutes to 100 hours, 5 minutes to 48 hours, 5 minutes to 24 hours, 5 minutes to 6 hours, 5 minutes to 2 hours, 5 minutes to 90 minutes, 5 minutes to 60 minutes, 5 minutes to 30 minutes, 30 minutes to 150 hours, 30 minutes to 100 hours, 30 minutes to 48 hours, 30 minutes to 24 hours, 30 minutes to 6 hours, 30 minutes to 2 hours, 30 minutes to 90 minutes, 30 minutes to 60 minutes, 60 minutes to 150 hours, 60 minutes to 100 hours, 60 minutes to 48 hours, 60 minutes to 24 hours, 60 minutes to 6 hours, 60 minutes to 2 hours, 60 minutes to 90 minutes, 90 minutes to 150 hours, 90 minutes to 100 hours, 90 minutes to 48 hours, 90 minutes to 24 hours, 90 minutes to 6 hours, 90 minutes to 2 hours, 2 hours to 150 hours, 2 hours to 100 hours, 2 hours to 48 hours, 2 hours to 24 hours, 2 hours to 6 hours, 6 hours to 150 hours, 6 hours to 100 hours, 6 hours to 48 hours, 6 hours to 24 hours, 24 hours to 150 hours, 24 hours to 100 hours, 24 hours to 48 hours, 48 hours to 150 hours, 48 hours to 100 hours or 100 hours to 150 hours. In some embodiments, the contacting is carried out for a time that is from 5 minutes to 6 hours, such as 5 minutes to 4 hours, 5 minutes to 2 hours, 5 minutes to 60 minutes, 5 minutes to 30 minutes, such as about 5 minutes to 20 minutes, such as about 10 minutes to 15 minutes. In some embodiments, the method includes contacting, such as by an incubation of the phthalocyanine dye (e.g. IR700) and the targeting molecule (e.g. antibody), for at least or about 15 minutes, at least or about 30 minutes, at least or about 60 minutes, at least or about 90 minutes, at least or about 120 minutes, or at least or about 150 minutes. In some embodiments, the method includes contacting, such as reacting the dye and the targeting molecule for between or between about 90 and 150 minutes, such as 120 minutes.

In some embodiments, the dye and targeting molecule are mixed in aqueous buffer that can include an organic solvent, such as DMSO or DMF. In some embodiments, the solvent is a water-based solvent. In some embodiments, the pH of the buffer is between or between about 6 and 10, such as between or between about 7 and 10, between or between about 8 and 10, or between or between about 8 and 9.

In some embodiments, the contacting step is carried out under light-protected conditions. For example, in some embodiments, during the contacting step, the dye and conjugate are not exposed to any environmental light or are not exposed to light with an intensity greater than 700 lux, greater than 600 lux, greater than 500 lux, greater than 400 lux, greater than 300 lux, greater than 200 lux, or greater than 100 lux. In some embodiments, the dye and conjugate are not exposed to light with an intensity of greater than 700 lux for more than 10 minutes, or for more than 5 minutes. In some embodiments, the dye and/or conjugate is not exposed to light with an intensity of greater than 200 lux for more than 10 minutes, or for more than 5 minutes.

In some embodiments, during the contacting step, the dye and conjugate are protected from environmental light, such as light in the near infrared (IR) range. In some embodiments, the only light to which the dye and conjugate are exposed prior to, during, and following the contacting step has a wavelength that is not absorbed by the dye or is not substantially absorbed by the dye. In some embodiments, the only light to which the dye and conjugate are exposed prior to, during, and following the contacting step is green light. In some embodiments, the only light to which the dye and conjugate are exposed prior to, during, and following the contacting step has a wavelength in a range from or from about 400 nm to 600 nm, such as 425 nm to 575 nm or 450 nm to 550 nm.

In some embodiments, the only light to which the dye and conjugate are exposed during the contacting step has a wavelength that is not absorbed by the dye or is not substantially absorbed by the dye and has an intensity of less than 700 lux, less than 600 lux, less than 500 lux, less than 400 lux, less than 300 lux, less than 200 lux, or less than 100 lux. In some embodiments, the only light to which the dye and conjugate are exposed during the contacting step has a wavelength in a range from or from about 400 nm to 600 nm, such as 425 nm to 575 nm or 450 nm to 550 nm and has an intensity of less than 700 lux, less than 600 lux, less than 500 lux, less than 400 lux, less than 300 lux, less than 200 lux, or less than 100 lux. In some embodiments, the only light to which the dye and conjugate are exposed during the contacting step is green light, such as light with a wavelength of 425 nm to 575 nm, that has an intensity of less than 700 lux, less than 600 lux, less than 500 lux, less than 400 lux, less than 300 lux, less than 200 lux, or less than 100 lux. In some embodiments, the total exposure of the dye and/or conjugate to any light during the contacting step is for no more than 5000 lux hours, no more than 2500 lux hours, no more than 1000 lux hours, no more than 500 lux hours, no more than 250 lux hours, no more than 100 lux hours or no more than 80 lux hours, no more than 50 lux hours or no more than 25 lux hours.

In some embodiments, the dye and conjugate are protected from light during the contacting step using containers that protect contents from light, or certain wavelengths or intensities of light. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and 725 nm, such as between or between about 650 nm and 725 nm, or does not transmit an intensity of light greater than 700 lux, 600 lux, 500 lux, 400 lux, 300 lux, 200 lux, or 100 lux. In some embodiments, the dye and/or conjugate is prepared in a translucent or opaque container. In some embodiments, the container is green, blue or amber. In some embodiments, the container is covered with an opaque substance, such as a foil, such as aluminum foil.

In some embodiments, in any of the methods provided herein, the targeting molecule (e.g. antibody) is linked directly or indirectly to the phthalocyanine dye (e.g. IR700). In some embodiments, the targeting molecule (e.g. antibody) is linked, directly or indirectly, to the phthalocyanine dye (e.g. IR700) via a covalent bond or a non-covalent interaction. In some embodiments, the covalent or non-covalent interactions or linkage is direct or indirect. In some embodiments, the attachment includes an indirect link, such as through a linker (e.g. such as any of the exemplary linkers described above), binding moiety or domain or reactive group. In some embodiments, the linkage includes a direct interaction between the targeting molecule and a phthalocyanine dye (e.g., IR700). In other embodiments, one or both of the targeting molecule and the phthalocyanine dye are linked to one or more linkers, and the interaction is indirect, e.g., between a linker attached to one of the molecules and another molecule, or between two linkers, each attached to the targeting molecule or the phthalocyanine dye.

In some embodiments, the phthalocyanine dye is non-covalently linked to or associated with the targeting molecule. For example, the phthalocyanine dye forms a complex with the targeting molecule via a non-covalent interaction.

In some embodiments, the phthalocyanine dye (e.g. IR700) contains a moiety or domain capable of non-covalently interacting with an attachment group of the targeting molecule. In some embodiments, the method includes incubating or binding the phthalocyanine dye (e.g. IR700) with the targeting molecule (e.g. antibody) to form a non-covalent interaction between the dye and the targeting molecule. In some examples, the non-covalent interaction between the targeting molecule and the phthalocyanine dye include, for example, electrostatic interactions, van der Waals force, hydrophobic interactions, π-effects, ionic interactions, hydrogen bonding, halogen bonding and/or combinations thereof, or any interactions that depend on one or more of the forces. In some embodiments, the targeting molecule and the phthalocyanine dye are linked using or using interactions that mimic non-covalent molecular interactions such as, for example, ligand-receptor interaction, antibody-antigen interaction, avidin-biotin interaction, streptavidin-biotin interaction, histidine-divalent metal ion interaction (e.g., Ni, Co, Cu, Fe), interactions between multimerization (e.g., dimerization) domains, glutathione S-transferase (GST)-glutathione interaction and/or any combination thereof.

In some embodiments, a non-covalent interaction moiety or domain is attached to or is a part of the targeting molecule, and forms a non-covalent interaction, e.g. a complex, with the phthalocyanine dye (e.g. IR700). In other embodiments, non-covalent interaction molecule or domain is attached to or is a part of the phthalocyanine dye molecule, and forms a non-covalent interaction e.g. a complex, with the targeting molecule. In some embodiments, the method includes incubating or contacting a targeting molecule conjugated to biotin (e.g. antibody-biotin, such as a cetuximab-biotin) and the phthalocyanine dye conjugated to an avidin or analog thereof or a streptavidin or analog thereof, including monomeric forms thereof (e.g. monomeric avidin-IR700 or monomeric streptavidin-IR700). By virtue of the non-covalent interaction between avidin, streptavidin or analogs thereof and biotin, in some embodiments, the phthalocyanine dye (e.g. IR700) forms a non-covalent complex with the targeting molecule.

In some embodiments, the phthalocyanine dye is covalently linked, e.g., covalently bound, to the targeting molecule. In some embodiments, the phthalocyanine dye (e.g. IR700) contains a reactive group to link it to the targeting molecule. In some embodiments, the contacting of the targeting molecule (e.g. antibody) with the phthalocyanine dye (e.g. IR700), such as a dye containing the reactive chemical group, produces a conjugate containing the dye linked to an attachment group of the targeting molecule. In some embodiments, the attachment includes an indirect link, such as through a linker. Exemplary linkers are described above. In some embodiments, the attachment includes a direct link, or a covalent linkage, wherein the covalent linkage is linear or branched, cyclic or heterocyclic, saturated or unsaturated, having 1-60 atoms, such as selected from among C, N, P, O, and S. In some embodiments, the attachment may contain any combination of ether, thioether, amine, ester, carbamate, urea, thiourea, oxy or amide bonds. In some embodiments, the attachment may include single, double, triple or aromatic carbon-carbon bonds, phosphorus-oxygen, phosphorus-sulfur, nitrogen-nitrogen, nitrogen-oxygen, nitrogen-platinum bonds, or aromatic or heteroaromatic bonds.

In some embodiments, the method includes reacting the phthalocyanine dye (e.g. IR700) with the targeting molecule (e.g. antibody) to form a covalent bond between the dye and the targeting molecule. In some embodiments, the bond is for example, an amide, a secondary or tertiary amine, a carbamate, an ester, an ether, an oxime, a phosphate ester, a sulfonamide, a thioether, a thiourea, or a urea. In some embodiments, the bond is covalent, such as an amide or carbamate bond. In some embodiments, the covalent bond is a phosphate or other linkage group. In some embodiments, the bond is a phosphate diester bond (e.g., for DNA, RNA).

In some embodiments, the reactive group of the dye reacts with the attachment group of the targeting molecule, for example, a thiol, a hydroxyl, a carboxyl, or an amino group, forming the attachment between the dye and the targeting molecule. In some embodiments, the attachment group of the targeting molecule a lysine residue. Thus, in some embodiments, the phthalocyanine dye (e.g. IR700) is covalently bound to a lysine residue of the targeting molecule.

In some embodiments, following the contacting step, the reaction is quenched, such as by adding a quenching agent, such as glycine. The term "quenching" refers to the process by which an unreacted reactive group is reacted with an excess of non-specific quenching agent (also called quencher), such as to stop the reaction between the dye and targeting molecule. The particular agent or quencher that is used depends on the particular reactive group associated with the dye. For example, NHS-ester crosslinking reactions can be quenched in the in presence of buffers containing amines, such as buffers containing Tris or glycine.

In some embodiments, the quenching step removes any unreacted dye. In some embodiments, the amount of quenching agent added is at least or about 200 mM, at least or about 500 mM, at least or about 1 M, at least or about 2 M, at least or about 5 M, or at least or about 10 M. In some embodiments, the quenching reaction involves the addition of 1 M glycine. In some embodiments, the final concentration of the quenching reagent after it is added to the conjugation reaction is at least or about 1 mM, at least or about 2 mM, at least or about 3 mM, at least or about 4 mM, at least or about 5 mM, or at least or about 10 mM. In some embodiments, the final concentration of the quenching regent, such as glycine, is or is about 4.2 nM.

In some embodiments, during the quenching step, the contents of the reaction vessel are mixed, such as stirred, such as on a stir plate. In some embodiments, the contents of the reaction vessel are stirred at between or between about 100 rpm and 1000 rpm, between or between about 200 rpm and 500 rpm, or are stirred at 300±50 rpm, or at 300 rpm. In some embodiments, the quenching reaction is mixed for at least or about 5 minutes, at least or about 10 minutes, or at least or about 15 minutes. In some embodiments, the quenching reaction is mixed for about 10 to 12 minutes.

In some embodiments, following the mixing of the quenching reaction, the container, such as the reaction vessel, is returned to a controlled temperature, such as in an incubator. In some embodiments, the contents of the vessel are incubated, such as from or from about 21° C. to 30° C., such as from or from about 23° C. to 27° C., such as at or about 25° C. In some embodiments, the incubation, such as additional incubation following the mixing of the quenching reagent with the contents of the reaction vessel, of the quenching step is carried out for at least or about 10 minutes, at least or about 15 minutes, at least or about 20 minutes, at least or about 25 minutes, or at least or about 30 minutes. In some embodiments, the incubation is carried out for from or from about 20 to 25 minutes.

In some embodiments, the quenching step is carried out under light-protected conditions. For example, in some embodiments, during the quenching step, the conjugate is not exposed to any environmental light or is not exposed to light with an intensity greater than 700 lux, greater than 600 lux, greater than 500 lux, greater than 400 lux, greater than 300 lux, greater than 200 lux, or greater than 100 lux. In some embodiments, the conjugate is not exposed to light with an intensity of greater than 700 lux for more than 10 minutes, or for more than 5 minutes. In some embodiments, the conjugate is not exposed to light with an intensity of greater than 200 lux for more than 10 minutes, or for more than 5 minutes.

In some embodiments, during the quenching step, the conjugate is protected from environmental light, such as light in the near infrared (IR) range. In some embodiments, the only light to which the conjugate is exposed during the quenching step has a wavelength that is not absorbed by the dye or conjugate or is not substantially absorbed by the dye or conjugate. In some embodiments, the only light to which the conjugate is exposed during the quenching step is green light. In some embodiments, the only light to which the conjugate is exposed during the quenching step has a wavelength in a range from or from about 400 nm to 600 nm, such as 425 nm to 575 nm or 450 nm to 550 nm.

In some embodiments, the only light to which the conjugate is exposed during the quenching step has a wavelength that is not absorbed by the conjugate or is not substantially absorbed by the conjugate and has an intensity of less than 700 lux, less than 600 lux, less than 500 lux, less than 400 lux, less than 300 lux, less than 200 lux, or less than 100 lux. In some embodiments, the only light to which the conjugate is exposed during the quenching step has a wavelength in a range from or from about 400 nm to 600 nm, such as 425 nm to 575 nm or 450 nm to 550 nm and has an intensity of less than 700 lux, less than 600 lux, less than 500 lux, less than 400 lux, less than 300 lux, less than 200 lux, or less than 100 lux. In some embodiments, the only light to which the conjugate is exposed during the quenching step is green light, such as light with a wavelength of 425 nm to 575 nm, that has an intensity of less than 700 lux, less than 600 lux, less than 500 lux, less than 400 lux, less than 300 lux, less than 200 lux, or less than 100 lux. In some embodiments, the total exposure of the dye and/or conjugate to any light during the quenching step is for no more than 5000 lux hours, no more than 2500 lux hours, no more than 1000 lux hours, no more than 500 lux hours, no more than 250 lux hours, no more than 100 lux hours or no more than 80 lux hours, no more than 50 lux hours or no more than 25 lux hours.

In some embodiments, the conjugate is protected from light during the quenching step using containers that protect contents from light, or certain wavelengths or intensities of light. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and 725 nm, such as between or between about 650 nm and 725 nm, or does not transmit an intensity of light greater than 700 lux, 600 lux, 500 lux, 400 lux, 300 lux, 200 lux, or 100 lux. In some embodiments, the conjugate is prepared in a translucent or opaque container. In some embodiments, the container is green, blue or amber. In some embodiments, the container is covered with an opaque substance, such as a foil, such as aluminum foil.

In some embodiments, the methods of manufacturing provided herein include a step or steps in which the conjugate is formulated, purified, or isolated to produce a drug substance. In some embodiments, the conjugate is formulated to a concentration within a range from or from about 0.1 mg/mL to about 1000 mg/mL, 0.1 mg/mL to about 500 mg/mL, 0.1 mg/mL to about 200 mg/mL, 0.1 mg/mL to about 100 mg/mL, 0.1 mg/mL to about 50 mg/mL, 0.1 mg/mL to about 10 mg/mL, 0.5 mg/mL to about 10 mg/mL, or 0.5 mg/mL to about 5 mg/mL.

In some embodiments, methods of formulating the conjugate can include concentrating or diluting the conjugate, exchanging the conjugate into a pharmaceutically acceptable buffer, or sterile processing.

In some embodiments, the formulating step includes concentrating the conjugate. In some embodiments, the concentrating step includes reducing the volume of the conjugate. In some embodiments, the volume reduction is achieved using an ultrafiltration/diafiltration system. In some embodiments, the volume of the conjugate is reduced from or from about 10 L, 15 L, 20 L, 25 L, 30 L, 40 L, or 50 L, to or to about 5 L, 8 L, 9 L, 10 L, 12 L or 15 L. In some embodiments, the final volume after concentration is between or between about 8 L and 10 L. In some embodiments, the conjugate is concentrated to a concentration within a range from or from about 0.1 mg/mL to about 1000 mg/mL, 0.1 mg/mL to about 500 mg/mL, 0.1 mg/mL to about 200 mg/mL, 0.1 mg/mL to about 100 mg/mL, 0.1 mg/mL to about 50 mg/mL, 0.1 mg/mL to about 10 mg/mL, 0.5 mg/mL to about 10 mg/mL, 0.5 mg/mL to about 5 mg/mL, or 1.8 mg/mL to about 2.1 mg/mL. In some embodiments, the conjugate is concentrated to or to about 2.0 mg/mL.

In some embodiments, the formulating step includes diluting the conjugate. In some embodiments, dilution of the conjugate involves increasing the volume of the buffer comprising the conjugate, such as from or from about 5 L, 10 L, 15, L, 20 L, 30 L, 40 L, or 50 L, to or to about 20 L, 30 L, 40 L, 50 L, or 75 L. In some embodiments, the conjugate is diluted to a concentration within a range from or from about 0.1 mg/mL to about 1000 mg/mL, 0.1 mg/mL to about 500 mg/mL, 0.1 mg/mL to about 200 mg/mL, 0.1 mg/mL to about 100 mg/mL, 0.1 mg/mL to about 50 mg/mL, 0.1 mg/mL to about 10 mg/mL, 0.5 mg/mL to about 10 mg/mL, or 0.5 mg/mL to about 5 mg/mL.

In some embodiments, the formulating step includes purifying the conjugate. In some embodiments, the conjugate is purified by gel permeation chromatography using equipment such as a SEPHADEX G-50 column, or by dialysis to remove unconjugated dye. In some embodiments, the conjugate is ultrafiltered or diafiltered, such as by using tangential flow filtration (TFF). In some embodiments, ultrafiltration/diafiltration is performed under dark or light-protected conditions to avoid exposure of the conjugate to environmental light.

In some embodiments, the formulating step includes exchanging the phthalocyanine dye-targeting molecule conjugate (e.g. IR700-targeting molecule conjugate, such as IR700-antibody conjugate) from the reaction buffer to a pharmaceutically acceptable buffer. In some embodiments, the buffer exchange may be carried out by ultrafiltration/diafiltration.

In some embodiments, the conjugate is formulated in a pharmaceutically acceptable buffer, such as that containing a pharmaceutically acceptable carrier or vehicle. Generally, the pharmaceutically acceptable carriers or vehicles, such as those present in the pharmaceutically acceptable buffer, are can be any known in the art. Remington's Pharmaceutical Sciences, by E. W. Martin, Mack Publishing Co., Easton, Pa., 19th Edition (1995), describes compositions and formulations suitable for pharmaceutical delivery of one or more therapeutic compounds.

In some embodiments, the pH of the composition is between or between about 6 and 10, such as between or between about 6 and 8, between or between about 6.9 and 7.3, such as about pH 7.1. In some embodiments, the pH of the pharmaceutically acceptable buffer is at least or about 5, at least or about 6, at least or about 7, at least or about 8, at least or about 9 or at least or about 10, or is 7.1.

In some embodiments, the nature of the pharmaceutically acceptable buffer, or carrier, depends on the particular mode of administration being employed. For instance, in some embodiments, parenteral formulations may comprise injectable fluids that include pharmaceutically and physiologically acceptable fluids such as water, physiological saline, balanced salt solutions, aqueous dextrose, or glycerol as a vehicle. In some embodiments, for solid compositions, for example powder, pill, tablet, or capsule forms, non-toxic solid carriers can include, for example, pharmaceutical grades of mannitol, lactose, starch, or magnesium stearate. In addition to biologically-neutral carriers, pharmaceutical compositions to be administered can in some embodiments contain minor amounts of non-toxic auxiliary substances, such as wetting or emulsifying agents, preservatives, and pH buffering agents, for example sodium acetate or sorbitan monolaurate.

In some embodiments, the pharmaceutically acceptable buffer is phosphate buffered saline (PBS). In some embodiments, the PBS has a pH of or of about 7.1.

In some embodiments, the formulating step includes filtering of the conjugate, such as by sterile filtering. In some embodiments, the conjugate is filtered through a sterile filter, such as through an about 0.2 µm filter, such as a 0.22 µm filter.

In some embodiments, during the formulating step, the conjugate is protected from wavelengths of light that are strongly absorbed by the conjugate. For example, in some embodiments, the concentrating is performed in a light-protected refrigerator.

In some embodiments, the formulating step is carried out under light-protected conditions. For example, in some embodiments, during the formulating step, the conjugate is not exposed to any environmental light or is not exposed to light with an intensity greater than 700 lux, greater than 600 lux, greater than 500 lux, greater than 400 lux, greater than 300 lux, greater than 200 lux, or greater than 100 lux. In some embodiments, the conjugate is not exposed to light with an intensity of greater than 700 lux for more than 10 minutes, or for more than 5 minutes. In some embodiments, the conjugate is not exposed to light with an intensity of greater than 200 lux for more than 10 minutes, or for more than 5 minutes.

In some embodiments, during the formulating step, the conjugate is protected from environmental light, such as light in the near infrared (IR) range. In some embodiments, the only light to which the conjugate is exposed during the formulating step has a wavelength that is not absorbed by the conjugate or is not substantially absorbed by the conjugate. In some embodiments, the only light to which the conjugate is exposed during the formulating step is green light. In some embodiments, the only light to which the conjugate is exposed during the formulating step has a wavelength in a range from or from about 400 nm to 600 nm, such as 425 nm to 575 nm or 450 nm to 550 nm.

In some embodiments, the only light to which the conjugate is exposed during the formulating step has a wavelength that is not absorbed by the conjugate or is not substantially absorbed by the conjugate and has an intensity of less than 700 lux, less than 600 lux, less than 500 lux, less than 400 lux, less than 300 lux, less than 200 lux, or less than 100 lux. In some embodiments, the only light to which the conjugate is exposed during the formulating step has a wavelength in a range from or from about 400 nm to 600 nm, such as 425 nm to 575 nm or 450 nm to 550 nm and has an intensity of less than 700 lux, less than 600 lux, less than 500 lux, less than 400 lux, less than 300 lux, less than 200 lux, or less than 100 lux. In some embodiments, the only light to which the conjugate is exposed during the formulating step is green light, such as light with a wavelength of 425 nm to 575 nm, that has an intensity of less than 700 lux, less than 600 lux, less than 500 lux, less than 400 lux, less than 300 lux, less than 200 lux, or less than 100 lux. In some embodiments, the total exposure of the dye and/or conjugate to any light during the formulating step is for no more than 5000 lux hours, no more than 2500 lux hours, no more than 1000 lux hours, no more than 500 lux hours, no more than 250 lux hours, no more than 100 lux hours or no more than 80 lux hours, no more than 50 lux hours or no more than 25 lux hours.

In some embodiments, the conjugate is protected from light during the formulating step by placing the container in which the reaction occurs in a light-protected, such as a dark area. For example, in some embodiments, the ultrafiltration/diafiltration is carried out in the dark, such as by placing the ultrafiltration/diafiltration apparatus, such as TFF, in a dark area, such as a refrigerator. In some embodiments, the conjugate is protected from light during the formulating step using containers that protect contents from light, or certain wavelengths or intensities of light. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and 725 nm, such as between or between about 650 nm and 725 nm, or does not transmit an intensity of light greater than 700 lux, 600 lux, 500 lux, 400 lux, 300 lux, 200 lux, or 100 lux. In some embodiments, the conjugate is prepared in a translucent or opaque container. In some embodiments, the container is green, blue or amber. In some embodiments, the container is covered with an opaque substance, such as a foil, such as aluminum foil. In some embodiments, the container is covered by material with light transmission of less than 50%, less than 40%, less than 30%, less than 20%, less than 10% or less than 5%.

In some embodiments, the formulated drug substance is stored prior to packaging, such as vialing, of the drug product. In some embodiments, the formulated conjugate is stored in the dark and/or is stored in an opaque or translucent container, such as a green or amber container, or is stored in a container that is covered, such as wrapped, in an opaque foil, such as aluminum foil. In some embodiments, the formulated drug substance is stored in a refrigerator, such as between or between about 2-8° C., such as at or about 4° C.

Packaging of Drug Substance to Produce Drug Product

In some embodiments, the method includes packaging the phthalocyanine dye-targeting molecule conjugate (e.g. IR700-targeting molecule conjugate, for example IR700-antibody conjugate), such as packaging the drug substance prepared as described above to result in a packaged drug product. In some embodiments, the drug substance is packaged, such as into one or more containers, within 4 weeks of preparation, such as within 1 week, 2 weeks, or 3 weeks of preparation. In some embodiments, the container is a vial, a tube, a syringe, a bag, a pouch or a box or combinations thereof.

Also provided herein are containers, such as light-protected containers, and/or devices, such as light-protected devices, that contain any of the conjugates or compositions described herein, or any conjugates or compositions produced or generated using any of the methods described herein. Also provided herein are packaging systems for protecting any of the conjugates or compositions described herein, or any conjugates or compositions produced or generated using any of the methods described herein. In some embodiments, such packaging systems comprise one or more of the containers described herein.

Also provided are kits or articles of manufacture containing the provided container, device, and/or packaging system, for protection of the conjugates or compositions, and for storage and/or administration. The kit may include a container and/or packaging system, a light-protected cover capable of covering a device capable of administering a composition comprising a phthalocyanine dye-targeting molecule conjugate, and optionally instructions for use. The kit can also contain a label or package insert on or associated with the contents of the kit. The kit or article of manufacture may further include a package insert indicating instructions for use, storage or administration of the conjugate or composition contained in the container and/or packaging system.

In some embodiments, the conjugate is packaged into one or more containers, such as a light-protected container. In some embodiments, the container is a vial, such as a depyrogenated, glass vial. In some embodiments, the container, such as a vial, blocks light of a particular wavelength, such as a wavelength of light that is absorbed by the dye or dye-targeting molecule conjugate. Thus, in some embodiments, the container protects the conjugate contained therein from light with a wavelength less than or less than about 250 nm or between or between about 550 nm and 750 nm. In some embodiments, the container protects from transmittance of light having a wavelength between or between about 500 nm and 725 nm, such as between or between about 650 nm and 725 nm. In some embodiments, the container only permits the transmittance of certain wavelengths of light, such as those from or from about 400 nm to 600 nm, such as from or from about 425 nm to 575 nm or from or from about 450 nm to 550 nm. In some embodiments, the container is green, blue, amber, translucent, opaque, or is wrapped in an opaque material, such as a foil, such as aluminum foil. In some embodiments, the container is sterile or depyrogenated. In some embodiments, the container protects from transmission of light such that the percentage of light transmission is less than 50%, less than 40%, less than 30%, less than 20%, less than 10% or less than 5%.

In some embodiments, the container has a maximum volume of at least or about 5 mL, at least or about 10 mL, at least or about 25 mL, at least or about 50 mL, such as 51±1 mL, at least or about 100 mL, at least or about 250 mL, at least or about 500 mL, or at least or about 1 L.

In some embodiments, such as where the containers are vials, the vials are stoppered and crimped prior to the fill. In some embodiments, the mean empty vial weight is determined and is used to determine the weigh range for filled vials.

In some embodiments, the packaging includes a semi-automated, aseptic fill. For example, in some embodiments, the conjugate is filled into the containers, e.g., vials, using a peristaltic pump and filling needle assembly. In some embodiments, the conjugate is aseptically filtered prior to filling, such as through an about 0.2 µm filter, such as a 0.22 µm filter. In some embodiments, the sterile filtrate is weighed to determine the approximate number of containers, e.g. vials, to be filled.

In some embodiments, the method includes filling a vial with a volume amount of dye-conjugate drug substance that is at least 0.2 mL, 0.3 mL, 0.4 mL, 0.5 mL, 1 mL, 1.5 mL, 2.0 mL, 3.0 mL, 5.0 mL, 10.0 mL, 20.0 mL, 30.0 mL, 40.0 mL, 50.0 mL or more, such as generally 0.5 mL to 50 mL or 1 mL to 10 mL. In some embodiments, all vials that are filled are filled to contain the same volume and amount of the dye conjugate. In some embodiments, the manufacturing method results in a fill of a plurality of vials, such as at least 2, 3, 4, 5, 6, 7, 8, 9, 10, 15, 20, 30, 40, 50 or more vials.

In some embodiments, a single dosage amount of the conjugate is contained in a single container. In some embodiments, a single dosage amount is provided in a plurality of containers, such as 2, 3, 4, 5, 6, 7, 8, 9, 10, or more containers.

In some embodiments, following the filling step, the containers, e.g., vials, are stoppered, sealed and crimped. In some embodiments, the containers are stored protected from light, such as in a non-transparent bin, such as at a temperature less than or equal to or about 26° C., such as less than or equal to or about 20° C., 15° C., 8° C., 0° C., −20° C., or −80° C. In some embodiments, the temperature is from or from about 20 to 26° C., such as 23±3° C., or from or from about 2 to 8° C., such as 5±3° C., such as at or about 4° C. or at or about 5° C., or less than 0° C., such as about −20 or −80° C.

In some embodiments, the containers, such as vials, are labeled. In some embodiments, labeling is performed at room temperature and care is taken to avoid the time of exposure of the conjugate to room temperature. For example, in some embodiments, the containers are exposed to ambient temperature for less than or about 30 minutes, such as less than or about 20 minutes, less than or about 10 minutes, less than or about 2 minutes, or less than or about 1 minute.

In some embodiments, the containers are further packaged to protect the contents from light. In some embodiments, a packaging system is provided that includes an internal packaging material comprising a container comprising the phthalocyanine dye-targeting molecule conjugate (e.g. IR700-targeting molecule conjugate, such as IR700-antibody conjugate). In some embodiments, the internal packaging material has a light transmittance of less than 20%, such as less than 15%, less than 10%, less than 5%, or less than 1%. In some embodiments, the packaging system includes an external packaging material comprising the internal packaging material. In some embodiments, the external packaging material has a light transmittance of less than 20%, such as less than 15%, less than 10%, less than 5%, or less than 1%. In some embodiments, the internal or external packaging material includes an opaque foil, such as aluminum foil. In some embodiments, the container is covered by material with light transmission of less than 50%, less than 40%, less than 30%, less than 20%, less than 10% or less than 5%. In some embodiments, the secondary packaging material is an aluminum pouch. In some embodiments, the external packaging material comprises cardboard.

In some embodiments, the internal and/or external packaging material is suitable for storage of the conjugate. In some embodiments, the internal and/or external packaging material is suitable for shipping of the conjugate.

Also provided is a packaging system for protecting a phthalocyanine dye-targeting molecule conjugate from light that includes one or more containers, such as one, two, three or more containers. Each or all of the containers in the packaging system provided herein can be light-protected containers, such as any light-protected containers described herein.

In some embodiments, the packaging system includes two containers: a first container comprising any of the containers described herein, and a second container comprising the first container, wherein the second container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

In some embodiments, the second container protects from transmission of light such that the percentage of light transmission is less than 50%, less than 40%, less than 30%, less than 20%, less than 10% or less than 5%. In some embodiments, the second container is green, blue, amber, translucent, opaque, or is covered by a material with light transmission of less than 50%, less than 40%, less than 30%, less than 20%, less than 10% or less than 5%. In some embodiments, the first and second containers are independently selected from among a vial, a tube, a syringe, a bag, a pouch, and a box.

In some embodiments, any of the provided packaging system further includes a third container comprising the second container, wherein the third container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the third container protects from transmission of light such that the percentage of light transmission is less than 50%, less than 40%, less than 30%, less than 20%, less than 10% or less than 5%. In some embodiments, the third container is green, blue, amber, translucent, opaque, or is covered by a material with light transmission of less than 50%, less than 40%, less than 30%, less than 20%, less than 10% or less than 5%. In some embodiments, the third container is selected from among a vial, a tube, a syringe, a bag, a pouch, and a box.

In some embodiments, the containers or containers or packaging systems comprising the conjugate, such as a single container or plurality of containers comprising a single dosage amount, are packaged in a kit. Thus, in some embodiments, the kit includes one or more single dosage amount. In some embodiments, the kit includes instructions, such as for administering the conjugate, such as under light-protected conditions. In some embodiments, the kit contains materials to be used for light protection of the conjugate, such as opaque foil, opaque containers, opaque intravenous (IV) bags, or opaque sleeves, such as for covering the IV bag.

For example, in some embodiments, the kit includes any of the containers described herein or any of the packaging systems described herein; a light-protected cover capable of covering a device capable of administering a composition comprising a phthalocyanine dye-targeting molecule conjugate; and optionally instructions for use. In some embodiments, the administration device is an intravenous infusion bag or a syringe. In some embodiments, the light-protected cover protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the light-protected cover protects from transmission of light such that the percentage of light transmission is less than 50%, less than 40%, less than 30%, less than 20%, less than 10% or less than 5%. In some embodiments, the light-protected cover is green, blue, amber, translucent, opaque, or is covered by a material with light transmission of less than 50%, less than 40%, less than 30%, less than 20%, less than 10% or less than 5%.

In some embodiments, prior to, during, and following the packaging of the conjugate, the conjugate is protected from environmental light, such as light in the near infrared (IR) range. In some embodiments, the only light to which the dye and conjugate are exposed prior to, during, and following the preparation of the drug substance is green light. In some embodiments, the only light to which the dye and conjugate are exposed prior to, during, and following the preparation of the drug substance has a wavelength in a range from or from about 400 nm to 600 nm, such as 425 nm to 575 nm or 450 nm to 550 nm. In some embodiments, the only light to which the dye and conjugate are exposed prior to, during, and following the preparation of the drug substance has a wavelength that is not absorbed by the dye or is not substantially absorbed by the dye.

In some embodiments, prior to, during, and following the preparation of the drug substance, the dye and conjugate are not exposed to any environmental light or are not exposed to light with an intensity greater than 700 lux, greater than 600 lux, greater than 500 lux, greater than 400 lux, greater than 300 lux, greater than 200 lux, or greater than 100 lux. In some embodiments, the total exposure of the dye and/or conjugate to any light during the packaging step is for no more than 5000 lux hours, no more than 2500 lux hours, no more than 1000 lux hours, no more than 500 lux hours, no more than 250 lux hours, no more than 100 lux hours or no more than 80 lux hours, no more than 50 lux hours or no more than 25 lux hours.

Characteristics of Phthalocyanine Dye-Targeting Molecule Conjugate

Provided in some embodiments is a stable phthalocyanine dye-targeting molecule conjugate, such as an IR700 dye-targeting molecule conjugate, for example an IR700-antibody conjugate. Also provided are conjugates, e.g., stable conjugates, produced, formulated or packaged according to any of the methods of manufacturing described herein.

In some embodiments, the conjugate has a molar ratio of dye to targeting molecule (e.g. IR700 to targeting molecule) is from or from about 1:1 to 1000:1, from or from about 1:1 to 100:1, from or from about 1:1 to 10:1, from or from about 1:1 to 4:1, or about 4:1 or 4:1.

In some embodiments, the conjugate (e.g. IR700-targeting molecule, for example IR700-antibody) has a concentration within a range from or from about 0.1 mg/mL to 1000 mg/mL, 0.1 mg/mL to 500 mg/mL, 0.1 mg/mL to 200 mg/mL, 0.1 mg/mL to 100 mg/mL, 0.1 mg/mL to 50 mg/mL, 0.1 mg/mL to 10 mg/mL, 0.5 mg/mL to 10 mg/mL, 0.5 mg/mL to 5 mg/mL, or 1.8 mg/mL to 2.1 mg/mL. In some embodiments, the conjugate has a concentration of about 2.0 mg/mL, or has a concentration of 2.0 mg/mL.

In some embodiments, the amount of the conjugate produced by the method is greater than or greater than about 1 gram, greater than or greater than about 2 grams, greater than or greater than about 3 grams, greater than or greater than about 4 grams, greater than or greater than about 5 grams or greater than or greater than about 10 grams. In some embodiments, the conjugate is produced using good manufacturing practice (GMP).

In some embodiments, the provided phthalocyanine dye-targeting molecule conjugate (e.g. IR700-targeting molecule conjugate, for example IR700-antibody conjugate) is stable and displays minimal aggregation, such as light-induced aggregation, during or following storage, such as for 3 months or more. Thus, in some embodiments, the conjugate is stable for at least 3, 4, 5, 6, 7, 8, or 9 months, or is stable for about or at least a year or more. In some embodiments, the conjugate is stable for more than 1 year.

In some embodiments, stability of the conjugate can be measured by assessing the percent monomer content of the conjugate. In some embodiments, the conjugate displays greater than 90% monomer content, such as at least 91%, 92%, 93%, 94%, 95%, 96%, 97%, 98%, or 99% monomer content at or greater than 3 months or more following preparation or storage. In some embodiments, stability of the conjugate is present if the conjugate displays less than 10% high molecular weight (HMW) species, such as less than 9%, 8%, 7%, 6%, 5%, 4%, 3%, 2%, or 1% HMW at 3 months or more following preparation or storage.

In some embodiments, potency or activity of the conjugate can be measured by assessing the ED50 of the conjugate or by assessing the ability of the conjugate to induce or mediate PIT killing. In some embodiments, the conjugate displays greater than or greater than about 30% of the potency or activity, such as greater than or greater than about 40%, 50%, 60%, 70%, 80%, 90% or 95% of the potency or activity, at or greater than 3 months or more following storage compared to the conjugate prior to the storage, e.g. compared to a conjugate at t=0.

In some embodiments, the stable phthalocyanine dye-targeting molecule conjugate, such as a IR700 dye-targeting molecule conjugate (e.g. IR700-antibody conjugate), is stable as a result of preparing or producing or storing the dye or dye-conjugate under light protection conditions, such as described above.

In some embodiments, a factor influencing the stability of the conjugate is protection of the conjugate from light, and thus, light-induced aggregation. Thus, in some embodiments, stability of the conjugated is imparted by protecting it from light, or certain wavelengths or intensities of light. For example, in some embodiments, the conjugate is not exposed to any environmental light or is not exposed to light with an intensity greater than 700 lux, greater than 600 lux, greater than 500 lux, greater than 400 lux, greater than 300 lux, greater than 200 lux, or greater than 100 lux. In some embodiments, the conjugate is not exposed to light with an intensity of greater than 700 lux for more than 10 minutes, or for more than 5 minutes. In some embodiments, the conjugate is not exposed to light with an intensity of greater than 200 lux for more than 10 minutes, or for more than 5 minutes. In some embodiments, during the steps of the provided methods, the total exposure of the dye and conjugate to any light is for no more than 5000 lux hours, no more than 2500 lux hours, no more than 1000 lux hours, no more than 500 lux hours, no more than 250 lux hours, no more than 100 lux hours or no more than 80 lux hours.

In some embodiments, the conjugate is protected from environmental light, such as light in the near infrared (IR) range. In some embodiments, the only light to which the conjugate is exposed has a wavelength that is not absorbed by the conjugate or is not substantially absorbed by the conjugate. In some embodiments, the only light to which the conjugate is exposed is green light. In some embodiments, the only light to which the conjugate is exposed has a wavelength in a range from or from about 400 nm to 600 nm, such as 425 nm to 575 nm or 450 nm to 550 nm.

In some embodiments, the only light to which the conjugate is exposed has a wavelength that is not absorbed by the conjugate or is not substantially absorbed by the conjugate and an intensity of less than 700 lux, less than 600 lux, less than 500 lux, less than 400 lux, less than 300 lux, less than 200 lux, or less than 100 lux. In some embodiments, the only light to which the conjugate is exposed has an intensity of less than 700 lux, less than 600 lux, less than 500 lux, less than 400 lux, less than 300 lux, less than 200 lux, or less than 100 lux. In some embodiments, the only light to which the conjugate is exposed has a wavelength in a range from or from about 400 nm to 600 nm, such as 425 nm to 575 nm or 450 nm to 550 nm and has an intensity of less than 700 lux, less than 600 lux, less than 500 lux, less than 400 lux, less than 300 lux, less than 200 lux, or less than 100 lux.

In some embodiments, the stability of the conjugate is present after storage in a light protected container. In some embodiments, the conjugate is protected from light using containers that protect contents from light, or certain wavelengths or intensities of light. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and 725 nm, such as between or between about 650 nm and 725 nm, or does not transmit an intensity of light greater than 700 lux, 600 lux, 500 lux, 400 lux, 300 lux, 200 lux, or 100 lux. In some embodiments, the conjugate is stored in a translucent or opaque container. In some embodiments, the container is green or amber. In some embodiments, the container is covered with an opaque substance, such as a foil, such as aluminum foil.

In some embodiments, the stability of the conjugate is present following storage of the conjugate at a temperature less than or equal to or about 26° C., such as less than or equal to or about 20° C., 15° C., 8° C., 0° C., −20° C., or −80° C. In some embodiments, the temperature is from or from about 20 to 26° C., such as 23±3° C., or from or from about 2 to 8° C., such as 5±3° C., such as at or about 4° C. or at or about 5° C., or is less than 0° C., such as about −20 or −80° C.

In some embodiments, pH of the conjugate, e.g., the pH of a pharmaceutically acceptable buffer in which the conjugate is formulated, imparts stability to the conjugate. In some embodiments, the pH is greater than 6.0, such as greater than or about 7.0, greater than or about 8.0 or greater than or about 9.0. In some embodiments, the pH is 6.0 to 9.0, such as 6.0 to 8.0, 6.5 to 7.4, such as about 7.1±3.0.

In some embodiments, the stable phthalocyanine dye-targeting molecule conjugate (e.g. IR700-targeting molecule conjugate, for example IR700-antibody conjugate) is produced by the methods provided herein, such as the light-protected methods described in subsection C.

In some embodiments, a stable conjugate is provided that is stable for greater than 3 months, such as when manufactured and stored under conditions of light protection as described above, at a temperature less than 26° C., such as 2 to 8° C., and when formulated at a pH of greater than 6.0, such as a pH of 6.0 to 8.0.

II. Methods of Treatment

In some embodiments, provided are methods for using and uses of a phthalocyanine dye-targeting molecule conjugate (e.g. IR700-targeting molecule conjugate, for example IR700-antibody conjugate) that targets to a cell or pathogen associated with a disease or condition, such as via binding to a cell surface molecule, cell surface protein or cell surface receptor expressed on a cell. Such methods and uses include therapeutic methods and uses, for example, involving administration of the molecules to a subject having a disease, condition or disorder followed by irradiation to achieve photoimmunotherapy, thereby resulting in photolysis of such cells or pathogens to effect treatment of the disease or disorder. Uses include uses of the conjugates in such methods and treatments, and in the preparation of a medicament in order to carry out such therapeutic methods. In some embodiments, provided are methods for using and uses of such molecules for treating a tumor in a subject with a phthalocyanine dye-targeting molecule conjugate (e.g. IR700-targeting molecule conjugate, for example a IR700-antibody conjugate) to treat a tumor in a subject. In some embodiments, the phthalocyanine-dye targeting molecule conjugate is a stable conjugate, such as any described herein. In some embodiments, the phthalocyanine dye targeting molecule conjugate is produced using the methods as described herein. In some embodiments, the methods thereby treat the disease or condition or disorder in the subject.

Also provided are methods of preparing a composition that contains any of the conjugates described herein, or conjugates prepared using the methods provided herein, for administration, to a subject, such as any of the phthalocyanine-dye conjugates (e.g. antibody-IR700 conjugate). In some embodiments, preparation of the conjugates takes place under light-protected conditions. In some embodiments, the method of preparation includes: unpacking one or more of any of the containers described herein or one or more of any of the packaging system described herein that includes any of the containers described herein; and transferring the composition present in the one or more containers into a device capable of administering the composition to a subject, wherein the only light to which the composition is exposed has a wavelength within a range from about 400 nm to about 650 nm, or the only light to which the composition is exposed has an intensity of less than 500 lux, such as less than 200 lux or less than 100 lux.

In some embodiments, the method provided is performed in a biosafety cabinet, biosafety hood or a sterile environment. In some embodiments, the one or more containers together comprise a therapeutically effective dose of the phthalocyanine-dye conjugate. In some embodiments, the one or more containers include at least or about at least or 2, 4, 6, 8, 10, 12, 18 or 24 containers.

In some embodiments, the provided method of preparing the phthalocyanine-dye conjugates (e.g. antibody-IR700 conjugate) is carried out for no more than 1 hour, no more than 30 minutes or no more than 15 minutes; or the total exposure of the composition to any light during the method is no more than 500 lux hours, no more than 250 lux hours, no more than 100 lux hours, no more than 50 lux hours or no more than 25 lux hours.

Also provided are light-protected devices that include the composition prepared by the methods provided herein. In some embodiments, the light-protective device is used for administration of the compositions or conjugates described herein.

In some embodiments, the administration device is an intravenous infusion bag or a syringe. In some embodiments, the administration device comprises a light-protected cover capable of covering the device. In some embodiments, the light-protected cover protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm. In some embodiments, the light-protected cover protects from transmission of light such that the percentage of light transmission is less than 50%, less than 40%, less than 30%, less than 20%, less than 10% or less than 5%. In some embodiments, the light-protected cover is green, blue, amber, translucent, opaque, or is covered by a material with light transmission of less than 50%, less than 40%, less than 30%, less than 20%, less than 10% or less than 5%.

In some embodiments, the methods include administration of a phthalocyanine dye-targeting molecule conjugate to the subject under conditions in which, generally, a cell targeted for killing is contacted with the conjugate. In some embodiments, the methods result in the binding of the targeting molecule (e.g., antibody) portion of the conjugate to a cell surface protein associated with a tumor or cancer. After contacting or administering the conjugate, a local area of the subject containing the targeted cells, e.g., the tumor, is exposed or irradiated with light absorbed by the dye, generally NIR light, thereby activating the conjugate to effect specific cell killing. For example, in some embodiments, the methods further include local irradiation of the disease region in the subject, such as local irradiation of the tumor. In some embodiments, irradiation is performed at a wavelength of 600 to 850 nm at a dose of at least 1 J cm$^{-2}$. In some embodiments, the conjugate is targeted to the diseased cell, such as tumor, and the irradiation results in cell killing, such as by photoimmunotherapy (PIT). In some embodiments, the methods include methods described in U.S. Pat. No. 8,524,239 or U.S. publication No. US2014/0120119.

In some embodiments, administration of the conjugate takes place under light-protected conditions. In some embodiments, the administration is performed under fluorescent lighting or LED lighting. In some embodiments, the administration is performed in the absence of direct or indirect sunlight.

In some embodiments, prior to and during administration, the conjugate is not exposed to environmental light or is not exposed to environmental light with an intensity greater than 700 lux, greater than 600 lux, greater than 500 lux, greater than 400 lux, greater than 300 lux, greater than 200 lux, or greater than 100 lux or greater than 50 lux.

In some embodiments, the conjugate is not exposed to light with an intensity of greater than 700 lux, greater than 600 lux, greater than 500 lux, greater than 400 lux, greater than 300 lux, greater than 200 lux, or greater than 100 lux or greater than 50 lux for more than 20 minutes, 10 minutes, or for more than 5 minutes. In some embodiments, the dye and/or conjugate is not exposed to light with an intensity of greater than 200 lux for more than 10 minutes, or for more than 5 minutes. In some embodiments, prior to and during administration, any exposure of the conjugate to light is for less than 20 minutes, less than 15 minutes, less than 10 minute, less than 5 minutes, less than 4 minutes, less than 3 minutes, less than 2 minutes, or less than 1 minute. In some embodiments, the total exposure of the dye and/or conjugate to any light prior to or during administration is for no more than 5000 lux hours, no more than 2500 lux hours, no more than 1000 lux hours, no more than 500 lux hours, no more than 250 lux hours, no more than 100 lux hours or no more than 80 lux hours, no more than 50 lux hours or no more than 25 lux hours.

In some embodiments, the conjugate is protected from environmental light, such as light in the near infrared (IR)

range. In some embodiments, the only light to which the conjugate is exposed has a wavelength that is not absorbed by the conjugate or is not substantially absorbed by the conjugate.

In some embodiments, the prior to administration to the subject, the conjugate is protected from light using containers that protect contents from light, or certain wavelengths or intensities of light. The container can be a tube, syringe, infusion bag or other container that is compatible with injection of transfer of the conjugate to the subject. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and 725 nm, such as between or between about 650 nm and 725 nm, or does not transmit an intensity of light greater than 700 lux, 600 lux, 500 lux, 400 lux, 300 lux, 200 lux, or 100 lux. In some embodiments, the conjugate is administered from or in a translucent or opaque container. In some embodiments, the container is green or amber. In some embodiments, the container is covered with an opaque substance, such as a foil, such as aluminum foil. In some embodiments, the container is an intravenous (IV) bag and the bag is covered in an opaque sleeve, such as foil, such as aluminum foil.

The target cell can be a cell that is not desired or whose growth is not desired, such as a tumor cell. In some embodiments, the cells can be growing in culture, or present in a mammal to be treated, such as a subject with cancer. Any target cell can be treated with the claimed methods. In some embodiments, the target cell expresses a cell surface protein that is not substantially found on the surface of other normal cells. In some embodiments, an antibody can be selected that specifically binds to such protein, and a phthalocyanine dye-antibody conjugate may be generated for that protein. In some embodiments, the cell surface protein is a tumor-specific protein. In some embodiments, the cell surface protein is CD25, which can be used to target cells associated with undesired transplant rejection.

Also provided are methods of removing unwanted cells or pathogens, such as a diseased cell, or a pathogen infected cell, from a subject, using any of the conjugates or compositions described herein, or any of the conjugates or compositions produced using any of the methods described herein. For example, in some embodiments, unwanted cells can include a stem cell, a proliferating cell, a cell in a hyperplasia, an inflammatory cell, a negative regulatory immune cell, which optionally is a T cell, a pathogen infected cell, a neuron, a fat cell or adipocyte. In some embodiments, the unwanted cell is a cancer cell or a tumor cell. In some embodiments, the unwanted cell is a cancer stem cell or a circulating tumor cell. In some embodiments, the unwanted pathogen can be a virus, a bacterial cell or a fungal cell.

In some embodiments, provided are methods of removing unwanted cells or pathogens, such as a diseased cell, or a pathogen infected cell, from a sample, using any of the conjugates or compositions described herein, or any of the conjugates or compositions produced using any of the methods described herein. For example, the unwanted cells or pathogens are removed from a biological sample from a subject, such as a blood sample or bone marrow sample or a biopsy. In some embodiments, the sample is a blood sample or a tissue sample. In some embodiments, the unwanted cells or pathogens are removed from a tissue, such as a tissue temporarily removed from a subject during surgery or treatment. In some embodiments, the unwanted cells are removed from a sample associated with a device, such as a biofilm on medical devices.

In some embodiments, the irradiation for removal or treatment is effected in vivo, e.g., administered directly to the subject. In some embodiments, the method is performed in vitro, or ex vivo, e.g., outside of the body of the subject. In some embodiments, the method is performed using an extracorporeal device. Exemplary extracorporeal devices include devices used for hemodialysis, extracorporeal oxygenation, $CO_2$ removal, and apheresis, or instruments that receive blood removed from a subject, processes (e.g., filters, purifies, treats, administers therapeutic agents to, etc.) the blood, and then returns the blood to the subject.

In some embodiments of the methods provided herein, removal of unwanted cells or pathogens from a sample, such as a blood sample or a tissue sample, include methods for treatment, such as treatment of a hyperplasia, a tumor or an infection.

In some embodiments, the unwanted cell is associated with, causes or contributes to the etiology of a disease or condition. In some embodiments, the disease of condition is a tumor or cancer, an infection, an inflammatory disease or condition, or a neuronal disease or condition. In some embodiments, the cell is a neuron and the disease or condition is a neurological disorder, which optionally is pain; the cell is a fat cell or adipocyte and the disease or condition involves excess fat; the cell is a pathogen infected cell and the disease or condition is an infection; the cell is a pathogen and the disease or condition is an infection; the cell is an inflammatory cell and the disease or condition is an inflammatory disease; the cell is a an immune cell, which optionally is a regulatory T cell, and the disease or condition is a tumor or cancer; or the cell is a tumor or cancer cell and the disease or condition is a tumor or a cancer. In some embodiments, the cell is present in the microenvironment of a lesion associated with a disease or condition or is in a hyperplasia. In some embodiments, the lesion is a tumor and the disease or condition is a tumor or cancer. In some embodiments, the method treats the disease or condition.

The methods generally include administering to a subject conjugates or compositions provided herein, or conjugates or compositions produced using methods described herein, and irradiating the unwanted cells or pathogens to activate the conjugate and thereby removing the cells.

In some embodiments, the method of removing unwanted cells or pathogens in a subject includes: (a) administering a composition comprising a phthalocyanine-dye conjugate from any of the light-protected device provided herein to a subject, wherein prior to and during the administration step the composition is not exposed to an intensity of environmental light greater than 500 lux; and (b) irradiating the unwanted cells or pathogens at a wavelength of 660 to 740 nm at a dose of at least 1 J $cm^{-2}$ or 1 J/cm of fiber length thereby removing the unwanted cell in the subject.

In some embodiments, the method of removing unwanted cells or pathogens in a subject includes: a) administering to a subject a therapeutically effective amount of any of the conjugates or compositions described herein, wherein prior to and during the administration step the conjugate is not exposed to an intensity of environmental light greater than 500 lux; and b) irradiating the unwanted cells or pathogens at a wavelength of 660 to 740 nm at a dose of at least 1 J $cm^{-2}$ or 1 J/cm of fiber length thereby removing the unwanted cell in the subject.

In some embodiments, the method of removing unwanted cells or pathogens in a subject includes: a) administering to a subject a therapeutically effective amount of a conjugate comprising IRDye 700DX (IR700) linked to a targeting molecule capable of binding an unwanted cell or pathogen, wherein prior to and during the administration step the conjugate is not exposed to an intensity of environmental light greater than 500 lux; and b) irradiating the unwanted cells or pathogens at a wavelength of 600 to 800 nm at a dose of at least 1 J cm$^{-2}$ or 1 J/cm of fiber length thereby removing the unwanted cells or pathogens in the subject.

In some embodiments, the method of removing unwanted cells or pathogens in a subject includes: a) administering to a subject a therapeutically effective amount of a first binding molecule capable of binding an unwanted cell or pathogen; b) administering to the subject a conjugate molecule comprising IRDye 700DX (IR700) linked to a targeting molecule, wherein the targeting molecule is a second binding molecule that is capable of binding to the first binding molecule; and c) irradiating the unwanted cells or pathogens at a wavelength of 600 to 800 nm at a dose of at least 1 J cm$^{-2}$ or 1 J/cm of fiber length thereby removing the unwanted cells or pathogens in the subject. In some embodiments of the methods provided herein, the first binding molecule is administered to the subject prior to the conjugate or the first binding molecule and conjugate are administered simultaneously to the subject. In some embodiments, the targeting molecule is a secondary antibody. In some embodiments, prior to and during the administration of the conjugate, the conjugate is not exposed to an intensity of environmental light greater than 500 lux.

In some embodiments, the method of removing unwanted cells or pathogens, such as pathogen infected cells, in a subject includes: a) administering to a subject a therapeutically effective amount of a conjugate molecule comprising IRDye 700DX (IR700) linked to a targeting molecule, wherein the targeting molecule is capable of binding to the pathogen infected cell directly or indirectly; and b) irradiating the pathogen infected cell at a wavelength of 600 to 800 nm at a dose of at least 1 J cm$^{-2}$ or 1 J/cm of fiber length thereby removing the pathogen infected cell in the subject. In some embodiments, the pathogen is a virus, bacterium, fungus, biofilm, or other prokaryote cell system. In some embodiments, prior to and during the administration of the conjugate, the conjugate is not exposed to an intensity of environmental light greater than 500 lux.

In some embodiments, the subject to be treated, or the subject where unwanted cells or pathogens are removed, has a tumor, and the phthalocyanine dye-targeting molecule conjugate is targeted to the tumor. In some embodiments, the tumor is a cancer. In some embodiments, the cancer is a cancer of the head and neck, breast, liver, colon, ovary, prostate, pancreas, brain, cervix, bone, skin, lung, or blood. In some embodiments, cancer may include a malignant tumor characterized by abnormal or uncontrolled cell growth. Other features that may be associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. Metastatic disease may refer to cancer cells that have left the original tumor site and migrated to other parts of the body, for example via the bloodstream or lymph system. In some embodiments, a cell targeted by the disclosed methods is a cancer cell. In some embodiments, the targeted cell is a cancer stem cell or a circulating tumor cell.

In some embodiments, the tumor cell is a cancer cell, such as a cell in a subject with cancer. Exemplary cells that can be targeted in the disclosed methods include cells of the following tumors: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrom's macroglobulinemia, heavy chain disease). In some embodiments, the cell is a solid tumor cell, such as a sarcoma or carcinoma, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinoma, lung cancer, colorectal cancer, squamous cell carcinoma, basal cell carcinoma, adenocarcinoma, for example adenocarcinoma of the pancreas, colon, ovary, lung, breast, stomach, prostate, cervix, or esophagus, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors, such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma. In some embodiments, the cancer is a squamous cell carcinoma of the head and neck.

Exemplary tumors, such as cancers, that can be treated with the claimed methods include solid tumors, such as breast carcinomas, such as lobular and duct carcinomas, sarcomas, carcinomas of the lung, such as non-small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma, such as serous cystadenocarcinoma and mucinous cystadenocarcinoma, ovarian germ cell tumors, testicular carcinomas and germ cell tumors, pancreatic adenocarcinoma, biliary adenocarcinoma, hepatocellular carcinoma, bladder carcinoma, including, for instance, transitional cell carcinoma, adenocarcinoma, and squamous carcinoma, renal cell adenocarcinoma, endometrial carcinomas, including, for instance, adenocarcinomas and mixed Mullerian tumors (carcinosarcomas), carcinomas of the endocervix, ectocervix, and vagina, such as adenocarcinoma and squamous carcinoma of each of same, tumors of the skin, such as squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma, esophageal carcinoma, carcinomas of the nasopharynx and oropharynx, including squamous carcinoma and adenocarcinomas of same, salivary gland carcinomas, brain and central nervous system tumors, including, for example, tumors of glial, neuronal, and meningeal origin, tumors of peripheral nerve, soft tissue sarcomas and sarcomas of bone and cartilage, and lymphatic tumors, including B-cell and T-cell malignant lymphoma. In some embodiments, the tumor is an adenocarcinoma.

The methods can also be used to treat liquid tumors, such as a lymphatic, white blood cell, or other type of leukemia. In some embodiments, the tumor treated is a tumor of the blood, such as a leukemia, for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia, lymphomas, such as Hodgkin's lymphoma and non-Hodgkin's lymphoma, and myelomas.

In some embodiments, the conjugate is targeted to a protein expressed in the tumor.

In some embodiments, the protein on the cell surface of the target cell to be targeted is not present in significant amounts on other cells. For example, the cell surface protein can be a receptor that is only found on the target cell type.

In some embodiments, the protein expressed in the tumor, e.g. tumor-specific protein, can be HER1/EGFR, HER2/ERBB2, CD20, CD25 (IL-2Rα receptor), CD33, CD52, CD133, CD206, CEA, cancer antigen 125 (CA125), alpha-fetoprotein (AFP), Lewis Y, TAG72, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen SK-lantigen or PD-L1. In some embodiments, the tumor-specific protein is PD-L1, HER1/EGFR, HER2, CD20, CD25, CD33, CD52, or prostate specific membrane antigen (PSMA). Other cell surface proteins include any as described above.

In some embodiments, the cell surface protein is a tumor-specific protein or tumor-specific antigen, such as members of the EGF receptor family (e.g., HER1, 2, 3, and 4) and cytokine receptors (e.g., CD20, CD25, IL-13R, CD5, CD52, etc.). In some embodiments, tumor specific proteins are those proteins that are unique to cancer cells or are much more abundant on them, as compared to other cells, such as normal cells. For example, HER2 is generally found in breast cancers, while HER1 is typically found in adenocarcinomas, which can be found in many organs, such as the pancreas, breast, prostate and colon.

Exemplary tumor-specific proteins that can be found on a target cell, and to which an antibody or antibody fragment specific for that protein can be used to formulate a phthalocyanine dye-antibody conjugate, include but are not limited to: any of the various MAGEs (Melanoma-Associated Antigen E), including MAGE 1, MAGE 2, MAGE 3, and MAGE 4, any of the various tyrosinases, mutant ras, mutant p53, p97 melanoma antigen, human milk fat globule (HMFG) which may be associated with breast tumors, any of the various BAGEs (Human B melanoma-Associated Antigen E), including BAGE1 and BAGE2, any of the various GAGEs (G antigen), including GAGE1, GAGE2-6, various gangliosides, and CD25.

Other tumor-specific antigens include the HPV 16/18 and E6/E7 antigens associated with cervical cancers, mucin (MUC 1)-KLH antigen which may be associated with breast carcinoma, CEA (carcinoembryonic antigen) which may be associated with colorectal cancer, gp100 which may be associated with for example melanoma, MARTI antigens which may be associated with melanoma, cancer antigen 125 (CA125, also known as mucin 16 or MUC16) which may be associated with ovarian and other cancers, alpha-fetoprotein (AFP) which may be associated with liver cancer, Lewis Y antigen which may be associated with colorectal, biliary, breast, small-cell lung, and other cancers, tumor-associated glycoprotein 72 (TAG72) which may be associated with adenocarcinomas, and the PSA antigen which may be associated with prostate cancer.

Other exemplary tumor-specific proteins further include, hut are not limited to, PMSA (prostate membrane specific antigen), which may be associated with solid tumor neovasculature, as well prostate cancer, HER-2 (human epidermal growth factor receptor 2) which may be associated with breast cancer, ovarian cancer, stomach cancer and uterine cancer, HER-1 which may be associated with lung cancer, anal cancer, and glioblastoma as well as adenocarcinomas, NY-ESO-1 which may be associated with melanoma, sarcomas, testicular carcinomas, and other cancers, hTERT (aka telomerase), proteinase 3, and Wilms tumor 1 (WT-1).

In some embodiments, the tumor-specific protein is CD52 and may be associated with chronic lymphocytic leukemia, CD33 and may be associated with acute myelogenous leukemia, or CD20 and may be associated with Non-Hodgkin lymphoma.

Thus, the disclosed methods can be used to treat any cancer that expresses a tumor-specific protein.

In some embodiments, the subject is a human or non-human mammal. In some embodiments, the subject is a human or veterinary subject, such as a mouse. In some embodiments, the subject is a mammal, such as a human, who has cancer, or is being treated for cancer. In some embodiments the disclosed methods are used to treat a subject who has a tumor, such as a tumor described herein. In some embodiments, the tumor has been previously treated, such as surgically or chemically removed, and the disclosed methods are used subsequently to kill any remaining undesired tumor cells that may remain in the subject.

The disclosed methods can be used to treat any mammalian subject, such as a human, who has a tumor, such as a cancer, or has had such previously removed or treated. Subjects in need of the disclosed therapies can include human subjects having cancer, wherein the cancer cells express a tumor-specific protein on their surface that can specifically bind to phthalocyanine dye-targeting molecule conjugate. For example, the disclosed methods can be used as initial treatment for cancer either alone, or in combination with radiation or other chemotherapy. The disclosed methods can also be used in patients who have failed previous radiation or chemotherapy. Thus, in some embodiments, the subject is one who has received other therapies, but those other therapies have not provided a desired therapeutic response. The disclosed methods can also be used in patients with localized and/or metastatic cancer.

In some embodiments, the method includes selecting a subject that will benefit from the disclosed therapies, such as selecting a subject having a tumor that expresses a cell surface protein, such as a tumor-specific protein, that can specifically hind to a phthalocyanine dye-targeting molecule conjugate. For example, if the subject is determined to have a breast cancer that expresses HER1, the subject may be selected to be treated with an anti-HER1-IR700 molecule, such as cetuximab-IR700.

In some embodiments, the composition used for administration of the conjugate contains an effective amount of the conjugate along with conventional pharmaceutical carriers and excipients appropriate for the type of administration contemplated.

In some embodiments, a single dosage amount of the conjugate is comprised within a single container, such as a container in which the conjugate is stored. In some embodiments, the container, such as vial, is one that is packaged under light protected conditions as described above. In some embodiments, a single dosage amount of the conjugate is comprised in a plurality of containers. Thus, in some embodiments, a plurality of containers, such as vials, are combined, in a container to be used for administration of the conjugate, such as an intravenous (IV) bag. In some embodiments, the container used for administration, such as IV bag, is prepared by opening one or a plurality of containers comprising the conjugate and placing the contents in the bag, such as until a desired dose of conjugate for administration, e.g., infusion, is achieved. During the preparation of the administration container, such as IV bag, light precautions were taken to avoid exposure of the conjugate to light, such as the various light precautions described herein.

In some embodiments, the method includes administering to a subject a therapeutically effective amount of the conjugate drug product. In some embodiments, the method includes administering to a subject a therapeutically effective amount of a conjugate containing a dye conjugated to a targeting molecule, e.g., IRDye 700DX-targeting molecule conjugate. In some embodiments, the IRDye 700DX-targeting molecule conjugate is targeted to the tumor.

In some embodiments, a therapeutically effective amount is an amount of a composition that alone, or together with an additional therapeutic agent, such as a chemotherapeutic agent, is sufficient to achieve a desired effect in a subject, or in a cell, being treated with the composition. The effective amount of the therapeutic agent, such as the phthalocyanine dye-targeting molecule conjugate, can be dependent on several factors, including, but not limited to the subject or cells being treated, the particular therapeutic agent, and the manner of administration of the therapeutic composition. In some embodiments, a therapeutically effective amount or concentration is one that is sufficient to prevent advancement, such as metastasis, delay progression, or to cause regression of a disease, or which is capable of reducing symptoms caused by the disease, such as cancer. In some embodiments, a therapeutically effective amount or concentration is one that is sufficient to increase the survival time of a patient with a tumor.

In some embodiments, a desired response of treatment according to the provided methods is to reduce or inhibit one or more symptoms associated with cancer. In some embodiments, the one or more symptoms do not have to be completely eliminated for the composition to be effective. For example, administration of a composition containing the phthalocyanine dye-targeting molecule conjugate followed by irradiation can decrease the size of a tumor, such as the volume or weight of a tumor, or metastasis of a tumor, for example by at least 20%, at least 50%, at least 80%, at least 90%, at least 95%, at least 98%, or at least 100%, as compared to the tumor size, volume, weight, or metastasis in the absence of the conjugate.

In some embodiments, a desired response of treatment according to the provided methods is to kill a population of cells by a desired amount, for example by killing at least 20%, at least 50%, at least 60%, at least 70%, at least 80%, at least 90%, at least 95%, at least 98%, or at least 100% of the cells, as compared to cell killing in the absence of the conjugate and irradiation.

In some embodiments, a desired response is to increase the survival time of a patient with a tumor, or who has had a tumor recently removed, by a desired amount, for example to increase survival by at least 20%, at least 50%, at least 60%, at least 70%, at least 80%, at least 90%, at least 95%, at least 98%, or at least 100%, as compared to the survival time in the absence of the conjugate and irradiation.

The amount of an agent that includes the phthalocyanine dye-targeting molecule conjugate that is administered to a human or veterinary subject will vary depending upon a number of factors associated with that subject, for example the overall health of the subject. In some embodiments, an effective amount of an agent can be determined by varying the dosage of the product and measuring the resulting therapeutic response, such as the regression of a tumor. In some embodiments, effective amounts can be determined through various in vitro, in vivo or in situ immunoassays. In some embodiments, the disclosed agents can be administered in a single dose, or in several doses, as needed to obtain the desired response. In some embodiments, the effective amount is dependent on the source applied, the subject being treated, the severity and type of the condition being treated, and the manner of administration.

In some embodiments, a therapeutically effective dose of the conjugate is at least 0.5 milligram per 60 kilogram (mg/kg), at least 5 mg/60 kg, at least 10 mg/60 kg, at least 20 mg/60 kg, at least 30 mg/60 kg, at least 50 mg/60 kg, for example 0.5 to 50 mg/60 kg, such as a dose of 1 mg/60 kg, 2 mg/60 kg, 5 mg/60 kg, 20 mg/60 kg, or 50 mg/60 kg, for example when administered intravenously. In some embodiments, the dose of the conjugate is at least 10 µg/kg, such as at least 100 µg/kg, at least 500 µg/kg, or at least 500 µg/kg, for example 10 µg/kg to 1000 µg/kg, such as a dose of 100 µg/kg, 250 µg/kg, about 500 µg/kg, 750 µg/kg, or 1000 µg/kg, for example when administered intratumorally or ip. In some embodiments, the dose is at least 1 µg/ml, such as at least 500 µg/ml, such as between 20 µg/ml to 100 µg/ml, such as 10 µg/ml, 20 µg/ml, 30 µg/ml, 40 µg/ml, 50 µg/ml, 60 µg/ml, 70 µg/ml, 80 µg/ml, 90 µg/ml or 100 µg/ml, for example administered in topical solution.

In some embodiments, a therapeutically effective dose of the conjugate is between or between about 10 mg/m$^2$ and 2000 mg/m$^2$, such as between or between about 10 mg/m$^2$ and 1500 mg/m$^2$, 25 mg/m$^2$ and 2000 mg/m$^2$, 200 mg/m$^2$ and 1250 mg/m$^2$, 500 mg/m$^2$ and 1250 mg/m$^2$, 500 mg/m$^2$ and 750 mg/m$^2$, or 750 mg/m$^2$ and 1250 mg/m$^2$. In some embodiments, the therapeutically effective amount is at least or about at least 0.01 mg, 0.1 mg, 0.5 mg, 1 mg, 5 mg, 10 mg, 50 mg, 100 mg, 200 mg, 500 mg, 600 mg, 700 mg, 800 mg, 900 mg, 1000 mg, 2000 mg, 3000 mg or more.

One skilled in the art will recognize that higher or lower dosages also could be used, for example depending on the particular conjugate. In some embodiments, dosages, such as daily dosages, are administered in one or more divided doses, such as 2, 3, or 4 doses, or in a single formulation. The disclosed conjugate can be administered alone, in the presence of a pharmaceutically acceptable carrier, or in the presence of other therapeutic agents, such as other antineoplastic agents.

In some embodiments, the targeting molecule is an antibody, an antigen binding fragment, a protein, a glycoprotein, a peptide, a polypeptide, a virus, a viral capsid, or a viral particle. In some embodiments, the targeting molecule is an antibody or an antigen binding fragment.

In some embodiments, prior to administration of the conjugate, the subject is administered the targeting molecule alone in a form that is non-conjugated, such as an antibody, such as cetuximab. Generally, the targeting molecule that is administered prior to the conjugate is the same targeting molecule that will be administered as part of the conjugate. In some embodiments, the dose of targeting molecule administered is between or between about 10 mg/m$^2$ and 2000 mg/m$^2$, such as between or between about 10 mg/m$^2$ and 1500 mg/m$^2$, 25 mg/m$^2$ and 2000 mg/m$^2$, 200 mg/m$^2$ and 1250 mg/m$^2$, 500 mg/m$^2$ and 1250 mg/m$^2$, 500 mg/m$^2$ and 750 mg/m$^2$, or 25 mg/m$^2$ and 100 mg/m$^2$.

In some embodiments, the targeting molecule is administered at least 1 week, at least 6 days, at least 5 days, at least 96 hours, at least 72 hours, at least 48 hours, at least 24 hours, or at least 12 hours prior to administration of the conjugate. In some embodiments, the targeting molecule is administered within a range from or from about 1 hour to 1 week prior to administration of the conjugate, such as within a range from or from about 1 hour to 96 hours, 1 hour to 48 hours, 1 hour to 24 hours, 24 hours to 96 hours, or 24 hours to 48 hours. In some embodiments, the targeting molecule is administered at or about 96 hours prior to the administration of the conjugate.

In some embodiments, the conjugate may be administered either systemically or locally to the organ or tissue to be treated. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes. In some embodiments, the conjugate is administered intravenously. In some embodiments, the conjugate is administered parenterally. In some embodiments, the conjugate is administered enterally. In some embodiments, the conjugate is administered by local injection. In some embodiments, the conjugate is administered as a topical application.

The composition comprising the conjugate can be administered locally or systemically using any method known in the art, for example to subjects having a tumor, such as a cancer, or who has had a tumor previously removed, for example via surgery. Although specific examples are provided, one skilled in the art will appreciate that alternative methods of administration of the disclosed conjugate can be used. Such methods may include for example, the use of catheters or implantable pumps to provide continuous infusion over a period of several hours to several days into the subject in need of treatment.

In some embodiments, the conjugate is administered by parenteral means, including direct injection direct injection or infusion into a tumor, such as intratumorally. In some embodiments, the conjugate is administered to the tumor by applying the conjugate to the tumor, for example by bathing the tumor in a solution containing the phthalocyanine dye-targeting molecule conjugate or by pouring the conjugate onto the tumor.

In addition, or alternatively, the disclosed compositions can be administered systemically, for example intravenously, intramuscularly, subcutaneously, intradermally, intraperitoneally, subcutaneously, or orally, to a subject having a tumor, such as cancer.

The dosages of the conjugate to be administered to a subject are not subject to absolute limits, but will depend on the nature of the composition and its active ingredients and its unwanted side effects, such as immune response against the antibody, the subject being treated, and the type of condition being treated and the manner of administration. Generally, the dose will be a therapeutically effective amount, such as an amount sufficient to achieve a desired biological effect, for example an amount that is effective to decrease the size, such as volume and/or weight, of the tumor, or attenuate further growth of the tumor, or decrease undesired symptoms of the tumor.

In some embodiments, for example for intravenous administration of the conjugate, exemplary dosages for administration to a subject for a single treatment can range from 0.5 to 100 mg/60 kg of body weight, 1 to 100 mg/60 kg of body weight, 1 to 50 mg/60 kg of body weight, 1 to 20 mg/60 kg of body weight, for example, about 1 or 2 mg/60 kg of body weight. In some embodiments, a therapeutically effective amount of intraperitoneally or intratumorally administered conjugate can vary from 10 µg to 5000 µg of conjugate to 1 kg of body weight, such as 10 µg/kg to 1000 µg/kg, 10 µg/kg to 500 µg/kg, or 100 µg/kg to 1000 µg/kg. In some embodiments, the conjugate is administered in an amount that is from or from about 0.5 mg/kg to about 100 mg/kg or 20 mg/m$^2$ to about 4000 mg/m$^2$. In some embodiments, the conjugate is administered in an amount that is at least or about at least or is or is about 0.5 mg/kg, 2.0 mg/kg, 4.0 mg/kg, 8.0 mg/kg, 16.0 mg/kg, 32.0 mg/kg or 64 mg/kg; or the conjugate is administered in an amount that is at least or about at least or is or is about 20 mg/m$^2$, 40 mg/m$^2$, 160 mg/m$^2$, 320 mg/m$^2$, 640 mg/m$^2$, 1280 mg/m$^2$ or 2560 mg/m$^2$.

In some embodiments, the dose of conjugate administered to a human patient is at least 50 mg, such as at least 100 mg, at least 300 mg, at least 500 mg, at least 750 mg, or even 1 g.

Treatments with disclosed conjugate can be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals.

In some embodiments, the composition used for administration of the conjugate contains an effective amount of the conjugate along with conventional pharmaceutical carriers and excipients appropriate for the type of administration contemplated. For example, in some embodiments, parenteral formulations may contain a sterile aqueous solution or suspension of the conjugate. In some embodiments, compositions for enteral administration may contain an effective amount of the conjugate in aqueous solution or suspension that may optionally include buffers, surfactants, thixotropic agents, and flavoring agents.

In some embodiments, the method includes irradiating the tumor. In some embodiments, the irradiation is effected between or between about 30 minutes and 96 hours after administering the conjugate, such as between 30 minutes and 48 hours, 30 minutes and 24 hours or 12 hours and 48 hours, such as generally at least 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more after administering the conjugate. For example, the irradiation can be performed within about 24 hours after administering the conjugate.

In some embodiments, after the cells are contacted with the phthalocyanine dye-targeting molecule conjugate, they are irradiated. Methods of irradiation are known in the art. As only cells expressing the cell surface protein will typically be recognized by the targeting molecule, generally only those cells will have sufficient amounts of the conjugate bound to it. This may decrease the likelihood of undesired side effects, such as killing of normal cells, as the irradiation may only kill the cells to which the conjugate is bound, and generally not other cells.

In some embodiments, cells are irradiated in vitro, such as in a tissue culture dish. In some embodiments, a cell is irradiated in vivo, for example irradiating a subject who has previously been administered the phthalocyanine dye-targeting molecule conjugate. In some embodiments, the subject is irradiated, for example a tumor in the subject can be irradiated.

In some embodiments, a light or laser may be applied to the dye molecules, such as cells containing the conjugate, for from about 5 seconds to about 5 minutes. For example, in some embodiments, the light or laser is applied for or for about 5, 10, 15, 20, 25, 30, 35, 40, 45 50 or 55 seconds, or for within a range between any of two such values, to activate the dye molecules. In some embodiments, the light or laser is applied for or for about 1, 1.5, 2, 2.5, 3, 3.5, 4, 4.5 or 5 minutes, or more, or within a range between any two of such values. In some embodiments, the length of time a light or laser is applied can vary depending, for example, on the energy, such as wattage, of the light or laser. For example, lights or lasers with a lower wattage may be applied for a longer period of time in order to activate the dye molecule.

In some embodiments, a light or laser may be applied about 30 minutes to about 48 hours after administering the conjugate. For example, in some embodiments, the light or laser is applied at or at about 30, 35, 40, 45, 50 or 55 minutes after administering the conjugate, or within a range between any two of such values. In some embodiments, the light or laser is applied at or at about 1, 2, 3, 4, 5, 6, 7, 8, 9, 10, 11, 12, 13, 14, 15, 16, 17, 18, 19, 20, 21, 22, 23 or 24 hours after administering the conjugate, or is administered within a range between or between about any two of such values. In some embodiments, the light or laser is applied for between or between about 1 and 24 hours, such as between or between about 1 and 12 hours, 12 and 24 hours, 6 and 12 hours, or may be administered more than 24 following administration of the conjugate. In some embodiments, the light or laser is applied 36 or 48 hours after administering the conjugate. In some embodiments, the cells, hyperplasia or tumor is irradiated within or within about or about 12 hours, 24 hours, 36 hours, 72 hours or 96 hours after administering the conjugate.

In some embodiments, the dye molecules of the conjugate can be activated at a suitable wavelength. Thus, in some embodiments, the cells are irradiated with a therapeutic dose of radiation at a wavelength of from or from about 660-710 nm, such as 660-700 nm or 670-690 nm, for example, 680 nm. In some embodiments, activation of the dye molecules renders them cytotoxic or able to produce a cytotoxic molecule. Suitable wavelengths include, without limitation, ultraviolet wavelengths, visible wavelengths, infrared wavelengths and near infrared wavelengths. In some embodiments, the dye molecules are activated and become cytotoxic at a wavelength of from or from about 600 nm to 800 nm, or 660 nm to 740 nm. In some embodiments, the dye molecules are activated and become cytotoxic at a wavelength of about or at least about 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm or 800 nm, or within a range between or between about any 2 of such wavelengths. In some embodiments, the dye molecules are activated at a wavelength of less than 600 nm or more than 800 nm.

In some embodiments, the tumor is irradiated at a wavelength within a range from or from about 600 nm to 800 nm or 600 nm to 740 nm, such as 640 nm to 760 nm, 660 nm to 740 nm, 680 nm to 720 nm, or 690 nm to 710 nm. In some embodiments, the tumor is irradiated at a wavelength of 690±50 nm.

Suitable wavelengths for dye molecule activation may depend on the particular dye molecule used.

In some embodiments, the cells, hyperplasia or tumor are irradiated at a dose of at least or about 1 J cm$^{-2}$ (1 J/cm$^2$), such as at least or about 10 J cm$^{-2}$, at least or about 30 J cm$^{-2}$, at least or about 50 J cm$^{-2}$, at least or about 100 J cm$^{-2}$, or at least or about 500 J cm$^{-2}$, such as at least about 2 J cm$^{-2}$, 5 J cm$^{-2}$, 10 J cm$^{-2}$, 25 J cm$^{-2}$, 50 J cm$^2$, 75 J cm$^{-2}$, 100 J cm$^{-2}$, 150 J cm$^{-2}$, 200 J cm$^{-2}$, 300 J cm$^{-2}$, 400 J cm$^{-2}$, or 500 J cm$^{-2}$. For example, in some embodiments, the cells, hyperplasia or tumor are irradiated at from or from about 1-1000 J cm$^{-2}$, 1-500 J cm$^{-2}$, 10-100 J cm$^{-2}$, or 10-50 J cm$^{-2}$. In some embodiments, the tumor is irradiated at a dose of at least 0.5 J cm$^{-2}$, at least 1 J cm$^{-2}$, at least 2 J cm$^{-2}$, at least 3 J cm$^{-2}$, at least 4 J cm$^{-2}$, or at least 5 J cm$^{-2}$. In some embodiments, the cells, hyperplasia or tumor is irradiated at a dose of 1 J cm$^{-2}$. In some embodiments, the cells, hyperplasia or tumor are irradiated at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length. In some embodiments, the cells are irradiated at a dose of at least 1 J cm$^{-J}$ or 1 J/cm of fiber length. In some embodiments, the cell, hyperplasia or tumor is irradiated at a dose of from or from about 2 J cm$^{-2}$ to about 400 J cm$^{-2}$ or from or from about 2 J/cm fiber length to about 500 J/cm fiber length.

In some embodiments, the tumor is a superficial tumor. In some embodiments, the tumor is irradiated at a dose of at least or about at least or about 10 J/cm$^2$, 25 J/cm$^2$, 50 J/cm$^2$, 150 J/cm$^2$, or 250 J/cm$^2$.

In some embodiments, the tumor is an interstitial tumor. In some embodiments, the tumor is irradiated at a dose of at least or about at least or about 50 J/cm fiber length, 100 J/cm fiber length, 200 J/cm fiber length, or 300 J/cm fiber length.

In some embodiments, the dose of irradiation following administration of the composition comprising the phthalocyanine dye-targeting molecule conjugate is at least 1 J cm$^{-2}$ at a wavelength of 660-740 nm, for example, at least 10 J cm$^{-2}$ at a wavelength of 660-740 nm, at least 50 J cm$^{-2}$ at a wavelength of 660-740 nm, or at least 100 J cm$^{-2}$ at a wavelength of 660-740 nm, for example 1 to 500 1.0 J cm$^{-2}$ at a wavelength of 660-740 nm. In some embodiments, the wavelength is 660-710 nm. In some embodiments, the dose of irradiation following administration of the composition comprising the phthalocyanine dye-targeting molecule conjugate is at least 1.0 J cm$^{-2}$ at a wavelength of 680 nm for example, at least 10 J cm$^{-2}$ at a wavelength of 680 nm, at least 50 J cm$^{-2}$ at a wavelength of 680 nm, or at least 100 J cm$^{-2}$ at a wavelength of 680 nm, for example 1 to 500 1.0 J cm$^{-2}$ at a wavelength of 680 nm. In some embodiments, multiple irradiations are performed, such as at least 2, at least 3, or at least 4 irradiations, such as 2, 3, 4, 5, 6, 7, 8, 9 or 10 separate administrations.

In some embodiments, cells, or subjects, can be irradiated one or more times. Thus, irradiation can be completed in a single day, or may be done repeatedly on multiple days with the same or a different dosage, such as irradiation at least 2 different times, 3 different times, 4 different times 5 different times or 10 different times. In some embodiments, repeated irradiations may be done on the same day, on successive days, or every 1-3 days, every 3-7 days, every 1-2 weeks, every 2-4 weeks, every 1-2 months, or at even longer intervals.

In some embodiments, prior to, during, or following administration of the conjugate, the subject can receive one or more other therapies. In some embodiments, the subject receives one or more treatments to remove or reduce the tumor prior to administration of the conjugate.

Additional Treatments

Prior to, during, or following administration of the phthalocyanine dye-targeting molecule conjugate, the subject can receive one or more other therapies. In one example, the subject receives one or more treatments to remove or reduce the tumor prior to administration of the conjugate.

In some embodiments, the other or additional agent or agents administered, or the additional agent in a combination therapy, is an unconjugated targeting molecule. In some embodiments, the unconjugated targeting molecule is the same or substantially the same targeting molecule as the targeting molecule of the conjugate. For example, in some embodiments, prior to administration of the conjugate, the targeting molecule, e.g., an unconjugated antibody that targets a protein or antigen, is administered to the subject. In some embodiments, the targeting molecule is administered up to 96 hours prior to administration of the conjugate. In some embodiments, the targeting molecule is administered at a dose within a range from or from about 10 mg/m$^2$ to about 500 mg/m$^2$. For example, the targeting molecule is cetuximab, and cetuximab is administered to the subject up to 96 hours prior to administration of the conjugate.

Examples of such therapies that can be used in combination with the disclosed PIT methods, which may enhance accessibility of the tumor to additional therapeutic agents for about 8 hours after the PIT, include but are not limited to, surgical treatment for removal or reduction of the tumor, such as surgical resection, cryotherapy, or chemoembolization, as well as anti-tumor pharmaceutical treatments which can include radiotherapeutic agents, anti-neoplastic chemotherapeutic agents, antibiotics, alkylating agents and antioxidants, kinase inhibitors, and other agents. In some examples, the additional therapeutic agent is conjugated to a nanoparticle. Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, and gene regulators. These agents, which are administered at a therapeutically effective amount, and treatments can be used alone or in combination. Methods and therapeutic dosages of such agents are known to those skilled in the art, and can be determined by a skilled clinician.

In some embodiments, microtubule binding agent refers to an agent that interacts with tubulin to stabilize or destabilize microtubule formation thereby inhibiting cell division. Examples of microtubule binding agents that can be used in conjunction with the disclosed conjugate therapies include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used. For example, suitable epothilones and epothilone analogs may be used. Taxoids, such as paclitaxel and docetaxel also can be used.

The following classes of compounds can be used with the PIT methods disclosed herein: suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof. Kinase inhibitors include Gleevac, Iressa, and Tarceva that prevent phosphorylation and activation of growth factors.

Other therapeutic agents, for example anti-tumor agents, that may or may not fall under one or more of the classifications above, also are suitable for administration in combination with the disclosed PIT therapies. By way of example, such agents include adriamycin, apigenin, rapamycin, zebularine, cimetidine, and derivatives and analogs thereof.

In some examples, the subject receiving the therapeutic conjugate composition is also administered interleukin-2 (IL-2), for example via intravenous administration. In some embodiments, IL-2 is administered, such as at a dose of at least 500,000 IU/kg as an intravenous bolus, such as over a 15 minute period every eight hours, beginning on the day after administration of the peptides and continuing for up to 5 days. Doses can be skipped depending on subject tolerance.

Further examples of therapies that can be used in combination with administration of the conjugate include, but are not limited to, surgical treatment for removal or reduction of the tumor, such as surgical resection, cryotherapy, or chemoembolization, as well as anti-tumor pharmaceutical treatments which can include radiotherapeutic agents, anti-neoplastic chemotherapeutic agents, antibiotics, alkylating agents and antioxidants, kinase inhibitors, and other agents. Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, gene regulators, and DARPins (designed ankyrin repeat proteins), such as mono-DARPins. These agents, which may be administered at a therapeutically effective amount, and treatments, can be used alone or in combination. Methods and therapeutic dosages of such agents can be determined by a skilled clinician.

In some embodiments, at least a portion of the tumor, such as a metastatic tumor, is surgically removed, for example via cryotherapy, irradiated, chemically treated, for example via chemoembolization, or combinations thereof, prior to administration of the disclosed therapies, such as administration of phthalocyanine dye-targeting molecule conjugate. For example, a subject having a metastatic tumor can have all or part of the tumor surgically excised prior to administration of the disclosed therapies. In some embodiments, one or more chemotherapeutic agents are administered following treatment with conjugate and irradiation. In some embodiments, the subject has a metastatic tumor and is administered radiation therapy, chemoembolization therapy, or both concurrently with the administration of the disclosed therapies.

III. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a "conjugate" refers to a polypeptide linked directly or indirectly to one or more other molecules, such as polypeptides or chemical moieties. Such conjugates include fusion proteins, those produced by chemical conjugates and those produced by any other methods. For example, a conjugate can refer to a phthalocyanine dye, such as an IR700 molecule, linked directly or indirectly to one or more other molecules, such as polypeptides or chemical moieties, such as to a targeting molecule that binds to or targets to a cell surface protein.

As used herein, a composition refers to any mixture of two or more products, substances, or compounds, including cells. It may be a solution, a suspension, liquid, powder, a paste, aqueous, non-aqueous or any combination thereof.

As used herein, a "pharmaceutical composition" or "pharmaceutical formulation" refers to a preparation which is in such form as to permit the biological activity of an active ingredient contained therein to be effective, and which contains no additional components which are unacceptably toxic to a subject to which the formulation would be administered.

As used herein, a "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, a kit is a packaged combination that optionally includes other elements, such as additional reagents and instructions for use of the combination or elements thereof.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, an "article of manufacture" is a product that is made and, in some cases, that can be sold. In some embodiments, the term can refer to compositions contained in articles of packaging, such as in a container.

As used herein, "disease or disorder" refers to a pathological condition in an organism resulting from cause or condition including, but not limited to, infections, acquired conditions, genetic conditions, and characterized by identifiable symptoms. Diseases and disorders of interest herein are those that are treatable by immune globulin.

As used herein, "treating" a subject with a disease or condition means that the subject's symptoms are partially or totally alleviated, or remain static following treatment. Hence treating encompasses prophylaxis, therapy and/or cure. Prophylaxis refers to prevention of a potential disease and/or a prevention of worsening of symptoms or progression of a disease.

As used herein, "treatment" means any manner in which the symptoms of a condition, disorder or disease or other indication, are ameliorated or otherwise beneficially altered.

As used herein, "therapeutic effect" means an effect resulting from treatment of a subject that alters, typically improves or ameliorates the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect. Hence, it is the quantity necessary for preventing, curing, ameliorating, arresting or partially arresting a symptom of a disease or disorder.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, the term "subject" refers to an animal, including a mammal, such as a human being.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

IV. Exemplary Embodiments

Among the embodiments provided herein are:

1. A method of manufacturing a phthalocyanine dye-targeting molecule conjugate, comprising:

a) contacting a targeting molecule with a phthalocyanine dye under conditions to produce a conjugate comprising the phthalocyanine dye linked to the targeting molecule; and b) formulating the conjugate in a pharmaceutically acceptable buffer, wherein in each of steps a)-b):

the only light to which the dye and conjugate are exposed has a wavelength within a range from about 400 nm to about 650 nm, or the only light to which the dye and conjugate are exposed has an intensity of less than 500 lux.

2. A method of manufacturing a phthalocyanine dye-targeting molecule conjugate, comprising:

a) contacting a targeting molecule with a phthalocyanine dye at a molar ratio of dye to targeting molecule of from or from about 1:1 to 1000:1 under conditions to produce a conjugate comprising the phthalocyanine dye covalently linked to the targeting molecule; and b) formulating the conjugate in a pharmaceutically acceptable buffer to a concentration from or from about 0.01 mg/mL to about 200.0 mg/mL, wherein in each of steps a)-b):

the only light to which the dye and conjugate are exposed has a wavelength within a range from about 400 nm to about 650 nm, or the only light to which the dye and conjugate are exposed has an intensity of less than 500 lux.

3. The method of embodiment 1 or embodiment 2, wherein the conjugate is formulated to a concentration from or from about 0.01 mg/mL to about 200.0 mg/mL or from about 0.5 mg/mL to about 10.0 mg/mL.

4. The method of any of embodiments 1-3, wherein the conjugate is formulated to a concentration from or from about 0.5 mg/mL to about 5.0 mg/mL.

5. The method of any of embodiments 1-4, wherein prior to the contacting step, the phthalocyanine dye is dissolved in a solvent under conditions in which the only light to which the dye is exposed has a wavelength within a range from about 400 nm to about 650 nm, or the only light to which the dye is exposed has an intensity of less than 500 lux.

6. The method of embodiment 5, wherein the dye is dissolved in the solvent to a concentration in a range from or from about 0.1 mg/mL to about 100 mg/mL.

7. The method of embodiment 5 or embodiment 6, wherein the dye is dissolved in the solvent to a concentration from or from about 1 mg/mL to about 50 mg/mL.

8. The method of any of embodiments 1-7, wherein the concentration of the phthalocyanine dye in the solvent is about 10 mg/mL.

9. The method of any of embodiments 5-8, wherein the solvent is selected from dimethylsulfoxide (DMSO) and DMF and water-based solvent.

10. The method of any of embodiments 5-9, wherein the solvent is DMSO.

11. The method of any of embodiments 1-10, wherein the formulating step comprises concentrating the conjugate.

12. The method of any of embodiments 1-11, wherein the contacting step is carried out for at least 15 minutes at a temperature between or between about 4° C. and about 37° C.

13. The method of any of embodiments 1-12, wherein the contacting step is carried out for 90 minutes to 150 minutes.

14. The method of any of embodiments 1-13, wherein the contacting step is carried out at a temperature of about 25° C.±1.0° C.

15. The method of any of embodiments 1-14, wherein the phthalocyanine dye is covalently or non-covalently linked to the targeting molecule.

16. The method of any of embodiments 1-14, wherein the phthalocyanine dye comprises a reactive chemical group and contacting the phthalocyanine dye and targeting molecule produces a conjugate comprising the phthalocyanine dye covalently bound to an attachment group of the targeting molecule.

17. The method of embodiment 16, further comprising quenching the conjugate prior to the concentrating step, wherein:

the only light to which the conjugate is exposed during the quenching step has a wavelength within a range from about 400 nm to about 650 nm, or the only light to which the conjugate is exposed during the quenching step has an intensity of less than 500 lux.

18. The method of any of embodiments 1-17, wherein the formulating step comprises ultrafiltration, diafiltration or dialysis.

19. The method of any of embodiments 1-18, further comprising sterile filtration of the conjugate.

20. The method of any of embodiments 1-19, further comprising d) packaging the conjugate in one or more light-protected container, wherein during the packaging step:

the only light to which the conjugate is exposed has a wavelength within a range from about 400 nm to about 650 nm, or the only light to which the dye and conjugate are exposed has an intensity of less than 500 lux.

21. A method of manufacturing a phthalocyanine dye-targeting molecule conjugate, comprising:

a) dissolving a phthalocyanine dye in a solvent to a concentration of about 0.1-100 mg/mL;

b) contacting a targeting molecule with the phthalocyanine dye at a molar ratio of dye to targeting molecule from 1:1 to 1000:1 under conditions to produce a conjugate comprising the phthalocyanine dye linked to the targeting molecule;

c) formulating the conjugate in a pharmaceutically acceptable buffer to a concentration from or from about 0.01 to about 200.0 mg/mL; and d) packaging the conjugate in one or more light-protected container, wherein in each of steps a)-d):

the only light to which the dye and conjugate are exposed has a wavelength within a range from about 400 nm to about 650 nm, or the only light to which the dye and conjugate are exposed has an intensity of less than 500 lux.

22. The method of embodiment 21, wherein the phthalocyanine dye is covalently or non-covalently linked to the targeting molecule.

23. The method of embodiment 21 or embodiment 22, wherein the phthalocyanine dye comprises a reactive chemical group and contacting the phthalocyanine dye and targeting molecule produces a conjugate comprising the phthalocyanine dye covalently bound to an attachment group of the targeting molecule.

24. The method of any of embodiments 1-23, wherein during the method the total exposure of the dye and conjugate to any light is for no more than 5000 lux hours, no more than 2500 lux hours, no more than 1000 lux hours, no more than 500 lux hours, no more than 250 lux hours, no more than 100 lux hours or no more than 80 lux hours.

25. The method of any of embodiments 20-24, wherein during the packaging step the total exposure of the conjugate to any light is for no more than 5000 lux hours, no more than 2500 lux hours, no more than 1000 lux hours, no more than 500 lux hours, no more than 250 lux hours, no more than 100 lux hours or no more than 80 lux hours.

26. The method of any of embodiments 1-25, wherein the dye has a maximum absorption wavelength from or from about 600 nm to about 850 nm.

27. The method of any of embodiments 1-26, wherein the dye has a maximum absorption wavelength from or from about 650 nm to about 850 nm.

28. The method of any of embodiments 1-27, wherein the dye has a maximum absorption wavelength from or from about 680 nm to about 850 nm.

29. The method of any of embodiments 1-28, wherein the phthalocyanine dye comprises the formula:

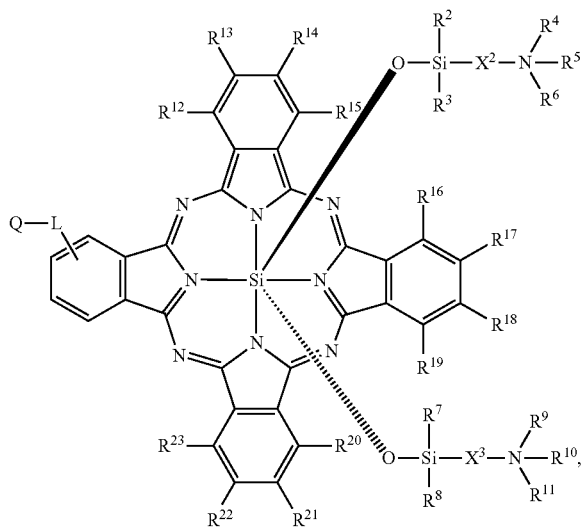

wherein:

L is a linker;

Q is a reactive group for attachment of the dye to the targeting molecule;

$R^2$, $R^3$, $R^7$, and $R^8$ are each independently selected from among optionally substituted alkyl and optionally substituted aryl;

$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from among hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

30. The method of any of embodiments 1-29, wherein the reactive group is selected from among an amine-reactive chemical group, a sulfhydryl-reactive chemical group, an activated ester, an acyl halide, an alkyl halide, an anhydride, a carboxylic acid, a carbodiimide, a carbonate, a carbamate, a haloacetamide, an isocyanate, an isothiocyanate, a maleimide, a phosphoramidite, a platinum complex, a sulfonate ester and a thiocyanate.

31. The method of any of embodiments 30, wherein the reactive chemical group is a sulfhydryl-reactive chemical group selected from among maleimides, haloacetyls and pyridyl disulfides.

32. The method of any of embodiments 1-30, wherein the phthalocyanine dye is covalently bound to a lysine residue of the targeting molecule.

33. The method of embodiment 32, wherein the reactive group is an amine-reactive chemical group that is an N-hydroxysuccinimide (NHS) ester.

34. The method of any of embodiments 1-30 and 32-33, wherein the phthalocyanine dye comprises the formula:

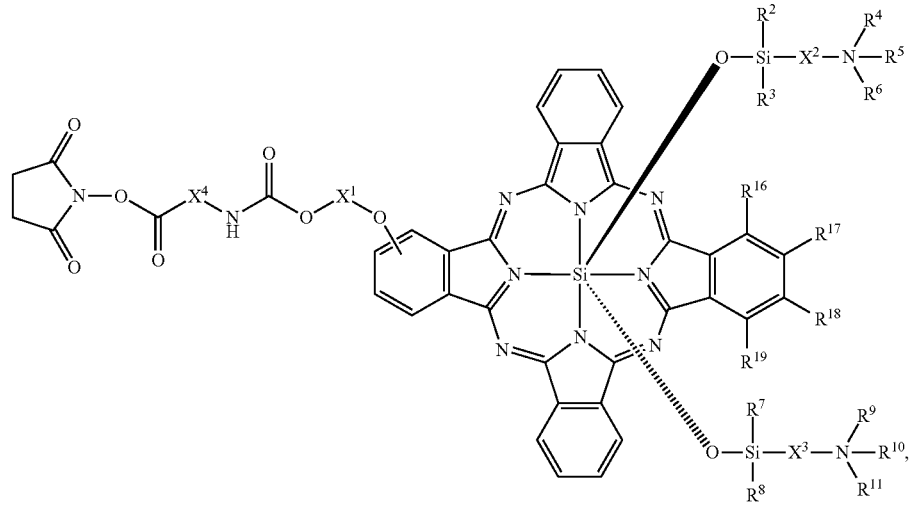

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from among hydrogen, halogen, optionally substituted alkylthio, optionally substituted alkylamino and optionally substituted alkoxy.

35. The method of any of embodiments 1-34, wherein the phthalocyanine dye comprises IRDye 700DX-NHS (IR700-NHS).

36. The method of any of embodiments 1-35, wherein the targeting molecule binds to an antigen or protein directly or indirectly.

37. The method of embodiment 36, wherein the targeting molecule is a second binding molecule that binds to a first binding molecule, said first binding molecule being capable of binding to the antigen or protein.

38. The method of embodiment 36 or embodiment 37, wherein the targeting molecule is a secondary antibody.

39. The method of any of embodiments 1-38, wherein the targeting molecule binds a cell surface target molecule on a surface of a cell or a pathogen.

40. The method of embodiment 39, wherein the cell is a stem cell, a proliferating cell, a cell in a hyperplasia, or a pathogen infected cell.

41. The method of embodiment 39 or embodiment 40, wherein the pathogen is selected from among viruses, bacteria, fungi, biofilms, and other prokaryote cell systems.

42. The method of embodiment 39 or embodiment 40, wherein the cell is a cancer cell, a tumor cell, an inflammatory cell or a neuron.

43. The method of any of embodiments 39-42, wherein the cell is present in the microenvironment of a lesion associated with a disease or condition.

44. The method of embodiment 43, wherein the lesion is a tumor and the cell is a cancer cell or a tumor cell.

45. The method of embodiment 39 or embodiment 40, wherein the cell is a cancer stem cell or a circulating tumor cell.

46. The method of embodiment 42, wherein the inflammatory cell is a leukocyte selected from among a neutrophil, an eosinophil, a basophil, a lymphocyte, and a monocyte.

47. The method of embodiment 42, wherein the neuron is a peripheral nervous system neuron or a central nervous system neuron.

48. The method of embodiment 42 or embodiment 47, wherein the neuron is a nociceptor selected from among thermal nociceptors, mechanical nociceptors, chemical nociceptors and polymodal nociceptors.

49. The method of any of embodiments 39-48, wherein the cell surface target molecule comprises an antigen, a polypeptide, a lipid, or a carbohydrate, or a combination thereof.

50. The method of any of embodiments 39-49, wherein the cell surface target molecule is selected from among cell membrane phospholipids, prokaryotic peptidoglycans, bacterial cell envelop proteins, viral capsid proteins, ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p'75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g. P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g. TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

51. The method of any of embodiments 39-50, wherein the cell surface target molecule is selected from among HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-lantigen, Bcr-abl, RET, MET, TRKB, TIE2, ALK, ROS, EML4-ALK, ROS1, BRAFV600E, SRC, c-KIT, PDGFR, mTOR, TSC1, TSC2, BTK, KIT, BRCA, CDK 4/6, JAK1, JAK2, BRAF, FLT-3, MEK1, MEK2, and SMO.

52. The method of any of embodiments 39-51, wherein the cell surface target molecule is HER1/EGFR, HER2, PD-L1, CD25, EpCAM, EphA2, CD206, CD20, CD44, CD133, Mesothelin, Glypican-3, or carcinoembryonic antigen (CEA).

53. The method of any of embodiments 1-52, wherein at least part of the targeting molecule is selected from or is a combination of a protein, a glycoprotein, an antibody, an antibody fragment, an antigen, an antigen binding fragment, a peptide, a polypeptide, a tissue homing peptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, an aptamer, nucleotide triphosphates, acyclo terminator triphosphates, or PNA.

54. The method of any of embodiments 1-53, wherein the targeting molecule is a tissue-specific homing peptide.

55. The method of embodiment 54, wherein the homing peptide has the sequence of amino acids as set forth in any of SEQ ID NOS: 1-52.

56. The method of any of embodiments 1-53, wherein the targeting molecule is an RGD polypeptide, an iRGD polypeptide, a Lyp-1 polypeptide, a cripto-1 binding polypeptide, a somatostatin receptor binding polypeptide, a prohibitin binding polypeptide, a NGR polypeptide, an iNGR polypeptide, or an activatable cell penetrating peptide (ACPP) comprised of a polycationic cell penetrating peptide (CPP) connected via a cleavable linker to a neutralizing polyanion.

57. The method of any of embodiments 1-53, wherein the targeting molecule is selected from among adrenocorticotropic hormone (ACTH), angiotensin II, atrial natriuretic factor (ANF), bombesin, bradykinin, brain derived neurotropihic factor (BDNF), bone morphogenetic protein 2 (BMP-2), bone morphogenetic protein 6 (BMP-6), bone morphogenetic protein 7 (BMP-7), calcitonin, cardiotrophin 1 (BMP-2), CD22, CD40, cholecystokinin (CCK), ciliary neurotrophic factor (CNTF), CCL1-CCL28, CXCL1-CXCL17, XCL1, XCL2, CX3CL1, cripto 1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-a), interferon beta (IFN-b), interferon gamma (IFNg), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 3G (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMA5A), semaphorin 5B (SEMA5B), semaphorin 6A (SEMA6A), semaphorin 6B (SEMA6B), semaphorin 6D (SEMA6D), semaphorin 7A (SEMA7A), SLIT1, SLIT2, SLIT3, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-α), transforming growth factor beta (TGF-b), tumor necrosis factor alpha (TNF-α), thrombin, vasoactive intestinal peptide (VIP), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

58. The method of any of embodiments 1-53, wherein the targeting molecule is an antibody or an antibody fragment.

59. The method of embodiment 58, wherein the antibody is selected from among cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, BMS-935559, MPDL3280A, Pidilizumab (CT-011), AMP-224, MSB001078C, and MEDI4736, or is an antigen-binding fragment thereof.

60. The method of embodiment 58, wherein the antibody binds to a cell surface target molecule selected from among HER1/EGFR, HER2, PD-L1, and carcinoembryonic antigen (CEA).

61. The method of any of embodiments 58-60, wherein the antibody is selected from among cetuximab, Panitumumab, Trastuzumab, BMS-935559, MEDI4736, MPDL3280A and MSB0010718C, or is an antigen-binding fragment thereof.

62. The method of any of embodiments 1-61, wherein the dye-targeting molecule conjugate is selected from among cetuximab-IR700, Panitumumab-IR700, Trastuzumab-IR700, BMS-935559-IR700, MEDI4736-IR700, MPDL3280A-IR700 and MSB0010718C-IR700.

63. The method of any of embodiments 1-62, wherein step b) of contacting a targeting molecule with the phthalocyanine dye is at a molar ratio of dye to targeting molecule from 1:1 to 100:1 or 1:1 to 10:1.

64. The method of any of embodiments 1-63, wherein the molar ratio of dye to targeting molecule is at least or at least about 4:1 or is at least or at least about 10:1.

65. The method of any of embodiments 1-64, wherein the produced conjugate comprises from or from about 1 to about 1000 phthalocyanine dye molecules per targeting molecule, from or from about 1 to about 10 phthalocyanine dye molecules per targeting molecule or from or from about 2 to about 5 phthalocyanine dye molecules per targeting molecule.

66. The method of any of embodiments 1-65, wherein the conjugate is formulated to a concentration that is from or from about 1.0 to about 5.0 mg/mL.

67. The method of any of embodiments 1-66, wherein the pharmaceutically acceptable buffer is phosphate buffered saline.

68. The method of any of embodiments 1-67, wherein the pharmacologically acceptable buffer comprises a pH from or from about pH 6.0 to about pH 8.0, wherein the conjugate is stable for greater than 3 months.

69. The method of embodiment 68, wherein the conjugate is stable if it retains greater than or greater than about 30%, 40%, 50%, 60%, 70%, 80%, 90% or more of its potency, activity or purity for greater than 3 months compared to the conjugate prior to the storage for the time.

70. The method of embodiment 68, wherein the conjugate is stable if greater than 90% of the conjugate is present as a main monomer component.

71. The method of any of embodiments 68-70, wherein the pharmacologically acceptable buffer comprises a pH from or from about pH 6.8 to about pH 7.4.

72. The method of any of embodiments 1-71, wherein the only light to which the dye and conjugate are exposed has a wavelength within a range from about 425 nm to about 575 nm.

73. The method of any of embodiments 1-72, wherein the only light to which the dye and conjugate are exposed has an intensity of less than 200 lux.

74. The method of any of embodiments 20-73, wherein the container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

75. The method of embodiment 74, wherein the container protects from transmission of light such that the percentage of light transmission is less than 50%, less than 40%, less than 30%, less than 20%, less than 10% or less than 5%.

76. The method of any of embodiments 20-75, wherein the container is green, blue, amber, translucent, opaque, or is covered by a material with light transmission of less than 50%, less than 40%, less than 30%, less than 20%, less than 10% or less than 5%.

77. The method of any of embodiments 20-76, wherein the container is selected from among a vial, a tube, a syringe, a bag, a pouch, and a box.

78. The method of any of embodiments 20-77, wherein the light-protected container is a first light-protected container and the method further comprises packing the first light-protected container into a second light-protected container.

79. The method of embodiment 78, wherein the second container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

80. The method of embodiment 78 or embodiment 79, wherein the second container protects from transmission of light such that the percentage of light transmission is less than 50%, less than 40%, less than 30%, less than 20%, less than 10% or less than 5%.

81. The method of any of embodiments 78-80, wherein the second container is green, blue, amber, translucent, opaque, or is covered by a material with light transmission of less than 50%, less than 40%, less than 30%, less than 20%, less than 10% or less than 5%.

82. The method of any of embodiments 78-81, wherein the second container is selected from among a vial, a tube, a syringe, a bag, a pouch, and a box.

83. The method of any of embodiments 78-82, further comprising packaging the second container into a third light-protected container.

84. The method of embodiment 83, wherein the third container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

85. The method of embodiment 84, wherein the third container protects from transmission of light such that the percentage of light transmission is less than 50%, less than 40%, less than 30%, less than 20%, less than 10% or less than 5%.

86. The method of embodiment 84 or embodiment 85, wherein the third container is green, blue, amber, translucent, opaque, or is covered by a material with light transmission of less than 50%, less than 40%, less than 30%, less than 20%, less than 10% or less than 5%.

87. The method of any of embodiments 83-86, wherein the third container is selected from among a vial, a tube, a syringe, a bag, a pouch, and a box.

88. The method of any of embodiments 1-87, wherein the amount of the conjugate produced by the method is greater than or greater than about 1 gram, greater than or greater than about 2 grams, greater than or greater than about 3 grams, greater than or greater than about 4 grams, greater than or greater than about 5 grams or greater than or greater than about 10 grams.

89. The method of any of embodiments 1-88, wherein the conjugate is produced using good manufacturing practice (GMP).

90. A conjugate produced, formulated or packaged by the method of any of embodiments 1-89.

91. The conjugate of embodiment 90, that is stable for greater than three months.

92. A stable conjugate, comprising a phthalocyanine dye linked to a targeting molecule, wherein the conjugate is stable for greater than three months.

93. The conjugate or stable conjugate of embodiment 91 or embodiment 92, wherein the conjugate is stable if it retains greater than or greater than about 30%, 40%, 50%, 60%, 70%, 80%, 90% or more of its potency, activity or purity for greater than 3 months compared to the conjugate prior to the storage for the time.

94. The conjugate or stable conjugate of embodiment 91 or embodiment 92, wherein the conjugate is stable if greater than 90% of the conjugate is present as a main monomer component.

95. The conjugate or stable conjugate of embodiment 94, wherein the conjugate is stable if greater than 95% of the conjugate is present as a main monomer component.

96. The conjugate or stable conjugate of any of embodiments 90-95, wherein the conjugate is stable for greater than 6 months or greater than 12 months.

97. The conjugate or stable conjugate of any of embodiments 90-96, wherein the conjugate is stable at a temperature of less than 30° C.

98. The conjugate or stable conjugate of any of embodiments 90-97, wherein the phthalocyanine dye comprises the formula:

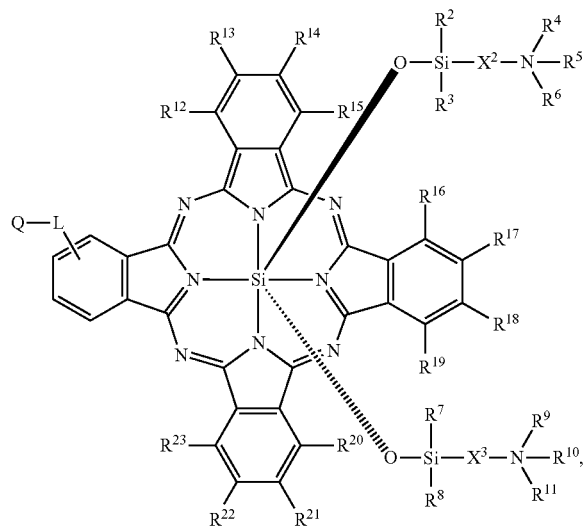

wherein:
L is a linker;
Q is a reactive group for attachment of the dye to the targeting molecule;
$R^2$, $R^3$, $R^7$, and $R^8$ are each independently selected from among optionally substituted alkyl and optionally substituted aryl;
$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;
$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from among hydrogen, halogen, optionally substituted alkylthio, optionally substituted alkylamino and optionally substituted alkoxy; and
$X^2$ and $X^3$ are each independently $C_1$-$C_{10}$ alkylene, optionally interrupted by a heteroatom.

99. The conjugate or stable conjugate of any of embodiments 90-98, wherein the phthalocyanine dye comprises the formula:

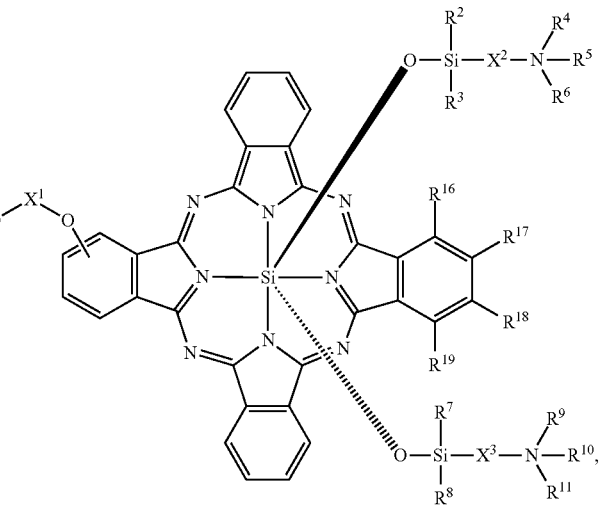

wherein:
$X^1$ and $X^4$ are each independently a $C_1$-$C_{10}$ alkylene optionally interrupted by a heteroatom;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and
$R^{16}$, $R^{17}$, $R^{18}$ and $R^{19}$ are each independently selected from among hydrogen, halogen, optionally substituted alkylthio, optionally substituted alkylamino and optionally substituted alkoxy.

100. The conjugate or stable conjugate of any of embodiments 90-99, wherein the dye has a maximum absorption wavelength from or from about 600 nm to about 850 nm, from or from about 650 nm to about 850 nm, or from or from about 680 nm to about 850 nm.

101. The conjugate or stable conjugate of any of embodiments 90-100, wherein the dye comprises IRDye 700DX (IR700).

102. The conjugate or stable conjugate of any of embodiments 90-101, wherein the targeting molecule binds a cell surface target molecule on a surface of a cell or a pathogen.

103. The conjugate or stable conjugate of any of embodiments 90-102, wherein the cell is a stem cell, a proliferating cell, a cell in a hyperplasia, or a pathogen infected cell.

104. The conjugate or stable conjugate of embodiment 102 or embodiment 103, wherein the pathogen is selected from among viruses, bacteria, fungi, biofilms, and other prokaryote cell systems.

105. The conjugate or stable conjugate of embodiment 102 or embodiment 103, wherein the cell is a proliferating cell, a cancer cell, a cell in a hyperplasia, a tumor cell, an inflammatory cell, a neuron, or a pathogen.

106. The conjugate or stable conjugate of embodiment 105, wherein the inflammatory cell is a leukocyte selected from among neutrophils, eosinophils, basophils, lymphocytes, and monocytes.

107. The conjugate or stable conjugate of embodiment 105, wherein the neuron is a peripheral nervous system neuron or a central nervous system neuron.

108. The conjugate or stable conjugate of embodiment 105 or embodiment 107, wherein the neuron is a nociceptor selected from among thermal nociceptors, mechanical nociceptors, chemical nociceptors and polymodal nociceptors.

109. The conjugate or stable conjugate of any of embodiments 102-108, wherein the cell surface target molecule comprises an antigen, a polypeptide, a lipid, or a carbohydrate, or a combination thereof.

110. The conjugate or stable conjugate of any of embodiments 102-109, wherein the cell surface target molecule is selected from among cell membrane phospholipids, prokaryotic peptidoglycans, bacterial cell envelop proteins, viral capsid proteins, ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g. P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g. TRPV1-6, TRPA1, TRPC1-7, TRPM1-8, TRPP1-5, TRPML1-3), TSH receptor, VEGF receptors (VEGFR1 or Flt-1, VEGFR2 or FLK-1/ KDR, and VEGF-3 or FLT-4), voltage-gated ion channels, VPAC1, VPAC2, Wilms tumor 1, Y1, Y2, Y4, and Y5.

111. The conjugate or stable conjugate of any of embodiments 102-110, wherein the cell surface target molecule is selected from among HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-lantigen, Bcr-abl, RET, MET, TRKB, TIE2, ALK, ROS, EML4-ALK, ROS1, BRAFV600E, SRC, c-KIT, PDGFR, mTOR, TSC1, TSC2, BTK, KIT, BRCA, CDK 4/6, JAK1, JAK2, BRAF, FLT-3, MEK1, MEK2, and SMO.

112. The conjugate or stable conjugate of any of embodiments 102-111, wherein the cell surface target molecule is HER1/EGFR, HER2, PD-L1, CD25, EpCAM, EphA2, CD206, CD20, CD44, CD133, Mesothelin, Glypican-3, or carcinoembryonic antigen (CEA).

113. The conjugate or stable conjugate of any of embodiments 90-112, wherein at least part of the targeting molecule is selected from or is a combination of a protein, a glycoprotein, an antibody, an antibody fragment, an antigen, an antigen binding fragment, a peptide, a polypeptide, a tissue homing peptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, an aptamer, nucleotide triphosphates, acyclo terminator triphosphates, or PNA.

114. The conjugate or stable conjugate of any of embodiments 90-113, wherein the targeting molecule is a tissue-specific homing peptide.

115. The conjugate or stable conjugate of embodiment 114, wherein the homing peptide has the sequence as set forth in any of SEQ ID NOs: 1-52.

116. The conjugate or stable conjugate of any of embodiments 90-113, wherein the targeting molecule is an RGD polypeptide, an iRGD polypeptide, a Lyp-1 polypeptide, a cripto-1 binding polypeptide, a somatostatin receptor binding polypeptide, a prohibitin binding polypeptide, a NGR polypeptide, an iNGR polypeptide, or an activatable cell penetrating peptide (ACPP) comprised of a polycationic cell penetrating peptide (CPP) connected via a cleavable linker to a neutralizing polyanion.

117. The conjugate or stable conjugate of any of embodiments 90-113, wherein the targeting molecule is selected from among adrenocorticotropic hormone (ACTH), angiotensin II, atrial natriuretic factor (ANF), bombesin, bradykinin, brain derived neurotropihic factor (BDNF), bone morphogenetic protein 2 (BMP-2), bone morphogenetic protein 6 (BMP-6), bone morphogenetic protein 7 (BMP-7), calcitonin, cardiotrophin 1 (BMP-2), CD22, CD40, cholecystokinin (CCK), ciliary neurotrophic factor (CNTF), CCL1-CCL28, CXCL1-CXCL17, XCL1, XCL2, CX3CL1, cripto 1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-a), interferon beta (IFN-b), interferon gamma (IFNg), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 3G (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMA5A), semaphorin 5B (SEMA5B), semaphorin 6A (SEMA6A), semaphorin 6B (SEMA6B), semaphorin 6D (SEMA6D), semaphorin 7A (SEMA7A), SLIT1, SLIT2, SLITS, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-α), transforming growth factor beta (TGF-b), tumor necrosis factor alpha (TNF-α), thrombin, vasoactive intestinal peptide (VIP), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

118. The conjugate or stable conjugate of any of embodiments 90-113, wherein the targeting molecule is an antibody or an antibody fragment.

119. The conjugate or stable conjugate of embodiment 118, wherein the antibody is selected from among cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, BMS-935559, MPDL3280A, Pidilizumab (CT-011), AMP-224, MSB001078C, and MEDI4736, or is an antigen-binding fragment thereof.

120. The conjugate or stable conjugate of embodiment 118 or embodiment 119, wherein the antibody binds to a cell surface target molecule selected from among HER1/EGFR, HER2 PD-L1, and carcinoembryonic antigen (CEA).

121. The conjugate or stable conjugate of any of embodiments 118-120, wherein the antibody is selected from among cetuximab, Panitumumab, Trastuzumab, BMS-935559, MEDI4736, MPDL3280A and MSB0010718C, or is an antigen-binding fragment thereof.

122. The conjugate or stable conjugate of any of embodiments 118-121, wherein the dye-targeting molecule conjugate is selected from among cetuximab-IR700, Panitumumab-IR700, Trastuzumab-IR700, BMS-935559-IR700, MEDI4736-IR700, MPDL3280A-IR700 and MSB0010718C-IR700.

123. The conjugate or stable conjugate of any of embodiments 90-122, wherein the conjugate comprises from or from about 1 to about 1000 phthalocyanine dye molecules per targeting molecule, from or from about 1 to about 10 or from or from about 2 to about 5 phthalocyanine dye molecules per targeting molecule.

124. A composition comprising the conjugate or stable conjugate of any of embodiments 90-123 and 234-236.

125. A pharmaceutical composition comprising the conjugate or stable conjugate of any of embodiments 90-123 and 234-236 and a pharmaceutically acceptable excipient.

126. The composition of embodiment 124 or embodiment 125, that is formulated in phosphate buffered saline.

127. The composition of any of embodiments 124-126 that has a pH of greater than 6.0.

128. A pharmaceutical composition, comprising a phthalocyanine dye linked to a targeting molecule and a pharmaceutically acceptable excipient, wherein:
the composition has a pH of greater than 6.0; and
the conjugate in the composition is stable for greater than three months.

129. The pharmaceutical composition of embodiment 128, wherein the conjugate in the composition is stable if it retains greater than or greater than about 30%, 40%, 50%, 60%, 70%, 80%, 90% or more of its potency, activity or purity for greater than 3 months compared to the conjugate prior to the storage for the time.

130 The pharmaceutical composition of embodiment 128, wherein the conjugate in the composition is stable if greater than 90% of the conjugate is present as a main monomer component.

131. The composition of any of embodiments 127-130, wherein the pH is greater than 6.0 or is from or from about pH 6.0 to about 8.0, inclusive.

132. The composition of any of embodiments 124-131, wherein the concentration of the conjugate in the composition is from or from about 0.01 mg/mL to about 200 mg/mL.

133. The composition of any of embodiments 124-132, wherein the concentration of the conjugate in the composition is from or from about 0.5 mg/mL to about 10 mg/mL.

134. The composition of any of embodiments 124-133, wherein the concentration of the conjugate in the composition is from or from about 1.0 to about 5.0 mg/mL.

135. The composition of any of embodiments 124-134, wherein the concentration of the conjugate in the composition is from or from about 1.8 to about 2.1 mg/mL.

136. The composition of any of embodiments 124-135, wherein the volume of the composition is from or from about 0.5 mL to about 100 mL, from or from about 1 mL to about 50 mL or from or from about 1 mL to about 10 mL.

137. A container comprising the conjugate or stable conjugate of any of embodiments 90-123 and 234-236 or composition of any of embodiments 124-136.

138. The container of embodiment 137, wherein the container protects from transmission of light having a wavelength from or from about 500 nm to about 725 nm or from about 650 nm to about 725 nm.

139. The container of embodiment 137 or embodiment 138, wherein the container protects from transmission of light such that the percentage of light transmission is less than 50%, less than 40%, less than 30%, less than 20%, less than 10% or less than 5%.

140. The container of any of embodiments 137-139, wherein the container is green, blue, amber, translucent, opaque, or is covered by a material with light transmission of less than 50%, less than 40%, less than 30%, less than 20%, less than 10% or less than 5%.

141. A packaging system for protecting a phthalocyanine dye-targeting molecule conjugate from light comprising:
a first container comprising the container of any of embodiments 137-140; and
a second container comprising the first container, wherein the second container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

142. The packaging system of embodiment 141, wherein the second container protects from transmission of light such that the percentage of light transmission is less than 50%, less than 40%, less than 30%, less than 20%, less than 10% or less than 5%.

143. The packaging system of embodiment 141 or embodiment 142, wherein the second container is green, blue, amber, translucent, opaque, or is covered by a material with light transmission of less than 50%, less than 40%, less than 30%, less than 20%, less than 10% or less than 5%.

144. The packaging system of any of embodiments 141-143, wherein the first binding molecule and second container are independently selected from among a vial, a tube, a syringe, a hag, a pouch, and a box.

145. The packaging system of any of embodiments 141-144, further comprising a third container comprising the second container, wherein the third container protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

146. The packaging system of embodiment 145, wherein the third container protects from transmission of light such that the percentage of light transmission is less than 50%, less than 40%, less than 30%, less than 20%, less than 10% or less than 5%.

147. The packaging system of embodiment 145 or embodiment 146, wherein the third container is green, blue, amber, translucent, opaque, or is covered by a material with light transmission of less than 50%, less than 40%, less than 30%, less than 20%, less than 10% or less than 5%.

148. The packaging system of any of embodiments 145-147, wherein the third container is selected from among a vial, a tube, a syringe, a bag, a pouch, and a box.

149. A kit, comprising:
the container of any of embodiments 137-140 or the packaging system of any of embodiments 141-148;
a light-protected cover capable of covering a device capable of administering a composition comprising a phthalocyanine dye-targeting molecule conjugate; and
optionally instructions for use.

150. The kit of embodiment 149, wherein the administration device is an intravenous infusion bag.

151. The kit of embodiment 149 or embodiment 150, wherein the light-protected cover protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

152. The kit of any of embodiments 149-151, wherein the light-protected cover protects from transmission of light such that the percentage of light transmission is less than 50%, less than 40%, less than 30%, less than 20%, less than 10% or less than 5%.

153. The kit of any of embodiments 149-152, wherein the light-protected cover is green, blue, amber, translucent, opaque, or is covered by a material with light transmission of less than 50%, less than 40%, less than 30%, less than 20%, less than 10% or less than 5%.

154. A method of preparing a composition comprising a phthalocyanine-dye conjugate for administration, comprising:
unpacking one or more containers of any of embodiments 137-140 or one or more of the packaging system of any of embodiments 141-148; and
transferring the composition present in the one or more containers into a device capable of administering the composition to a subject, wherein
the only light to which the composition is exposed has a wavelength within a range from about 400 nm to about 650 nm, or
the only light to which the composition is exposed has an intensity of less than 500 lux.

155. The method of embodiment 154, wherein the only light in which the composition is exposed has an intensity of less than 200 lux or less than 100 lux.

156. The method of embodiment 154 or embodiment 155 that is performed in a biosafety cabinet, biosafety hood or a sterile environment.

157. The method of any of embodiments 154-156, wherein the one or more containers together comprise a therapeutically effective dose of the phthalocyanine-dye conjugate.

158. The method of any of embodiments 154-157, wherein the one or more containers comprise at least or about at least or 2, 4, 6, 8, 10, 12, 18 or 24 containers.

159. The method of any of embodiments 154-158, wherein:
the method is carried out for no more than 1 hour, no more than 30 minutes or no more than 15 minutes; or the total exposure of the composition to any light during the method is no more than 500 lux hours, no more than 250 lux hours, no more than 100 lux hours, no more than 50 lux hours or no more than 25 lux hours.

160. The method of any of embodiments 154-159, wherein the administration device is an intravenous infusion bag.

161. The method of any of embodiments 154-160, wherein the administration device comprises a light-protected cover capable of covering the device.

162. The method of embodiment 161, wherein the light-protected cover protects from transmission of light having a wavelength from or from about 250 nm to about 800 nm, from about 250 nm to about 450 nm, from about 400 nm to about 800 nm, from about 450 nm to about 650 nm, or from about 600 nm to about 720 nm.

163. The method of embodiment 161 or embodiment 162, wherein the light-protected cover protects from transmission of light such that the percentage of light transmission is less than 50%, less than 40%, less than 30%, less than 20%, less than 10% or less than 5%.

164. The method of any of embodiments 154-163, wherein the light-protected cover is green, blue, amber, translucent, opaque, or is covered by a material with light transmission of less than 50%, less than 40%, less than 30%, less than 20%, less than 10% or less than 5%.

165. A light-protected device comprising the composition prepared by the method of any of embodiments 154-164.

166. A method of removing unwanted cells or pathogens in a subject, comprising:
(a) administering a composition comprising a phthalocyanine-dye conjugate from the light-protected device of embodiment 165 to a subject, wherein prior to and during the administration step the composition is not exposed to an intensity of environmental light greater than 500 lux; and
(b) irradiating the unwanted cells or pathogens at a wavelength of 660 to 740 nm at a dose of at least 1 J cm$^{-2}$ or 1 J/cm of fiber length thereby removing the unwanted cell in the subject.

167. A method of removing unwanted cells or pathogens in a sample, comprising:
(a) administering a composition comprising a phthalocyanine-dye conjugate from the light-protected device of embodiment 165 to a sample, wherein prior to and during the administration step the composition is not exposed to an intensity of environmental light greater than 500 lux; and
(b) irradiating the unwanted cells or pathogens at a wavelength of 660 to 740 nm at a dose of at least 1 J cm$^{-2}$ or 1 J/cm of fiber length thereby removing the unwanted cell in the sample.

168. A method of removing unwanted cells or pathogens in a subject comprising:
a) administering to a subject a therapeutically effective amount of the conjugate or stable conjugate of any of embodiments 90-123 and 234-236 or composition of any of embodiments 124-136, wherein prior to and during the administration step the conjugate is not exposed to an intensity of environmental light greater than 500 lux; and
b) irradiating the unwanted cells or pathogens at a wavelength of 660 to 740 nm at a dose of at least 1 J cm$^{-2}$ or 1 J/cm of fiber length thereby removing the unwanted cell in the subject.

169. A method of removing unwanted cells or pathogens in a sample comprising:
a) administering to a sample a therapeutically effective amount of the conjugate or stable conjugate of any of embodiments 90-123 and 234-236 or composition of any of embodiments 124-136, wherein prior to and during the administration step the conjugate is not exposed to an intensity of environmental light greater than 500 lux; and
b) irradiating the unwanted cells or pathogens at a wavelength of 660 to 740 nm at a dose of at least 1 J cm$^{-2}$ or 1 J/cm of fiber length thereby removing the unwanted cell in the sample.

170. A method of removing unwanted cells or pathogens in a subject comprising:
a) administering to a subject a therapeutically effective amount of a conjugate comprising IRDye 700DX (IR700) linked to a targeting molecule capable of binding an unwanted cell or pathogen, wherein prior to and during the administration step the conjugate is not exposed to an intensity of environmental light greater than 500 lux; and
b) irradiating the unwanted cells or pathogens at a wavelength of 600 to 800 nm at a dose of at least 1 J cm$^{-2}$ or 1 J/cm of fiber length thereby removing the unwanted cells or pathogens in the subject.

171. A method of removing unwanted cells or pathogens in a sample comprising:
a) administering to a sample a therapeutically effective amount of a conjugate comprising IRDye 700DX (IR700) linked to a targeting molecule capable of binding an unwanted cell or pathogen, wherein prior to and during the administration step the conjugate is not exposed to an intensity of environmental light greater than 500 lux; and
b) irradiating the unwanted cells or pathogens at a wavelength of 600 to 800 nm at a dose of at least 1 J cm$^{-2}$ or 1 J/cm of fiber length thereby removing the unwanted cells or pathogens in the sample.

172. A method of removing unwanted cells or pathogens in a subject comprising:
a) administering to a subject a therapeutically effective amount of a first binding molecule capable of binding an unwanted cell or pathogen;
b) administering to the subject a conjugate molecule comprising IRDye 700DX (IR700) linked to a targeting molecule, wherein the targeting molecule is a second binding molecule that is capable of binding to the first binding molecule; and
c) irradiating the unwanted cells or pathogens at a wavelength of 600 to 800 nm at a dose of at least 1 J cm$^{-2}$ or 1 J/cm of fiber length thereby removing the unwanted cells or pathogens in the subject.

173. The method of embodiment 172, wherein the first binding molecule is administered to the subject prior to the conjugate or the first binding molecule and conjugate are administered simultaneously to the subject.

174. A method of removing unwanted cells or pathogens in a sample comprising:
a) administering to a sample a therapeutically effective amount of a first binding molecule capable of binding an unwanted cell or pathogen;
b) administering to the sample a conjugate molecule comprising IRDye 700DX (IR700) linked to a targeting molecule, wherein the targeting molecule is a second binding molecule that is capable of binding to the first binding molecule; and
c) irradiating the unwanted cells or pathogens at a wavelength of 600 to 800 nm at a dose of at least 1 J cm$^{-2}$ or 1 J/cm of fiber length thereby removing the unwanted cells or pathogens in the sample.

175. The method of any of embodiments 167, 169, 171 and 174, wherein the sample is a blood sample or a tissue sample.

176. The method of any of embodiments 167, 169, 171 174 and 175, wherein the method is performed in vitro or ex vivo.

177. The method of embodiment 175, wherein the method is performed using an extracorporeal device.

178. The method of any of embodiments 172-177, wherein the first binding molecule is administered to the sample prior to the conjugate or the first binding molecule and conjugate are administered simultaneously to the sample.

179. The method of any of embodiments 166-178, wherein the targeting molecule is a secondary antibody.

180. The method of any of embodiments 166-179, wherein prior to and during the administration of the conjugate, the conjugate is not exposed to an intensity of environmental light greater than 500 lux.

181. The method of any of embodiments 166-180, wherein the cell is a stem cell, a proliferating cell, a cell in a hyperplasia, an inflammatory cell, a negative regulatory immune cell, which optionally is a T cell, a pathogen infected cell, a neuron, a fat cell or adipocyte.

182. The method of any of embodiments 166-181, wherein the cell is a cancer cell or a tumor cell.

183. The method of any of embodiments 166-182, wherein the cell is associated with, causes or contributes to the etiology of a disease or condition.

184. The method of embodiment 183, wherein the disease of condition is a tumor or cancer, an infection, an inflammatory disease or condition, or a neuronal disease or condition.

185. The method of embodiment 183 or embodiment 184, wherein:
the cell is a neuron and the disease or condition is a neurological disorder, which optionally is pain;
the cell is a fat cell or adipocyte and the disease or condition involves excess fat;
the cell is a pathogen infected cell and the disease or condition is an infection;
the cell is a pathogen and the disease or condition is an infection;
the cell is an inflammatory cell and the disease or condition is an inflammatory disease;
the cell is a an immune cell, which optionally is a regulatory T cell, and the disease or condition is a tumor or cancer; or
the cell is a tumor or cancer cell and the disease or condition is a tumor or a cancer.

186. The method of any of embodiments 166-185, wherein the cell is present in the microenvironment of a lesion associated with a disease or condition or is in a hyperplasia.

187. The method of embodiment 186, wherein the lesion is a tumor and the disease or condition is a tumor or cancer.

188. The method of any of embodiments 183-187, wherein the method treats the disease or condition.

189. A method of removing a pathogen infected cell in a subject comprising:
a) administering to a subject a therapeutically effective amount of a conjugate molecule comprising IRDye 700DX (IR700) linked to a targeting molecule, wherein the targeting molecule is capable of binding to the pathogen infected cell directly or indirectly; and
b) irradiating the pathogen infected cell at a wavelength of 600 to 800 nm at a dose of at least 1 J cm$^{-2}$ or 1 J/cm of fiber length thereby removing the pathogen infected cell in the subject.

190. A method of removing a pathogen infected cell in a sample comprising:
a) administering to a sample a therapeutically effective amount of a conjugate molecule comprising IRDye 700DX (IR700) linked to a targeting molecule, wherein the targeting molecule is capable of binding to the pathogen infected cell directly or indirectly; and
b) irradiating the pathogen infected cell at a wavelength of 600 to 800 nm at a dose of at least 1 J cm$^{-2}$ or 1 J/cm of fiber length thereby removing the pathogen infected cell in the sample.

191. The method of embodiment 190, wherein the sample is a blood sample or a tissue sample.

192. The method of embodiment 190 or embodiment 191, wherein the method is performed in vitro or ex vivo.

193. The method of embodiment 192, wherein the method is performed using an extracorporeal device.

194. The method of any of embodiments 189-192, wherein the pathogen is a virus, bacterium, fungus, biofilm, or other prokaryote cell system.

195. The method of any of embodiments 189-194, wherein prior to and during the administration of the conjugate, the conjugate is not exposed to an intensity of environmental light greater than 500 lux.

196. A method of treating a hyperplasia or a tumor in a subject comprising:
a) administering to the subject a therapeutically effective amount of the conjugate or stable conjugate of any of embodiments 90-123 and 234-236 or composition of any of embodiments 124-136, wherein prior to and during the administration step the conjugate is not exposed to an intensity of environmental light greater than 500 lux; and
b) irradiating the hyperplasia or the tumor at a wavelength of 660 to 740 nm at a dose of at least 1 J cm$^{-2}$ or 1 J/cm of fiber length thereby treating the tumor in the subject.

197. A method of treating a hyperplasia or a tumor in a sample comprising:
a) administering to the sample a therapeutically effective amount of the conjugate or stable conjugate of any of embodiments 90-123 and 234-236 or composition of any of embodiments 124-136, wherein prior to and during the administration step the conjugate is not exposed to an intensity of environmental light greater than 500 lux; and
b) irradiating the hyperplasia or the tumor at a wavelength of 660 to 740 nm at a dose of at least 1 J cm$^{-2}$ or 1 J/cm of fiber length thereby treating the tumor in the sample.

198. A method of treating a hyperplasia or a tumor in a subject comprising:
a) administering to the subject a therapeutically effective amount of a conjugate comprising IRDye 700DX (IR700) linked to a targeting molecule that targets the conjugate to the tumor or hyperplasia, wherein prior to and during the administration step the conjugate is not exposed to an intensity of environmental light greater than 500 lux; and
b) irradiating the hyperplasia or a tumor at a wavelength of 600 to 800 nm at a dose of at least 1 J cm$^{-2}$ or 1 J/cm of fiber length thereby treating the tumor in the subject.

199. A method of treating a hyperplasia or a tumor in a sample comprising:
a) administering to the sample a therapeutically effective amount of a conjugate comprising IRDye 700DX (IR700) linked to a targeting molecule that targets the conjugate to the tumor or hyperplasia, wherein prior to and during the administration step the conjugate is not exposed to an intensity of environmental light greater than 500 lux; and b) irradiating the hyperplasia or a tumor at a wavelength of 600 to 800 nm at a dose of at least 1 J cm$^{-2}$ or 1 J/cm of fiber length thereby treating the tumor in the sample.

200. The method of embodiment 197 or embodiment 199, wherein the sample is a blood sample or a tissue sample.

201. The method of any of embodiments 197, 199 or 200, wherein the method is performed in vitro or ex vivo.

202. The method of embodiment 201, wherein the method is performed using an extracorporeal device.

203. The method of any of embodiments 196-202 that is for treating a tumor, wherein the targeting molecule of the conjugate targets the conjugate to the tumor or a microenvironment of the tumor.

204. The method of embodiment 203, wherein irradiating the tumor is at a wavelength of 600 to 800 nm and at a dose of at least 1 J cm$^{-2}$ or 1 J/cm of fiber length, thereby treating the tumor.

205. The method of any of embodiments 166-204, wherein the targeting molecule is an antibody, an antigen binding fragment, a protein, a glycoprotein, a peptide, a polypeptide, a virus, a viral capsid, or a viral particle.

206. The method of any of embodiments 166-205, wherein the targeting molecule is an antibody or an antibody fragment.

207. The method of any of embodiments 166-206, wherein administration is performed under fluorescent lighting or LED lighting and in the absence of direct or indirect sunlight.

208. The method of any of embodiments 166-207, wherein prior to and during the administration step any exposure of the conjugate to light less than 500 lux is for less than 20 minutes, less than 15 minutes, less than 10 minutes or less than 5 minutes.

209. The method of embodiment 208, wherein the exposure of the conjugate to any light is light with an intensity that is not greater than 50 lux.

210. The method of any of embodiments 196-209, wherein the tumor is a cancer.

211. The method of any of embodiments 184, 185, 187 and 210, wherein the cancer is a cancer located at the head and neck, breast, liver, colon, ovary, prostate, pancreas, brain, cervix, bone, skin, eye, bladder, stomach, esophagus, peritoneum, or lung.

212. The method of embodiment 210 or embodiment 211, wherein the cancer is a cancer of the blood.

213. The method of any of embodiments 196-212, wherein the conjugate is targeted to a protein expressed on the surface of a cell present in the tumor microenvironment.

214. The method of embodiment 213, wherein the cell is a tumor cell, an immune cell or a cancer stem cell.

215. The method of any of embodiments 166-214, wherein the protein expressed on the surface of a cell is selected from among ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g. P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g. TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

216. The method of any of embodiments 166-215, wherein the protein expressed on the surface of a cell is selected from among HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), VEGFR2, VEGF-A, integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, SK-lantigen, Bcr-abl, RET, MET, TRKB, TIE2, ALK, ROS, EML4-ALK, ROS1, BRAFV600E, SRC, c-KIT, PDGFR, mTOR, TSC1, TSC2, BTK, KIT, BRCA, CDK 4/6, JAK1, JAK2, BRAF, FLT-3, MEK1, MEK2, and SMO.

217. The method of any of embodiments 166-216, wherein the conjugate is targeted to a protein expressed in the tumor.

218. The method of any of embodiments 166-217, wherein the cell, hyperplasia or tumor is irradiated at a wavelength from or from about 600 nm to about 850 nm.

219. The method of any of embodiments 166-218, wherein the cell, hyperplasia or tumor is irradiated at a wavelength of 690±50 nm or 690±20 nm.

220. The method of any of embodiments 166-219, wherein the cell, hyperplasia or tumor is irradiated at a dose of from or from about 2 J cm$^{-2}$ to about 400 J cm$^{-2}$ or from or from about 2 J/cm fiber length to about 500 J/cm fiber length.

221. The method of any of embodiments 166-220, wherein:

the cells, hyperplasia or tumor are irradiated at a dose of at least or at least about 2 J cm$^{-2}$, 5 J cm$^{-2}$, 10 J cm$^{-2}$, 25

J cm⁻², 50 J cm⁻², 75 J cm⁻², 100 J cm⁻², 150 J cm⁻², 200 J cm⁻², 300 J cm⁻², 400 J cm⁻², or 500 J cm⁻²; or the cells, tumor or hyperplasia are irradiated at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.

222. The method of any of embodiments 184-188 and 196-221, wherein the disease or condition is a tumor and the tumor is a superficial tumor.

223. The method of embodiment 222, wherein the tumor is irradiated at a dose of at least or about at least or about 10 $J/cm^2$, 25 $J/cm^2$, 50 $J/cm^2$, 150 $J/cm^2$, or 250 $J/cm^2$.

224. The method of any of embodiments 184-188 and 196-221, wherein the disease or condition is a tumor and the tumor is an interstitial tumor.

225. The method of embodiment 224, wherein the tumor is irradiated at a dose of at least or about at least or about 50 J/cm fiber length, 100 J/cm fiber length, 200 J/cm fiber length, or 300 J/cm fiber length.

226. The method of any of embodiments 166-225, wherein the cells, hyperplasia or tumor is irradiated within or within about or about 12 hours, 24 hours, 36 hours, 72 hours or 96 hours after administering the conjugate.

227. The method of any of embodiments 166-226, wherein the conjugate is administered in an amount that is from or from about 0.5 mg/kg to about 100 mg/kg or 20 $mg/m^2$ to about 4000 $mg/m^2$.

228. The method of any of embodiments 166-227, wherein:

the conjugate is administered in an amount that is at least or about at least or is or is about 0.5 mg/kg, 2.0 mg/kg, 4.0 mg/kg, 8.0 mg/kg, 16.0 mg/kg, 32.0 mg/kg or 64 mg/kg; or the conjugate is administered in an amount that is at least or about at least or is or is about 20 $mg/m^2$, 40 $mg/m^2$, 160 $mg/m^2$, 320 $mg/m^2$, 640 $mg/m^2$, 1280 $mg/m^2$ or 2560 $mg/m^2$.

229. The method of any of embodiments 166-228, wherein prior to administration of the conjugate the targeting molecule is administered.

230. The method of any of embodiments 166-229, wherein the targeting molecule is administered up to 96 hours prior to administration of the conjugate.

231. The method of embodiment 229 or embodiment 230, wherein the targeting molecule is administered at a dose within a range from or from about 10 $mg/m^2$ to about 500 $mg/m^2$.

232. The method of any of embodiments 166-231, wherein the targeting molecule is an antibody or antigen binding fragment.

233. The method of embodiment 232, wherein the antibody is cetuximab.

234. A conjugate, comprising a phthalocyanine dye and a targeting molecule, wherein the targeting molecule is selected from among a tissue-specific homing peptide, an RGD polypeptide, an iRGD polypeptide, a Lyp-1 polypeptide, a cripto-1 binding polypeptide, a somatostatin receptor binding polypeptide, a prohibitin binding polypeptide, a NGR polypeptide, an iNGR polypeptide, an activatable cell penetrating peptide (ACPP) comprised of a polycationic cell penetrating peptide (CPP) connected via a cleavable linker to a neutralizing polyanion, and an antibody selected from Ado-trastuzumab emtansine, Afatinib, Axitinib, Bosutinib, Cabozantinib, Ceritinib, Crizotinib, Dabrafenib, Dasatinib, Everolimus, Ibrutinib, Imatinib, Lenvatinib, Nilotinib, Ola- parib, Palbociclib, Pazopanib, Ramucirumab, Regorafenib, Ruxolitinib, Sorafenib, Sunitinib, Temsirolimus, Trametinib, Vandetanib, Vemurafenib, Vismodegib, Ipilimumab, Nivolumab, pembrolizumab, pidilizumab, lambrolizumab, BMS-935559, MPDL3280A, Pidilizumab (CT-011), AMP-224, MSB001078C, or MEDI4736, or an antigen-binding fragment thereof.

235. The conjugate of embodiment 234, wherein the homing peptide has a sequence as set forth in any of SEQ ID NOs: 1-52.

236. The conjugate of embodiment 234 or embodiment 235, wherein the dye is IR700.

V. Examples

The following examples are included for illustrative purposes only and are not intended to limit the scope of the invention.

Example 1: Conjugation of Cetuximab to IRDye 700DX NHS Ester

This example describes the procedures used to produce a 12 g scale batch of Cetuximab-IRDye 700DX conjugate. The methods were performed using opaque or translucent containers and, in some cases, aluminum foil to wrap containers or vessels.

A volume of 6 L (12 g) of Cetuximab (Myoderm USA, Norristown, Pa.) was buffer-exchanged into 100 mM sodium phosphate buffer (pH 8.5) using tangential flow filtration (TFF) with a regenerated cellulose membrane until the pH of the filtrate was 8.46. Approximately 6 L (12 g: 78.95 µmol) of diafiltered Cetuximab antibody (2 mg/mL) was placed into a 2 mg/mL carboy container containing a sterile stir bar.

A 25 mg vial, two 50 mg vials and two 250 mg vials of IRDye 700DX NHS Ester (dye; Cat. No. 929-70011; Li-COR, Lincoln, Nebr.) stored at 20° C. were allowed to warm to room temperature for 30 minutes until moisture on the surface of the vials was vaporized. To make a 10 mg/mL solution, 2.5 mL of DMSO was added to the 25 mg vial, 5 mL of DMSO was added to each of the two 50 mg vials, and 500 mg of the dye was dissolved in 50 mL of DMSO.

A volume of 61.7 mL (315.8 µmol) of the suspended dye was added to the 2 mg/mL container wrapped in aluminum foil less than five minutes after dissolving IRDye 700DX NHS ester in DMSO. The container was sealed and stirred for 15±5 minutes at 300±50 rpm at room temperature until the dye dissolved completely and distributed evenly in the antibody solutions. The reaction vessel wrapped in aluminum foil was placed in a stability chamber that was protected from light at 25° C. for 2 hours without further mixing.

Upon completion of the incubation time, the reaction was quenched by adding 25 mL of 1 M glycine (25 mmol) to the 2 mg/mL container. The container was sealed and stirred for 10±5 minutes at 300±50 rpm. The carboy was placed back into the stability chamber at 25° C. for 20 minutes without further mixing.

After the quenching reaction was complete, the conjugate was transferred to the TFF system that was set in the light-protected refrigerator. Six liters of the conjugate were concentrated to approximately 2.5 L using the TFF system with the regenerated cellulose membrane. The concentrated conjugated product (2.5 L; approximately 5 mg/mL) was diafiltered against approximately 25 L (10 volumes) of 1×PBS, pH 7.1±0.2 pre-chilled to 2-8° C. Diafiltration was performed at 2-8° C. under dark conditions.

The buffer-exchanged conjugates (approximately 2.2 L) were filtered using a 0.22 µm Millipak 40 pre-equilibrated filter with 1×PBS, pH 7.1±0.2.

After preparing the conjugated material, the sample was submitted at approximately 5 mg/mL for the following tests: SDS-PAGE, HPLC-SEC, and Binding ELISA. Other tests for appearance, pH, bacteriostasis and fungistasis, bioburden, endotoxin level, osmolality and residual DMSO also were performed.

Example 2: Photo-Degradation of Cetuximab-IRDye 700DX Drug Product

This example describes the photo-degradation effects that white fluorescent light exposure has on the Cetuximab-IRDye 700DX drug product contained in both clear and amber vials using fluorescent light intensities typically used to light indoor facilities.

A 10 mL sample of IR-700DX conjugated drug product at a concentration of 2.1 mg/mL in phosphate buffered saline (PBS, pH=7.1) was placed into one clear and one amber 50 mL Type 1 20 mm finish vial and capped with a 20 mm Septa cap. The samples contained in the two different types of vials were then exposed to white fluorescent light at an intensity measured to be 550±10 lux at the samples with a Digi-Sense Data Logging Light Meter, Model #: 20250-00 (Cole-Palmer, Vernon Hills, Ill.).

After a total exposure time period of: 1, 2, 24 and 44 hours, a sample volume of 500 µL was removed from each vial under low light (less than 50 lux) and placed into a HPLC vial and stored fully protected from light at 5° C.±3° C. until analysis of each sample was performed by High Pressure Liquid Chromatography using a Size Exclusion column (HPLC-SEC) analysis.

Figure 1B:
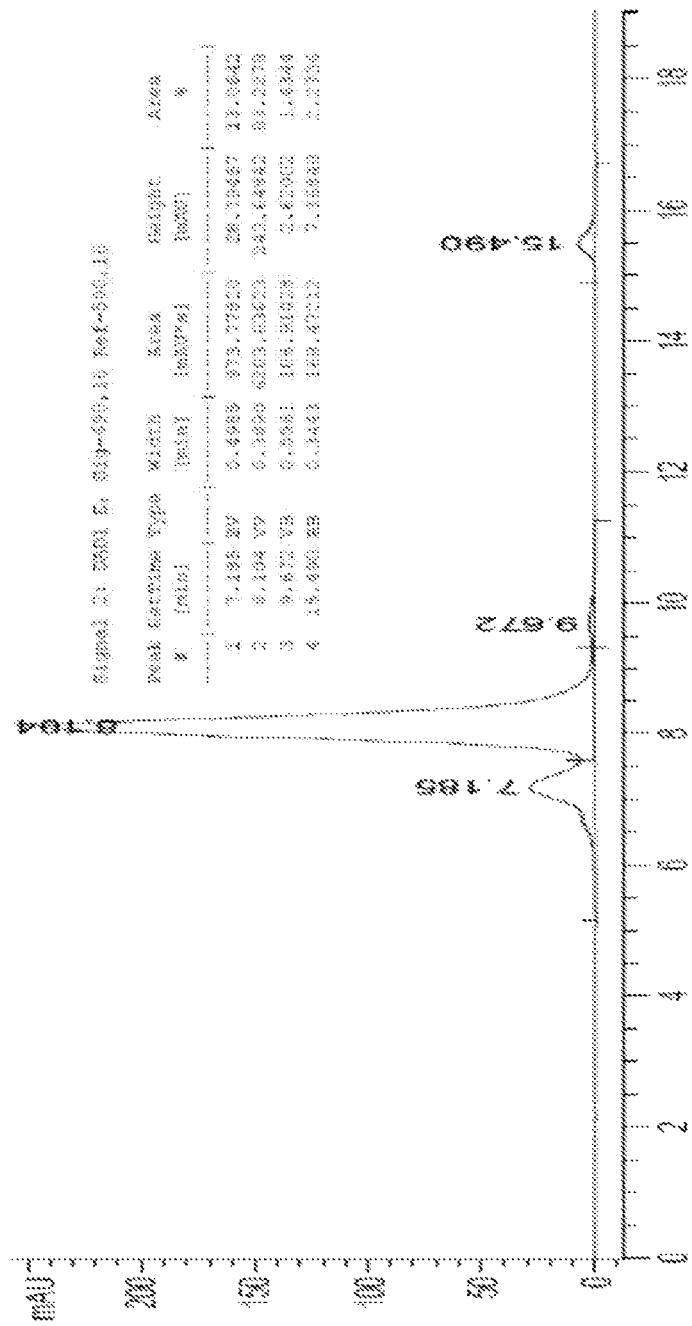
FIG. 1B displays the relative amounts of high molecular weight species (aggregates) and monomer form of the Cetuximab-IRDye 700DX as assessed by High Pressure Liquid Chromatography using a Size Exclusion column (HPLC-SEC) analysis of a sample in a clear vial after 24 hours of light exposure.

Using this method, the relative amounts of high molecular weight species (aggregates) and monomer form of the Cetuximab-IRDye 700DX present in each sample were quantitated. The results of that analysis are shown in Table 1 below, demonstrating a significant increase in the amount of aggregates present in the samples as the light exposure time increases. An exemplary HPLC-SEC chromatogram of Cetuximab-IRDye 700DX sample in a clear vial before and after 24 hours of light exposure is depicted in FIGS. 1A and 1B.

TABLE 1

HPLC-SEC Determined % Aggregate Found in White Light Exposed Samples

| Light Exposure Time (hours) | % Aggregate Clear Vial | % Aggregate Amber Vial |
| --- | --- | --- |
| 0 | 1.0 | 1.0 |
| 1 | 2.9 | 2.0 |
| 2 | 4.9 | 2.8 |
| 24 | 13.0 | 9.2 |
| 44 | 14.7 | 11.3 |

In another example, a 2 mL sample of the Cetuximab-IRDye 700DX at a concentration of 5.5 mg/mL in phosphate buffered saline (PBS, pH=7.1) was placed into two clear vials. One of the vials was exposed to white fluorescent light at an intensity of 500 lux for a total time period of 15 and 30 minutes. The other 2 mL sample in a clear vial was exposed to green LED light (Ecosmart GP19, HomeDepot, Atlanta Ga.) with an intensity at the sample of 500 lux as measured with the Digi-Sense Light Meter. After light exposure, 200 µL samples were taken from each of the vials for HPLC-SEC analysis at each time point of 15 and 30 minutes. In Table 2 below the HPLC-SEC quantitation of the relative amounts of aggregate species found in each of the 200 µL samples tested is shown.

TABLE 2

% Aggregate Found in Green versus White Light Exposed Samples

| Light Exposure Time (minutes) | % Aggregate Green Light | % Aggregate White Light |
| --- | --- | --- |
| 0 | 1.3 | 1.3 |
| 15 | 1.6 | 3.5 |
| 30 | 1.8 | 5.8 |

The data in Table 2 demonstrate that the white light exposed Cetuximab-IRDye 700DX samples had significantly higher amounts of aggregate species present at both time points relative to the samples exposed for the same period of time to an intensity of green light.

Example 3: Good Manufacturing Practices (GMP) Method for Preparing Conjugated Drug Substance This example describes a method for preparing a conjugated drug substance under Good Manufacturing Practices (GMP), including the preparation of final intermediates and the conjugation of the final intermediates. To ensure that pharmaceutical quality of the final product was met, extra precautions were taken during manufacture to limit exposure of the dye and conjugate to light due to the photosensitivity of the dye. These included the use of low levels of green light having a wavelength from 425 to 575 nm and an intensity of less than 200 Lux in the manufacturing facility. In addition, the methods also employed the use of a translucent carboy for conjugation, wrapping of the conjugation vessel with aluminum foil, and steps with potential light exposure were performed as quickly as possible.

This example describes a method for preparing IRDye 700DX NHS ester (dye) conjugated to Cetuximab to produce Cetuximab-IRDye 700DX conjugate. The provided methods may be employed to prepare any drug substance, such as one containing a dye conjugated to a macromolecule and the following description is provided for exemplary purposes only.

A. Preparation of Buffers

Buffers were prepared using Highly Purified Water (HPW) or Water for Injection (WFI) and were filtered through a 0.22 µm filter prior to storage at ambient temperature. Tables 3-5 show in-process controls and tests for prepared buffers: conjugation buffer (100 mM sodium phosphate, pH 8.65), quenching buffer (1.0 M glycine, pH 9) and final phosphate buffered saline (PBS) formulation buffer: (5.60 mM $Na_2HPO_4$, 1.058 $KH_2PO_4$, 154 mM NaCl, pH 7.1), respectively.

TABLE 3

Preparation of Conjugation Buffer (100 mM sodium phosphate, pH 8.65)

| In-process Controls and Tests | Specification or Range |
| --- | --- |
| Mixing time | ≥30 min |
| pH | 8.5-8.8 |
| Conductivity | 11.7-14.1 mS/cm |
| Filter integrity testing | Pass |
| Endotoxin | ≤1.5 EU/mL |

TABLE 4

Preparation of Quenching Buffer (1.0M glycine, pH 9)

| In-process Controls and Tests | Specification or Range |
|---|---|
| Mixing time | ≥30 min |
| pH | 8.9-9.1 |
| Conductivity | 5-11 mS/cm |
| Filter integrity testing | Pass |
| Endotoxin | ≤1.5 EU/mL |

TABLE 5

Buffer release test for 1x PBS

| Tests | Specification or Range |
|---|---|
| Appearance | Clear solution |
| pH | 7.0-7.2 |
| Osmolality | 280-330 mOsm/kg |
| Sterility | No growth |
| Cytotoxicity | Non-toxic |

B. Preparation of Dye and Cetuximab Intermediates

1. Cetuximab Preparation

Prior to conjugation, Cetuximab vials (Myoderm USA, Norristown, Pa.) were sprayed with sterile isopropyl alcohol and placed in a Laminar Flow Hood. A total of 423 vials were used to prepare drug substance. The vials were de-crimped using an electronic decrimper, the stoppers were removed with autoclaved forceps, and the contents were poured into sterile 2 L PETG bottles. The bottles were capped when filled. The Cetuximab was then filtered through a 0.22 μm filter and pooled into a 50 L HyQtainer. Pooled, filtered Cetuximab was stored at 2-8° C.

A concentration and buffer exchange step was then performed by ultrafiltration/diafiltration (UF/DF). Cleaning of the UF/DF device was performed prior to use. The storage solution was drained and the membrane flushed with at least 20 L of HPW. The unit was flushed with 0.1 M NaOH for 30-40 min and then flushed with HPW. The pH of the rinsate was confirmed. The system was equilibrated with 100 mM sodium phosphate, pH 8.65 buffer. Permeate and retentate effluent pH and conductivity were confirmed prior to use. Endotoxin testing was also performed; the system was used within 48 hours of endotoxin testing.

Prior to UF/DF operations, the pooled, filtered Cetuximab was warmed by placing it in an incubator at 25° C. for 120-150 min. The material was first concentrated to a target of 5 mg/mL and then diafiltered into 100 mM sodium phosphate, pH 8.65 buffer. Diafiltration was performed until the permeate pH and conductivity targets were met. The system was flushed with buffer and the flush was added to the diafiltered retentate. UF/DF system pressures were monitored and recorded during the operation as described in Table 6.

The diafiltered Cetuximab product concentration was determined and then diluted to a target concentration of 2 mg/mL (1.8-2.4 mg/mL) using 100 mM sodium phosphate, pH 8.65 buffer. The product was aseptically filtered through a 0.22 μm filter and split into two autoclaved product-dedicated 40 L carboys containing stir bars and forward-processed directly into the conjugation operation. The weight of Cetuximab in each carboy was determined.

TABLE 6

In-process controls and tests for Cetuximab processing

| In-process Controls and Tests | Specification or Range |
|---|---|
| Cetuximab pooling | |
| Filter integrity test (0.22 μm) (after pooling) | Pass |
| Protein concentration after pooling | Report results |
| TFF Unit Preparation | |
| TFF parts 1.0M NaOH contact time | ≥60 min |
| pH of TFF rinsed parts | <7 |
| TOC of UF/DF rinsed parts | <1000 ppb |
| HPW volume rinse with membrane | >20 L |
| UF/DF Integrity testing prior to use | Air displacement <90 mL/min |
| 0.1M NaOH flush time | 30-40 min |
| UF/DF permeate and retentate pH after HPW rinsing | <7 |
| TFF Equilibration | |
| UF/DF permeate and retentate effluent pH | 8.5-8.8 |
| UF/DF permeate and retentate effluent conductivity | 11.7-14.1 mS/cm |
| UF/DF permeate and retentate effluent endotoxin | ≤0.134 EU/mL |
| Cetuximab Diafiltration | |
| Pooled, filtered Cetuximab incubation temperature | 25° C. |
| Pooled, filtered Cetuximab incubation time | 120-150 min |
| Feed inlet pressure during concentration | <25 psi |
| Retentate outlet pressure during concentration | 10-12 psi |
| Retentate pressure during diafiltration | 10-12 psi |
| UF/DF system pressure during diafiltration | <32 psi |
| UF/DF permeate pH after diafiltration | 8.5-8.8 |
| UF/DF permeate conductivity after diafiltration | 11.7-14.1 mS/cm |
| Cetuximab concentration ($A_{280}$) after diafiltration | 4.5 mg/mL |
| Cetuximab concentration ($A_{280}$) after dilution | 1.8-2.4 mg/mL |

2. Dye Preparation

Prior to conjugation, IRDye 700DX NHS Ester (dye; Cat. No. 929-70011; Li-COR, Lincoln, Nebr.) was prepared by dissolving it to a concentration of 10 mg/mL in anhydrous DMSO. The steps were performed under green light (e.g., wavelength from 425 to 575 nm and an intensity of less than 200 Lux) to protect the dye from the wavelengths of light that are strongly absorbed by the dye.

C. Conjugation

The conjugation and quenching steps were performed in the 2×40 L carboys (wrapped in aluminum foil for light protection) containing diafiltered Cetuximab. The steps were performed at room temperature under green light (e.g., wavelength from 425 to 575 nm and an intensity of less than 200 Lux) to protect the conjugate from photo-degradation.

For the conjugation reaction, the appropriate amount of IRDye 700DX NHS ester in DMSO was calculated (based on the weight of Cetuximab in each carboy, typically from 80-120 g) to achieve a final molar ratio of 4:1 (IRDye 700DX NHS ester: Cetuximab). Process development studies have determined that this ratio, in conjugation with the targeted conjugation incubation time, should incorporate 2-3 dye residues per Cetuximab molecule. The calculated amount of the IRDye 700DX NHS ester was added to the carboys containing Cetuximab and mixed on a stir plate for 10-15 min. The conjugation reaction then proceeded for 120 min by placing the carboys in a 25° C. incubator.

The conjugation reaction was quenched by the addition of 1 M glycine to a final concentration of 4.2 mM and mixing for 10-12 min. The carboys were incubated for an additional 20-25 min in the 25° C. incubator. Table 7 displays in-process controls and tests for the conjugation and quenching steps.

TABLE 7

In-process controls and tests for conjugation and quenching steps

| In-process Controls and Tests | Specification or Range |
|---|---|
| Conjugation step mixing time | 10-15 min |
| Conjugation step incubation time | 120 (115-125) min |
| Conjugation step incubation temperature | 25 (23-27) ° C. |
| Quenching step mixing time | 10-12 min |
| Quenching step incubation time | 20-25 min |
| Quenching step incubation temperature | 25 (23-27) ° C. |

A final UF/DF step was performed to exchange the conjugated product into the final PBS formulation buffer. Cleaning of the UF/DF system was performed prior to use. The unit was cleaned and parts were soaked in 1.0 M NaOH and then rinsed with HPW. The system was equilibrated with PBS, pH 7.1 until the permeate was within specifications. Permeate and retentate were tested for endotoxin.

The quenched conjugate was transferred to the UF/DF system and was first concentrated to 8-10 L followed by diafiltration with 8-12 diavolumes of PBS in order to exchange the product into the final formulation buffer. The pH and conductivity were confirmed. The system was flushed with buffer and the flush was added to the final product. The protein concentration was determined and if needed, further dilution with PBS was performed to reach a final target product concentration of 2.0 mg/mL (1.8-2.1 mg/mL).

Table 8 displays in-process controls and tests for the final UF/DF, filtration, and storage. In some cases, dilution was required.

TABLE 8

In-process controls and tests for final UF/DF, filtration, and storage

| In-process Controls and Tests | Specification or Range |
|---|---|
| TFF Unit Preparation | |
| 0.1M NaOH flush time | 30-40 min |
| HPW rinse volume | ≥20 L |
| TFF Equilibration | |
| pH of permeate after equilibration | 7.0-7.2 |
| UF/DF permeate and retentate effluent endotoxin | ≤0.134 EU/mL |
| Cetuximab-IRDye 700DX Conjugate Diafiltration | |
| pH of permeate after diafiltration | 7.0-7.2 |
| Conductivity of permeate after diafiltration | 11-16 mS/cm |
| Target conjugate protein concentration (SEC-HPLC) after diafiltration | 1.8-2.1 mg/mL |
| Filter integrity test | Pass |

After preparing the conjugated material, the sample was submitted for SEC-HPLC to determine concentration, dye to antibody ratio (DAR), identity and purity. Other tests for appearance, pH, bioburden, and endotoxin level also were performed. Table 9 shows the results of these tests for an exemplary batch product with reference to general acceptance criterion for the drug substance.

TABLE 9

Drug Substance Specifications

| Test | Acceptance Criterion | Result | Pass/Fail |
|---|---|---|---|
| Appearance | Green to blue liquid May contain visible particulates | Conforms | Pass |
| Bioburden | <1 CFU/mL | 0 CFU/mL | Pass |
| Endotoxin (LAL) | ≤0.067 EU/mg | <0.06 EU/mg | Pass |
| pH | 7.1 ± 0.5 | 7.1 | Pass |
| Concentration by SEC-HPLC | 1.8 to 2.1 mg/mL | 2.0 mg/mL | Pass |
| DAR by SEC-HPLC (A690/A280 with dye correction) | 1.5 to 4.0 | 2.9 | Pass |
| Identity by SEC-HPLC (A690) | Relative retention time of monomer peak: 0.90 to 1.10 of Reference Standard monomer peak | Relative retention time of monomer peak: 0.99 of Reference Standard monomer peak | Pass |
| Purity by SEC-HPLC (A690) | Monomer ≥ 92.0% HMW ≤ 5.0% LMW ≤ 5.0% Free Dye: ≤3% | Monomer 100.0% HMW 0.0% LMW 0.0% Free Dye: 0% | Pass |

A final filtration through a 0.22 μm filter was performed and the Cetuximab-IRDye 700DX conjugate drug substance was stored in the dark at 2-8° C. in a 50 L HyQtainer covered with aluminum foil to protect the contents from light. The steps were performed at room temperature under green light to protect the Cetuximab-IRDye 700DX conjugate. The Cetuximab-IRDye 700DX conjugate drug substance was forward-processed directly into drug product stability within 4 weeks of manufacture. In some instances the drug product was vialed within about 1 week of preparation of the drug substance.

Example 4: Completion and Packaging of Drug Product

The final Cetuximab-IRDye 700DX conjugate drug product was prepared and packaged using methods that included a semi-automated aseptic fill into sterile, depyrogenated amber glass vials. The vials were stoppered, sealed, and then inspected. Precautions were in place during all product exposure operations to minimize exposure to light, including the use of low intensity green light (e.g., wavelength from 425 to 575 nm and an intensity of less than 200 Lux) during the sterile filtration, filling operations, and inspection processes. In addition to the use of low intensity green light during all steps requiring some light exposure, the bulk and vialed product was covered by opaque materials or containers at all other times. Environmental monitoring of the room, equipment, and personnel was performed throughout the sterile filtration and fill processes.

Prior to the fill, the vials, stoppers, and seals were cleaned and sterilized as appropriate. Glass vials were cleaned with Highly Purified Water (HPW) and Water for Injection (WFI). Vials were then visually inspected and defective vials were removed prior to further preparation. The vials were placed in racks and covered, followed by depyrogenation. Seals were washed with HPW/WFI. Both vials and seals were sterilized (autoclaved) prior to use. Stoppers were purchased ready-to-use (cleaned and sterile).

Cetuximab-IRDye 700DX conjugate drug product was aseptically filtered using a 0.22 μm sterile filter and the filter was integrity tested after the filtration step. The sterile filtrate was then weighed to determine the approximate number of vials to be filled and stored at 2 to 8° C. overnight, protected from light, prior to the fill.

Prior to the filling operations, the crimper was tested. Ten empty vials were stoppered and crimped and the pressure (20-40 psi) was confirmed. Empty vial weights for five vials were measured to determine the mean empty vial weight. This result was used to determine the weight range for filled vials, assuming a 51±1 mL fill and a density of 1 g/mL for the Cetuximab-IRDye 700DX conjugate bulk solution. A fill check was performed on three vials prior to fill start to ensure the filled vial weight was within specification. Sterile filtered Cetuximab-IRDye 700DX conjugate was filled into vials using a peristaltic pump and filling needle assembly. Vials were stoppered and transferred for scaling and crimping. Vial weight checks were performed on filled vials containing the solution, stoppers, and overseals for each tray during the fill process; 5 vials were checked per tray and each tray held up to 30 vials. The fill duration was established at <8 hr 49 min based on media fill qualification results. Filled vials were placed in containers to protect them from the light and stored at 2 to 8° C.

All filled vials in the lot were visually inspected for overfill, underfill, defective seals, and other defects and any defective vials were segregated from the lot. Vials were stored at 5±3° C., protected from light, prior to labeling operations.

Labeling of the vials was performed using light protection with green light. Vials were labeled at ambient room temperature, taking care to avoid excessive exposure to ambient temperature. After labeling, vials were stored in a non-transparent bin and returned to storage at 5±3° C. A second 100% visual inspection was performed, and any defective vials were removed. Vials were returned to storage at 5±3° C., protected from light, prior to final secondary packaging operations.

Secondary/tertiary packaging was performed by placing a single unit vial into a single aluminum pouch. The pouch provided 100% protection from light. The pouch containing the vial was then placed in a paperboard box for an additional measure of light protection. Vials stored in their secondary packaging were held at 5±3° C. prior to distribution and clinical use.

After preparing the conjugated material, the sample was submitted for SEC-HPLC to determine concentration, dye to antibody ratio (DAR), identity and purity. Other tests for appearance, pH, bioburden, and endotoxin level also were performed. Table 9 shows the results of these tests for an exemplary batch product with reference to general acceptance criterion for the drug substance.

Following preparation of the drug product, samples were submitted for SEC-HPLC to determine concentration, dye to antibody ratio (DAR), identity and purity. Other tests for appearance, pH, fill volume, sterility, endotoxin level, particulates, and purity by SDS-PAGE also were performed. Table 10 depicts general acceptance criterion for the drug product based on these tests.

TABLE 10

| | Drug Product Specifications | |
|---|---|---|
| Test | Release Acceptance Criterion | Stability Acceptance Criterion |
| Appearance | Green to blue liquid May contain visible particulates | Same |
| pH | 7.1 ± 0.5 | Same |
| Fill Volume | Not less than 50 mL | NA |
| Concentration by SEC-HPLC | Release: 1.8 to 2.2 mg/mL | 1.8 to 2.4 mg/mL |
| Identity by SEC-HPLC (A690) | Relative retention time of monomer peak: 0.90 to 1.10 of Reference Standard monomer peak | Same |
| Purity by SEC-HPLC (A690) | Monomer ≥ 90.0% Release: HMW ≤ 5.0% Release: LMW ≤ 5.0% Release: Free dye ≤ 7.0% | Same HMW ≤ 10.0% LMW ≤ 10.0% Free dye ≤ 10.0% |
| Purity by SDS-PAGE, Reduced, Coomassie | Purity (heavy and light chains together) ≥ 90% Main bands conform to Reference Standard | Same Same |
| Purity by SDS-PAGE, Non-reduced, Coomassie | Main band ≥ 90.0% purity Main band conforms to Reference Standard | Same Same |
| DAR SEC-HPLC (A690/A280 with A280 dye correction) | Release: DAR 1.5 to 4.0 | Report results |
| ELISA for EGFR antigen binding | 50-150% of Reference Standard | Report results |

TABLE 10-continued

Drug Product Specifications

| Test | Release Acceptance Criterion | Stability Acceptance Criterion |
| --- | --- | --- |
| Sterility | Negative for Growth | Same |
| Endotoxin | <0.067 EU/mg | Same |
| Particulates | Not performed | Report Results |

Example 5: Methods of Treatment with Cetuximab-IRDye 700DX Conjugate

This example describes therapeutic methods for treating head and neck cancer by intravenously administering to a subject cetuximab-IRDye 700DX conjugate, prepared for instance, as described in Example 3. Under light-controlled conditions, the subject was administered 160 mg/m$^2$ of cetuximab-IRDye 700DX conjugate followed by irradiation with near infrared light to induce photoimmunotherapy. In some cases a subject is administered a dose of cetuximab-IRDye 700DX conjugate within a range from 750 mg/m$^2$ to 1250 mg/m$^2$.

Preparation of Intravenous (IV) Bags for Infusion

Prior to infusion of the cetuximab-IRDye 700DX conjugate, the conjugate was not exposed to direct or indirect sunlight. Operations with cetuximab-IRDye 700DX conjugate were conducted in rooms under fluorescent lighting. Tungsten lighting was not used. Protection from exposure to environmental light was implemented.

Intravenous (IV) bags containing the conjugate were prepared from vials containing 50 mL of a 2 mg/mL solution of cetuximab-IRDye 700DX conjugate. The packaging of each vial containing the conjugate was opened and the contents of that vial were placed into a sterile IV bag. The process of opening each individual vial and placing the contents into the IV hag was repeated until the desired dose of conjugate for infusion was achieved. Each vial was opened separately and placed into the IV bag so as to reduce the exposure of the drug product to ambient room light. The process was performed in less than 15 min. The IV bag was covered at all times by an opaque sleeve to protect the conjugate from light exposure. After preparation, the IV hag was stored at 2-8° C.

Administration

The subject was administered the conjugate via IV infusion over 2 hours on Day 1. During the infusion, the lighting in the treatment room was less than 200 lux of fluorescent light. Any windows in the room were covered with shades. The IV bag was covered during the administration by an opaque sleeve to protect the conjugate from light exposure. Any light exposure was limited to less than 5 minutes.

To induce photoimmunotherapy, one light application of with a light having a wavelength of 690 nm was performed at 24 hours±2 h (Day 2) post conjugate administration.

The subject returned for a follow up on Day 4 and all treated tumors exhibited necrosis. The subject showed no adverse effects and did not report any pain. No skin photosensitivity was detected.

Optionally, prior to conjugate administration, the subject was pretreated with 100 mg of Erbitux® administered by IV infusion over 30 minutes. During the infusion, the subject was evaluated for possible infusion reactions to Erbitux®. After the 100 mg Erbitux® infusion, but just prior to cetuximab-IRDye 700DX conjugate infusion, the subject was pre-treated with 50 mg of anti-histaminic Benadryl (Diphenhydramine) and 10 mg of the steroid Decadron (Dexamethasone) by IV administration to limit the risk of hypersensitivity to cetuximab-IRDye 700DX conjugate infusion.

Example 6: pH Stability of Drug Product

To assess the effect of pH, concentration and/or buffer formulation on long term stability of the conjugate, a series of four buffer formulations containing the Cetuximab-IRDye 700DX conjugate at two concentrations, 2 mg/mL and 5 mg/mL, for a total of eight buffer formulations were prepared at either pH 5.5 or pH 7.1. The eight buffer formulations prepared were as follows:

BF #1: [2 mg/mL conjugate] HyClone Phosphate Buffered Saline (1×), 6.7 mM PO4 (pH 7.0-7.2) without Calcium, Magnesium (HyClone Cat # SH30256).

BF #2: [2 mg/mL conjugate] 10 mM Sodium citrate, 100 mM glycine, 100 mM NaCl, 0.01% Tween 80, pH 5.5±0.1

BF #3: [2 mg/mL conjugate] 20 mM Sodium Citrate, 120 mM Sodium Chloride, 2 mM EDTA, 0.01% Tween 80, pH 5.5±0.1

BF #4: [2 mg/mL conjugate] 20 mM Sodium Citrate, 4% Mannitol, 2 mM EDTA, 0.01% Tween 80, pH 5.5±0.1

BF #5: [5 mg/mL conjugate] HyClone Phosphate Buffered Saline (1×), 6.7 mM PO4 (pH 7.0-7.2) without Calcium, Magnesium (HyClone Cat # SH30256).

BF #6: [5 mg/mL conjugate] 10 mM Sodium Citrate, 100 mM glycine, 100 mM NaCl, 0.01% Tween 80, pH 5.5±0.1

BF #7: [5 mg/mL conjugate] 20 mM Sodium Citrate, 120 mM Sodium Chloride, 2 mM EDTA, 0.01% Tween 80, pH 5.5±0.1

BF #8: [5 mg/mL conjugate] 20 mM Sodium Citrate, 4% Mannitol, 2 mM EDTA, 0.01% Tween 80, pH 5.5±0.1

In this example, stability was performed on BF #5-BF #8 using conditions to induce forced degradation as follows: A sample volume of 750 μL of each of the 4 formulations BF #5-8 were placed into 2 mL screw-cap polypropylene vials and covered with aluminum foil to protect the samples from light. The four tubes were placed into a 45° C. water bath and allowed to incubate for 16 hours. The vials were then transferred to a refrigerator and stored at 2-8° C. for a period of 1 week. The samples were removed from the refrigerator and centrifuged at 5,000×g for 5 minutes. Upon inspection of the tubes it was observed that the 3 samples of Cetuximab-IRDye 700DX conjugate formulated in the pH 5.5 buffers systems (BF #6, BF #7 and BF #8) all had a significant amount of precipitated blue material in the bottom of each tube. However, the BF #5 sample which was formulated in PBS at pH=7.1 did not show any visual precipitate.

A sample of the supernatant solution was obtained from each of the four samples and HPLC-SEC analysis was performed to determine the concentration of the monomer form of the Cetuximab-IRDye 700DX conjugate that remained in each of the samples. The results of that analysis are shown below in Table 11 along with the initial concentrations determined for each of samples prior to being subjected to the forced degradation study conditions.

TABLE 11

Forced Degradation Study Results

| Sample | Initial Concentration (mg/mL) | Final Concentration (mg/mL) |
|---|---|---|
| BF#5 | 5.2 | 5.1 |
| BF#6 | 5.3 | 3.7 |
| BF#7 | 5.3 | 4.1 |
| BF#8 | 5.2 | 3.6 |

The data in Table 11 show that all samples of the Cetuximab-IRDye 700DX conjugate formulated in the pH 5.5 buffers systems (BF #6, BF #7 and BF #8) displayed a significant loss (20% or more) in the concentration of the monomer form of the conjugate product. In contrast to these results, the BF #5 (pH=7.1) sample showed little change in concentration. These results indicated that the Cetuximab-IRDye 700DX conjugate drug product could also be less stable in pH=5.5 buffer systems upon long term storage (e.g., greater than 6 months) of the product under 2-8° C. storage conditions.

Example 7: Long Term Storage Stability of Cetuximab-IRDye 700DX Conjugate in pH=5.5 Buffer Systems Versus pH=7.1 PBS Samples of the Cetuximab-IRDye 700DX conjugate in the four buffer formulations described above containing the conjugate at the two concentrations, 2 mg/mL and 5 mg/mL (BF #1-8), were stored for a period of 12 months at 2-8° C. protected from light in 15 mL polypropylene tubes. After the 12 months of storage at 2-8° C. the samples were visually inspected for the formation of a precipitate. It was observed upon this inspection that all of the pH=5.5 samples (BF #2, BF #3, BF #4, BF #6, BF #7 and BF #8) contained a significant amount of insoluble blue material that had adhered to the bottom and sides of their storage tubes. Conversely, the two samples in the PBS pH=7.1 buffer system (BF #1, BF #5) did not show any indication of insoluble material. This observation indicates that the Cetuximab-IRDye 700DX conjugate is not stable and can precipitate after long-term storage in a buffer system at a pH<6, even at temperatures of 2-8° C. and protected from light. In contrast, the Cetuximab-IRDye 700DX conjugate that was formulated in a buffer greater than pH 6.0, such as about pH 7.1, results in stability of the drug product even after long-term storage at 2-8° C. for up to 1 year.

Example 8: Assessment of Cell Killing Activity and Composition of Various Antibody: IRDye 700 DX Conjugates Studies were performed to assess whether antibody-IRDye 700DX conjugates pre-exposed to different wavelengths of light differentially affect soluble aggregate formation. Two different antibodies—mouse anti-human anti-PD-L1 (Catalog No: 329728, Biolegend, San Diego, Calif.) and anti-EGFR (cetuximab; Myoderm USA, Norristown, Pa.)—were labeled with IRDye 700DX and were evaluated to assess if pre-exposure to different wavelengths of light affected soluble aggregate formation.

A. Antibody Conjugation

Both antibodies were conjugated with IRDye 700DX using the same approach. For all conjugates described below, the general protocol used to conjugate the antibodies was similar to that of larger scale conjugation with cetuximab-IRDye 700DX described in Example 1. Modifications to the protocol were made for smaller scale reaction volumes that used 3 mg or less of protein.

The antibody solution (either anti-PD-L1 antibody or anti-EGFR antibody) was first exchanged with phosphate buffer saline pH 7 using a 30,000 Dalton molecular weight cutoff centrifugal filter, then the antibody solution pH was adjusted to a pH of 8.5 with addition of phosphate buffer at pH=9. Frozen solid aliquots of IRDye 700DX NHS Ester (Catalog No. 929-70011; Li-COR, Lincoln, Nebr.) were thawed at room temperature, then dissolved with DMSO to achieve a 10 mg/mL concentration. In a dark environment, the solubilized IRDye 700 DX NHS Ester was then added to the antibody solution at a 4 (IRDye 700 DX NHS Ester) to 1 (antibody) molar ratio. The conjugation reaction proceeded at 25° C. for 2 hours protected from light. Glycine (pH 8.2) was added to a final concentration of 10 mM for 15 minutes to quench the reaction. The antibody conjugate solution was then exchanged with a 30,000 Dalton molecular weight cutoff centrifugal filter with 24 mL of PBS pH 7 to remove free dye, glycine, and glycine-IRDye 700 DX, and to adjust the pH of the solution back to pH 7. The antibody conjugates were analyzed with size exclusion chromatography to evaluate antibody-IRDye 700 DX concentration, monomer purity, % soluble aggregate, and dye to antibody ratio (DAR).

B. Effects of Light Pre-Exposure on Composition of IRDye 700DX Conjugate

The antibody-IRDye 700DX conjugate was tested for formation of soluble aggregates under four different conditions with at least 30 μL, of conjugate at an antibody conjugate concentration of 850 μg/mL. The four treatment conditions were as follows: (1) antibody-IRDye 700DX conjugate stored at 4° C. protected from light ("4° C." control); (2) antibody-IRDye 700DX conjugate placed in a clear glass HPLC tube under a halogen lamp (Catalog No: PL-800, Dolan-Jenner, Boxborough, Mass.) at 2500 lux for 24 hrs ("white light"); (3) antibody-IRDye 700DX conjugate placed in a clear glass HPLC tube wrapped in aluminum foil to protect from light exposure under halogen lamp at 2500 lux for 24 hrs ("no light", used to control for thermal heating effects on the formation of aggregates); and (4) antibody-IRDye 700DX conjugate placed in a clear glass HPLC tube and exposed to green LED lamp (Catalog No: Green-ECS GP19 EcoSmart) at 2500 lux for 24 hrs ("green light"). After 24 hours under each treatment condition, monomer purity and soluble aggregate formation was assessed by size exclusion chromatography.

The results for the anti-PD-L1-IRDye 700DX conjugate are shown in Table 12. As shown, anti-PD-L1-IRDye 700DX conjugate (DAR~3) that was stored at 4° C. exhibited low soluble aggregate formation (<1.5%) and high monomer purity (>96%) as measured by 280 nm absorbance and 690 nm absorbance. Exposure of the anti-PD-L1-IRDye 700DX conjugate to 2500 lux of white light from a halogen lamp resulted in a significant increase in soluble aggregate formation (~30%) and concomitant decrease in monomer purity (~65%) as measured by 280 nm absorbance and 690 nm absorbance. Anti-PD-L1 IRDye 700DX exposed to the thermal heating effects of 2500 lux white light from a halogen lamp, but protected from light illumination using aluminum foil, did not induce any increase in soluble aggregate formation when compared to that of the 4° C. control sample. Anti-PD-L1 IRDye 700DX conjugate exposed to light from a green LED lamp resulted in a very minor increase in soluble aggregate formation (~5%), which was a significantly lower amount of soluble aggregate formation than that of anti-PD-L1 IRDye 700DX exposed to white light.

TABLE 12

Anti-PD-L1 IRDye 700DX aggregate formation with different types of light exposures.

| Treatment | Aggregate Retention time [min] | Monomer Retention time [min] | % Aggregate (Aggregate/Total) | % monomer (Monomer/Total) |
|---|---|---|---|---|
| 1) Anti-PD-L1-IRDye 700DX: 4° C. | 7.2 | 8.3 | 1.2% (280 nm)<br>1.1% (690 nm) | 96.7% (280 nm)<br>98.4% (690 nm) |
| 2) Anti-PD-L1-IRDye 700DX: 2500 Lux white light, 24 hours | 6.8 | 7.6 | 30.9% (280 nm)<br>29.5% (690 nm) | 65.0% (280 nm)<br>64.7% (690 nm) |
| 3) Anti-PD-L1-IRDye 700DX: No light, 24 hours | 7.2 | 8.3 | 1.1% (280 nm)<br>1.1% (690 nm) | 98.9% (280 nm)<br>98.2% (690 nm) |
| 4) Anti-PD-L1-IRDye 700DX: 2500 Lux green light, 24 hours | 7.2 | 8.3 | 5.4% (280 nm)<br>5.1% (690 nm) | 94.6% (280 nm)<br>94.4% (690 nm) |

The results for the cetuximab-IRDye 700DX conjugate are shown in Table 13. Cetuximab-IRDye 700DX conjugates (DAR~3) that were stored at 4° C. did not have any detectable soluble aggregate formation (~0%) and high monomer purity (~100%) as measured at 280 nm absorbance and 690 nm absorbance. Exposure of the cetuximab-IRDye 700DX conjugate to white light of 2500 lux from a halogen lamp resulted in a significant increase in soluble aggregate formation (~40%) and concomitant decrease in monomer purity (~55%) as measured by 280 nm absorbance and 690 nm absorbance. Cetuximab-IRDye 700DX exposed to the thermal heating effects of 2500 lux white light from a halogen lamp, but protected from light illumination using aluminum foil, did not induce any increase in soluble aggregate formation when compared to that of the 4° C. control sample. Cetuximab-IRDye 700DX conjugate exposure to light from a green LED lamp resulted in a minor increase in soluble aggregate formation (~4%), which was significantly lower amount of soluble aggregate formation than that of cetuximab-IRDye 700DX exposed to white light.

Example 9: Duration of Pre-Exposure of White Fluorescent Vs. Green LED Lighting and their Effect on Cetuximab-IRDye 700DX Soluble Aggregate Formation and PIT Potency The following studies were performed to assess whether cetuximab-IRDye 700DX conjugates pre-exposed to different wavelengths of light and for different durations of exposure differentially affect soluble aggregate formation and pharmacological activity.

Cetuximab-IRDye 700DX was conjugated as described in Example 1. The following 14 different conditions were assessed: sample was exposed to 500 lux white fluorescent lighting at 25° C. for different durations of light exposure at 24 hours, 12 hours, 6 hours, 3 hours, 1.5 hours, and 45 minutes; sample was exposed to 500 lux of green LED lighting (Catalog No: Green-ECS GP19 EcoSmart) at 25° C. for different durations of light exposure at 24 hours, 12 hours, 6 hours, 3 hours, 1.5 hours, and 45 minutes; sample was exposed to no light at 25° C.; and sample was exposed to no light at 4° C. The duration of the light exposure for 24 hours, 12 hours, 6 hours, 3 hours, 1.5 hours, 45 minutes corresponds to 12,000 lux-hours, 6,000 lux-hours, 3,000 lux-hours, 1,500 lux-hours, 750 lux-hours, or 375 lux-hours, respectively. For each condition, 30 μL of conjugate was placed in a clear HPLC vial per sample at an antibody conjugate concentration of 2 mg/mL and the sample was exposed to each light condition.

TABLE 13

Cetuximab-IRDye 700DX aggregate formation with different types of light exposures.

| Sample | Aggregate Retention time [min] | Monomer Retention time [min] | % Aggregate (Aggregate/Total) | % monomer (Monomer/Total) |
|---|---|---|---|---|
| 1) Cetuximab-IRDye 700DX: 4° C. | ND | 8.2 | 0% (280 nm)<br>0.2% (690 nm) | 100% (280 nm)<br>99.3% (690 nm) |
| 2) Cetuximab-IRDye 700DX: 2500 Lux white light, 24 hours | 7.1 | 7.9 | 40.5% (280 nm)<br>41.8% (690 nm) | 55.3% (280 nm)<br>53.8% (690 nm) |
| 3) Cetuximab-IRDye 700DX: No light, 24 hours | 7.3 | 8.2 | 0.3% (280 nm)<br>0.2% (690 nm) | 99.6% (280 nm)<br>99.6% (690 nm) |
| 4) Cetuximab-IRDye 700DX: 2500 Lux green light, 24 hours | 7.3 | 8.2 | 3.9% (280 nm)<br>3.5% (690 nm) | 96.1% (280 nm)<br>96.0% (690 nm) |

The stability of fetuximab-IRDye 700DX conjugate following white light or green light exposure for different durations of time was assessed by monitoring formation of soluble aggregates and PIT killing activity.

1. Aggregate Formation

Cetuximab-IRDye 700DX was analyzed with HPLC size exclusion chromatography to evaluate the monomer purity and soluble aggregate formation. The percent soluble aggregate formation was measured as a function of cetuximab-IRDye 700DX lux-hours exposure to white light, green light, or no light.

Figure 2A:
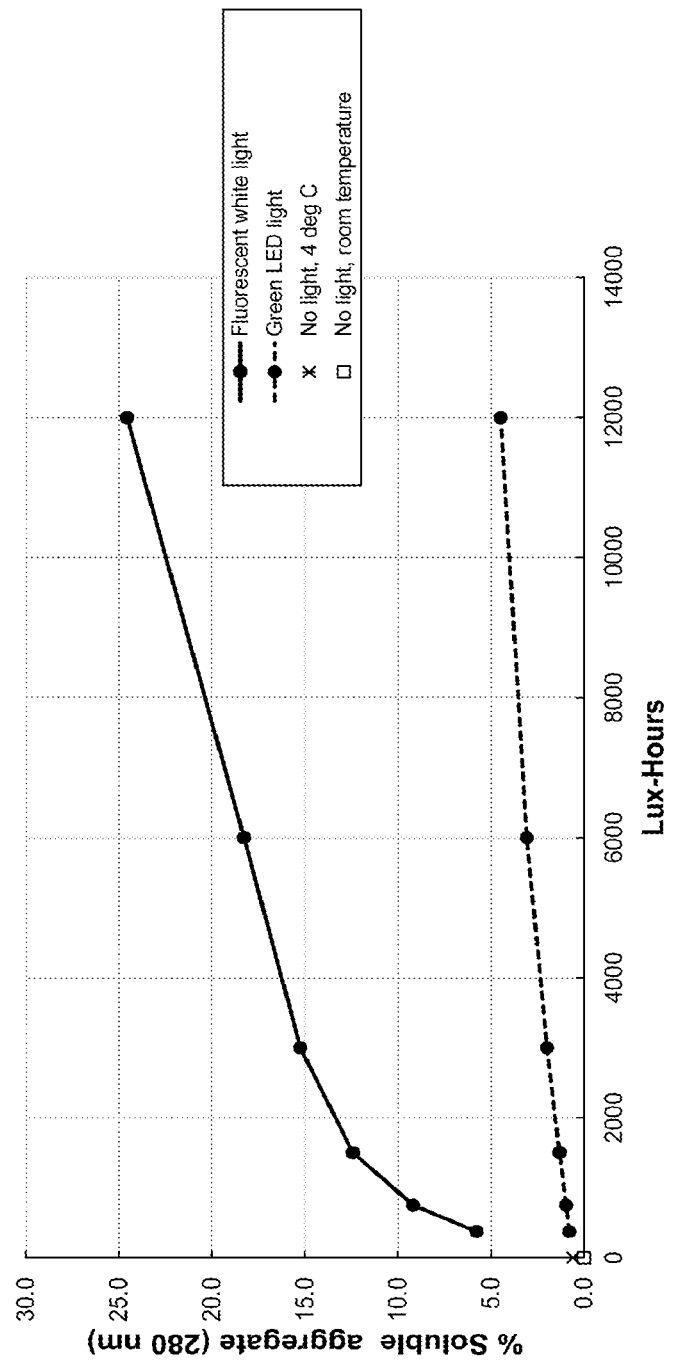
FIG. 2A shows the duration of exposure of Cetuximab-IRDye 700DX to 500 Lux white fluorescent light or green LED light and its effect on soluble aggregate formation.

As shown in FIG. 2A, the duration of exposure of cetuximab-IRDye 700DX to 500 lux white fluorescent light had a direct effect on the formation of soluble aggregates. Cetuximab-IRDye 700DX exposure to white fluorescent light resulted in a rapid increase in soluble aggregate formation with the presence of greater than 5.0% soluble aggregate formation observed even after only 375 lux-hours (45 minutes at 500 lux) of exposure to white light, which increased further with the increased duration of exposure to white fluorescent lighting. Cetuximab-IRDye 700DX green light exposure also slightly increased soluble aggregate formation albeit at a rate much slower than that of white light; the percentage of aggregates formed even after exposure to 12,000 lux-hours (24 hours at 500 lux) of green light was no more than 5.0%. The results showed that there was a greater cetuximab-IRDye 700DX soluble aggregate formation with an increase in time of exposure to white light than that of green light. Less than 1% soluble aggregate formation was observed in samples either incubated at 4° C. or 25° C. when protected from any light exposure.

2. PIT Killing

To evaluate PIT killing activity by the cetuximab-IRDye 700DX pre-exposed to the various light conditions, BxPC3 cells (#CRL-1687, ATCC, Manassas Va.) were incubated for one hour at 4° C. with or without 1 μg/mL cetuximab-IRDye 700DX in RPMI-1640 media supplemented with 10% FBS and 1% Penicillin/Streptomycin (complete culture media), and then washed one time with complete culture media to remove unbound cetuximab-IRDye 700DX. The cells were then illuminated with a 690 nm laser at a light dose of 32 $J/cm^2$ or protected from light (0 $J/cm^2$).

The effect of different treatment regimens on cell death was measured using the fluorescent stain, CellTox Green (Cat No: G8731, Promega, Madison, Wis.). CellTox Green is a non-permeable fluorescent dye that exhibits increased fluorescence upon binding to DNA. Therefore, only cells that have compromised plasma membranes exhibit strong CellTox Green staining. After the light treatment, all cells were incubated with 1× CellTox Green reagent diluted in RPMI-1640 supplemented with 10% fetal bovine serum and 1% Penicillin/Streptomycin (complete culture media). Wells that did not include any cells were also incubated with 1×CellTox Green reagent diluted in complete culture media to serve as background subtraction wells during fluorescent signal detection. The CellTox Green fluorescence signal was measured at 24 hours after light treatment using a fluorescence plate reader. The cells were then lysed with detergent, incubated at 37° C. for 30 minutes, and the CellTox Green fluorescence signal was measured again post lysis. The percent dead cells was calculated by taking the ratio between background (1× CellTox Green in complete culture media without cells) subtracted CellTox Green signal per well prior to and post lysis and multiplying the ratio by 100.

Figure 2B:
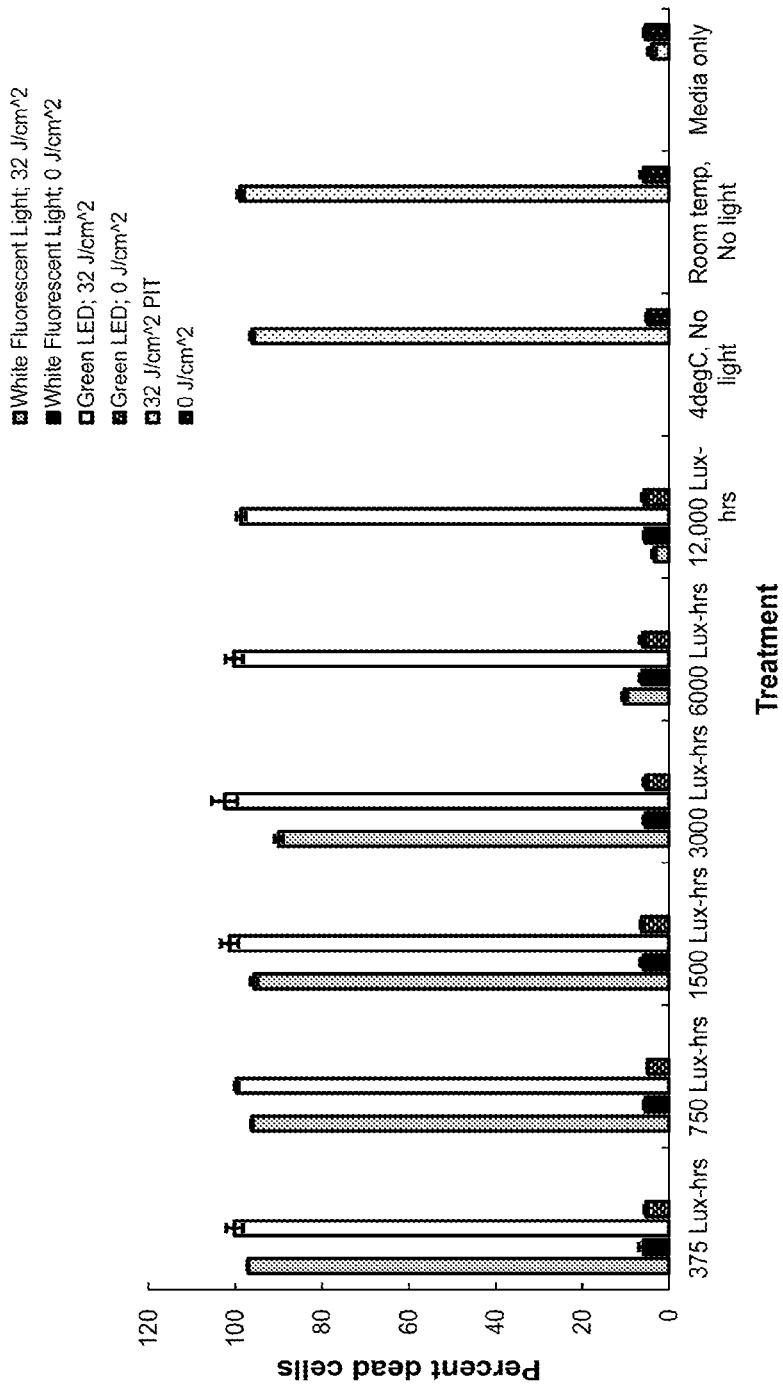
FIG. 2B shows the effect of pre-exposure of Cetuximab-IRDye 700DX to white fluorescent light or green LED light on BxPC3 PIT activity at various light doses and durations.

As shown in FIG. 2B, no effect on cell death was observed for all samples exposed to 0 $J/cm^2$ during the PIT treatment, indicating that, despite the increase in soluble aggregates after pre-exposure to white light, the soluble aggregates were not cytotoxic in that absence of light irradiation. In contrast, cell killing was observed for samples that were subsequently irradiated with a 690 nm laser at a light dose 32 $J/cm^2$, although the extent of cell killing was substantially reduced by the cetuximab-IRDye 700DX exposed to increased durations of white light. As shown, cetuximab-IRDye 700DX pre-exposed to 3,000 Lux-Hours (500 lux for 6 hours) or more of white fluorescent light exhibited less than 90% or less effect on PIT activity. However, cetuximab-IRDye 700DX exposed to all lux-hour doses of green light evaluated did not result in an effect in PIT potency, indicating that pre-exposure to green light did not substantially impact light-activated killing activity.

Figure 2C:
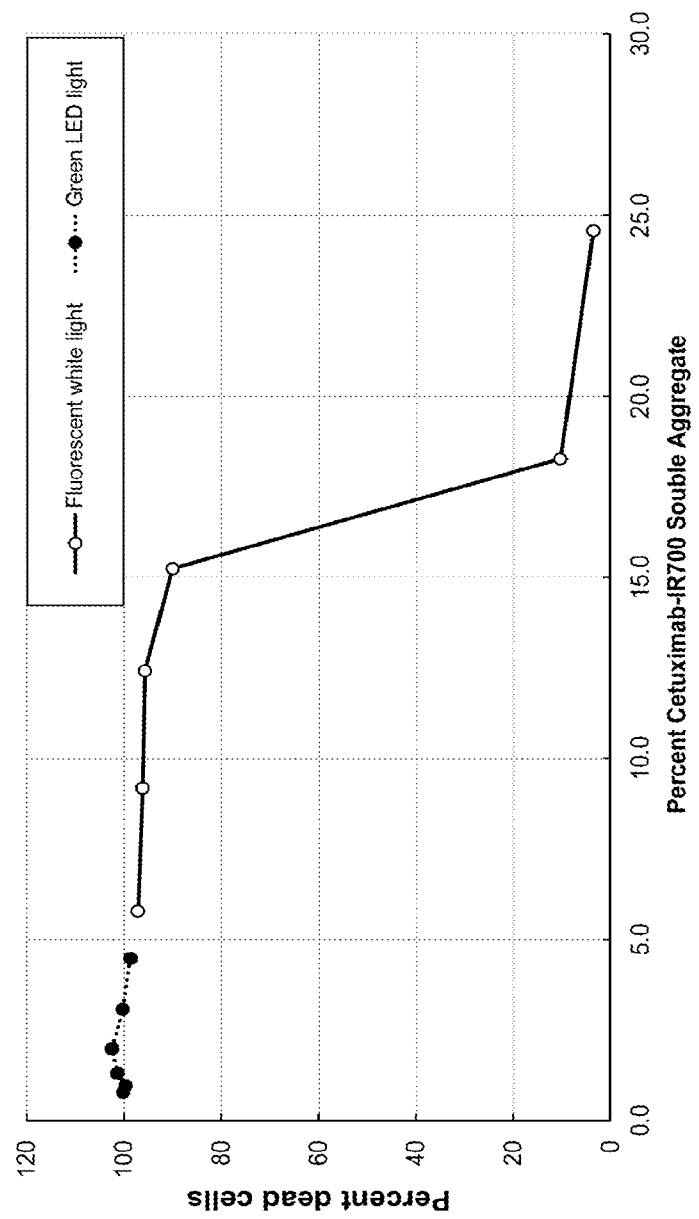
FIG. 2C shows the effect of percent Cetuximab-IRDye 700DX soluble aggregate formation on PIT activity.

The effect of aggregate formation on PIT activity is shown in FIG. 2C. As shown, the PIT potency (percent dead cells) for all cetuximab-IRDye 700 DX treatment regimens for evaluating white light and green light exposure were plotted as a function of the measured percent soluble aggregate for each respective sample. The results showed that greater than 15% soluble aggregate formation of cetuximab-IRDye 700DX results in a significant decrease in PIT potency.

Example 10: Effect of Indirect Conjugation with Phthalocyanine Dye on PIT Killing and Specificity of PIT The following studies were performed to assess whether antibodies that hind directly to cell surface molecules require direct conjugation with a phthalocyanine photosensitizer, such as IRDye 700DX, to mediate PIT killing activity.

A. IRDye 700 DX Conjugation of Secondary Antibody Against Cell Targeting Antibody Instead of directly conjugating a targeting antibody targeted against a cell surface molecule (e.g., on a cancer cell) with IRDye 700 DX, a secondary anti-human IgG antibody that bound the targeting antibody was conjugated with IRDye 700 DX. Specifically, AffiniPure Donkey Anti-Human IgG, Fcγ Fragment Specific (DxHu) antibody (Catalog number: 709-005-098, Jackson ImmunoResearch Laboratories, West Grove, Pa.) was labeled with IRDye 700DX to evaluate whether non-covalent labeling of primary antibodies with secondary antibody-IRDye 700DX could be used in PIT-mediated killing. The protocol used for conjugating the DxHu antibody with IRDye 700DX was substantially the same as the protocol for antibody conjugation used in Example 8.

PIT killing of BxPC3 cells was evaluated similar to the method described in Example 9, except the cells were first incubated for one hour at 4° C. with or without anti-EGFR antibody, cetuximab (Myoderm USA, Norristown, Pa.) in RPMI-1640 media supplemented with 10% FBS and 1% Penicillin/Streptomycin (complete culture media). The cells were then washed one time with complete culture media, incubated for 30 minutes at 4° C. with or without IRDye 700DX conjugated (DxHu IRDye 700DX) secondary antibody diluted with complete culture media, and then washed one time with complete culture media. As a control, BxPC3 cells were incubated with cetuximab-IRDye 700DX in which the cetuximab was directly conjugated to IRDye 700DX. To induce cell killing, the cells were then illuminated with a 690 nm laser at a light dose of 16 $J/cm^2$ or protected from light ("no light"). Cell death was evaluated as described in Example 9 using CellTox Green.

Figure 3:
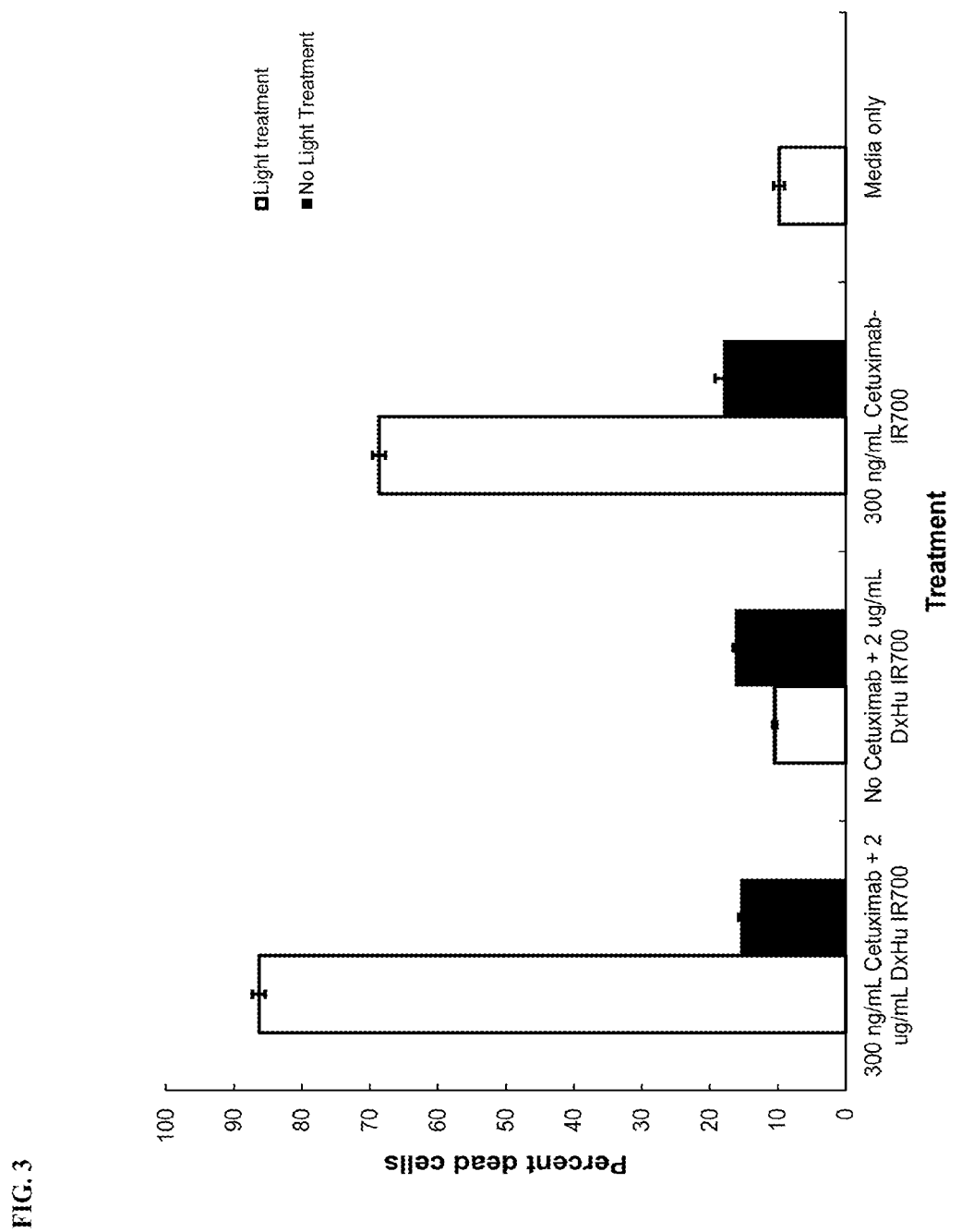
FIG. 3 shows the PIT killing activity with sequential staining using Cetuximab and donkey anti-human-IRDye 700DX (DxHu IR700) secondary antibody.

As shown in FIG. 3, BxPC3 cells that were sequentially labeled with cetuximab and donkey anti-human IRDye 700DX secondary antibody and treated with light exhibited ~90% cell death. The same treatment with the primary and secondary antibody did not result in cell death when cells were not exposed to the 690 nm light treatment. Light illumination of cells treated only with the secondary antibody did not lead to cell death because the DxHu IRDye 700DX secondary antibody does not bind directly to cells in the absence of pre-incubation with a human-derived primary antibody targeting a cell surface antigen. The extent of cell killing induced by sequential exposure to the antibodies was even slightly greater than in BxPC3 cells incubated with cetuximab that had been directly labeled with IRDye 700DX. Light treatment of BxPC3 cells treated only with media alone with no incubation with either cetuximab or DxHu IRDye 700DX resulted in a basal cell death level of ~10%, which was similar to the background cell death in cells that were not irradiated with light (no light treatment). Thus, the results showed that antibodies that bind directly to cancer cells do not require direct conjugation of a phthalocyanine photo sensitizer such as IRDye 700DX to mediate PIT killing activity. Indirect labeling of anti-cancer antibodies mediated by a secondary antibody conjugated IRDye 700DX can also induce effective PIT killing activity.

B. IRDye 700 DX Conjugation of Monomeric Streptavidin Against a Biotinylated Cell Targeting Antibody In another study, the PIT killing activity of cells sequentially incubated with a biotinylated anti-EGFR antibody (biotinylated cetuximab) and monomeric streptavidin-conjugated IRDye 700DX was examined. Furthermore, the effect of pre-exposure of the monomeric streptavidin-IRDye 700 DX to white light on the PIT killing activity was also examined.

1. Conjugations a. Conjugation of Biotin to Cetuximab

To conjugate the anti-EGFR antibody Cetuximab to biotin, a 5 mL volume of anti-EGFR antibody (Cetuximab; Myoderm USA, Norristown, Pa.) supplied at a concentration of 2 mg/mL in PBS pH 7.2 was concentrated to a volume of 2 mL (5 mg/mL) using a 30,000 Dalton molecular weight cutoff centrifugal filter (Cat No: UFC903024, Merck-Millipore, Cork, IRL.) The solution was diluted to 5 mL with 100 mM $Na_2HPO_4$ (pH 8.9) to final volume of 5 mL and pH of ~8.5.

EZ-Link Sulfo-NHS-LC-Biotin (sulfocussinimidyl-6-[biotin-amido]hexanoate) was used to label the antibody according to the manufacturer's instructions (Cat. No. 21327, ThermoScientific, Rockford, Ill.). Specifically, a 2 mg sample of Sulfo-NHS-Biotin ($SO_3$-biotin-NHS ester, Cat #: 1854200, Thermo Scientific) was thawed at room temperature, then dissolved with deionized (DI) water to achieve a 10 mg/mL concentration. A volume of 130 μL of the solubilized $SO_3$-biotin-NHS ester was added to the cetuximab antibody solution at a 20 (SO3-Biotin-NHS Ester) to 1 (cetuximab antibody) molar ratio. The conjugation reaction proceeded at 25° C. for 2 hours protected from light where upon, excess glycine was added to quench the reaction for 15 minutes. The Cetuximab-biotin conjugate solution was then exchanged with ten times the equivalent conjugation volume with PBS pH 7.2 using a 30,000 Dalton molecular weight cutoff centrifugal filter to remove free dye, glycine, and glycine-IRDye 700DX, and to adjust the pH back to pH 7.2.

The cetuximab-biotin conjugate was analyzed with size exclusion chromatography (SE-HPLC) to evaluate monomeric cetuximab-biotin purity, % soluble aggregate and reaction product residual impurity levels. The average molar Biotin to Antibody Ratio (BAR) for the conjugate was determined using the Pierce Colorimetric Biotin Quantification Assay (Cat No: 128005, Thermo Scientific, Rockford, Ill.) according to supplier instructions. The results are shown in Table 14.

TABLE 14

Cetuximab-Biotin Analysis Results

| | | |
|---|---|---|
| Biotin to Antibody Ratio (BAR) | 7.2 | |
| SE-HPLC Purity | A210 | 99.1% monomer, 0.3% HMW, 0.6 LMW |
| | A280 | 100% | b. Conjugation of Monomeric Streptavidin to IRDye 700 DX

The general protocol used to conjugate engineered monomeric streptavidin 2 (mSA2) (Catalog No: EBU001/2, Kerafast, Boston, Mass.) with IRDye 700 DX was substantially the same as the protocol for antibody conjugation described in Example 8, except that prior to conjugation, the mSA2 solution was first exchanged with phosphate buffer saline pH 7 using a 3,000 Dalton molecular weight cutoff centrifugal filter. For the conjugation, the solubilized IRDye 700 DX NHS Ester was then added to the mSA2 solution at a 2 (IRDye 700 DX NHS Ester) to 1 (monomeric streptavidin) molar ratio. After the conjugation reaction performed substantially as described in Example 8, the monomeric streptavidin conjugate solution was then exchanged with 24 mL of PBS pH 7 using a 10,000 Dalton molecular weight cutoff centrifugal filter to remove free dye, glycine, and glycine-IRDye 700 DX, and to adjust the pH back to pH 7.

2. PIT Killing

Biotinylated cetuximab was pre-incubated with monomeric streptavidin-IRDye 700DX at a 20 (monomeric streptavidin IRDye 700DX) to 1 (1 μg/mL biotinylated cetuximab) molar ratio for 1 hour at room temperature. BxPC3 cells were incubated with RPMI media supplemented with 10% FBS and 1% Penicillin/Streptomycin (complete culture media) containing 1 μg/mL of biotinylated cetuximab pre-complexed with monomeric streptavidin-IRDye 700DX or complete culture media only for one hour at 37° C. The cells were then washed one time with complete culture media. The cells were either protected from light (light dose 0 J/cm$^2$) or were illuminated with a 690 nm laser with different light dosimetries (2 J/cm$^2$, 8 J/cm$^2$, 32 J/cm$^2$ or 64 J/cm$^2$). Cell death was evaluated as described in Example 9 using CellTox Green.

Figure 4A:
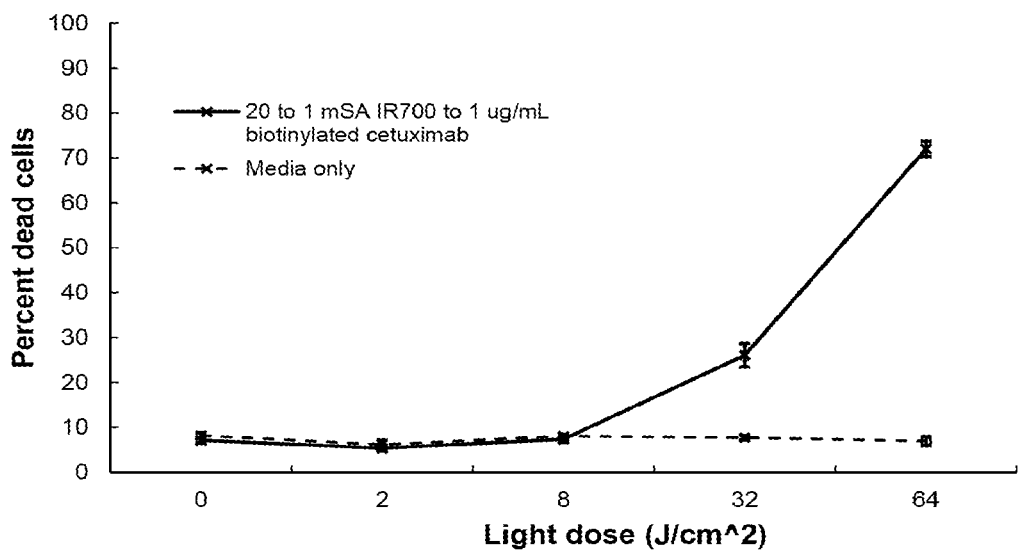
FIG. 4A shows the light-dependent killing of BxPC3 cells with biotinylated cetuximab pre-complexed with monomeric streptavidin-IRDye 700DX (mSA IR700).

As shown in FIG. 4A, the light-dependent PIT killing activity of BxPC3 cells with biotinylated cetuximab pre-complexed with monomeric streptavidin-IRDye 700DX (mSA IRDye 700DX) was light dose dependent. No light-dependent killing activity was observed with cells incubated with complete culture media alone.

To confirm specificity of the effect, the effect of biotinylated cetuximab pre-complexed with monomeric streptavidin-IRDye 700DX was evaluated in the presence of either unconjugated cetuximab or unconjugated monomeric streptavidin to assess if the effect could be competed. In one condition, BxPC3 cells were first pre-incubated with 100 μg/mL unconjugated cetuximab or complete culture media alone for one hour at 37° C. The cells were then washed one time. The cells pre-incubated with unconjugated cetuximab were then incubated with complete culture media containing 1 μg/mL biotinylated cetuximab pre-complexed with 2 μg/mL monomeric streptavidin IRDye 700DX. In another condition, cells that had been pre-incubated with complete culture media alone (but not preincubated with unconjugated cetuximab) were incubated with 1 µg/mL biotinylated cetuximab that had been pre-complexed in the presence of 10-fold excess unconjugated monomeric streptavidin (complexing performed with 20 µg/mL unconjugated monomeric streptavidin and 2 µg/mL monomeric streptavidin IRDye 700DX). In addition, cells that had been preincubated with cell culture media (but not preincubated with unconjugated cetuximab) either incubated with 2 µg/mL monomeric streptavidin IRDye 700DX alone or complete culture media only for one hour at 37° C. The cells were then washed one time with complete culture media.

Figure 4B:
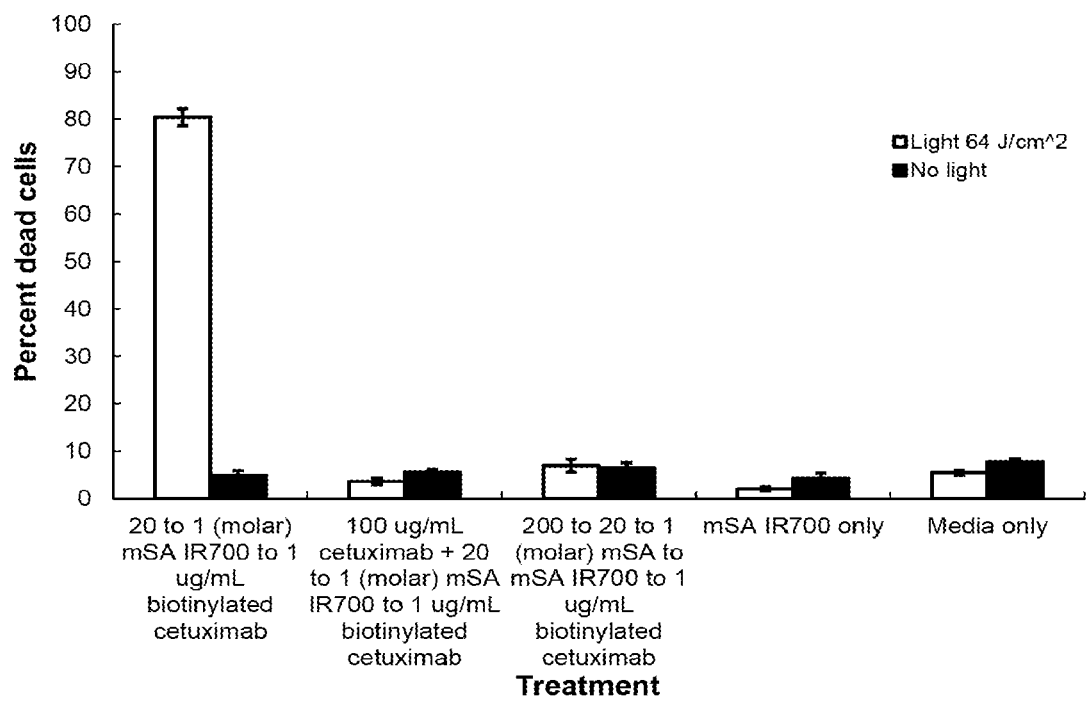
FIG. 4B shows the specificity of PIT with biotinylated cetuximab pre-complexed with monomeric streptavidin-IRDye 700DX (mSA IR700).

The results shown in FIG. 4B demonstrated the PIT-mediated killing with biotinylated cetuximab pre-complexed with monomeric streptavidin-IRDye 700DX (mSA IRDye 700DX) was specific to cells having bound cetuximab associated with IRDye 700 DX. No light-dependent PIT killing was observed when BxPC3 cells were pre-exposed to 100 µg/mL unconjugated cetuximab prior to incubation with biotinylated cetuximab pre-complexed with monomeric streptavidin-IRDye 700DX. The results also showed that the PIT killing was dependent on the association of the IRDye 700 DX conjugated monomeric streptavidin and biotinylated antibody, since no light-dependent PIT killing of BxPC3 cells incubated with biotinylated cetuximab pre-complexed with 10× molar excess of unconjugated monomeric streptavidin over monomeric streptavidin-IRDye 700DX was observed. Further, the results demonstrated that no light-dependent PIT killing of BxPC3 cells was observed in cells incubated with monomeric streptavidin-IRDye 700DX alone in the absence of biotinylated cetuximab or BxPC3 cells incubated in culture media alone.

3. Effects of Light Pre-Exposure on Composition and Activity

The effect of indirect killing of cells using monomeric streptavidin-IRDye 700DX that had been exposed to different types of light was also evaluated. Thirty microliters of monomeric streptavidin-IRDye 700DX conjugate (DAR 1.35) was added per clear HPLC vial at a monomeric streptavidin conjugate concentration of 865 µg/mL. The following conditions were tested: (1) the monomeric streptavidin-IRDye 700DX conjugate was placed in a clear glass HPLC tube wrapped in aluminum foil to protect from light exposure under a halogen lamp at 2500 lux for 24 hrs ("no light"; to control for thermal heating effects); (2) the monomeric streptavidin-IRDye 700DX conjugate was placed in a clear glass HPLC tube under a halogen lamp at 2500 lux for 24 hrs ("white light"); (3) the monomeric streptavidin-IRDye 700DX conjugate was placed in a clear glass HPLC tube and exposed to green LED lamp at 2500 lux for 24 hrs ("green light").

Cell killing induced by the monomeric streptavidin-IRDye 700DX pre-exposed under the various conditions and that had been complexed with biotinylated cetuximab was assessed on BxPC3 cells as described above. Thus, all BxPC3 cell treatments were incubated with either complete culture media or complete culture media containing biotinylated cetuximab pre-complexed monomeric streptavidin-IRDye 700DX that had undergone pre-exposure to light of different wavelengths of light as described above.

Figure 4C:
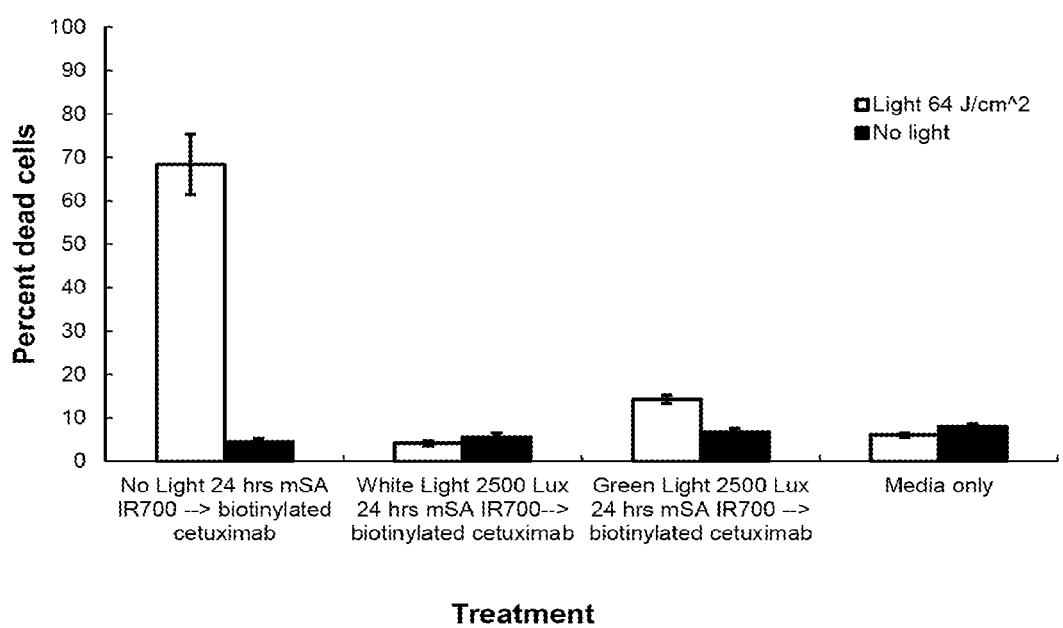
FIG. 4C shows the effect of monomeric streptavidin-IRDye 700DX pre-exposure to white light on the PIT killing activity with biotinylated Cetuximab in BxPC3 cells.

As shown in FIG. 4C, the results revealed that monomeric streptavidin-IRDye 700DX pre-exposure to white light inhibits potential for PIT killing activity. The expected light-dependent killing of BxPC3 cells was observed when cells were incubated with biotinylated cetuximab pre-complexed with monomeric streptavidin-IRDye 700DX that had been protected from light exposure with aluminum foil. In contrast, no light-dependent PIT killing of BxPC3 cells was observed when cells were incubated with biotinylated cetuximab pre-complexed with monomeric streptavidin that had been exposed to white light from a halogen lamp at 2500 lux for 24 hours. The results showed that the loss of PIT killing upon light exposure was reduced when BxPC3 cells were incubated with biotinylated cetuximab pre-complexed with monomeric streptavidin-IRDye 700DX that had been exposed to green light from a green LED lamp at 2500 lux for 24 hours, although in this experiment there was some decrease in PIT killing even when the IRDye 700 DX conjugate was pre-exposed to green light. No light-dependent PIT killing of BxPC3 cells incubated with complete culture media alone.

Example 11: Effect of Anti-EpCAM Antibody-IRDye 700 DX Conjugate on PIT Killing

A further additional study was performed to assess the effect on cell killing of an anti-mouse CD326 (EpCAM) (Catalog No: 118202, BioLegend, San Diego, Calif.) conjugated to a phthalocyanine photosensitizer such as IRDye 700DX. The antibody targets a further alternative cell surface molecule, EpCAM. To prepare the anti-EpCAM-IRDye 700DX, conjugation was performed as described in Example 8.

To evaluate PIT killing activity by the anti-EpCAM-IRDye 700DX conjugate, 4T1 cells were incubated with RPMI media supplemented with 10% FBS and 1% Penicillin/Streptomycin (complete culture media) containing increasing concentrations of anti-EpCAM-IRDye 700DX as indicated or complete culture media only for one hour at 37° C. The cells were then washed one time with complete culture media. The cells were then illuminated with a 690 nm laser at 0 or 32 J/cm$^2$ light dosimetries. Cell death was evaluated as described in Example 9 using CellTox Green.

Figure 5A:
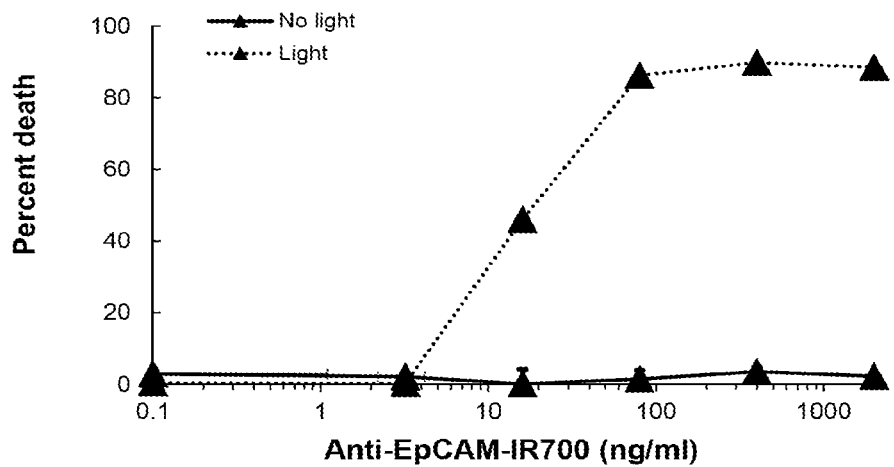
FIG. 5A shows the antibody dose-dependent killing of 4T1 cells with directly conjugated anti-EpCAM-IRDye 700DX.

As shown in FIG. 5A, the results showed that 4T1 cells incubated with anti-EpCAM-IRDye 700DX and illuminated at 32 J/cm$^2$ were killed in an antibody dose dependent manner. No significant cell death was observed at any antibody concentration without light illumination.

To confirm specificity of the cell killing, 4T1 cells were incubated with a molar excess unconjugated anti-EpCAM antibody to block binding of the anti-EpCAM-IRDye 700DX conjugate to the cell surface. Specifically, 10, 1, or 0.1 µg/mL unconjugated anti-EpCAM antibody or complete culture media alone for one hour at 37° C. Without washing the cells, anti-EpCAM-IRDye 700DX was added to 4T1 cells to achieve a final concentration of 0.1 µg/mL and incubated for one hour at 37° C. Cell killing was induced by illumination with a 690 nm laser at a 32 J/cm$^2$ light dose and cell killing determined using CellTox Green as described above.

Figure 5B:
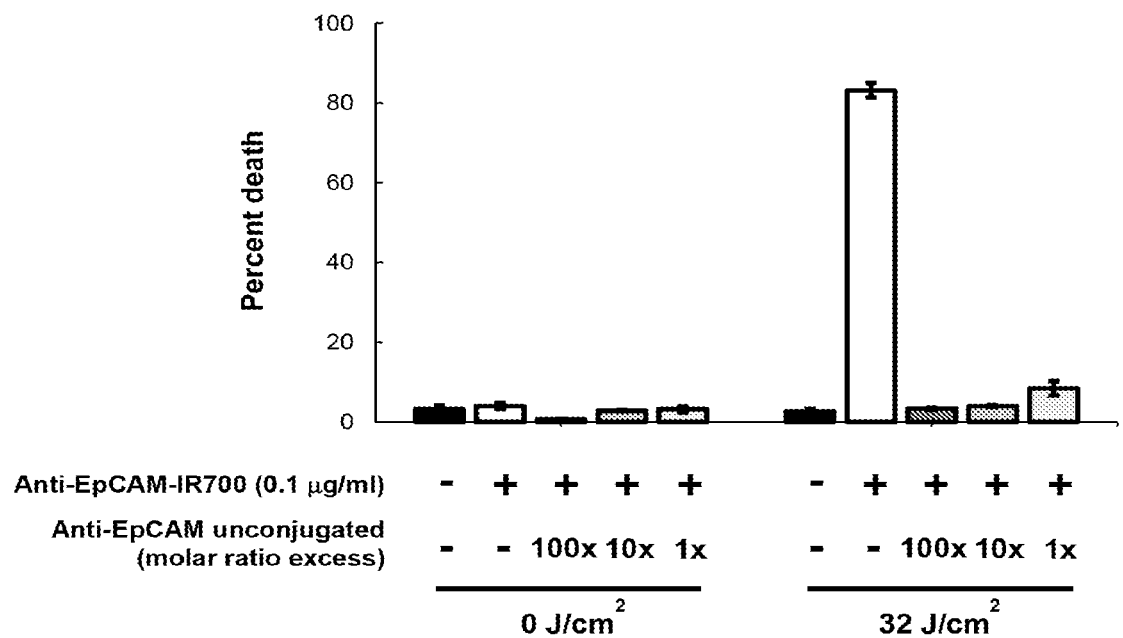
FIG. 5B shows the specificity of anti-EpCAM-IRDye 700DX PIT killing activity.

The results are shown in FIG. 5B, which shows the specificity of anti-EpCAM-IRDye 700DX PIT killing activity. The results showed that 4T1 cells that were pre-incubated with unconjugated anti-EpCAM antibody prior to incubation with anti-EpCAM-IRDye 700DX displayed significantly less cell death after exposure to 32 J/cm$^2$ laser illumination in comparison to the 4T1 cells that did not undergo the blocking step, demonstrating that cell binding of anti-EpCAM and conjugation with IRDye 700DX is necessary for photoimmunotherapy-based killing.

Example 12: PIT Killing of Fc Receptor-Expressing Target Cells with Cetuximab-IRDye 700DX The following studies were performed to assess whether antibody-IRDye 700DX drug conjugate can bind to Fc receptor (FcR) and whether activation with near infrared (~690 nm) light results in FcR+ cell killing. FcR are commonly found on wide variety of immune cells such as, monocytes, macrophages and myeloid derived suppressor cells (MDSCs). The role of these cells in solid tumors have been found to be detrimental and tumor promoting. Human monocytic cell line THP1 express surface Fc receptors and was used as the model cell system for this assay.

THP1 cells (ATCC, TIB-202) grown in complete RPMI 1640 medium were plated at 5000 cells in 100 µL total volume per well in a 96 well tissue culture plate for adherence overnight. The viability of the cells prior to plating was checked via trypan blue exclusion method and >95% cells were viable. The cells were divided into three groups (all in triplicate) as follows: (1) THP1 cells only (untreated); (2) THP1 cells treated with the drug Cetuximab-IRDye 700DX at 500 ng/mL; and (3) THP1 cells first incubated with Fc receptor blocking solution (Catalog No: 564220, BD, Franklin Lakes, N.J.) at 1 µg/well for 20 min at room temperature followed by treatment with drug Cetuximab-IRDye 700DX (500 ng/mL, 1 hr at 37° C. in incubator protected from light).

To induce killing, cells in each group were subjected to 690 nm laser light at a dose of 32 J/cm2. The controls represented wells corresponding to the groups described above but not treated with light. Cell killing was assessed using CellTox Green as described substantially as described Example 9. CellTox Green dye (1×) was added to the wells and cells were incubated for 24 hours at 37° C. in an incubator. The dye was also added to couple of wells just containing 100 µL of the medium for background subtraction later. After the incubation, the tissue culture plate was immediately read on a plate reader. The cells were then subjected to lysis by adding 5 µL of diluted lysis solution (Promega, cat # G1821) including also the control wells containing just the media. The dilution was performed by adding culture medium to the lysis solution at 40% (lysis solution): 60% (culture medium) ratio. The plate was then read again to obtain values for 100% cell death. For each read, the two background wells were averaged and their values subtracted from all other wells. In order to calculate the % cell death for each well, the background subtracted value from the first read was divided by the value from the second read (after lysis), and multiplied by 100.

Figure 6:
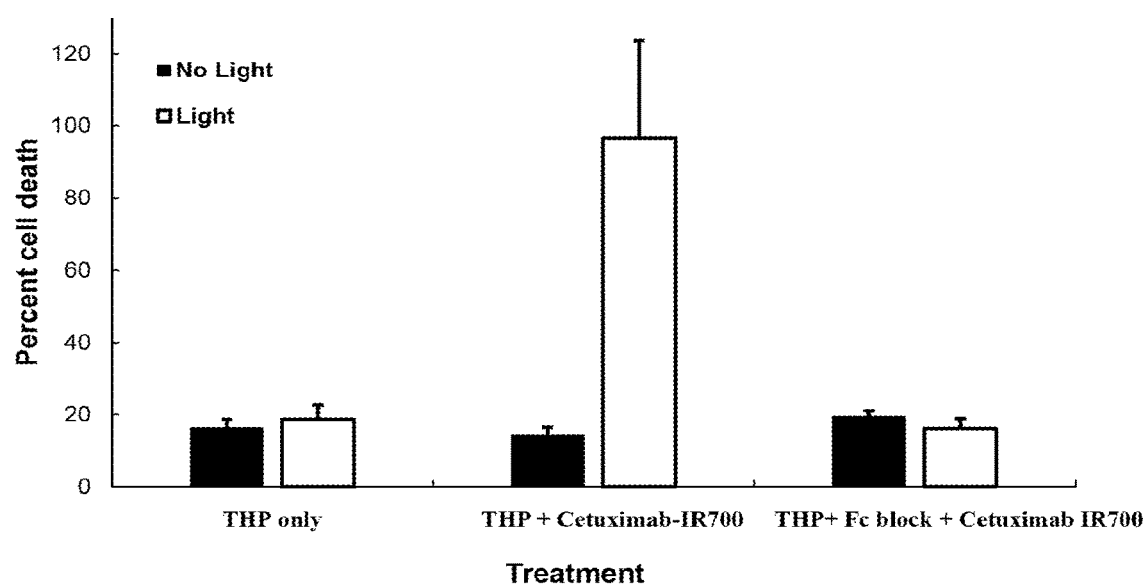
FIG. 6 shows the Fc receptor-specific killing of THP1 cells by Cetuximab-IRDye 700DX.

As shown in FIG. 6, the results showed the Fc receptor-specific killing of THP1 cells by Cetuximab-IRDye 700DX. Maximum killing was observed in the group represented by drug treated THP1 cells subjected to 32 J/cm$^2$ light. The percent killing values are relative to the light and drug treated THP1 cells. Thus, the results showed that antibody-mediated killing can be mediated by specific binding to target molecules on the cell surface as well as, in some cases, binding of the antibody to the FcR.

Example 13: Assessment of Cell Killing Activity and Effect of White Light Exposure on Cell Killing Activity of Non-Antibody Molecule: IRDye 700 DX DX Conjugates The following studies were performed to assess if non-antibody proteins, small proteins, and viruses can be conjugated with a phthalocyanine dye, such as IRDye 700 DX, to target cell killing. As shown below, the results showed that various other non-antibody molecules mediate cell killing that is dependent on activation with near infrared light (e.g., about 690 nm light), binding to cells, and/or affected by pre-exposure of the macromolecule conjugate to white light.

A. Non-Antibody Protein: IR700 Conjugate

Human recombinant epidermal growth factor (EGF) (Catalog No: 01-401, EMD Millipore, Billerica, Mass.) was conjugated to IRDye 700DX and evaluated to assess its killing activity and if pre-exposure to different wavelengths of light affected soluble aggregate formation.

1. EGF Conjugation

The protocol used for labeling of the human recombinant EGF with IRDye 700DX was substantially the same as the protocol for antibody conjugation described in Example 8, except that the prior to conjugation, the EGF solution was first exchanged with phosphate buffer saline pH 7 using a 3,000 Dalton molecular weight cutoff centrifugal filter. For the conjugation, the solubilized IR700 NHS Ester was then added to the EGF solution at a 4 (IR700 NHS Ester) to 1 (EGF) molar ratio or at a molar ratio of 1.2 (IR700 NHS Ester) to 1 (EGF). After the conjugation reaction performed as described in part A, the EGF conjugate solution was then exchanged with six times the equivalent conjugation volume with PBS pH 7 using a 3,000 Dalton molecular weight cutoff centrifugal filter to remove free dye, glycine, and glycine-IR700, and to adjust the pH back to pH 7.

2. EGF-IR700 Light-Dependent Killing Activity

To assess if EGF-IR700 cell killing was assessed in A431 cells. A431 cells were seeded at 5000 cells per well in 96 well white clear bottom dishes one day prior to the experiment. The following day, the A431 cells were washed three times with EMEM supplemented with 1% Penicillin/Streptomycin (serum free media). The A431 cells were then washed one time with serum free media, then incubated with serum free media containing 1 µg/mL of EGF-IRDye 700DX for one hour at 4° C. or serum free media only. As a control to assess the specificity of the activity, in one condition A431 cells were pre-incubated with 100 µg/mL unconjugated cetuximab diluted in serum free media for one hour at 4° C. prior to incubation with 1 µg/mL of EGF-IRDye 700DX. The cells were then washed one time with serum free media.

To induce IR700-dependent killing, the cells were then illuminated with a 690 nm laser with 32 J/cm$^2$ of light or protected from light ("no light"). Cell death was evaluated as described in Example 9 using CellTox Green. The normalized percentage of dead cells was calculated by subtracting all wells by the percentage of dead cells from the no light scrum free media only control, dividing by EGF-IRDye 700DX at 32 J/cm$^2$ minus the no light serum-free media only control, and multiplied 100.

Figure 7A:
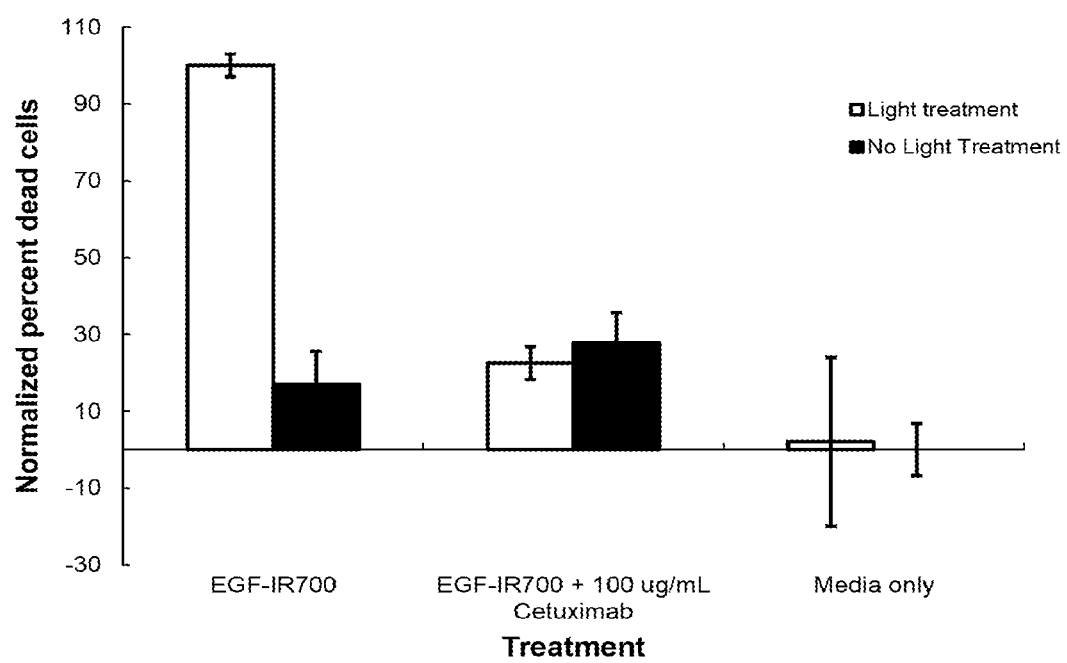
FIG. 7A shows the specificity of EGF-IRDye 700DX light-dependent killing in A431 cells.

As shown in FIG. 7A, the results showed that EGF-IRDye 700DX mediated cell killing is light-dependent killing with killing observed only when cells were treated with light to activate cell killing activity. Pre-exposure of A431 cells with 100 µg/mL unconjugated cetuximab prior to incubation with 1 µg/mL EGF-IRDye 700DX blocked light-dependent cell killing. A431 cells incubated with media alone did not exhibit any light-induced killing.

3. Effects of Light Pre-Exposure on Photo-Activated Activity

The effect of EGF-IRDye 700DX pre-exposure to white light versus green light on photo-activated cell killing was also evaluated in A431 cells. EGF-IRDye 700DX was pre-exposed to different types of light and the effect of light treatment on photo-activated killing activity was evaluated. Five microliters of EGF-IRDye 700DX conjugate (DAR 2) was added per clear HPLC vial at a EGF-IRDye 700DX concentration of 1.14 mg/mL. The following conditions were tested: (1) the antibody-IRDye 700DX conjugate stored at 4° C. protected from light ("4° C.", used as the control); (2). antibody-IRDye 700DX conjugate placed in a clear glass HPLC tube under a Halogen lamp at 2500 lux for 24 hrs ("white light"); (3) antibody-IRDye 700DX conjugate placed in a clear glass HPLC tube wrapped in aluminum foil to protect from light exposure under Halogen lamp at 2500 lux for 24 hrs ("no light", used as a control for thermal heating effects on the formation of aggregates); and (4) antibody-IRDye 700DX conjugate placed in a clear glass HPLC tube and exposed to green LED lamp at 2500 lux for 24 hrs ("green light").

To assess cell killing activity, A431 cells were washed two times with serum free media, and incubated in serum free media alone for one hour at 4° C. The cells were then washed one time with serum free media and incubated with serum free media alone or serum free media containing 1 µg/mL of EGF-IRDye 700DX ("no light"), serum free media containing 1 µg/mL of EGF-IRDye 700DX pre-exposed to white light ("2500 Lux White light"), or serum free media containing 1 µg/mL EGF-IRDye 700DX pre-exposed to green light for one hour at 4° C. ("2500 Lux Green light"). The cells were then washed one time with serum free media.

To induce cell killing, the cells were either protected from light (light dose 0 J/cm$^2$) or were illuminated with a 690 nm laser with different light dosimetries (8 J/cm$^2$, 32 J/cm$^2$ or 64 J/cm$^2$).

Figure 7B:
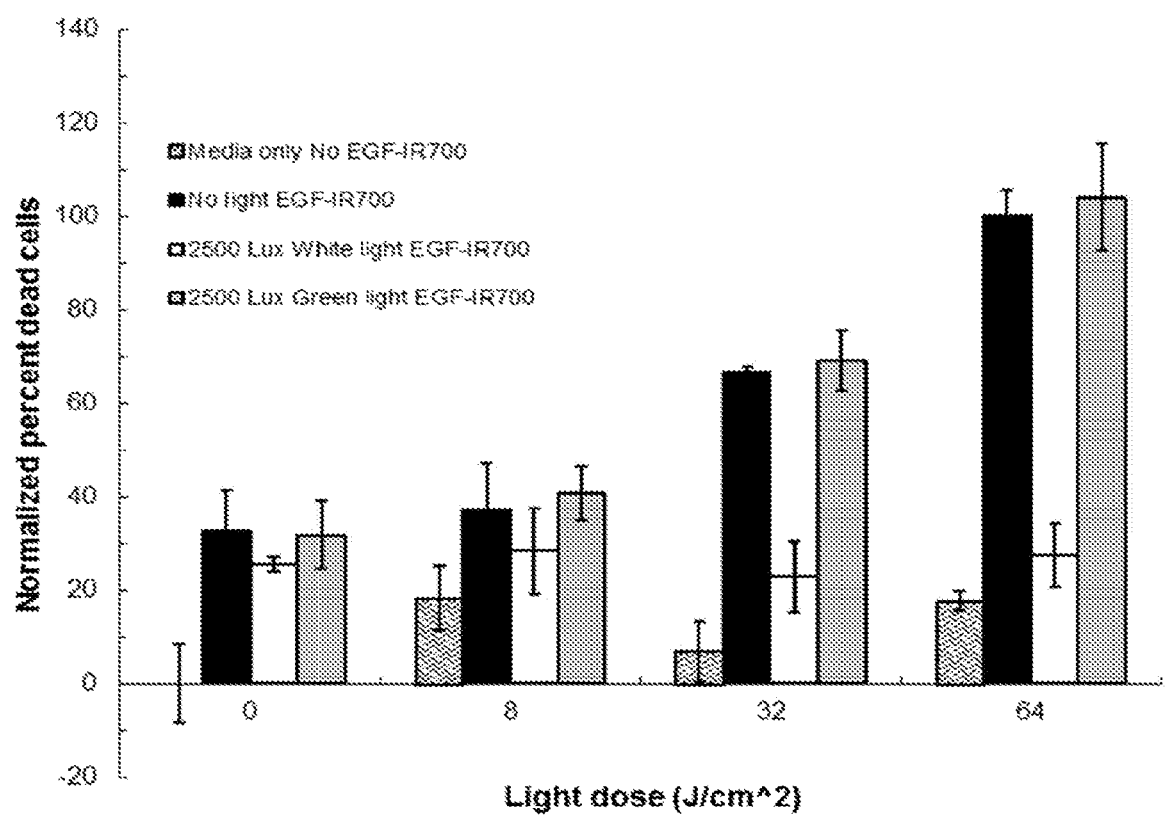
FIG. 7B shows the effect of EGF-IRDye 700DX pre-exposure to different types of light on light-dependent killing in A431 cells.

As shown in FIG. 7B, EGF-IRDye 700DX light-dependent killing activity was sensitive to pre-exposure to white light. A431 cells incubated with EGF-IRDye 700DX that had been protected from light exposure but not thermal heating under white light from a halogen lamp at 2500 lux for 24 hours exhibited light-dependent killing. A431 cells incubated with EGF-IRDye 700DX that had been exposed to white light from a halogen lamp at 2500 lux for 24 hours no longer exhibited light-dependent killing activity. A431 cells incubated with EGF-IRDye 700DX that had been exposed to green light from a green LED lamp at 2500 lux for 24 hours exhibited light-dependent killing activity comparable to that of the "no light" EGF-IRDye 700DX. A431 cells incubated with serum free media alone did not exhibit light-dependent killing activity.

B. Cholera Toxin B-IR700 Conjugate

To assess if cell killing can be mediated by a molecule that binds to non-protein molecules, Cholera Toxin B (Catalog No: C9903-2MG, Sigma Aldrich, St. Louis, Mo.) was conjugated to IRDye 700DX and evaluated to assess its killing activity upon pre-exposure to different wavelengths of light. Cholera toxin B binds specifically to glycolipid, GM1, which is a non-protein surface macromolecule moiety.

1. Cholera Toxin B Conjugation

The protocol used for labeling of the Cholera Toxin B with IRDye 700DX was substantially the same as the protocol for antibody conjugation described in Example 8, except that the prior to conjugation, the Cholera Toxin B solution was first exchanged with phosphate buffer saline pH 7 using a 3,000 Dalton molecular weight cutoff centrifugal filter. For the conjugation, the solubilized IR700 NHS Ester was then added to the cholera toxin solution at a 2 (IR700 NHS Ester) to 1 (Cholera Toxin B) molar ratio. After the conjugation reaction, which was performed substantially as described in Example 8, the Cholera Toxin B conjugate solution was then exchanged then exchanged with 24 mL of PBS pH 7 using a 10,000 Dalton molecular weight cutoff filter to remove free dye, glycine, and glycine-IR700, and to adjust the pH back to pH 7.

2. Cholera Toxin B-IR700 Killing Activity

Photo-activated cell killing using cholera toxin B-IR700 was assessed in BxPC3 cells. BxPC3 cells were washed three times with RPMI media supplemented with 1% Penicillin/Streptomycin (serum free media), then incubated with serum free media only or serum free media containing 2 µg/mL of cholera toxin B-IRDye 700DX (DAR ~2.9 per pentamer) for one hour at 4° C. The cells were then washed two times with serum free media.

To induce IR700-dependent killing, the cells were either protected from light (light dose 0 J/cm2) or were illuminated with a 690 nm laser with different light dosimetries (2 J/cm, 8 J/cm$^2$ or 32 J/cm$^2$ or 96 J/cm$^2$). Cell death was evaluated as described in Example 9 using CellTox reagent. The normalized percentage of dead cells was calculated by subtracting all wells by the percentage of dead cells from the no light complete culture media only control, dividing by cholera toxin B-IRDye 700DX at 96 J/cm$^2$ minus no light complete culture media, and multiplied 100.

Figure 8A:
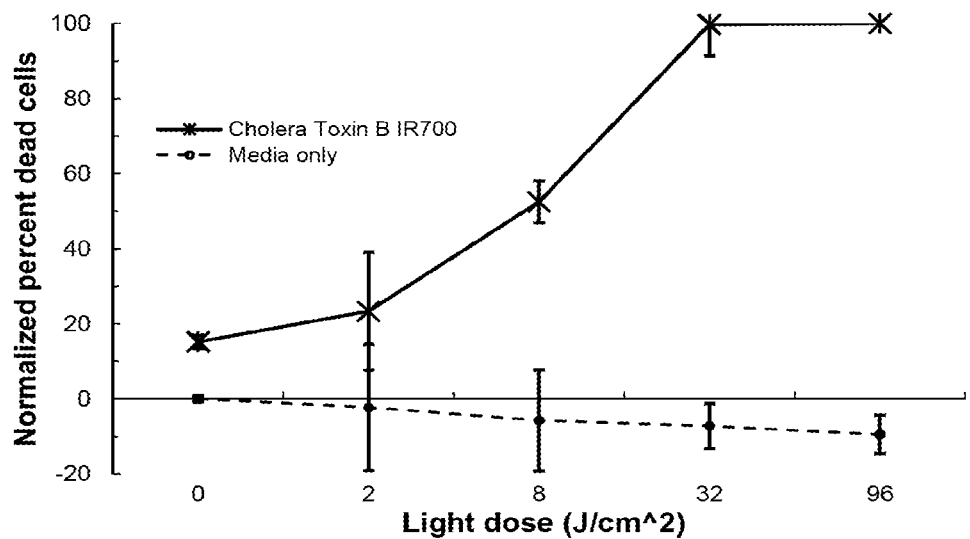
FIG. 8A shows the light-dependent killing of BxPC3 cells using Cholera Toxin B-IRDye 700DX.

As shown in FIG. 8A, the effect of light dose on light-dependent killing of BxPC3 cells was dose dependent, as evidenced by an increase in the normalized percent of dead BxPC3 cells that had been incubated with 2 µg/mL Cholera Toxin B-IRDye 700DX for 1 hour at 4° C. followed by irradiation in the presence of increasing light dose. No light dose dependent killing of BxPC3 cells treated only with complete culture media was observed.

To assess specificity of the photo-activated cell killing activity, BxPC3 cells were washed three times with serum free media, then incubated with complete culture media alone or complete culture media containing 100 µg/mL unconjugated cholera toxin B for one hour at 4° C. The cells were then washed one time with serum free media, and incubated for one hour at 4° C. with serum free media only, serum free media containing 2 µg/mL of cholera toxin B-IRDye 700DX, or 100 µg/mL unconjugated cholera toxin B with 2 µg/mL of cholera toxin B-IRDye 700DX. The cells were then washed two times with serum free media. To induce IR700-dependent killing, the cells were either protected from light (light dose 0 J/cm$^2$) or were illuminated with a 690 nm laser with at 96 J/cm$^2$ and cell death was evaluated as described above.

Figure 8B:
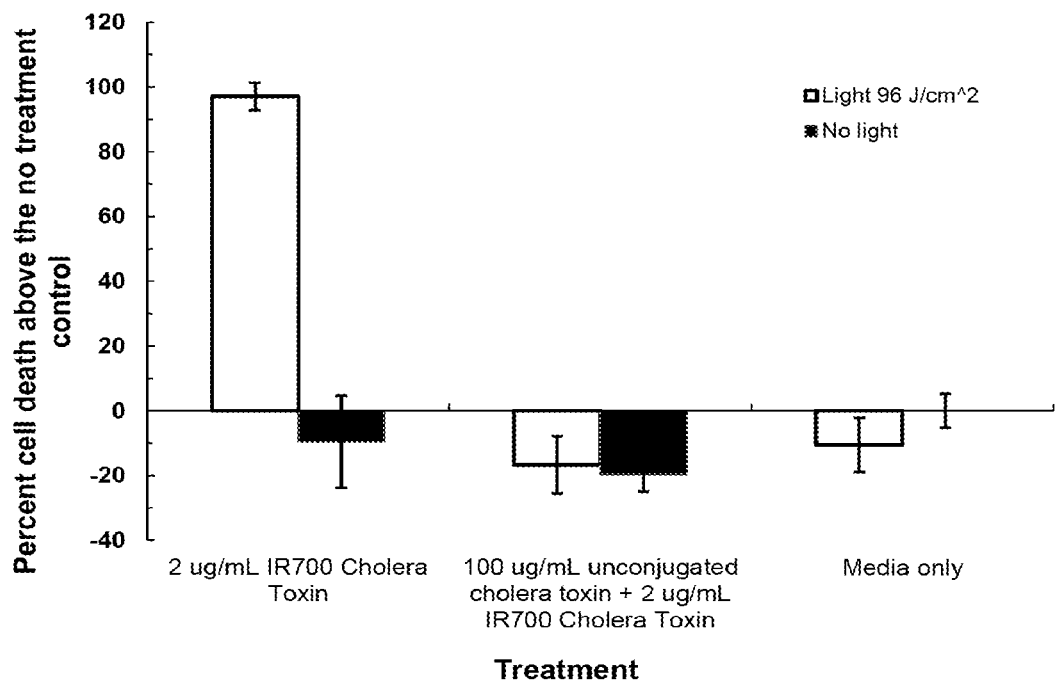
FIG. 8B shows the specificity of Cholera Toxin B-IRDye 700DX light-activated killing.

As shown in FIG. 8B, the results showed that pre-incubation of BxPC3 cells with 100× excess of the unconjugated cholera toxin B blocked Cholera Toxin B-IRDye 700DX light-dependent killing in BxPC3 cells, thereby indicating that the killing activity is dependent on binding of the Cholera toxin B to cells.

3. Effects of Light Pre-Exposure on Cell Killing Activity

The effect of cholera Toxin B-IRDye 700DX pre-exposure to white versus green light on photo-activated killing activity was evaluated. Ten microliters of Cholera Toxin B-IRDye 700DX conjugate (DAR 2.9) was added per clear HPLC vial at a Cholera Toxin B-IRDye 700DX concentration of 1 mg/mL. The following conditions were tested: (1) Cholera Toxin B-IRDye 700DX conjugate placed in a clear glass HPLC tube wrapped in aluminum foil to protect from light exposure under Halogen lamp at 2500 lux for 24 hrs ("no light", used as a control for thermal heating effects on the formation of aggregates); (2) Cholera Toxin B-IRDye 700DX conjugate was placed in a clear glass HPLC tube under a Halogen lamp at 2500 lux for 24 hrs ("white light"); or (3) Cholera Toxin B-IRDye 700DX conjugate was placed in a clear glass HPLC tube and exposed to green LED lamp at 2500 lux for 24 hrs ("green light").

Cell killing induced by the cholera Toxin B-IRDye 700DX pre-exposed under the various conditions was assessed on BxPC3 cells as described above. Thus, all BxPC3 cell treatments were incubated with either serum free media alone or serum free media containing Cholera Toxin B-IRDye 700DX that had undergone pre-exposure to light of different wavelengths of light as described above.

Figure 8C:
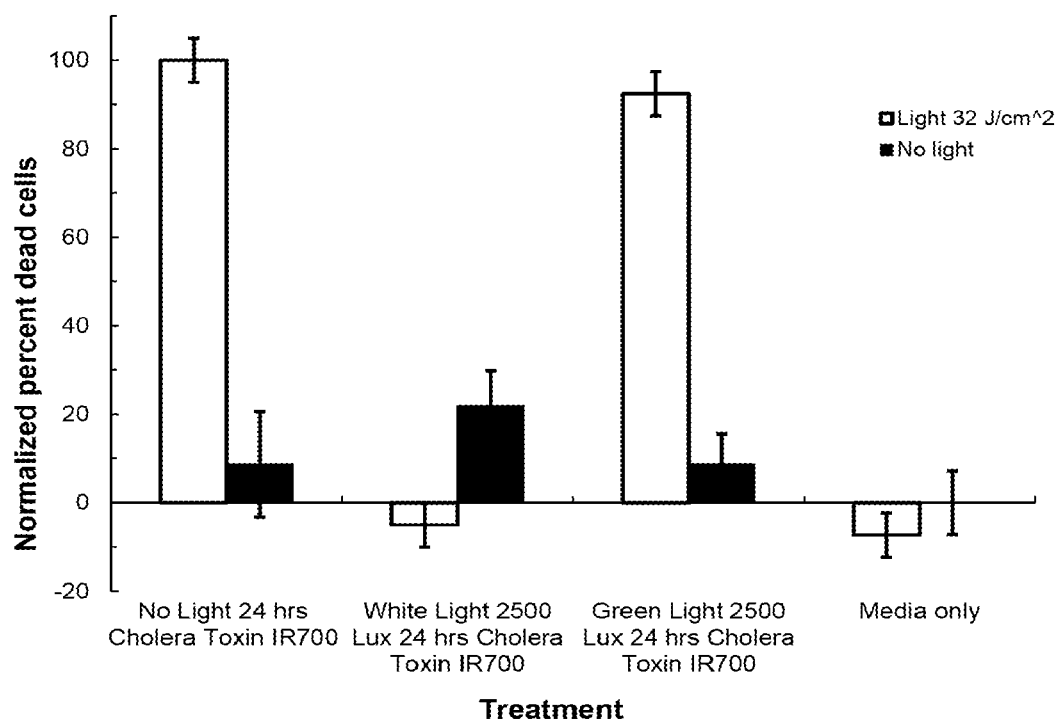
FIG. 8C shows the effect of pre-exposure of Cholera Toxin B-IRDye 700DX to different wavelengths of light on light-activated killing in BxPC3 cells.

As shown in FIG. 8C, light-dependent killing activity mediated by Cholera Toxin B-IRDye 700DX was sensitive to pre-exposure to white light. BxPC3 cells incubated with Cholera Toxin B-IRDye 700DX that had been protected from light exposure but not thermal heating under white light from a halogen lamp at 2500 lux for 24 hours exhibited light-dependent killing. BxPC3 cells incubated with Cholera Toxin B-IRDye 700DX that had been exposed to white light from a halogen lamp at 2500 lux for 24 hours no longer exhibited light-dependent killing activity. BxPC3 cells incubated with Cholera Toxin B-IRDye 700DX that had been exposed to green light from a green LED lamp at 2500 lux for 24 hours exhibited a slight decrease in light-dependent killing activity, but substantially less than that of the white light exposed Cholera Toxin B-IRDye 700DX treated cells. BxPC3 cells incubated with serum free media alone did not exhibit light-dependent killing activity.

C. Influenza Virus-IR700

The following studies were performed to assess whether virus particles can be conjugated with phthalocyanine dyes such as IRDye 700DX for photo-activated cell killing. Effect of pre-exposure to white light on photo-activated virus-IR700 conjugate killing was also assessed.

1. Influenza Virus (X-31) Conjugation

Frozen solid aliquots of IRDye 700DX NHS Ester (Cat. No. 929-70011; Li-COR, Lincoln, Nebr.) were thawed at room temperature, then dissolved with DMSO to achieve a 10 mg/mL concentration. In a dark environment, 10 µg of IRDye 700DX NHS Ester was added to a 65,536 HA titer units of Influenza A X-31, A/Aichi/68 (H3N2) stock (Catalog No: 10100375, Charles River Laboratories, Wilmington, Mass.), and placed on the lowest setting possible on a table top vortexor for 2 hours at 25° C. A gravity flow column was used to separate the virus conjugate from the free dye by loading 100 µL of virus solution to a pre-phosphate buffer saline equilibrated Nap 5 gravity flow column (Catalog No: 17-0853-02, GE Healthcare Life Sciences, Pittsburgh, Pa.). After adding 650 µL of phosphate buffer saline, the flow through was discarded. An additional 400 µL phosphate buffer saline was loaded to the column and the flow through, which contained the conjugated virus, was collected. Prior to using the virus for experiments, the virus conjugate solution was filtered with a 0.2 µm pore size PVDF filter to remove any insoluble aggregates.

2. Influenza Virus (X-31)-IRDye 700DX Killing Activity

Vero cells were incubated with influenza virus (X-31)-IR700 to assess if cells associated with the influenza virus (X-31)-IR700 were susceptible to killing after light irradiation. Vero cells were washed four times with EMEM media supplemented with 1% Penicillin/Streptomycin (serum free media). Virus inoculation media was made by mixing 1200 µL serum free media with 400 µL of purified influenza virus (X-31)-IRDye 700DX flow through (prepared as described above), which was then filtered with a 0.2 µm pore size PVDF filter to remove any aggregates. 100 µL of virus inoculation media or 100 µL of serum free culture media was added to the cells, and incubated for 1 hr at 4° C. The cells then were washed once with 100 µL of serum free media.

Virus-associated cells or control Vero cells were then either protected from light (light dose 0 J/cm$^2$) or were illuminated with a 690 nm laser with different light dosimetries (2 J/cm$^2$, 8 J/cm$^2$, 32 J/cm$^2$ or 96 J/cm$^2$). Cell death was evaluated as described in Example 9 using CellTox Green.

Figure 9A:
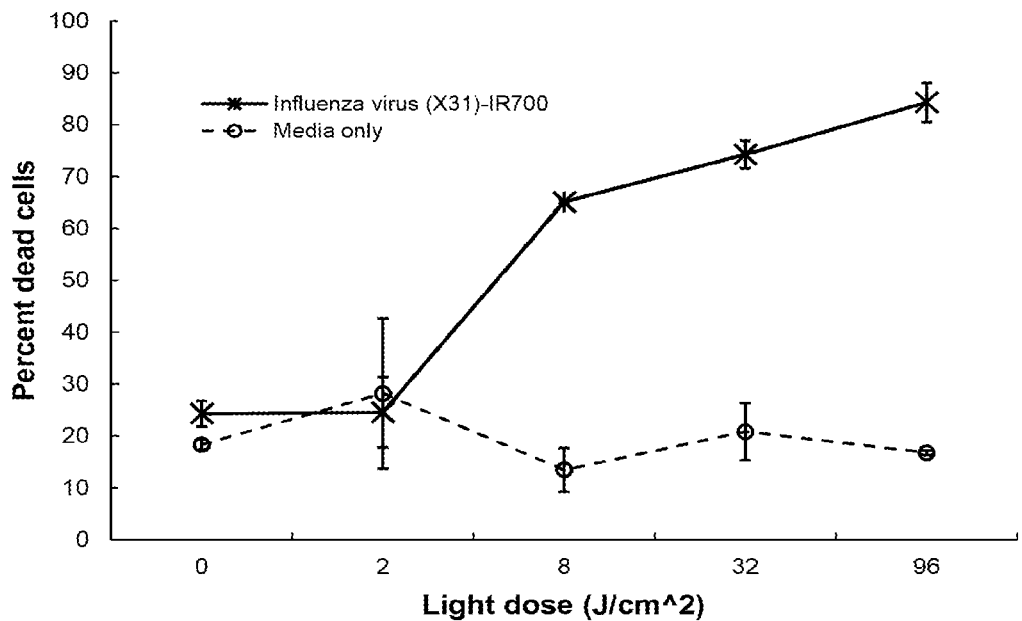
FIG. 9A shows the light-dependent killing of Vero cells with Influenza virus (X-31)-IRDye 700DX.

As shown in FIG. 9A, Vero cells that were inoculated with Influenza virus (X-31)-IRDye 700DX were killed in a light dose-dependent manner. Vero cells incubated in complete culture media without virus did not exhibit light dependent killing.

3. Effects of Light Pre-Exposure on Conjugate Activity

The influenza virus (X-31)-IRDye 700DX was tested for the effect of pre-exposure to light on photo-activated light-dependent killing activity under three different light-exposure conditions, including to the different wavelengths of white light vs. green light. Approximately 130 uL of influenza virus (X-31)-IRDye 700DX flow through was added per clear HPLC vial and tested after exposure to the following conditions: (1) influenza virus (X-31)-IRDye 700DX conjugate was placed in a clear glass HPLC tube wrapped in aluminum foil to protect from light exposure under a Halogen lamp (Catalog No: PL-800, Dolan-Jenner, Boxborough, Mass.) at 2500 lux for 18 hrs ("no light", to control for thermal heating effects); (2) the influenza virus (X-31)-IRDye 700DX conjugate was placed in a clear glass HPLC tube under a halogen lamp at 2500 lux for 18 hrs ("white light"); (3) influenza virus (X-31)-IRDye 700DX conjugate was placed in a clear glass HPLC tube and exposed to green LED lamp (Catalog No: Green-ECS GP19 EcoSmart) at 2500 lux for 18 hrs (("green light").

Cell killing induced by inoculation of Vero cells with influenza virus (X-31)-IRDye 700DX pre-exposed under the various conditions was assessed as described above after illumination with a 690 nm laser with a light dose of 96 J/cm$^2$. Thus, all Vero cell treatments were incubated with either serum free media alone or serum free media containing influenza virus (X-31)-IRDye 700DX that had undergone pre-exposure to light of different wavelengths of light.

Figure 9B:
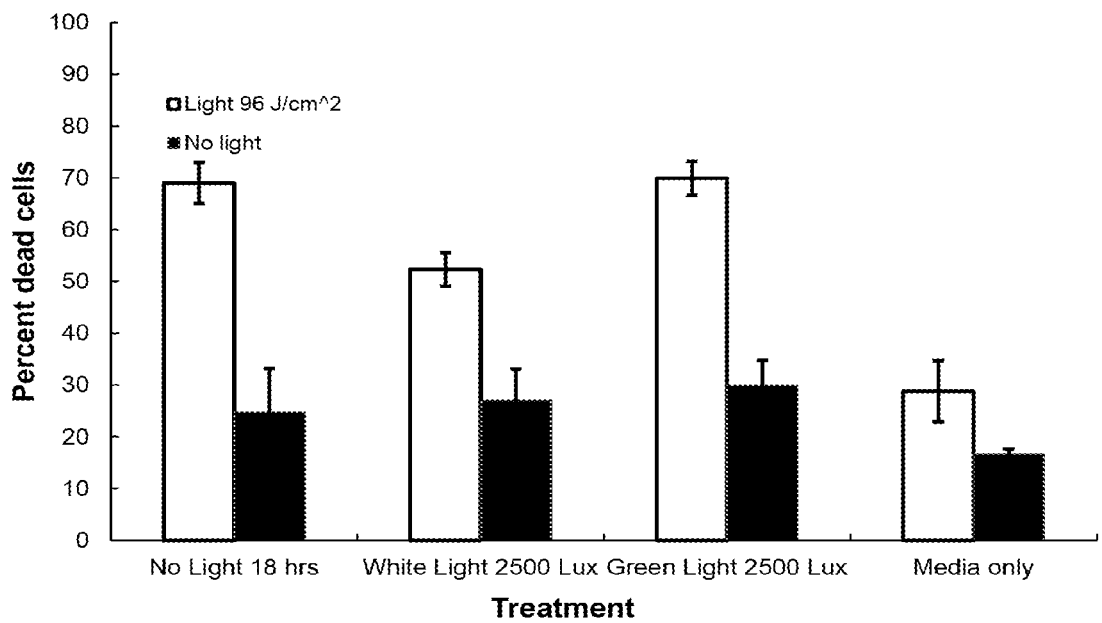
FIG. 9B shows the effect of pre-exposure of influenza virus (X-31)-IRDye 700DX to white light vs. green light on photo-activated cell killing.

As shown in FIG. 9B, light-dependent killing activity mediated by influenza virus (X-31)-IRDye 700DX is sensitive to pre-exposure to white light. Vero cells incubated with influenza virus (X-31)-IRDye 700DX that had been protected from light exposure with aluminum foil ("no light") exhibited light-dependent killing. However, the extent of cell killing was decreased in Vero cells incubated with influenza virus (X-31)-IRDye 700DX that had been exposed to white light from a halogen lamp at 2500 lux for 18 hours compared to cell treated with the "no light" influenza virus (X-31)-IRDye 700DX that had been protected from light. In contrast, incubation of Vero cells with influenza virus (X-31)-IRDye 700DX that had been exposed to green light from a green LED lamp at 2500 lux for 18 hours exhibited the same photo-activated killing activity as that of the "no light" influenza virus (X-31)-IRDye 700DX that had been protected from light. Vero cells incubated with serum free media alone did not exhibit light-dependent killing activity.

Example 14: Assessment of Cell Killing Activity of Additional Molecule: IR700 DX Conjugates Studies were performed to assess the cell killing activity of additional non-antibody IRDye 700 DX conjugates that can bind to non-protein surface molecules. In an exemplary additional study, the effect of *Sambucus Nigra* Lectin (SNA; also called Elderberry lectin, EBL) (Catalog No: L-1300, Vector Labs, Burlingame, Calif.) conjugated to IRDye 700DX was evaluated to assess its killing activity. SNA binds specifically to alpha(2,6)-linked sialic acids on glycoproteins on cells. The SNA-IR700 also was assessed for light-induced aggregation using size exclusion chromatography, but in this exemplary experiment there was no effect on the size exclusion chromatography of the SNA-IR700 conjugate exposed to white light versus green light.

1. Elderberry Lectin (SNA) Conjugation

The protocol used for labeling of the SNA with IRDye 700DX is substantially the same as the protocol for antibody conjugation described in Example 8.

2. SNA-IR700-Light-Dependent Killing Activity

To assess if SNA-IR700 was able to elicit cell killing after light irradiation, cell killing was assessed in BxPC3 cells. BxPC3 cells were dissociated from the cell culture plate and the cell culture media containing RPMI media supplemented with 10% Fetal Bovine Serum and 1% Penicillin/Streptomycin (complete culture media) was exchanged for RPMI media supplemented with 1% BSA and 1% Penicillin/Streptomycin (binding media). The BxPC3 cells were transferred to separate tubes containing binding media only or binding media containing 10 μg/mL SNA-IRDye 700DX at a dye antibody ratio (DAR) of ~2.5), and incubated for one hour at 4° C. The cells were then transferred to plates pre-coated with 200 μg/mL unconjugated SNA (1 hr coating treatment at 37° C., and washed 3 times with serum free media) to block non-specific binding of the SNA-IRDye 700DX to the plates.

To induce IR700-dependent killing, the cells were either protected from light (light dose 0 J/cm$^2$) or were illuminated with a 690 nm laser with different light dosimetries (8 J/cm$^2$, 32 J/cm$^2$ or 96 J/cm$^2$). Cell death was evaluated as described in Example 9 using CellTox Green.

Figure 10A:
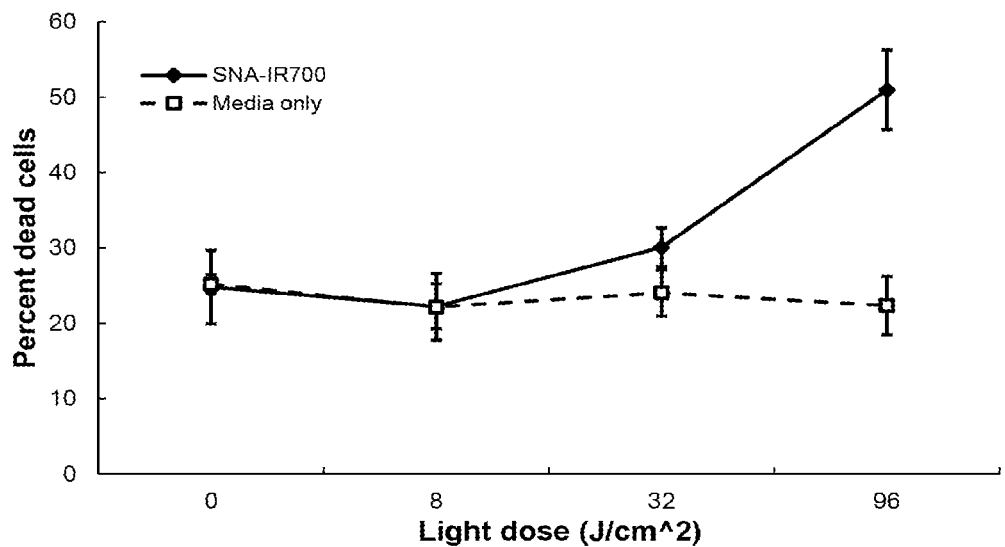
FIG. 10A shows the effect of light dose on SNA-IRDye 700DX killing activity in BxPC3 cells.

As shown in FIG. 10A, BxPC3 cells incubated with SNA-IRDye 700DX exhibited light dependent killing. BxPC3 cells treated with complete culture media in the absence of an IR700 conjugate did not exhibit light dependent killing.

To assess the specificity of the cell killing, BxPC3 cells were treated with sialidase A, which cleaves alpha(2,6)-linked sialic acids, the receptor for SNA. BxPC3 cells were dissociated from the tissue culture flask, and fixed with 10% formalin for 20 minutes. The cells were then washed 3 times with PBS, and treated with a 1× reaction buffer alone (diluted from a 5× Glyco Sialidase A-51 reaction buffer, catalog number GK80045, Prozyme), 1× reaction buffer containing 0.025 U sialidase A, or 1× reaction buffer containing 0.075 U sialidase A for 2 hours at 37° C. The cells were then washed three times with PBS, and then incubated with PBS alone or PBS containing 10 μg/mL SNA-IRDye 700DX for 1 hour at 4° C.

After the incubation, the cells were washed three times with PBS, stained with DAPI nuclear stain, and then plated onto 96 well dish and imaged on an epi-illumination fluorescent microscope. At least 10 regions were chosen and imaged to detect DAPI nuclear stain and SNA-IRDye 700DX fluorescent signal. To compare fluorescent intensity of the tested groups, background subtraction was performed by subtracting the minimum pixel intensity of a given image from all other pixels in the same image. The DAPI nuclear signal was thresholded and used as the representative area for each cell. The segmented DAPI image was then used to determine the area for each individual cell to be quantified for average fluorescence intensity in the channel used to image the SNA-IRDye 700DX. Because the SNA-IRDye 700DX staining is a membrane stain that is diffuse and because an epi-illumination microscope was used, the average fluorescent signal measured from the masked region as defined by the DAPI nuclear stain could be used as a representative average fluorescent intensity for SNA-IRDye 700DX staining per cell. The average fluorescence intensity was collect for hundreds of cells per treatment condition and plotted in a box and whisker plot.

Figure 10B:
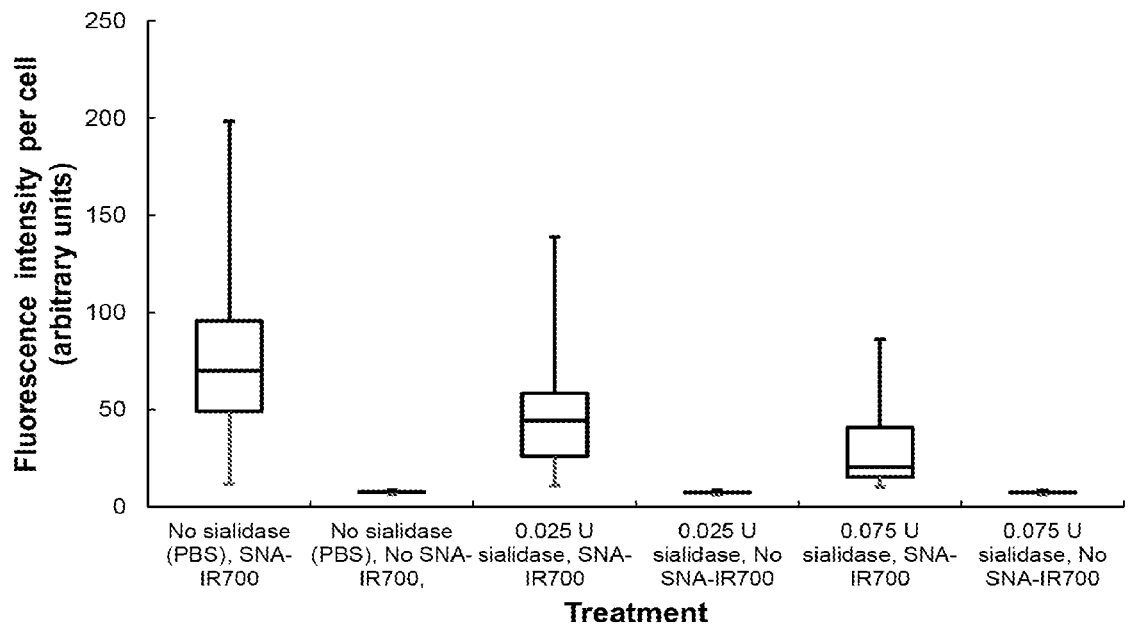
FIG. 10B shows the effect of sialidase treatment on the specificity of SNA-IRDye 700DX binding to cells.

The fluorescent intensity results of the tested groups after treatment of cells with sialidase A is shown in FIG. 10B. The results showed that a dose dependent increase in sialidase A treatment resulted in a concomitant decrease in SNA-IRDye 700DX staining in the sample. Dose dependent increase in sialidase A treatment did not result in any change in fluorescence from the channel used to detect the SNA-IRDye 700DX when BxPC3 cells were not stained with SNA-IRDye 700DX.

Example 15: IR700-Conjugate-Mediated PIT Killing of Bacterial Pathogens

The following studies were performed to assess whether antibodies directly conjugated to a phthalocyanine photosensitizer such as IRDye 700DX can kill bacterial cells by binding to proteins displayed on its cell surface. Protein A is a protein displayed on the cell surface of *Staphylococcus aureus* (*S. aureus*) that binds to the Fc region of antibodies.

Cetuximab-IR700, conjugated substantially as described in Example 1, was used in these studies. *S. aureus* was acquired from American Type Culture Collection (ATCC) ID 6538. *S. aureus* was grown on either Brain Heart Infusion (BHI) agar plates for colony selection and counting, or BHI broth (complete culture media) for population expansion.

To evaluate bacterial cell-induced PIT killing, *S. aureus* was incubated with 100 μg/mL of cetuximab-IRDye 700DX for one hour at room temperature. The cells were then illuminated with a 690 nm laser at 0 or 300 J/cm$^2$. The number of remaining viable bacterial cells was determined by counting colony forming units (CFU) on BHI agar plates under the following conditions. As a control, the number of viable bacterial cells also was assessed in cells treated with cetuximab-IRDye 700DX incubation alone but without laser illumination, laser illumination alone, or untreated. Percent of viable CFU was normalized to bacterial cells with no treatment.

Figure 11:
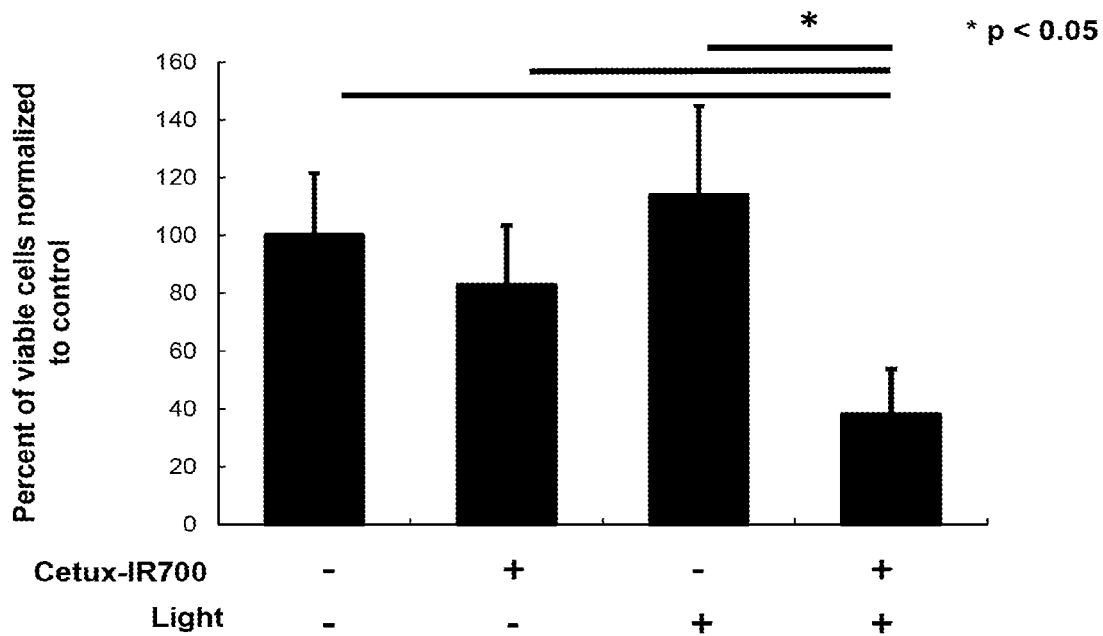
FIG. 11 shows the PIT killing of S. aureus by Cetuximab-IRDye 700DX in combination with laser illumination.

The results are shown in FIG. 11, which shows that PIT-mediated cell killing of *S. aureus* can occur in the presence of an antibody-IR700 conjugate that binds to Protein A. Only the bacterial cells that were incubated with cetuximab-IRDye 700DX with subsequent laser illumination had a statistically significant CFU reduction in comparison to the other three groups.

Example 16: IR700-Conjugate-Mediated PIT Killing of Virus Pathogens

The following studies were performed to assess whether virus infectivity can be inhibited by performing PIT on virus particles with phthalocyanine-labeled anti-virus antibodies. An exemplary study was performed using influenza virus as a specific example in which indirect PIT treatment was performed against influenza virus particles coated with mouse anti-influenza virus A (H3N2) and goat anti-mouse Fab-IRDye 700DX antibodies. Because indirect labeling of primary unconjugated antibodies with secondary antibody-IRDye 700DX conjugates can induce PIT killing similar to that of direct conjugated primary antibodies, the findings can be generalized to directly conjugated anti-virus-IRDye 700DX antibodies. Thus, these results demonstrate that PIT treatment can lead to inhibition of virus infection AffiniPure Fab Fragment Goat anti-mouse IgG1 specific (GtxMs Fab) antibody (Catalog number: 115-007-185, Jackson ImmunoResearch Laboratories, West Grove, Pa.) was conjugated to IR700 substantially as described in Example 8, except the GtxMs Fab antibody solution was first exchanged with phosphate buffer saline pH 7 using a 10,000 Dalton molecular weight cutoff centrifugal filter, then the antibody solution pH was adjusted to a pH of 8.5 with addition of phosphate buffer at pH=9. Frozen solid aliquots of IRDye 700DX NHS Ester (Cat. No. 929-70011; Li-COR, Lincoln, Nebr.) were thawed at room temperature, then dissolved with DMSO to achieve a 10 mg/mL concentration. In a dark environment, the solubilized IR700 NHS Ester was then added to the antibody solution at a 2 (IR700 NHS Ester) to 1 (antibody) molar ratio. The conjugation reaction proceeded at 25° C. for 2 hours protected from light. Glycine (pH 8.2) was added to a final concentration of 10 mM for 15 minutes to quench the reaction. The antibody conjugate solution was then exchanged with 24 mL of PBS pH 7 using a 10,000 Dalton molecular weight cutoff centrifugal filter to remove free dye, glycine, and glycine-IR700, and to adjust the pH back to pH 7.

For PIT, influenza A virus was indirectly associated with IR700 by mixing 1 µg of mouse Anti-Human Influenza A (H3N2) (F49) (Catalog No: M146, TaKaRa, Katsushika Tokyo, Japan) and 1 µg of GtxMs Fab-IRDye 700DX for 5 minutes at 25° C. in the dark, followed by a 30 minute incubation with 16,384 HA titer units of Influenza A X-31, A/Aichi/68 (H3N2) stock (Catalog No: 10100375, Charles River Laboratories, Wilmington, Mass.) for 30 minutes at 25° C. in the dark. Approximately 875 µL of EMEM supplemented with 1% Penicillin/Streptomycin (serum free media) was added, and the incubated virus was filtered with a 0.2 µm pore size PVDF filter to remove any insoluble aggregates (virus inoculation media). The incubation was performed in duplicate. For one of the duplicate samples, the antibody-virus solution was exposed to 144 J/cm$^2$ of 690 nm light, while the other sample was protected from light.

PIT-treated virus were evaluated for infectivity with Vero cells. Twenty for hours prior to labeling influenza virus (X-31) with the mouse-anti-influenza virus A (H3N2) and the GtxMs Fab-IRDye 700DX, 125,000 Vero cells were plated in a 6 well dish. The following day after seeding the cells and after labeling the influenza virus (X31) with the mouse anti-influenza virus (H3N2) antibody with GtxMs Fab-IRDye 700DX, the cells were washed four times with serum free media. The cells were then incubated with 100 µL of light-treated virus inoculation media, no light treated virus inoculation media, or serum free media for 1 hour at 37° C. The media was then replaced with EMEM supplemented with 0.3% bovine serum albumin (BSA) and 1% Penicillin/Streptomycin. After 14 hours post virus inoculation, the cells were trypsinized, and resuspended in EMEM supplemented with 10% fetal bovine serum and 1% Penicillin/Streptomycin, and placed into Eppendorf tubes. Cells were then fixed with 10% formalin for 20 minutes, and subsequently washed 3 times with phosphate buffer saline (PBS, pH 7). For each wash step, cells were spun down at 1500 rpm for 3 minutes, supernatant was removed, and the cell pellet was resuspended with 1 mL of PBS.

The cells were then incubated for 30 minutes at 25° C. with "block buffer" containing PBS supplemented with 3% Bovine Serum Albumin (IgG-Free, Protease-Free) (Catalog No: 001-000-162, Jackson ImmunoResearch Laboratories, Wilmington, Mass.) and 0.08% saponin. The cells were then incubated for 1 hour 10 minutes at 25° C. with 1:2000 mouse (IgG2a) Anti-Influenza A Virus Nucleoprotein antibody [AA5H] (Catalog no: ab20343, Abcam, Cambridge, United Kingdom) diluted in block buffer. The cells were subsequently washed 3 times with block buffer by spinning the cells down at 1500 rpm for 3 minutes, removing the supernatant, resuspending the cell pellet with 100 µL of block buffer, and incubating the cells for at least 5 minutes at 25° C. prior to the next wash. After washing out the primary antibody, the cells were incubated for 30 minutes at 25° C. with 1:250 AlexaFluor 488-conjugated AffiniPure Goat Anti-Mouse IgG FcGamma Subclass 2a specific (Catalog No: 115-545-206, Jackson ImmunoResearch Laboratories, Wilmington, Mass.) diluted in block buffer. The cells were then washed 3 times with 100 µL per wash of block buffer with at least 5 minutes per wash step, followed by 3 additional washes with PBS. The cells were then spotted on a 96 well plate, and imaged with a fluorescent microscope (Evos, Life Technologies). At least 12 random regions of interest were randomly chosen to obtain the brightfield image and corresponding fluorescent image taken with the GFP excitation and emission cube. The brightfield image was used to obtain the total number of cells, and the fluorescent image was used to detect the presence of nucleoprotein expression, a readout that the cell was infected with influenza virus infection.

Figure 12:
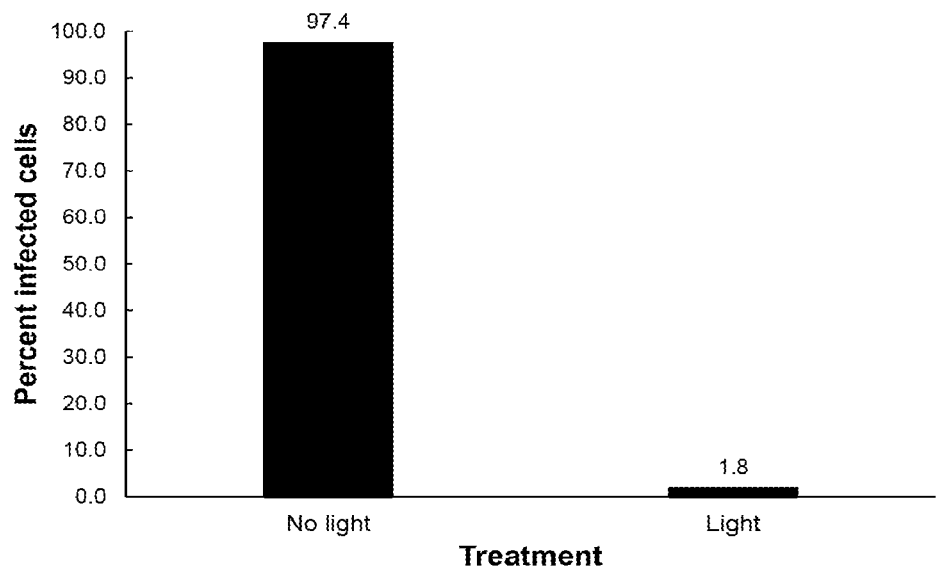
FIG. 12 shows the PIT of influenza virus particles using pre-complexed mouse anti-influenza virus (H3N2) with GtxMs Fab-IRDye 700DX.

The effect of influenza virus particles coated with anti-HA and goat anti-mouse IRDye 700DX (GtxMs Fab-IRDye 700DX) exposure to 690 nm light on virus infectivity was evaluated. The results in FIG. 12 show that PIT on influenza virus particles using pre-complexed mouse anti-influenza virus (H3N2) with GtxMs Fab-IRDye 700DX abrogates influenza virus infection. Vero cells incubated with virus coated with pre-complexed mouse anti-influenza virus (H3N2) and GtxMs Fab-IRDye 700DX that were not exposed to 690 nm light resulted in robust virus infection, with about 97.4% of the Vero cells staining for influenza virus nucleoprotein expression. In stark contrast, Vero cells incubated with PIT-treated virus coated with mouse anti-influenza virus (H3N2) and GtxMs Fab-IRDye 700DX exhibited a significant decrease in virus infection, with only 1.8% of the cells staining for influenza virus nucleoprotein expression.

Example 17: IR700-Conjugate-Mediated PIT Killing of Pathogen Infected Cells

The following studies were performed to assess whether virus-infected cells can be selectively treated with PIT with anti-virus antibodies labeled with phthalocyanine dyes (such as IRDye 700DX) either through direct conjugation or indirect labeling with secondary antibody conjugates. The exemplary data includes performing PIT on influenza virus-infected cells using indirect PIT with mouse anti-influenza virus (H3N2) antibodies and Goat anti-mouse-IRDye 700DX secondary antibodies.

In this study, conjugation of AffiniPure Fab Fragment Goat anti-mouse IgG1 specific (GtxMs Fab) antibody with IRDye 700 DX was performed substantially as described in Example 8.

Vero cells were infected with Influenza virus prior to treating the virus or cells with PIT. Approximately 5,000 Vero cells were plated in a 96 well clear bottom, black plates. The following day after seeding the cells, the cells were washed four times with 100 µL of EMEM supplemented with 1% Penicillin/Streptomycin (serum free media), then incubated with serum free media containing 327.68 HA titer units of Influenza A X-31, A/Aichi/68 (H3N2) (Catalog No: 10100375, Charles River Laboratories, Wilmington, Mass.) per well. The cells were then incubated with the virus inoculation media or serum free media for 90 minutes at 37° C., after which the virus inoculation media was then replaced with EMEM supplemented with 0.3% bovine serum albumin (BSA) and 1% Penicillin/Streptomycin.

Virus infected cells were then labeled with mouse anti-influenza virus (H3N2) antibodies and Goat anti-mouse-IRDye 700DX secondary antibodies 14 hours post virus inoculation. Briefly, the cells were incubated for one hour at 4° C. with 1 µg/mL of mouse Anti-Human Influenza A (H3N2) (F49) (Catalog No: M146, TaKaRa, Katsushika Tokyo, Japan) diluted with EMEM supplemented with 10% fetal bovine serum and 1% Penicillin/Streptomycin (complete culture media). The cells were then washed one time with complete culture media, and then incubated for one hour at 4° C. with 5 µg/mL of GtxMs-IRDye 700DX diluted in complete culture media. The cells were then washed once with 100 µL of complete culture media. To induce PIT, the cells were illuminated with a 690 nm laser at 64 $J/cm^2$ or protected from light ("no light").

Cell death was evaluated using CellTox Green reagent. After the light treatment, all cells were incubated with 1× CellTox Green reagent diluted in complete culture media for 15 minutes at 37° C., then imaged with a fluorescent microscope (Evos, Life Technologies). At least 5 random regions of interest per well for at least three different wells were randomly chosen to obtain the brightfield image, anti-influenza virus fluorescent image using a Cy5 excitation and emission cube, and CellTox Green fluorescent image using a GFP excitation and emission cube. Cells that were then scored for anti-influenza virus staining as an indication for the cell being virus infected. Of the virus infected cells, the cells were then scored for whether there was CellTox Green staining.

Figure 13:
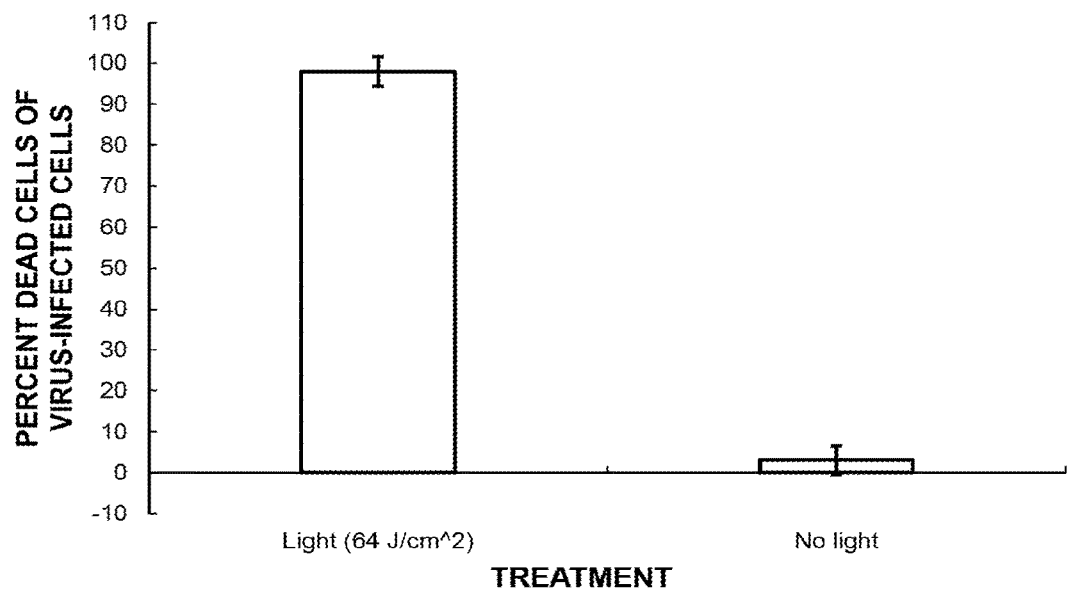
FIG. 13 shows the light-dependent killing of influenza virus infected cells with Mouse anti-influenza virus (H3N2) and Goat anti-Mouse IRDye 700DX (GtxMs-IR700).

As shown in FIG. 13, the results showed that PIT induced cell death was observed in influenza virus-infected Vero cells that had been sequentially labeled with mouse anti-influenza virus (H3N2) and goat anti-mouse IRDye 700DX (GtxMs-IRDye 700DX) followed by light irradiation. The extent of cell death that was observed was light-dependent, since only negligible cell death was observed in the absence of light treatment.

Example 18: IR700-Conjugate-Mediated PIT Killing of Neurons

The following study was performed to assess whether neurons can be killed by PIT using conjugates of IRDye 700DX. Dorsal Root Ganglion (DRG) neurons were subjected to PIT with the B subunit of Cholera Toxin conjugated with IRDye 700 DX. Irradiation with laser light of 690 nm resulted in complete cell death as measured in a luminescence based cell toxicity assay. Without light administration no significant cell death was observed. The findings demonstrate that PIT can be an effective treatment to kill neurons, and more broadly, to kill non-cancer cells, including primary cells.

Rat embryonic DRGs were obtained from Lonza (catalog number R-eDRG-515, Lonza Walkersville, Inc., Walkersville, Md.) in cryo-preserved format and stored in liquid Nitrogen until used. Black-wall 96-well plates were coated with 50 µL PBS per well containing 30 µg/mL poly-D-lysine (Sigma-Aldrich, catalog P0899, St. Louis, Mo.) and 2 µg/mL laminin (Sigma-Aldrich, L2020, St. Louis, Mo.) for 1 hour at room temperature, following stock solution preparation and procedures by Lonza. The coating solution was aspirated and the plates let dry for an hour (open lid in biosafety cabinet) and used immediately for cell seeding.

The instructions provided by Lonza were strictly followed for thawing and plating the cells. The culture medium was PNBM supplemented at all times with 2 mM L-glutamine, 50 µg/mL Gentamicin, 37 ng/mL Amphotericin and 2% NSF-1, but the latter was added fresh each time before use. These components were part of a kit (catalog number CC-4461, Lonza, Basel, Switzerland). Additionally, nerve growth factor (NGF, catalog number N2513, Sigma, St. Louis, Mo.) was also added fresh at the time of use to 100 ng/mL. To plate cells, a 0.25 mL vial was thawed and dropwise diluted with 3.75 mL culture medium, and 200 µL suspension was seeded into wells. Cells were incubated for 4 hours at 37° C. and 5% CO2, and the medium was replaced with medium also containing the mitotic inhibitors 5-fluoro-2'-deoxyuridine (7.5 µg/mL final concentration, catalog number F-0503, Sigma, St. Louis, Mo.) and uridine (17.5 µg/mL final concentration, catalog number U-3003, Sigma, St. Louis, Mo.) that were added just before use. The medium was changed again every 3-4 days.

The conjugation of Cholera Toxin B with IR700 was performed as described in Example 13.B.

After culturing rat embryonic DRGs for 11 days, 1 µg/mL stock solution of Cholera Toxin B-IR700 was diluted to 40 µg/mL with culture medium and 5 µL of the diluted conjugate was added directly to the wells of a 96-well plate containing DRG neurons in 200 µL medium, to achieve a final concentration of 5 µg/mL conjugate. Cells were incubated for 1 hour at 37° C. The culture medium was removed, the cells washed once with culture medium, and 100 µL fresh culture medium was added. The stained neurons were then illuminated with a 690 nm laser at a light dose of 64 $J/cm^2$ (150 $mW/cm^2$), or left protected from light as a control ("no light").

The effect of PIT on DRG neurons was measured with the luminescence based toxicity assay CytoTox Glo (catalog number G9291, Promega, Madison, Wis.). This assay is based on membrane integrity and employs a pro-substrate for luciferase that cannot penetrate intact cells. When cells die, damage in the plasma membrane allows enzymes to diffuse out of cells and activating the pro-substrate, now becoming a real substrate for luciferase, resulting in a luminescence signal. Plates were equilibrated to room temperature for 15 minutes, and 50 µL assay reagent was added. After incubating for 20 minutes at room temperature, luminescence was read on a multi-mode reader. To determine complete cell death, 50 µL digitonin solution was added to kill remaining viable cells, and after 20 minutes luminescence was read again. The background values from wells without cells were subtracted from each read, and percent cell death was calculated as the ratio between luminescence before and after lysis with digitonin, multiplied by 100.

Figure 14:
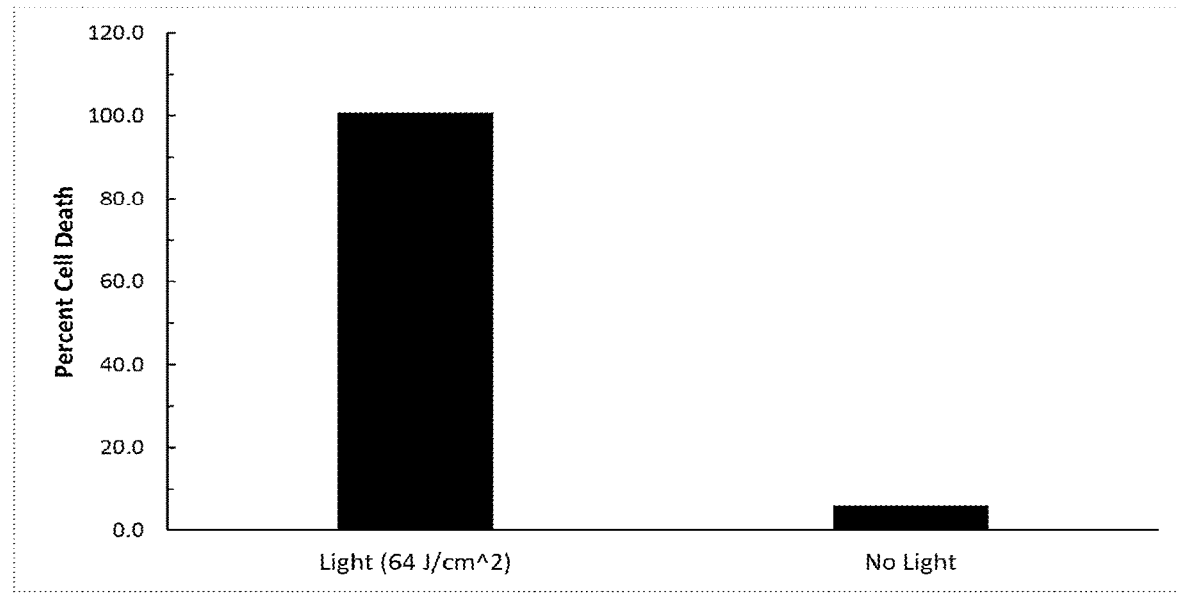
FIG. 14 shows the PIT killing of rat embryonic dorsal root ganglion (DRG) neurons using Cholera Toxin B-IRDye 700DX.

As shown in FIG. 14, PIT induced cell death in Rat Embryonic DRG Neurons. Irradiation with 690 nm laser light of 64 $J/cm^2$) lead to 100 percent cell death after 3 hours (left bar), whereas light protected cells ("No Light") remained unharmed (6% dead cells, right bar).

Example 19: Sensitivity of Cetuximab-IRDye 700DX Conjugate, Cetuximab-IRDye 680RD Conjugate, and Cetuximab-IRDye 700+IRDye 680RD Dual Conjugate to White Fluorescent Light Vs. Green LED Light Studies were performed to assess whether protection from light for IRDye 700DX conjugates is a specific property due to the unique sensitivity of IRDye 700DX conjugates to form soluble aggregate formation when exposed to light.

Three different conjugates were assessed: (1) a cetuximab-IRDye 700DX conjugate, (2) a cetuximab-IRDye 680RD conjugate, and (3) a cetuximab-IRDye 700 IRDye 680RD dual conjugate.

Although many fluorophores require protection from light because they are not very photostable such that exposure to light results in degradation of the fluorophore and a concomitant decrease in fluorescence properties, IRDye700DX is a uniquely photostable dye (see e.g. Peng et al. Proceedings of SPIE 6097, 2006; see also, www.licor.com/bio/products/reagents/irdye/700dx/photostability.html). Due to the extreme photo stability of the dye, this would suggest that IRDye 700DX does not need to be protected from light. However, it was observed that only when IR700 is conjugated to a macromolecule does IR700 require light protection due to an increased sensitivity for the conjugated molecule to induce soluble aggregate formation.

A. Antibody Conjugation

All antibodies were conjugated to the dyes (i.e., IRDye 700DX, IRDye 600RD, or both) using the same approach.

The cetuximab-IRDye 700DX conjugate was made as described in Example 1.

The cetuximab-IRDye 680RD conjugate was made using the same general protocol as described in Example 1, with the following modifications. A sample of Cetuximab was incubated with 4 molar equivalents of IRDye 680RD (Cat. No. 929-70050; Li-COR, Lincoln, Nebr.) dissolved at 5 mg/mL in DMSO. All other step in the conjugation, purification and characterization process for the conjugate were identical to that described above for the Cetuximab-IR700 conjugate preparation.

The cetuximab-IRDye 700DX+IRDye 680RD dual conjugate was made using the same general protocol as described in Example 1, with the following modifications. To a sample of Cetuximab-IRDye 700DX previously prepared by the protocol described above was added 4 molar equivalents of IRDye 680RD dissolved in DMSO at 5 mg/mL. All other steps in the conjugation, including the purification and characterization process for the conjugate, were identical to that described above for the cetuximab-IRDye 700DX conjugate preparation.

B. Effects of Light Pre-Exposure on Composition of Cetuximab-IRDye 700DX Conjugate, Cetuximab-IRDye 680RD Conjugate, and Cetuximab-IRDye 700+IRDye 680RD Dual Conjugate The conjugates were tested for formation of soluble aggregates under four different conditions with at least 30 μL of conjugate placed in a clear HPLC vial per sample at an antibody conjugate concentration of ~1.8 mg/mL. The samples were exposed to 500 lux white fluorescent lighting at 25° C., 500 lux of green LED lighting (Catalog No: Green-ECS GP19 EcoSmart) at 25° C., no light at 25° C., or no light at 4° C. for 24 hours. After 24 hours under each treatment condition, monomer purity, soluble aggregate formation, and fluorescence was assessed by size exclusion chromatography. The percent soluble aggregate formation was measured using size exclusion chromatography at an absorbance of 280 nm. To evaluate the effect of treatment on fluorescence, the fluorescence at 680 nm (areas for the monomer peak) divided by the area for 280 nm absorbance for the monomer was determined.

Figure 15A:
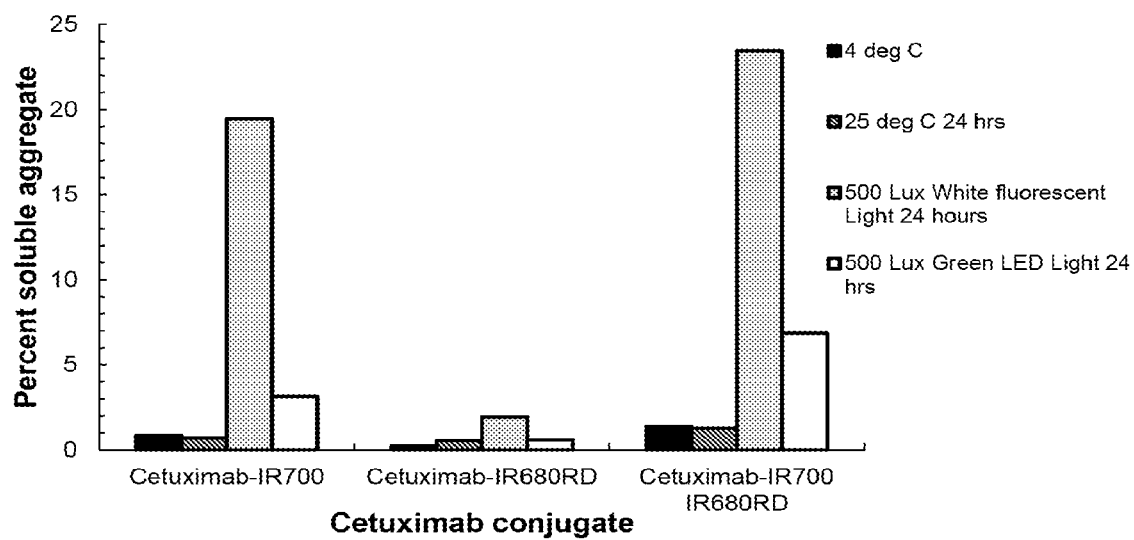
FIG. 15A shows the effect of pre-exposure of cetuximab-IRDye 700DX conjugate, cetuximab-IRDye 680RD conjugate, and cetuximab-IRDye 700+IRDye 680RD dual conjugate to white light or green light on soluble aggregate formation.

The results in FIG. 15A showed that cetuximab conjugated with IRDye 700DX resulted in increased sensitivity to soluble aggregate formation compared to cetuximab conjugated with IRDye 680RD when exposed to white light. Cetuximab-IRDye 700DX exposure to white fluorescent light induced a higher percentage of soluble aggregate formation. Cetuximab-IRDye 700DX green light exposure also increased soluble aggregate formation albeit at a rate much slower than that of white light. Less than 1% soluble aggregate formation was observed in samples either incubated at 4° C. or 25° C., but protected from light. In contrast, Cetuximab-IRDye 680RD exposure to white fluorescent light resulted in a very slight increased soluble aggregate formation, which was much less than that of cetuximab-IRDye 700DX. Cetuximab-IRDye 680RD samples incubated at 4° C. or 25° C., but protected from light or exposed to green light did not exhibit any increase in soluble aggregate formation. As shown, the dual conjugate in which IRDye 700DX was conjugated to cetuximab-IRDye 680RD, resulted in further sensitivity to white and green light exposure on soluble aggregate formation when compared to that of cetuximab-IRDye 680 or cetuximab-IR700 mono-label conjugates.

Figure 15B:
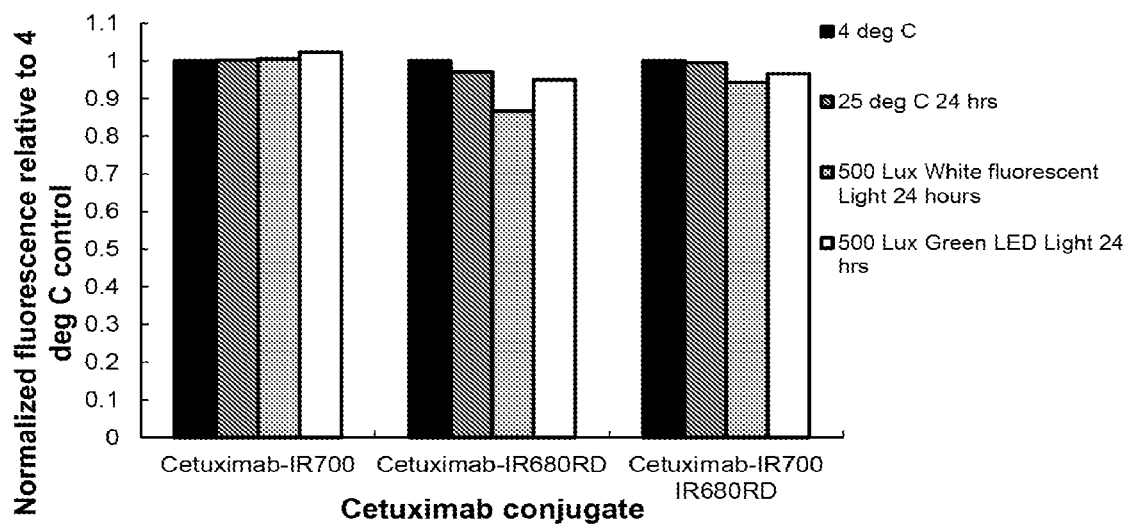
FIG. 15B shows the effect of pre-exposure of cetuximab-IRDye 700DX conjugate, cetuximab-IRDye 680RD conjugate, and cetuximab-IRDye 700+IRDye 680RD dual conjugate to white light or green light on fluorescence normalized to monomer content.

The results in FIG. 15B showed that the fluorescence of cetuximab-IRDye 680RD conjugate was more sensitive to white light exposure than that of cetuximab-IRDye 700DX conjugates. For all treatments for cetuximab-IRDye 700DX, the fluorescence of cetuximab-IRDye 700DX conjugate remained stable despite the significant increase in soluble aggregate formation with 500 lux white fluorescent light exposure for 24 hours. Cetuximab-IRDye 680RD exposed to white fluorescent light for 24 hours exhibited the largest decrease in fluorescence of all treatment conditions tested, indicating that some of the IRDye 680RD was likely bleached with white light exposure. A decrease in fluorescence was also observed when IRDye 700DX was dual conjugated with IRDye 680RD. Based on the mono-labeled cetuximab-IRDye 700DX, this decrease in fluorescence was likely due to the IRDye 680RD bleaching for the dual-labeled cetuximab-IRDye 700DX+IRDye 680RD conjugate.

Thus, the results showed that IRDye 700DX conjugates have a unique sensitivity of forming soluble aggregate formation when exposed to light. Despite the increase in soluble aggregate formation in the IRDye 700DX conjugates when exposed to light, the fluorescence properties of IRDye 700DX conjugate did not change, consistent with the reported published findings that IRDye 700DX is a photostable dye. In stark contrast, white light exposure of another conjugate labeled with IRDye 680RD resulted in only a modest increase in soluble aggregate formation when compared to that of IRDye 700DX conjugate. Only when the IRDye 680RD conjugate was labeled with both IRDye 700DX and IRDye 680RD did an increase in soluble aggregate formation occur with the IRDye 680RD conjugate. IRDye 680 conjugate was sensitive to photobleaching with exposure to light.

The data show that cetuximab-IRDye 700DX, cetuximab-IRDye 680RD, and cetuximab-IRDye 700DX+IRDye 680RD conjugates pre-exposed to different wavelengths of light exhibit differential sensitivity to soluble aggregate formation and fluorescence bleaching. The data provided support the need for light protection of conjugates to ensure consistency in product manufacturing. Specifically, for macromolecule IRDye 700DX conjugates such as antibody-IRDye 700DX conjugates, the fraction of monomer purity and pharmacological activity are essential and changes can lead to a significant impact on the light-activated killing activity.

The present invention is not to be limited in scope by the embodiments disclosed herein, which are intended as single illustrations of individual aspects of the invention, and any that are functionally equivalent are within the scope of the invention. Various modifications to the compositions and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

SEQUENCES

| SEQ ID NO. | Sequence |
| --- | --- |
| 1 | CRGDKGPDC |
| 2 | CCRGDKGPDC |
| 3 | AKPAPPKPEPKPKKAP |
| 4 | AKVKDEPQRRSARLS |
| 5 | CAGALCY |
| 6 | CAGRRSAYC |
| 7 | CARSKNKDC |
| 8 | CDCRGDCFC |
| 9 | CDTRL |
| 10 | CGKRK |
| 11 | CGLIIQKNEC |
| 12 | CGNKRTR |
| 13 | CGNKRTRGC |
| 14 | CGRRAGGSC |
| 15 | CKAAKNK |
| 16 | CKGGRAKDC-GG |
| 17 | CLSDGKRKC |
| 18 | CMYIEALDKYAC |
| 19 | KKCGGGGIRLRG |
| 20 | CNAGESSKNC |
| 21 | CNGRC |
| 22 | CNRRTKAGC |
| 23 | CPGPEGAGC |
| 24 | CPKTRRPVC |
| 25 | CPRECESIC |
| 26 | CRAKSKVAC |
| 27 | CREAGRKAC |
| 28 | CREKA |
| 29 | CRGDKGPDC |
| 30 | CRGRRST |
| 31 | CRKDKC |
| 32 | CRPPR |
| 33 | CRRETAWAC |
| 34 | CRSRKG |
| 35 | CSRPRRSEC |
| 36 | CTTHWGFTLC |
| 37 | CVPELGHEC |
| 38 | EKGEGALPTGKSK |
| 39 | FALGEA |
| 40 | GLNGLSSADPSSD |
| 41 | GSMSIARL |
| 42 | GVSFLEYR |
| 43 | IFLLWQR |
| 44 | IFLLWQR-C-RR |
| 45 | PEPHC |
| 46 | PISNDQKVSDDDK |
| 47 | RMWPSSTVNLSAGRR |
| 48 | RPARPAR |
| 49 | SMSIARL |
| 50 | VDEDRASLLKSQE |
| 51 | VSFLEYR |
| 52 | WNAPAEEWGNW |

The invention claimed is:

1. A method of manufacturing a phthalocyanine dye-targeting molecule conjugate, the method comprising:
   (a) contacting a targeting molecule with a phthalocyanine dye under conditions to produce a conjugate comprising the phthalocyanine dye linked to the targeting molecule; and
   (b) formulating the conjugate in a pharmaceutically acceptable buffer, wherein in each of steps (a)-(b):
   the only light to which the dye and conjugate are exposed has a wavelength within a range from at or about 400 nm to at or about 650 nm, or
   the only light to which the dye and conjugate are exposed has an intensity of less than at or about 200 lux wherein the targeting molecule is an antibody or an antibody fragment.

2. The method of claim 1, wherein the contacting step a) further comprises contacting the targeting molecule with the phthalocyanine dye at a molar ratio of dye to targeting molecule of from at or about 1:1 to at or about 100:1, and wherein the conjugate is formulated to a concentration from at or about 0.1 mg/mL to at or about 200.0 mg/mL.

3. The method of claim 1, wherein the conjugate is formulated to a concentration from at or about 0.5 mg/mL to at or about 10.0 mg/mL.

4. The method of claim 1, wherein the phthalocyanine dye comprises IRDye 700DX-NHS (IR700-NHS).

5. The method of claim 1, wherein the targeting molecule binds to an antigen, a protein or a cell surface target molecule.

6. The method of claim 1, wherein targeting molecule is cetuximab or a fragment thereof.

7. The method of claim 5, wherein the cell surface target molecule is selected from among cell membrane phospholipids, prokaryotic peptidoglycans, bacterial cell envelop proteins, viral capsid proteins, ACTHR, endothelial cell Anxa-1, aminopeptidase N, IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (Carcinoembryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family, P2X1-5, mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP, TRPV1-6, TRPA1, TRPC1-7, TRPM1-8, TRPP1-5, TRPML1-3, TSH receptor, VEGF receptors, VEGFR1, Flt- 1, VEGFR2, FLK-1/KDR, VEGF-3, FLT-4, voltage-gated ion channels, VPAC1, VPAC2, Wilms tumor 1, Y1, Y2, Y4, and Y5.

8. The method of claim 1, further comprising a quenching step subsequent to step (a) and before step (b), wherein, during the quenching step:
the only light to which the conjugate is exposed has a wavelength within a range from at or about 400 nm to at or about 650 nm, or
the only light to which the conjugate are exposed has an intensity of less than at or about 200 lux.

9. The method of claim 8, wherein the quenching step comprises contacting the conjugate with glycine.

10. The method of claim 1, wherein the phthalocyanine dye comprises the formula:

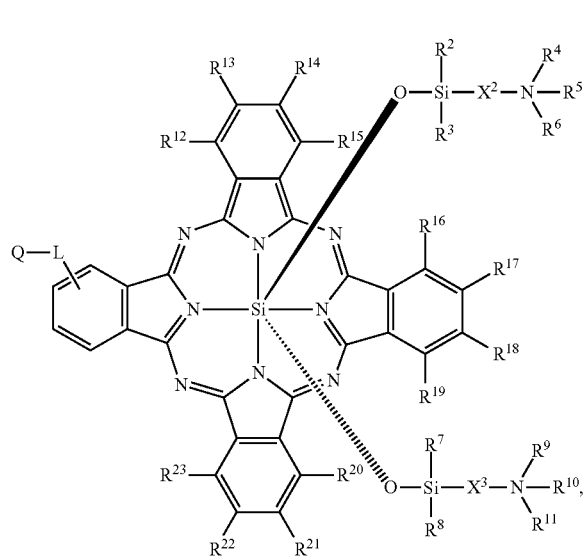

wherein:
L is a linker;
Q is a reactive group for attachment of the dye to the targeting molecule;
$R^2$, $R^3$, $R^7$, and $R^8$ are each independently selected from among optionally substituted alkyl and optionally substituted aryl;
$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;
$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from among hydrogen, halogen, optionally substituted alkylthio, optionally substituted alkylamino and optionally substituted alkoxy; and
$X^2$ and $X^3$ are each independently $C_1$-$C_{10}$ alkylene, optionally interrupted by a heteroatom.

11. The method of claim 10, wherein the phthalocyanine dye comprises the formula:

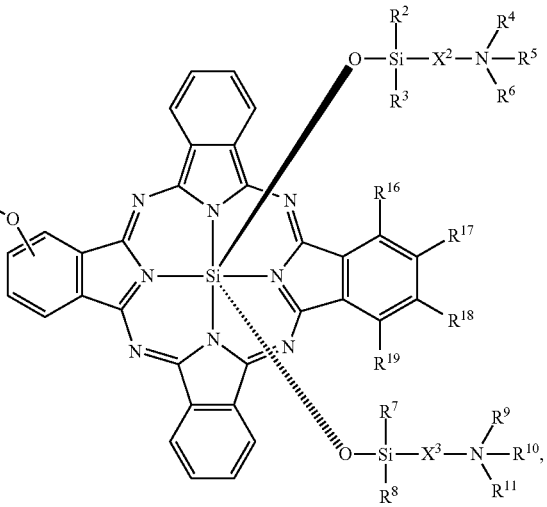

wherein:
$X^1$ and $X^4$ are each independently a $C_1$-$C_{10}$ alkylene optionally interrupted by a heteroatom;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$ are each independently selected from among hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and
$R^{16}$, $R^{17}$, $R^{18}$ and $R^{19}$ are each independently selected from among hydrogen, halogen, optionally substituted alkylthio, optionally substituted alkylamino and optionally substituted.

12. The method of claim 1, wherein the manufactured conjugate comprises two or more features selected from among:
(a) less than or equal to 3% free dye,
(b) high molecular weight species less than or equal to 5%,
(c) low molecular weight species less than or equal to 5%, and/or
(d) greater than or equal to 92% monomer.

13. The method of claim 4, wherein the manufactured conjugate comprises two or more features selected from among:

(a) less than or equal to 3% free dye,
(b) high molecular weight species less than or equal to 5%,
(c) low molecular weight species less than or equal to 5%, and/or
(d) greater than or equal to 92% monomer.

14. A method of manufacturing a phthalocyanine dye-targeting molecule conjugate, the method comprising:
    (a) contacting a targeting molecule with a phthalocyanine dye under conditions to produce a conjugate comprising the phthalocyanine dye linked to the targeting molecule;
    (b) quenching by contacting with glycine; and
    (c) formulating the conjugate in a pharmaceutically acceptable buffer, wherein in each of steps (a)-(c):
    the only light to which the dye and conjugate are exposed has a wavelength within a range from at or about 400 nm to at or about 650 nm wherein the targeting molecule is an antibody or an antibody fragment.

15. The method of claim 14, wherein the manufactured conjugate comprises two or more features selected from among:
    (a) less than or equal to 3% free dye,
    (b) high molecular weight species less than or equal to 5%,
    (c) low molecular weight species less than or equal to 5%, and/or
    (d) greater than or equal to 92% monomer.

16. A method of manufacturing a phthalocyanine dye-targeting molecule conjugate, the method comprising:
    (a) contacting a targeting molecule with a phthalocyanine dye under conditions to produce a conjugate comprising the phthalocyanine dye linked to the targeting molecule;
    (b) quenching by contacting with glycine; and
    (c) formulating the conjugate in a pharmaceutically acceptable buffer, wherein in each of steps (a)-(c):
    the only light to which the dye and conjugate are exposed has an intensity of less than at or about 200 lux wherein the targeting molecule is an antibody or an antibody fragment.

17. The method of claim 16, wherein the manufactured conjugate comprises two or more features selected from among:
    (a) less than or equal to 3% free dye,
    (b) high molecular weight species less than or equal to 5%,
    (c) low molecular weight species less than or equal to 5%, and/or
    (d) greater than or equal to 92% monomer.

* * * * *

SEQUENCE LISTING

<160> NUMBER OF SEQ ID NOS: 52

<210> SEQ ID NO 1
<211> LENGTH: 9
<212> TYPE: PRT
<213> ORGANISM: Artificial Sequence
<220> FEATURE:
<223> OTHER INFORMATION: homing peptide

<400> SEQUENCE: 1

Cys Arg Gly Asp Lys Gly Pro Asp Cys
1               5

<210> SEQ ID NO 2
<211> LENGTH: 10
<212> TYPE: PRT
<213> ORGANISM: Artificial Sequence
<220> FEATURE:
<223> OTHER INFORMATION: homing peptide

<400> SEQUENCE: 2

Cys Cys Arg Gly Asp Lys Gly Pro Asp Cys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: homing peptide

<400> SEQUENCE: 3

Ala Lys Pro Ala Pro Pro Lys Pro Glu Pro Lys Pro Lys Lys Ala Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: homing peptide

<400> SEQUENCE: 4

Ala Lys Val Lys Asp Glu Pro Gln Arg Arg Ser Ala Arg Leu Ser
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: homing peptide

<400> SEQUENCE: 5

Cys Ala Gly Ala Leu Cys Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: homing peptide

<400> SEQUENCE: 6

Cys Ala Gly Arg Arg Ser Ala Tyr Cys
1               5

<210> SEQ ID NO 7
<211> LENGTH: 9
<212> TYPE: PRT
<213> ORGANISM: Artificial Sequence
<220> FEATURE:
<223> OTHER INFORMATION: homing peptide

<400> SEQUENCE: 7

Cys Ala Arg Ser Lys Asn Lys Asp Cys
1               5

```
<210> SEQ ID NO 8
<211> LENGTH: 9
<212> TYPE: PRT
<213> ORGANISM: Artificial Sequence
<220> FEATURE:
<223> OTHER INFORMATION: homing peptide

<400> SEQUENCE: 8

Cys Asp Cys Arg Gly Asp Cys Phe Cys
1               5

<210> SEQ ID NO 9
<211> LENGTH: 5
<212> TYPE: PRT
<213> ORGANISM: Artificial Sequence
<220> FEATURE:
<223> OTHER INFORMATION: homing peptide

<400> SEQUENCE: 9

Cys Asp Thr Arg Leu
1               5

<210> SEQ ID NO 10
<211> LENGTH: 5
<212> TYPE: PRT
<213> ORGANISM: Artificial Sequence
<220> FEATURE:
<223> OTHER INFORMATION: homing peptide

<400> SEQUENCE: 10

Cys Gly Lys Arg Lys
1               5

<210> SEQ ID NO 11
<211> LENGTH: 10
<212> TYPE: PRT
<213> ORGANISM: Artificial Sequence
<220> FEATURE:
<223> OTHER INFORMATION: homing peptide

<400> SEQUENCE: 11

Cys Gly Leu Ile Ile Gln Lys Asn Glu Cys
1               5                   10

<210> SEQ ID NO 12
<211> LENGTH: 7
<212> TYPE: PRT
<213> ORGANISM: Artificial Sequence
<220> FEATURE:
<223> OTHER INFORMATION: homing peptide

<400> SEQUENCE: 12

Cys Gly Asn Lys Arg Thr Arg
1               5

<210> SEQ ID NO 13
<211> LENGTH: 9
<212> TYPE: PRT
<213> ORGANISM: Artificial Sequence
<220> FEATURE:
<223> OTHER INFORMATION: homing peptide

<400> SEQUENCE: 13

Cys Gly Asn Lys Arg Thr Arg Gly Cys
1               5
```

```
<210> SEQ ID NO 14
<211> LENGTH: 9
<212> TYPE: PRT
<213> ORGANISM: Artificial Sequence
<220> FEATURE:
<223> OTHER INFORMATION: homing peptide

<400> SEQUENCE: 14

Cys Gly Arg Arg Ala Gly Gly Ser Cys
1               5

<210> SEQ ID NO 15
<211> LENGTH: 7
<212> TYPE: PRT
<213> ORGANISM: Artificial Sequence
<220> FEATURE:
<223> OTHER INFORMATION: homing peptide

<400> SEQUENCE: 15

Cys Lys Ala Ala Lys Asn Lys
1               5

<210> SEQ ID NO 16
<211> LENGTH: 11
<212> TYPE: PRT
<213> ORGANISM: Artificial Sequence
<220> FEATURE:
<223> OTHER INFORMATION: homing peptide

<400> SEQUENCE: 16

Cys Lys Gly Gly Arg Ala Lys Asp Cys Gly Gly
1               5                   10

<210> SEQ ID NO 17
<211> LENGTH: 9
<212> TYPE: PRT
<213> ORGANISM: Artificial Sequence
<220> FEATURE:
<223> OTHER INFORMATION: homing peptide

<400> SEQUENCE: 17

Cys Leu Ser Asp Gly Lys Arg Lys Cys
1               5

<210> SEQ ID NO 18
<211> LENGTH: 12
<212> TYPE: PRT
<213> ORGANISM: Artificial Sequence
<220> FEATURE:
<223> OTHER INFORMATION: homing peptide

<400> SEQUENCE: 18

Cys Met Tyr Ile Glu Ala Leu Asp Lys Tyr Ala Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: homing peptide

<400> SEQUENCE: 19

Lys Lys Cys Gly Gly Gly Gly Ile Arg Leu Arg Gly
1               5                   10

<210> SEQ ID NO 20
```

```
<211> LENGTH: 10
<212> TYPE: PRT
<213> ORGANISM: Artificial Sequence
<220> FEATURE:
<223> OTHER INFORMATION: homing peptide

<400> SEQUENCE: 20

Cys Asn Ala Gly Glu Ser Ser Lys Asn Cys
1               5                   10

<210> SEQ ID NO 21
<211> LENGTH: 5
<212> TYPE: PRT
<213> ORGANISM: Artificial Sequence
<220> FEATURE:
<223> OTHER INFORMATION: homing peptide

<400> SEQUENCE: 21

Cys Asn Gly Arg Cys
1               5

<210> SEQ ID NO 22
<211> LENGTH: 9
<212> TYPE: PRT
<213> ORGANISM: Artificial Sequence
<220> FEATURE:
<223> OTHER INFORMATION: homing peptide

<400> SEQUENCE: 22

Cys Asn Arg Arg Thr Lys Ala Gly Cys
1               5

<210> SEQ ID NO 23
<211> LENGTH: 9
<212> TYPE: PRT
<213> ORGANISM: Artificial Sequence
<220> FEATURE:
<223> OTHER INFORMATION: homing peptide

<400> SEQUENCE: 23

Cys Pro Gly Pro Glu Gly Ala Gly Cys
1               5

<210> SEQ ID NO 24
<211> LENGTH: 9
<212> TYPE: PRT
<213> ORGANISM: Artificial Sequence
<220> FEATURE:
<223> OTHER INFORMATION: homing peptide

<400> SEQUENCE: 24

Cys Pro Lys Thr Arg Arg Pro Val Cys
1               5

<210> SEQ ID NO 25
<211> LENGTH: 9
<212> TYPE: PRT
<213> ORGANISM: Artificial Sequence
<220> FEATURE:
<223> OTHER INFORMATION: homing peptide

<400> SEQUENCE: 25

Cys Pro Arg Glu Cys Glu Ser Ile Cys
1               5

<210> SEQ ID NO 26
<211> LENGTH: 9
```

```
<212> TYPE: PRT
<213> ORGANISM: Artificial Sequence
<220> FEATURE:
<223> OTHER INFORMATION: homing peptide

<400> SEQUENCE: 26

Cys Arg Ala Lys Ser Lys Val Ala Cys
1               5

<210> SEQ ID NO 27
<211> LENGTH: 9
<212> TYPE: PRT
<213> ORGANISM: Artificial Sequence
<220> FEATURE:
<223> OTHER INFORMATION: homing peptide

<400> SEQUENCE: 27

Cys Arg Glu Ala Gly Arg Lys Ala Cys
1               5

<210> SEQ ID NO 28
<211> LENGTH: 5
<212> TYPE: PRT
<213> ORGANISM: Artificial Sequence
<220> FEATURE:
<223> OTHER INFORMATION: homing peptide

<400> SEQUENCE: 28

Cys Arg Glu Lys Ala
1               5

<210> SEQ ID NO 29
<211> LENGTH: 9
<212> TYPE: PRT
<213> ORGANISM: Artificial Sequence
<220> FEATURE:
<223> OTHER INFORMATION: homing peptide

<400> SEQUENCE: 29

Cys Arg Gly Asp Lys Gly Pro Asp Cys
1               5

<210> SEQ ID NO 30
<211> LENGTH: 7
<212> TYPE: PRT
<213> ORGANISM: Artificial Sequence
<220> FEATURE:
<223> OTHER INFORMATION: homing peptide

<400> SEQUENCE: 30

Cys Arg Gly Arg Arg Ser Thr
1               5

<210> SEQ ID NO 31
<211> LENGTH: 6
<212> TYPE: PRT
<213> ORGANISM: Artificial Sequence
<220> FEATURE:
<223> OTHER INFORMATION: homing peptide

<400> SEQUENCE: 31

Cys Arg Lys Asp Lys Cys
1               5

<210> SEQ ID NO 32
<211> LENGTH: 5
<212> TYPE: PRT
```

```
<213> ORGANISM: Artificial Sequence
<220> FEATURE:
<223> OTHER INFORMATION: homing peptide

<400> SEQUENCE: 32

Cys Arg Pro Pro Arg
1               5

<210> SEQ ID NO 33
<211> LENGTH: 9
<212> TYPE: PRT
<213> ORGANISM: Artificial Sequence
<220> FEATURE:
<223> OTHER INFORMATION: homing peptide

<400> SEQUENCE: 33

Cys Arg Arg Glu Thr Ala Trp Ala Cys
1               5

<210> SEQ ID NO 34
<211> LENGTH: 6
<212> TYPE: PRT
<213> ORGANISM: Artificial Sequence
<220> FEATURE:
<223> OTHER INFORMATION: homing peptide

<400> SEQUENCE: 34

Cys Arg Ser Arg Lys Gly
1               5

<210> SEQ ID NO 35
<211> LENGTH: 9
<212> TYPE: PRT
<213> ORGANISM: Artificial Sequence
<220> FEATURE:
<223> OTHER INFORMATION: homing peptide

<400> SEQUENCE: 35

Cys Ser Arg Pro Arg Arg Ser Glu Cys
1               5

<210> SEQ ID NO 36
<211> LENGTH: 10
<212> TYPE: PRT
<213> ORGANISM: Artificial Sequence
<220> FEATURE:
<223> OTHER INFORMATION: homing peptide

<400> SEQUENCE: 36

Cys Thr Thr His Trp Gly Phe Thr Leu Cys
1               5                   10

<210> SEQ ID NO 37
<211> LENGTH: 9
<212> TYPE: PRT
<213> ORGANISM: Artificial Sequence
<220> FEATURE:
<223> OTHER INFORMATION: homing peptide

<400> SEQUENCE: 37

Cys Val Pro Glu Leu Gly His Glu Cys
1               5

<210> SEQ ID NO 38
<211> LENGTH: 13
<212> TYPE: PRT
<213> ORGANISM: Artificial Sequence
```

```
<220> FEATURE:
<223> OTHER INFORMATION: homing peptide

<400> SEQUENCE: 38

Glu Lys Gly Glu Gly Ala Leu Pro Thr Gly Lys Ser Lys
1               5                   10

<210> SEQ ID NO 39
<211> LENGTH: 6
<212> TYPE: PRT
<213> ORGANISM: Artificial Sequence
<220> FEATURE:
<223> OTHER INFORMATION: homing peptide

<400> SEQUENCE: 39

Phe Ala Leu Gly Glu Ala
1               5

<210> SEQ ID NO 40
<211> LENGTH: 13
<212> TYPE: PRT
<213> ORGANISM: Artificial Sequence
<220> FEATURE:
<223> OTHER INFORMATION: homing peptide

<400> SEQUENCE: 40

Gly Leu Asn Gly Leu Ser Ser Ala Asp Pro Ser Ser Asp
1               5                   10

<210> SEQ ID NO 41
<211> LENGTH: 8
<212> TYPE: PRT
<213> ORGANISM: Artificial Sequence
<220> FEATURE:
<223> OTHER INFORMATION: homing peptide

<400> SEQUENCE: 41

Gly Ser Met Ser Ile Ala Arg Leu
1               5

<210> SEQ ID NO 42
<211> LENGTH: 8
<212> TYPE: PRT
<213> ORGANISM: Artificial Sequence
<220> FEATURE:
<223> OTHER INFORMATION: homing peptide

<400> SEQUENCE: 42

Gly Val Ser Phe Leu Glu Tyr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: homing peptide

<400> SEQUENCE: 43

Ile Phe Leu Leu Trp Gln Arg
1               5

<210> SEQ ID NO 44
<211> LENGTH: 10
<212> TYPE: PRT
<213> ORGANISM: Artificial Sequence
<220> FEATURE:
```

<223> OTHER INFORMATION: homing peptide

<400> SEQUENCE: 44

Ile Phe Leu Leu Trp Gln Arg Cys Arg Arg
1               5                   10

<210> SEQ ID NO 45
<211> LENGTH: 5
<212> TYPE: PRT
<213> ORGANISM: Artificial Sequence
<220> FEATURE:
<223> OTHER INFORMATION: homing peptide

<400> SEQUENCE: 45

Pro Glu Pro His Cys
1               5

<210> SEQ ID NO 46
<211> LENGTH: 13
<212> TYPE: PRT
<213> ORGANISM: Artificial Sequence
<220> FEATURE:
<223> OTHER INFORMATION: homing peptide

<400> SEQUENCE: 46

Pro Ile Ser Asn Asp Gln Lys Val Ser Asp Asp Lys
1               5                   10

<210> SEQ ID NO 47
<211> LENGTH: 15
<212> TYPE: PRT
<213> ORGANISM: Artificial Sequence
<220> FEATURE:
<223> OTHER INFORMATION: homing peptide

<400> SEQUENCE: 47

Arg Met Trp Pro Ser Ser Thr Val Asn Leu Ser Ala Gly Arg Arg
1               5                   10                  15

<210> SEQ ID NO 48
<211> LENGTH: 7
<212> TYPE: PRT
<213> ORGANISM: Artificial Sequence
<220> FEATURE:
<223> OTHER INFORMATION: homing peptide

<400> SEQUENCE: 48

Arg Pro Ala Arg Pro Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: homing peptide

<400> SEQUENCE: 49

Ser Met Ser Ile Ala Arg Leu
1               5

<210> SEQ ID NO 50
<211> LENGTH: 13
<212> TYPE: PRT
<213> ORGANISM: Artificial Sequence
<220> FEATURE:
<223> OTHER INFORMATION: homing peptide

```
<400> SEQUENCE: 50

Val Asp Glu Asp Arg Ala Ser Leu Leu Lys Ser Gln Glu
1               5                   10

<210> SEQ ID NO 51
<211> LENGTH: 7
<212> TYPE: PRT
<213> ORGANISM: Artificial Sequence
<220> FEATURE:
<223> OTHER INFORMATION: homing peptide

<400> SEQUENCE: 51

Val Ser Phe Leu Glu Tyr Arg
1               5

<210> SEQ ID NO 52
<211> LENGTH: 11
<212> TYPE: PRT
<213> ORGANISM: Artificial Sequence
<220> FEATURE:
<223> OTHER INFORMATION: homing peptide

<400> SEQUENCE: 52

Trp Asn Ala Pro Ala Glu Glu Trp Gly Asn Trp
1               5                   10
```

UNITED STATES PATENT AND TRADEMARK OFFICE
CERTIFICATE OF CORRECTION

PATENT NO. : 11,141,483 B2
APPLICATION NO. : 15/753151
DATED : October 12, 2021
INVENTOR(S) : Makings et al.

It is certified that error appears in the above-identified patent and that said Letters Patent is hereby corrected as shown below:

In the Claims

At Column 163, Claim number 6, Line 61: please replace "wherein targeting molecule" with -- wherein the targeting molecule --; and At Column 166, Claim number 11, Line 55: please replace "optionally substituted." with -- optionally substituted alkoxy. --.

Signed and Sealed this
Second Day of August, 2022

Katherine Kelly Vidal
*Director of the United States Patent and Trademark Office*